US012459953B2

(12) United States Patent
Busch-Petersen et al.

(10) Patent No.: US 12,459,953 B2
(45) Date of Patent: Nov. 4, 2025

(54) TREM2 MODULATORS

(71) Applicant: Muna Therapeutics ApS, Frederiksberg (DK)

(72) Inventors: Jakob Busch-Petersen, Frederiksberg (DK); Gavin Whitlock, Sandwich (GB)

(73) Assignee: Muna Therapeutics ApS, Frederiksberg (DK)

( * ) Notice: Subject to any disclaimer, the term of this patent is extended or adjusted under 35 U.S.C. 154(b) by 0 days.

(21) Appl. No.: 19/009,660

(22) Filed: Jan. 3, 2025

(65) Prior Publication Data

US 2025/0223294 A1 Jul. 10, 2025

(30) Foreign Application Priority Data

Jan. 4, 2024 (EP) .................................. 24150289.7

(51) Int. Cl.

| | |
|---|---|
| ***C07D 487/04*** | (2006.01) |
| ***A61K 31/5377*** | (2006.01) |
| ***A61P 25/00*** | (2006.01) |
| ***A61P 25/28*** | (2006.01) |
| ***C07D 471/04*** | (2006.01) |

(52) U.S. Cl.

CPC ........ *C07D 487/04* (2013.01); *A61K 31/5377* (2013.01); *A61P 25/00* (2018.01); *A61P 25/28* (2018.01); *C07D 471/04* (2013.01)

(58) Field of Classification Search

CPC . C07D 487/04; C07D 471/04; A61K 31/5377

See application file for complete search history.

(56) References Cited

U.S. PATENT DOCUMENTS

| | | | |
|---|---|---|---|
| 11,453,667 B2 | 9/2022 | Cai et al. | |
| 2021/0163443 A1 | 6/2021 | Shirude et al. | |
| 2025/0042897 A1* | 2/2025 | Houze .................. | A61K 31/519 |
| 2025/0223293 A1 | 7/2025 | Busch-Petersen et al. | |

FOREIGN PATENT DOCUMENTS

| | | |
|---|---|---|
| WO | WO-2004/043956 A1 | 5/2004 |
| WO | WO-2019/109055 A1 | 6/2019 |
| WO | WO-2020/021064 A1 | 1/2020 |
| WO | WO-2021/210970 A1 | 10/2021 |
| WO | WO-2021/226135 A1 | 11/2021 |
| WO | WO-2021/226629 A1 | 11/2021 |
| WO | WO-2022/032293 A2 | 2/2022 |
| WO | WO-2022/120390 A1 | 6/2022 |
| WO | WO-2022/236272 A2 | 11/2022 |
| WO | WO-2022/251868 A1 | 12/2022 |
| WO | WO-2023/086799 A1 | 5/2023 |
| WO | WO-2023/086800 A1 | 5/2023 |
| WO | WO-2023/086801 A1 | 5/2023 |
| WO | WO-2023/092146 A1 | 5/2023 |
| WO | WO-2024/008722 A2 | 1/2024 |
| WO | WO-2024/097798 A1 | 5/2024 |
| WO | WO-2024/233847 A2 | 11/2024 |
| WO | WO-2024/233848 A1 | 11/2024 |
| WO | WO-2024/246018 A1 | 12/2024 |
| WO | WO-2024/246019 A1 | 12/2024 |
| WO | WO-2024/260929 A1 | 12/2024 |
| WO | WO-2025/117599 A1 | 6/2025 |
| WO | WO-2025/128848 A1 | 6/2025 |
| WO | WO-2025/128873 A1 | 6/2025 |
| WO | WO-2025/136898 A1 | 6/2025 |
| WO | WO-2025/136936 A1 | 6/2025 |

OTHER PUBLICATIONS

T. Heinrich et al. CHIMIA International Journal for Chemistry, 58(3): 143-147, DOI:10.2533/000942904777678118. (Year: 2004).*

Atagi, Y. et al. Apolipoprotein E is a Ligand for Triggering Receptor Expressed on Myeloid Cells 2 (TREM2), J. Biol. Chem., 290(43):26043-50 (2015).

Colonna, M. and Wang, Y., TREM2 variants: new keys to decipher Alzheimer disease pathogenesis, Nat. Rev. Neurosci., 17:201-207 (2016).

Deczkowska, A. et al., The Physiology, Pathology, and Potential Therapeutic Applications of the TREM2 Signalinjg Pathway, Cell, 181(6):1207-1217 (2020).

Hammond, T. R. et al., Immune Signaling in Neurodegeneration, Immunity, 50(4):955-974 (2019).

International Search Report for PCT/EP2023/068406, 8 pages (mailed Jan. 26, 2024).

Kleinberger, G. et al., TREM2 mutations implicated in neurodegeneration impair cell surface transport and phagocytosis, Sci. Transl. Med., 6(243):243ra86 (2014).

Labadie, S. et al., Design and evaluation of novel 8-oxo-pyridopyrimidine Jak1/2 inhibitors, Bioorg. Med. Chem. Lett., 23:5923-930 (2013).

Paloneva, J. et al., CNS manifestations of Nasu-Hakola disease; A Frontal dementia with bone cysts, Neurology, 56(11):1552-1558 (2001).

Suarez-Calvet, M. et al., sTREM2 cerebrospinal fluid levels are a potential biomarker for microglia activity in early-stage Alzheimer's disease and associate with neuronal injury markers, EMBO Mol. Med., 8(5):466-476 (2016).

Ulrich, J. D. et al., Elucidating the Role of TREM2 in Alzheimer's Disease, Neuron., 94(2):237-248 (2017).

Written Opinion for PCT/EP2023/068406, 10 pages (mailed Jan. 26, 2024).

(Continued)

*Primary Examiner* — James H Alstrum-Acevedo

*Assistant Examiner* — Manahil Mirghani Ali Abdalhameed

(74) *Attorney, Agent, or Firm* — Choate, Hall & Stewart LLP; Brenda Herschbach Jarrell; Michael A. Shinall

(57) ABSTRACT

The present invention relates to compounds useful for modulating Triggering Receptor Expressed on Myeloid Cells-2 ("TREM2"). The invention also relates to the compounds for use in treatment of conditions related to loss of function of TREM2, such as neurodegenerative diseases, and to pharmaceutical compositions comprising the compounds.

23 Claims, No Drawings

(56) References Cited

OTHER PUBLICATIONS

Yamazaki, K. et al., A Case of Nasu-Hakola Disease without Fractures or Consanguinity Diagnosed Using Exome Sequencing and Treated with Sodium Valproate, Clinical Psychopharmacology and Neuroscience, Korean College of Neuropsychopharmacology, 13(3):324-326 (2015).
International Search Report for PCT/EP2025/050085, 4 pages (mailed Apr. 1, 2025).
International Search Report for PCT/EP2025/050090, 5 pages (mailed Apr. 7, 2025).
Written Opinion for PCT/EP2025/050085, 9 pages (mailed Apr. 1, 2025).
Written Opinion for PCT/EP2025/050090, 5 pages (mailed Apr. 7, 2025).

* cited by examiner

TREM2 MODULATORS

TECHNICAL FIELD

The present invention relates to compounds useful for modulating Triggering Receptor Expressed on Myeloid Cells-2 ("TREM2"). The invention also relates to the compounds for use in treatment of conditions related to loss of function of TREM2, such as neurodegenerative diseases, and to pharmaceutical compositions comprising the compounds.

BACKGROUND

Triggering receptor expressed on myeloid cells-2 (TREM2) is a transmembrane receptor belonging to the immunoglobulin superfamily and is encoded by the TREM2 gene, which maps to human chromosome 6p21. TREM2 consists of an extracellular part that includes a single immunoglobulin domain and a short ectodomain, a single transmembrane helix and a short cytosolic tail (Colonna, M. et al. (2016))).

Insight to the role of TREM2 is provided by its restricted expression pattern. It is expressed exclusively on myeloid lineage cells, such as macrophages, microglia, dendritic cells and osteoclasts. It plays a role in tissue maintenance, as a sensor of pathology and inducer of innate immune signalling in specific tissues. In the brain TREM2 is exclusively expressed in microglia and is functionally required e.g. in phagocytosis of cellular debris, but has also been assigned roles in restricting inflammation as well as promoting cell survival (Deczkowska, A. et al. (2020)).

TREM2 has a wide range of ligands such as bacterial anionic molecules/endotoxins, phospholipids incl phosphatidylserine, lipoproteins and apolipoproteins incl ApoE, as well as oligomeric Aβ (Hammond, T. R. (2019)).

Signaling via TREM2 is well described through co-receptor DAP12. The adaptor molecule DAP 12 is expressed as a homodimer at the surface of a variety of cells participating in the innate immune response, including microglia, macrophages, granulocytes, NK cells, and dendritic cells. After ligation of TREM2, ITAM (immunoreceptor tyrosine-based activation motif) tyrosine phosphorylation of DAP12 by SRC-family kinases drive the recruitment and activation of the Syk kinase and/or ZAP70 kinase. Downstream of TREM2/DAP12/Syk several signaling pathways have been described involved in cell survival, cell activation and differentiation, and in the control of the actin cytoskeleton.

Proteolytic cleavage of the ectodomain of TREM2 by metalloproteinases, including ADAM10 and ADAM17 and possibly matrix metalloproteinases, leads to the shedding of soluble TREM2 (sTREM2), which can be detected in human cerebrospinal fluid (CSF). sTREM2 has been suggested as a potential biomarker for microglia activity in early-stage Alzheimer's disease (Suarez-Calvet, M. et al. (2016)).

Deficiency of either TREM2 or DAP12 leads to a blunted microglial response to pathological agents. The impact of TREM2-deficiency in vitro has been shown in the context of stimulation with typical TLR ligands, such as LPS. Loss-of-function genetic variants of TREM2 are associated with neurodegenerative diseases and supports a central role of microglial function in disease pathogenesis. Homozygous loss-of-function TREM2 variants cause Nasu-Hakola disease (Yamazaki, K. et al. (2015); Paloneva BM, J. et al. (2001); Ulrich J. D. et al. (2017)), whereas heterozygous loss-of-function TREM2 variants are associated with an increased risk for several neurological and neurodegenerative disorders such as Alzheimer's disease (AD), Frontotemporal lobar degeneration (FTLD), Parkinson's disease, FTLD-like syndrome, and Amyotrophic lateral sclerosis (ALS). The most prevalent mutation associated with AD is the loss-of-function mutation R47H, which has been shown to abrogate ligand binding and phagocytosis (Atagi, Y. et al. (2015); Kleinberger, G. et al (2014)).

Neurodegenerative disorders that may be treated by modulation of TREM2 activity and/or signaling include, but is not limited to, Alzheimer's disease (AD), Frontotemporal lobar degeneration (FTLD), FTLD-like syndrome, Parkinson's disease, Huntington disease, Nasu-Hakola disease (also known as polycystic lipomembranous osteodysplasia with sclerosing leukoencephalopathy), Multiple sclerosis (MS), Guillain-Barre syndrome, chronic inflammatory demyelinating polyneuropathies, Charcot-Marie-Tooth disease andAmyotrophic lateral sclerosis (ALS). Thus, there is a high and unmet medical need for TREM2 modulators to address these indications.

SUMMARY

The present invention relates to compounds that modulates TREM2.

In one aspect, the present invention relates to a compound of Formula (I):

Formula (I)

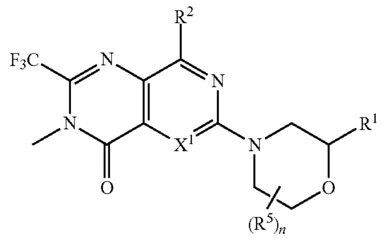

wherein $X^1$ is N or C(H);

$R^1$ is of Formula (II):

Formula (II)

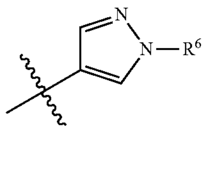

wherein $R^6$ is $C_{1-3}$ alkyl or cyclopropyl;

or $R^1$ is

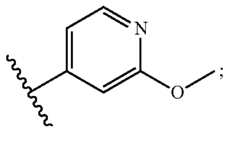 [SMILES: *c1ccnc(OC)c1]

$R^2$ is selected from the group consisting of:

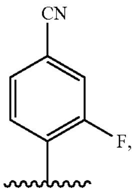, 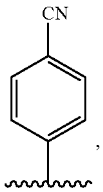, 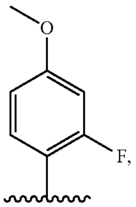, and

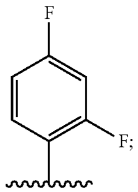 [SMILES: *c1ccc(F)cc1F]

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, with the proviso that when the compound is of Formula (VIII):

Formula (VIII)

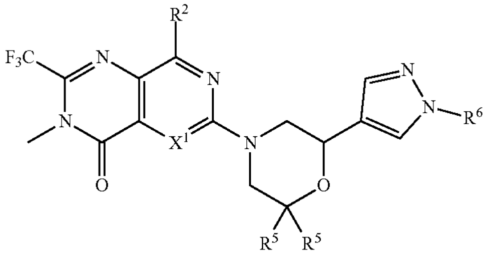

and $X^1$ is N, $R^5$ is C, alkanediyl and the two $R^5$ are linked together to form a 3-membered ring, $R^2$ is

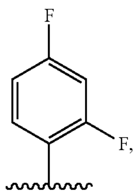

then $R^6$ is not methyl;

and with the proviso that when the compound is of Formula (VIII) and $X^1$ is C(H) or N, one $R^5$ is H and the other $R^5$ is $CH_3$, $R^2$ is

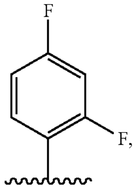

then $R^6$ is not cyclopropyl, or a pharmaceutically acceptable salt thereof.

In one aspect, the present invention relates a compound of Formula (I) as defined herein, or a pharmaceutically acceptable salt thereof, for use in the treatment of a disease associated with loss-of-function of TREM2, such as a neurodegenerative disease.

Definitions

As used herein, the singular forms "a," "an" and "the" include plural referents unless the content clearly dictates otherwise.

The terms "approximately" and "about" as referred herein are synonymous. In some embodiments, "about" refer to the recited amount, value, or duration ±20%, ±10%, ±5%, ±4%, ±3%, ±2%, ±1%, or ±0.5%.

The term, "compound," as used herein is meant to include all stereoisomers, geometric isomers, tautomers, and isotopes of the structures depicted, unless otherwise specified.

The terms "$C_{1-3}$ alkyl", "$C_{1-5}$ alkyl" and "$C_{1-6}$ alkyl" as used herein refer to a straight or branched hydrocarbon chains containing from 1 to 3, 1 to 5, and 1 to 6 carbon atoms, respectively. Representative examples of $C_{1-3}$ alkyl, $C_{1-5}$ alkyl and $C_{1-6}$ alkyl include, but are not limited to, methyl, ethyl, n-propyl, iso-propyl, n-butyl, sec-butyl, iso-butyl, tert-butyl, pentyl and hexyl.

The term "$C_{3-6}$ cycloalkyl" as used herein refers to a saturated carbocyclic molecule wherein the cyclic framework has 3 to 6 carbon atoms. Representative examples of $C_{3-6}$ cycloalkyl include, but are not limited to, cyclopropyl, cyclobutyl, cyclopentyl, and cyclohexyl.

The term "halogen" as used herein refers to —F, —Cl, —Br, or —I. In some embodiments, the halogen is F. In some embodiments, the halogen is Cl.

The term "halo" as used herein as a prefix to another term for a chemical group refers to a modification of the chemical group, wherein one or more hydrogen atoms are substituted with a halogen as defined herein. The halogen is independently selected at each occurrence. For example, the term "$C_{1-6}$ haloalkyl" refers to a $C_{1-6}$ alkyl as defined herein, wherein one or more hydrogen atoms are substituted with a halogen.

Representative examples of $C_{1-6}$ haloalkyl include, but are not limited to, $—CH_2F$, $—CHF_2$, $—CF_3$, —CHFCl, $—CH_2CF_3$, $—CFHCF_3$, $—CF_2CF_3$, $—CH(CF_3)_2$, $—CF(CHF_2)_2$, and $—CH(CH_2F)(CF_3)$.

The term "CN" is used herein to indicate a cyano group ( 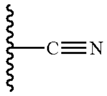 ).

As described herein, compounds of the present invention may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position, i.e. the substituent may be individually/independently selected from a group of substituents. Combinations of substituents envisioned by the present invention are preferably those that result in the formation of stable or chemically feasible compounds.

The term "stable," as used herein, refers to compounds that are not substantially altered when subjected to conditions to allow for their production, detection, and, in certain embodiments, their recovery, purification, and use for one or more of the purposes disclosed herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art.

DETAILED DESCRIPTION

In one aspect, the present invention relates to a compound of Formula (I):

Formula (I)

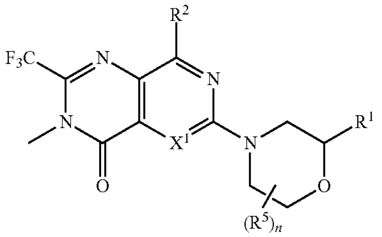

wherein $X^1$ is N or C(H);

$R^1$ is of Formula (II):

Formula (II)

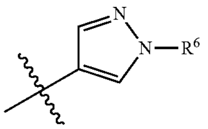

wherein $R^6$ is $C_{1-3}$ alkyl or cyclopropyl;

or $R^1$ is

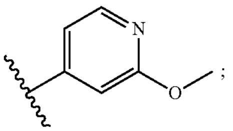

$R^2$ is selected from the group consisting of:

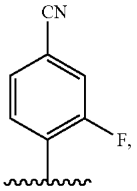

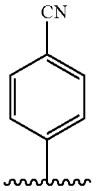

,

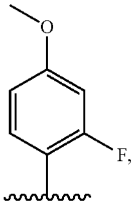

and

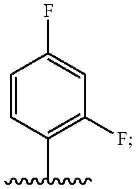 [SMILES: *c1ccc(F)cc1F]

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, or a pharmaceutically acceptable salt thereof.

In one aspect, the present invention relates to a compound of Formula (I):

Formula (I)

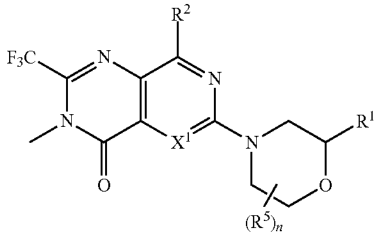

wherein $X^1$ is N or C(H);

$R^1$ is of Formula (II):

Formula (II)

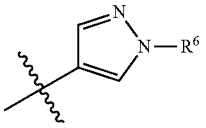

wherein $R^6$ is $C_{1-3}$ alkyl or cyclopropyl;

or $R^1$ is

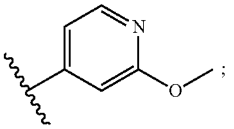 [SMILES: *c1ccnc(OC)c1]

$R^2$ is selected from the group consisting of:

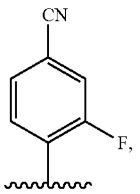

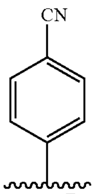

,

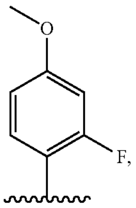

and

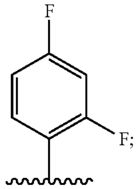 [SMILES: *c1ccc(F)cc1F]

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, with the proviso that when the compound is of Formula (VIII):

Formula (VIII)

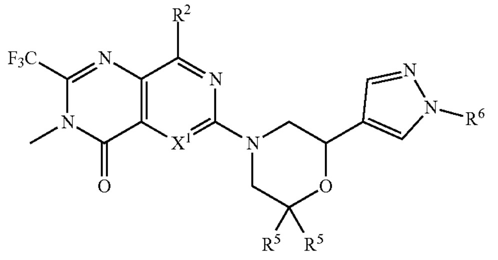

and $X^1$ is N, $R^3$ and $R^4$ are $C_1$ alkanediyl linked together to form a 3-membered ring, $R^2$ is

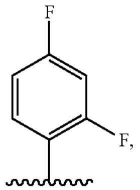

then $R^6$ is not methyl; and with the proviso that when the compound is of Formula (VIII) and $X^1$ is C(H) or N, $R^3$ is H, $R^4$ is $CH_3$, $R^2$ is

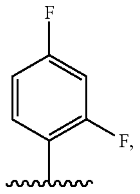

then $R^6$ is not cyclopropyl, or a pharmaceutically acceptable salt thereof.

In some embodiments, n is 1 and the

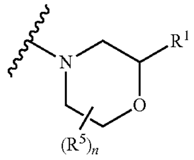

moiety is of Formula (VI):

Formula (VI)

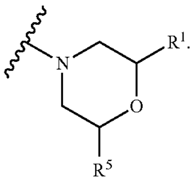

In some embodiments, the moiety of Formula (VI) is of Formula (VIa):

Formula (VIa)

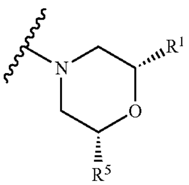

In some embodiments, the moiety of Formula (VI) is of Formula (VIb):

Formula (VIb)

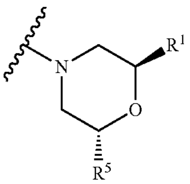

In some embodiments, the moiety of Formula (VI) is of Formula (VIc):

Formula (VIc)

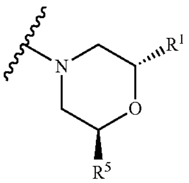

In some embodiments, the moiety of Formula (VI) is of Formula (VId):

Formula (VId)

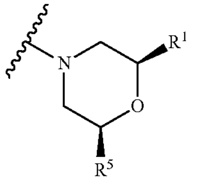

In some embodiments, the compound is of Formula (Ia):

Formula (Ia)

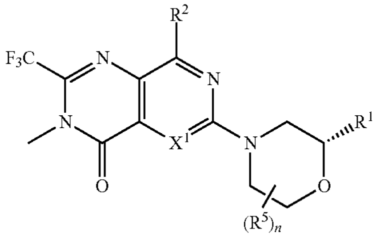

wherein $R^1$, $R^2$, $R^5$, n, and $X^1$ are as defined in classes and subclasses herein, both singly and in combination.

In some embodiments, the compound is of Formula (Ib):

Formula (Ib)

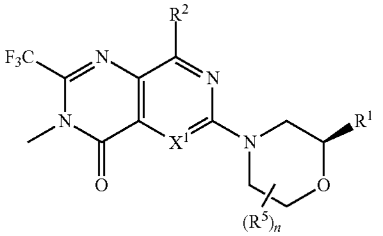

wherein $R^1$, $R^2$, $R^5$, n, and $X^1$ are as defined in classes and subclasses herein, both singly and in combination.

In some embodiments, the

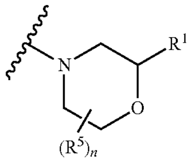

moiety is of Formula (VIIa):

Formula (VIIa)

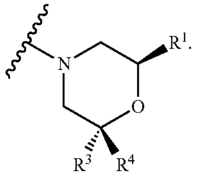

In some embodiments, the

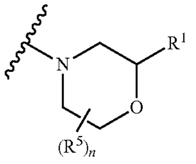

moiety is of Formula (VIIb):

Formula (VIIb)

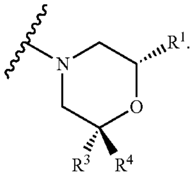

In some embodiments, the compound is of Formula (III):

Formula (III)

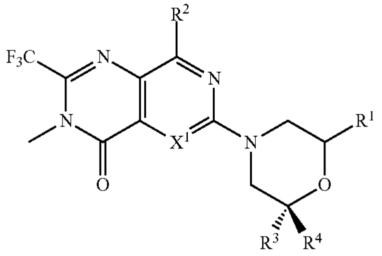

wherein $X^1$ is N or C(H);

$R^1$ is of Formula (II):

Formula (II)

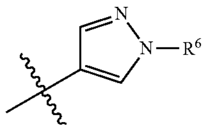

wherein $R^6$ is $C_{1-3}$ alkyl or cyclopropyl; or $R^1$ is

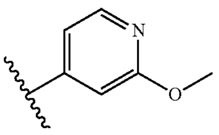

;

$R^2$ is selected from the group consisting of:

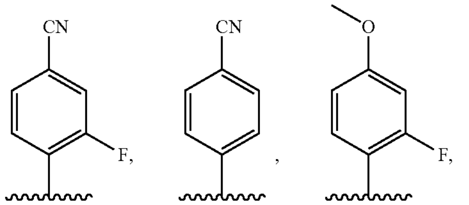

and

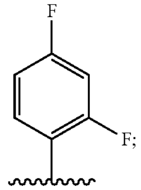 [SMILES: *c1ccc(F)cc1F]

$R^3$ is selected from the group consisting of H, F and $C_{1-3}$ alkyl; and $R^4$ is selected from the group consisting of H, F and $C_{1-3}$ alkyl;

or $R^3$ and $R^4$ are $C_{1-3}$ alkanediyl, $R^3$ and $R^4$ are linked together to form a 3- to 6-membered ring.

In some embodiments, the compound is of Formula (IIIa)

Formula (IIIa)

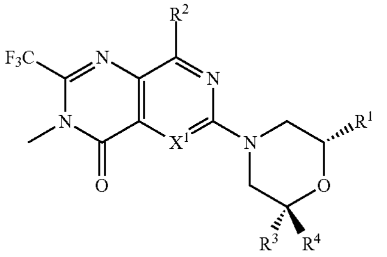

wherein $R^1$, $R^2$, $R^3$, $R^4$, and $X^1$ are as defined in classes and subclasses herein, both singly and in combination.

In some embodiments, the compound is of Formula (IIIb):

Formula (IIIb)

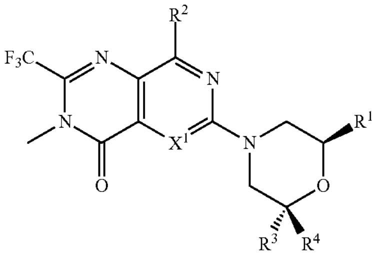

wherein $R^1$, $R^2$, $R^3$, $R^4$, and $X^1$ are as defined in classes and subclasses herein, both singly and in combination.

In some embodiments, the compound is of Formula (IV):

Formula (IV)

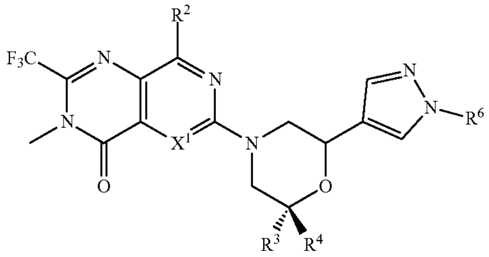

wherein $X^1$ is N or C(H);

wherein $R^6$ is $C_{1-3}$ alkyl or cyclopropyl;

$R^2$ is selected from the group consisting of:

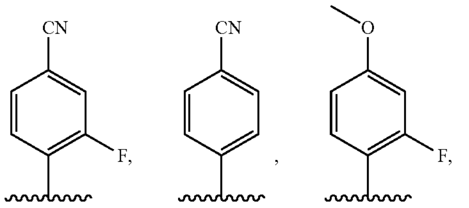

and

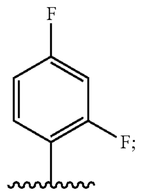

$R^3$ is selected from the group consisting of H, F and $C_{1-3}$ alkyl; and $R^4$ is selected from the group consisting of H, F and $C_{1-3}$ alkyl;

or $R^3$ and $R^4$ are $C_{1-3}$ alkanediyl, $R^3$ and $R^4$ are linked together to form a 3- to 6-membered ring.

In some embodiments, the compound is of Formula (IX):

Formula (IX)

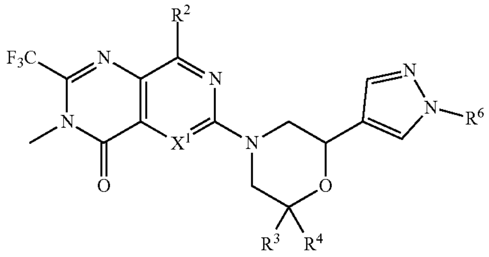

wherein $R^2$, $R^3$, $R^4$, $R^6$, and $X^1$ are as defined in classes and subclasses herein, both singly and in combination.

In some embodiments, the compound is of Formula (IVa):

Formula (IVa)

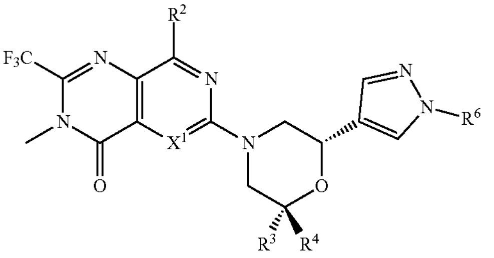

wherein $R^2$, $R^3$, $R^4$, $R^6$, and $X^1$ are as defined in classes and subclasses herein, both singly and in combination.

In some embodiments, the compound is of Formula (IVb):

Formula (IVb)

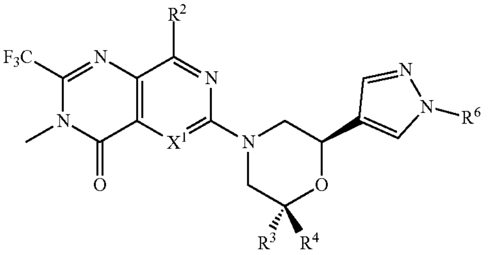

wherein $R^2$, $R^3$, $R^4$, $R^6$, and $X^1$ are as defined in classes and subclasses herein, both singly and in combination.

In some embodiments, the compound is of Formula (X):

Formula (X)

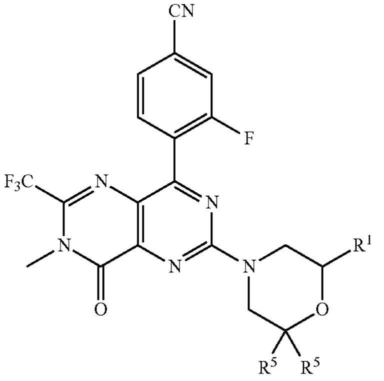

or a pharmaceutically acceptable salt thereof, wherein $R^1$ is of Formula (II):

Formula (II)

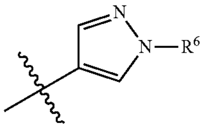

wherein $R^6$ is $C_{1-3}$ alkyl or cyclopropyl; or

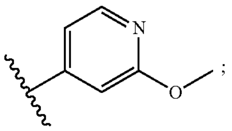 [SMILES: *c1ccnc(OC)c1]

each $R^5$ is individually selected from the group consisting of H, F and $C_{1-3}$ alkyl.

In some embodiments, the compound is of Formula (XI):

Formula (XI)

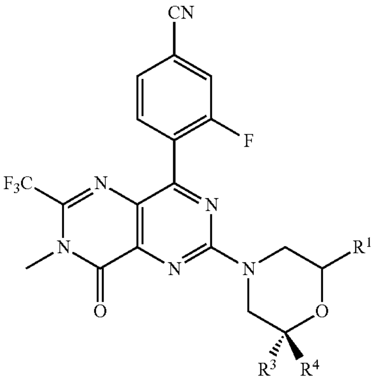

or a pharmaceutically acceptable salt thereof, wherein

Formula (II)

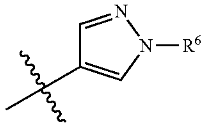

wherein $R^6$ is $C_{1-3}$ alkyl or cyclopropyl; or

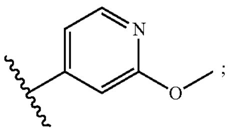 [SMILES: *c1ccnc(OC)c1]

$R^3$ is H, F or $C_{1-3}$ alkyl; and $R^4$ is H, F or $C_{1-3}$ alkyl.

In one aspect, the present invention relates to a compound of Formula (I):

Formula (I)

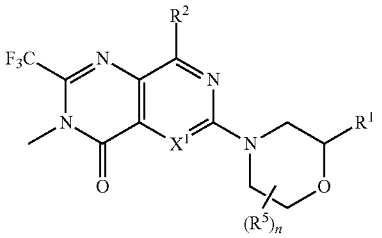

wherein $X^1$ is N or C(H);

$R^1$ is of Formula (II):

Formula (II)

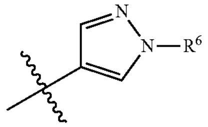

wherein $R^6$ is $C_{1-3}$ alkyl or cyclopropyl;

or $R^1$ is

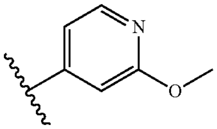 ;

$R^2$ is of Formula (XII):

Formula (XII)

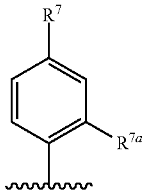

wherein $R^7$ is —CN, —$OC_{1-3}$ alkyl or F; and $R^{7a}$ is F or H;

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, or a pharmaceutically acceptable salt thereof.

In some embodiments, the compound is of Formula (V):

Formula (V)

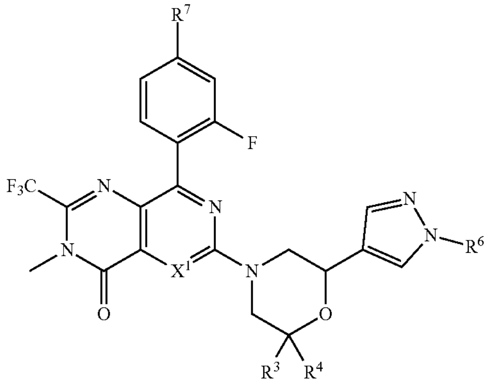

wherein $X^1$ is N or C(H);

$R^6$ is $C_{1-3}$ alkyl or cyclopropyl;

$R^7$ is —CN, —$OC_{1-3}$ alkyl or F;

$R^3$ is selected from the group consisting of H, F and $C_{1-3}$ alkyl; and $R^4$ is selected from the group consisting of H, F and $C_{1-3}$ alkyl.

In some embodiments, $X^1$ is N. In some embodiments, $X^1$ is C(H).

In some embodiments, $R^1$ is of Formula (II):

Formula (II)

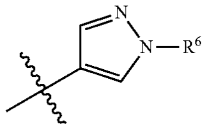

wherein $R^6$ is $C_{1-3}$ alkyl or cyclopropyl.

In some embodiments, $R^6$ is —$C_{1-3}$ alkyl. In some embodiments, $R^6$ is —$CH_3$. In some embodiments, $R^6$ is —$CH_2CH_3$. In some embodiments, $R^6$ is —$CH_2CH_2CH_3$. In some embodiments, $R^6$ is cyclopropyl.

In some embodiments, $R^1$ is

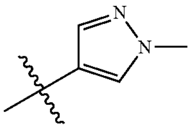 .

In some embodiments, $R^1$ is

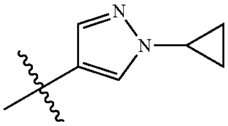 .

In some embodiments, $R^1$ is

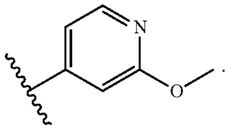 [SMILES: *c1ccnc(OC)c1]

In some embodiments, $R^2$ is of Formula (XII):

Formula (XII)

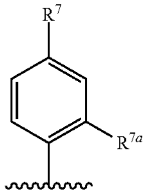

wherein $R^7$ is —CN, —$OC_{1-3}$ alkyl or and $R^{7a}$ is or H. In some embodiments, $R^{7a}$ is F. In some embodiments, $R^{7a}$ is H. In some embodiments, $R^2$ is of Formula (XII) and $R^7$ is —CN. In some embodiments, $R^2$ is of Formula (XII), $R^7$ is —$OC_{1-3}$ alkyl, and $R^{7a}$ is F.

In some embodiments, $R^7$ is —CN. In some embodiments, $R^7$ is —$OC_{1-3}$ alkyl. In some embodiments, $R^7$ is —$OCH_3$.

In some embodiments, $R^2$ is

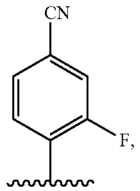 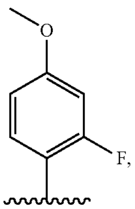 or 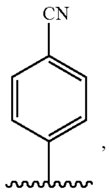 ,

In some embodiments, $R^2$ is

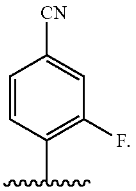 [SMILES: *c1ccc(C#N)cc1F]

In some embodiments, $R^2$ is

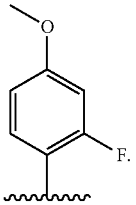 [SMILES: *c1ccc(OC)cc1F]

In some embodiments, $R^2$ is

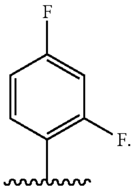 [SMILES: *c1ccc(F)cc1F]

In some embodiments, $R^2$ is

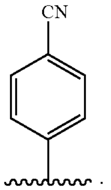 [SMILES: *c1ccc(C#N)cc1]

In some embodiments, n is 0, 1 or 2, and $R^5$ is individually H, F or $C_{1-3}$ alkyl. In some embodiments, n is 0, 1 or 2, and $R^5$ is individually F or $C_{1-3}$ alkyl.

In some embodiments, $R^5$ is H. In some embodiments, $R^5$ is individually F or $C_{1-3}$ alkyl. In some embodiments, $R^5$ is F. In some embodiments, $R^5$ is $C_{1-3}$ alkyl. In some embodiments, $R^5$ is $CH_3$. In some embodiments, $R^5$ is $R^3$. In some embodiments, $R^5$ is $R^4$.

In some embodiments, n is 0. In some embodiments, n is 1. In some embodiments, n is 2.

In some embodiments, $R^3$ is H, F or $C_{1-3}$ alkyl, and $R^4$ is H, F or $C_{1-3}$ alkyl.

In some embodiments, $R^3$ is H. In some embodiments, $R^3$ is F. In some embodiments, $R^3$ is $C_{1-3}$ alkyl. In some embodiments, $R^3$ is $CH_3$.

In some embodiments, $R^4$ is H. In some embodiments, $R^4$ is F. In some embodiments, $R^4$ is $C_{1-3}$ alkyl. In some embodiments, $R^4$ is $CH_3$.

In some embodiments, $R^3$ and $R^4$ are identical. In some embodiments, $R^3$ and $R^4$ are different.

In some embodiments, $R^3$ is $C_{1-3}$ alkyl and $R^4$ is $C_{1-3}$ alkyl. In some embodiments, $R^3$ is $CH_3$ and $R^4$ is $CH_3$. In some embodiments, $R^3$ is $CH_3$ and $R^4$ is H. In some embodiments, $R^3$ is H and $R^4$ is H. In some embodiments, $R^3$ is H and $R^4$ is $CH_3$. In some embodiments, $R^3$ is F and $R^4$ is F.

In some embodiments, $X^1$ is N; $R^3$ is H; and $R^4$ is H. In some embodiments, $X^1$ is C(H); $R^3$ is H; and $R^4$ is H. In some embodiments, $X^1$ is N; $R^3$ is F; and $R^4$ is F. In some embodiments, $X^1$ is C(H); $R^3$ is F; and $R^4$ is F. In some embodiments, $X^1$ is N; $R^3$ is $CH_3$; and $R^4$ is H. In some embodiments, $X^1$ is C(H); $R^3$ is $CH_3$; and $R^4$ is H.

In some embodiments, the compound is of Formula (III) and $X^1$ is N; $R^3$ is H; and $R^4$ is H. In some embodiments, the compound is of Formula (III) and $X^1$ is C(H); $R^3$ is H; and $R^4$ is H. In some embodiments, the compound is of Formula (III) and $X^1$ is N; $R^3$ is F; and $R^4$ is F. In some embodiments, the compound is of Formula (III) and $X^1$ is C(H); $R^3$ is F; and $R^4$ is F. In some embodiments, the compound is of Formula (III) and $X^1$ is N; $R^3$ is $CH_3$; and $R^4$ is H. In some embodiments, the compound is of Formula (III) and $X^1$ is C(H); $R^3$ is $CH_3$; and $R^4$ is H.

In some embodiments, $X^1$ is N; $R^6$ is $CH_3$; $R^3$ is H; and $R^4$ is H. In some embodiments, $X^1$ is C(H); $R^6$ is $CH_3$; $R^3$ is H; and $R^4$ is H. In some embodiments, $X^1$ is N; $R^6$ is $CH_3$; $R^3$ is F; and $R^4$ is F. In some embodiments, $X^1$ is C(H); $R^6$ is $CH_3$; $R^3$ is F; and $R^4$ is F. In some embodiments, $X^1$ is N; $R^6$ is cyclopropyl; $R^3$ is $CH_3$; and $R^4$ is H. In some embodiments, $X^1$ is C(H); $R^6$ is cyclopropyl; $R^3$ is $CH_3$; and $R^4$ is H. In some embodiments, $X^1$ is N; $R^6$ is $CH_3$; $R^3$ is $CH_3$; and $R^4$ is H. In some embodiments, $X^1$ is N; $R^6$ is cyclopropyl; $R^3$ is H; and $R^4$ is $CH_3$. In some embodiments, $X^1$ is C(H); $R^6$ is cyclopropyl; $R^3$ is H; and $R^4$ is $CH_3$. In some embodiments, $X^1$ is N; $R^6$ is $CH_3$; $R^3$ is H; and $R^4$ is $CH_3$.

In some embodiments, the compound is of Formula (IV) and $X^1$ is N; $R^6$ is $CH_3$; $R^3$ is H; and $R^4$ is H. In some embodiments, the compound is of Formula (IV) and $X^1$ is C(H); $R^6$ is $CH_3$; $R^3$ is H; and $R^4$ is H. In some embodiments, the compound is of Formula (IV) and $X^1$ is N; $R^6$ is $CH_3$; $R^3$ is F; and $R^4$ is F. In some embodiments, the compound is of Formula (IV) and $X^1$ is C(H); $R^6$ is $CH_3$; $R^3$ is F; and $R^4$ is F. In some embodiments, the compound is of Formula (IV) and $X^1$ is N; $R^6$ is cyclopropyl; $R^3$ is $CH_3$; and $R^4$ is H. In some embodiments, the compound is of Formula (IV) and $X^1$ is C(H); $R^6$ is cyclopropyl; $R^3$ is $CH_3$; and $R^4$ is H. In some embodiments, the compound is of Formula (IV) and $X^1$ is N; $R^6$ is $CH_3$; $R^3$ is $CH_3$; and $R^4$ is H. In some embodiments, the compound is of Formula (IVa) and $X^1$ is N; $R^6$ is $CH_3$; $R^3$ is H; and $R^4$ is H. In some embodiments, the compound is of Formula (IVa) and $X^1$ is C(H); $R^6$ is $CH_3$; $R^3$ is H; and $R^4$ is H. In some embodiments, the compound is of Formula (IVa) and $X^1$ is N; $R^6$ is $CH_3$; $R^3$ is F; and $R^4$ is F. In some embodiments, the compound is of Formula (IVa) and $X^1$ is C(H); $R^6$ is $CH_3$; $R^3$ is F; and $R^4$ is F. In some embodiments, the compound is of Formula (IVa) and $X^1$ is N; $R^6$ is cyclopropyl; $R^3$ is $CH_3$; and $R^4$ is H. In some embodiments, the compound is of Formula (IVa) and $X^1$ is C(H); $R^6$ is cyclopropyl; $R^3$ is $CH_3$; and $R^4$ is H. In some embodiments, the compound is of Formula (IVa) and $X^1$ is N; $R^6$ is $CH_3$; $R^3$ is $CH_3$; and $R^4$ is H. In some embodiments, the compound is of Formula (IVb) and $X^1$ is N; $R^6$ is $CH_3$; $R^3$ is H; and $R^4$ is H. In some embodiments, the compound is of Formula (IVb) and $X^1$ is C(H); $R^6$ is $CH_3$; $R^3$ is H; and $R^4$ is H. In some embodiments, the compound is of Formula (IVb) and $X^1$ is N; $R^6$ is $CH_3$; $R^3$ is F; and $R^4$ is F. In some embodiments, the compound is of Formula (IVb) and $X^1$ is C(H); $R^6$ is $CH_3$; $R^3$ is F; and $R^4$ is F. In some embodiments, the compound is of Formula (IVb) and $X^1$ is N; $R^6$ is cyclopropyl; $R^3$ is H; and $R^4$ is $CH_3$. In some embodiments, the compound is of Formula (IVb) and $X^1$ is C(H); $R^6$ is cyclopropyl; $R^3$ is H; and $R^4$ is $CH_3$. In some embodiments, the compound is of Formula (IVb) and $X^1$ is N; $R^6$ is $CH_3$; $R^3$ is H; and $R^4$ is $CH_3$.

In some embodiments, $R^3$ is $C_{1-3}$ alkanediyl, $R^4$ is $C_{1-3}$ alkanediyl, and $R^3$ and $R^4$ are linked together to form a ring. In some embodiments, $R^3$ is $—CH_2—$, $R^4$ is $—CH_2—$, and $R^3$ and $R^4$ are linked together to form a ring.

In some embodiments, when $R^2$ is

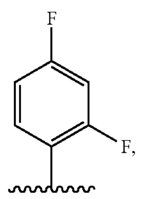

then $R^1$ is

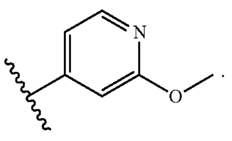 [SMILES: *c1ccnc(OC)c1]

In some embodiments, when $R^2$ is

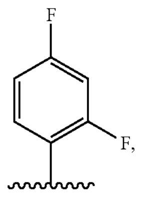

then n is 0.

In some embodiments, when $X^1$ is N, n is 2 and the two $R^5$ are $C_1$ alkanediyl, linked together to form a 3-membered ring, $R^2$ is

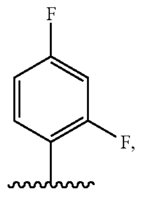

and $R^1$ is of Formula (II), then $R^6$ is not methyl. In some embodiments, when the compound is of Formula (VIII):

Formula (VIII)

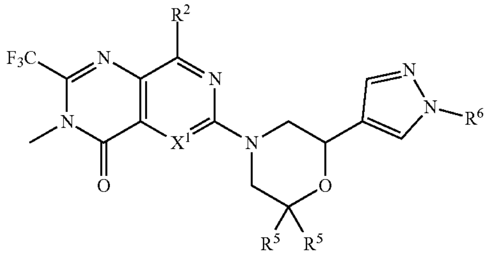

and $X^1$ is N, $R^5$ is $C_1$ alkanediyl and the two $R^5$ are linked together to form a 3-membered ring, $R^2$ is

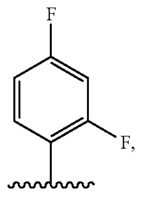

then $R^6$ is not methyl. In some embodiments, when the compound is of Formula (IX):

Formula (IX)

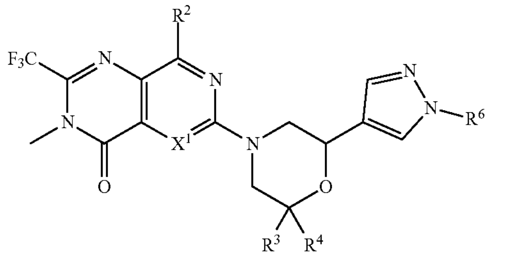

$X^1$ is N, $R^3$ and $R^4$ are $C_1$ alkanediyl, linked together to form a 3-membered ring, $R^2$ is

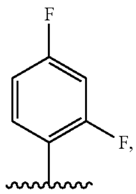

then $R^6$ is not methyl. In some embodiments, the compound is not 8-(2,4-difluorophenyl)-3-methyl-6-(5-(1-methyl-1H-pyrazol-4-yl)-4-oxa-7-azaspiro[2.5]octan-7-yl)-2-(trifluoromethyl)pyrimido[5,4-d]pyrimidin-4(3H)-one, or a pharmaceutically acceptable salt thereof. In some embodiments, the compound is not (R)-8-(2,4-difluorophenyl)-3-methyl-6-(5-(1-methyl-1H-pyrazol-4-yl)-4-oxa-7-azaspiro[2.5]octan-7-yl)-2-(trifluoromethyl)pyrimido[5,4-d]pyrimidin-4(3H)-one, or a pharmaceutically acceptable salt thereof. In some embodiments, the compound is not (S)-8-(2,4-difluorophenyl)-3-methyl-6-(5-(1-methyl-1H-pyrazol-4-yl)-4-oxa-7-azaspiro[2.5]octan-7-yl)-2-(trifluoromethyl)pyrimido[5,4-d]pyrimidin-4(3H)-one, or a pharmaceutically acceptable salt thereof.

In some embodiments, when n is 1, $R^5$ is $CH_3$, $R^2$ is

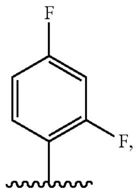

and $R^1$ is of Formula (II), then $R^6$ is not cyclopropyl. In some embodiments, when the compound is of Formula (VIII):

Formula (VIII)

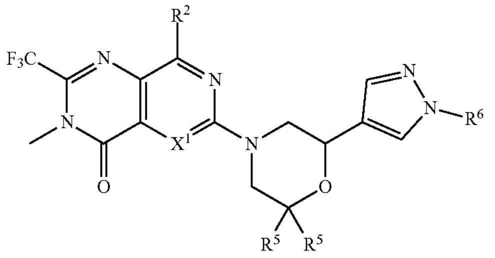

and $X^1$ is C(H) or N, one $R^5$ is H and the other $R^5$ is $CH_3$, $R^2$ is

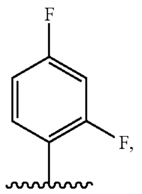

then $R^6$ is not cyclopropyl. In some embodiments, when the compound is of Formula (IX):

Formula (IX)

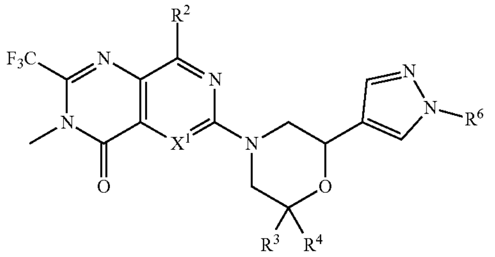

$X^1$ is N or C(H), $R^3$ is H, $R^4$ is $CH_3$, $R^2$ is

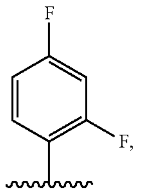

then $R^6$ is not cyclopropyl.

In some embodiments, when $X^1$ is N, n is 1, $R^5$ is $CH_3$, $R^2$ is

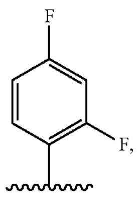

and $R^1$ is of Formula (II), then $R^6$ is not cyclopropyl.

In some embodiments, when the compound is of Formula (VIII):

Formula (VIII)

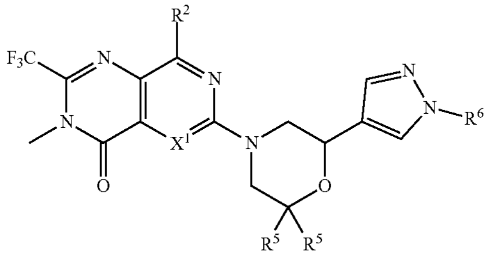

$X^1$ is N, one $R^5$ is H and the other $R^5$ is $CH_3$, $R^2$ is

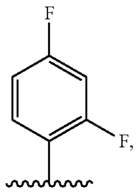

then $R^6$ is not cyclopropyl.

In some embodiments, when the compound is of Formula (IX):

Formula (IX)

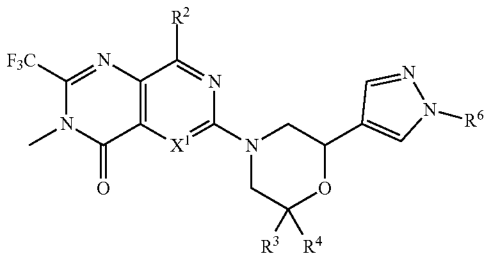

$X^1$ is N, $R^3$ is H, $R^4$ is $CH_3$, $R^2$ is

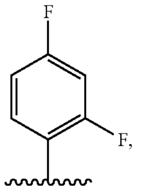

then $R^6$ is not cyclopropyl. In some embodiments, the compound is not 6-[2-(1-cyclopropyl-1H-pyrazol-4-yl)-6-methyl-4-morpholinyl]-8-(2,4-difluorophenyl)-3-methyl-2-(trifluoromethyl)-pyrimido[5,4-d]pyrimidin-4(3H)-one, or a pharmaceutically acceptable salt thereof. In some embodiments, the compound is not 6-[(2R,6S)-2-(1-cyclopropyl-1H-pyrazol-4-yl)-6-methyl-4-morpholinyl]-8-(2,4-difluorophenyl)-3-methyl-2-(trifluoromethyl)-pyrimido[5,4-d]pyrimidin-4(3H)-one, or a pharmaceutically acceptable salt thereof. In some embodiments, the compound is not 6-[(2S,6R)-2-(1-cyclopropyl-1H-pyrazol-4-yl)-6-methyl-4-morpholinyl]-8-(2,4-difluorophenyl)-3-methyl-2-(trifluoromethyl)-pyrimido[5,4-d]pyrimidin-4(3H)-one, or a pharmaceutically acceptable salt thereof.

In some embodiments, when $X^1$ is C(H), n is 1, $R^5$ is $CH_3$, $R^2$ is

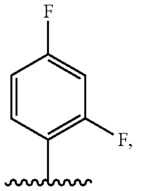

and $R^1$ is of Formula (II), then $R^6$ is not cyclopropyl. In some embodiments, when the compound is of Formula (VIII):

Formula (VIII)

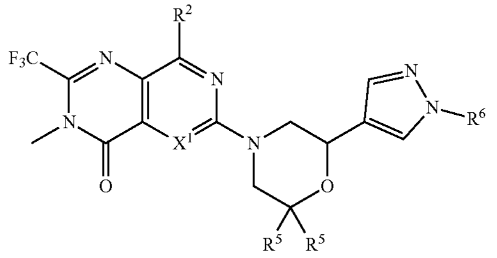

$X^1$ is C(H), one $R^5$ is H and the other $R^5$ is $CH_3$, $R^2$ is

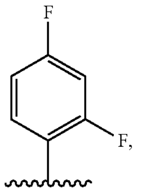

then $R^6$ is not cyclopropyl. In some embodiments, when the compound is of Formula (IX):

Formula (IX)

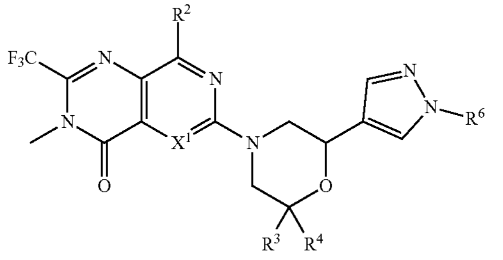

$X^1$ is C(H), $R^3$ is H, $R^4$ is $CH_3$, $R^2$ is

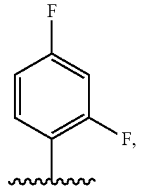

then $R^6$ is not cyclopropyl. In some embodiments, the compound is not 6-(2-(1-cyclopropyl-1H-pyrazol-4-yl)-6-methylmorpholino)-8-(2,4-difluorophenyl)-3-methyl-2-(trifluoromethyl)pyrido[3,4-d]pyrimidin-4(3H)-one, or a pharmaceutically acceptable salt thereof. In some embodiments, the compound is not 6-((2R,6S)-2-(1-cyclopropyl-1H-pyrazol-4-yl)-6-methylmorpholino)-8-(2,4-difluorophenyl)-3-methyl-2-(trifluoromethyl)pyrido[3,4-d]pyrimidin-4(3H)-one, or a pharmaceutically acceptable salt thereof. In some embodiments, the compound is not 6-((2S,6R)-2-(1-cyclopropyl-1H-pyrazol-4-yl)-6-methylmorpholino)-8-(2,4-difluorophenyl)-3-methyl-2-(trifluoromethyl)pyrido[3,4-d]pyrimidin-4(3H)-one, or a pharmaceutically acceptable salt thereof.

In some embodiments, the compound is 3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one, or a pharmaceutically acceptable salt thereof. In some embodiments, the compound is 4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 6-(2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one, or a pharmaceutically acceptable salt thereof. In some embodiments, the compound is 6-(3-((1-cyclopropyl-1H-pyrazol-4-yl)methyl)azetidin-1-yl)-8-(2,4-difluorophenyl)-3-methyl-2-(trifluoromethyl)pyrimido[5,4-d]pyrimidin-4(3H)-one, or a pharmaceutically acceptable salt thereof. In some embodiments, the compound is 3-fluoro-4-(7-methyl-2-(2-methyl-6-(1-methyl-1H-pyrazol-4-yl)morpholino)-8-oxo-6-(trifluoromethyl)-7,8-dihydropyrimido[5,4-d]pyrimidin-4-yl) benzonitrile, or a pharmaceutically acceptable salt thereof. In some embodiments, the compound is 4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile, or a pharmaceutically acceptable salt thereof. In some embodiments, the compound is 3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 3-fluoro-4-(2-(2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 4-(7-methyl-2-(2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 4-(2-(2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 8-(2,4-difluorophenyl)-6-(2-(2-methoxypyridin-4-yl)morpholino)-3-methyl-2-(trifluoromethyl)pyrimido[5,4-d]pyrimidin-4(3H)-one, or a pharmaceutically acceptable salt thereof. In some embodiments, the compound is 4-(6-(2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile, or a pharmaceutically acceptable salt thereof. In some embodiments, the compound is 4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile, or a pharmaceutically acceptable salt thereof. In some embodiments, the compound is 3-fluoro-4-(3-methyl-6-(2-(1-methyl-1H-pyrazol-4-yl)morpholino)-4-oxo-2-(trifluoromethyl)-3,4-dihydropyrido[3,4-d]pyrimidin-8-yl)benzonitrile, or a pharmaceutically acceptable salt thereof.

In some embodiments, the compound is (S)-3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is (R)-3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is (S)-8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one, or a pharmaceutically acceptable salt thereof. In some embodiments, the compound is (R)-8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one, or a pharmaceutically acceptable salt thereof. In some embodiments, the compound is (S)-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is (R)-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 6-((2S,6R)-2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one, or a pharmaceutically acceptable salt thereof. In some embodiments, the compound is 6-((2R,6S)-2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one, or a pharmaceutically acceptable salt thereof. In some embodiments, the compound is 4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile, or a pharmaceutically acceptable salt thereof. In some embodiments, the compound is 4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile, or a pharmaceutically acceptable salt thereof. In some embodiments, the compound is 3-fluoro-4-(7-methyl-2-((2R,6S)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 3-fluoro-4-(7-methyl-2-((2S,6R)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is (S)-4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile, or a pharmaceutically acceptable salt thereof. In some embodiments, the compound is (R)-4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile, or a pharmaceutically acceptable salt thereof. In some embodiments, the compound is (S)-3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is (R)-3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 3-fluoro-4-(2-((2S,6R)-2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 3-fluoro-4-(2-((2R,6S)-2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 4-(7-methyl-2-((2R,6S)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 4-(7-methyl-2-((2S,6R)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile, or a pharmaceutically acceptable salt thereof. In some embodiments, the compound is 4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is 4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile, or a pharmaceutically acceptable salt thereof. In some embodiments, the compound is (S)-8-(2,4-difluorophenyl)-6-(2-(2-methoxypyridin-4-yl)morpholino)-3-methyl-2-(trifluoromethyl)pyrimido[5,4-d]pyrimidin-4(3H)-one, or a pharmaceutically acceptable salt thereof. In some embodiments, the compound is (R)-8-(2,4-difluorophenyl)-6-(2-(2-methoxypyridin-4-yl)morpholino)-3-methyl-2-(trifluoromethyl)pyrimido[5,4-d]pyrimidin-4(3H)-one, or a pharmaceutically acceptable salt thereof. In some embodiments, the compound is 4-(6-((2R,6S)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile, or a pharmaceutically acceptable salt thereof. In some embodiments, the compound is 4-(6-((2S,6R)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile, or a pharmaceutically acceptable salt thereof. In some embodiments, the compound is (S)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile, or a pharmaceutically acceptable salt thereof. In some embodiments, the compound is (R)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile, or a pharmaceutically acceptable salt thereof. In some embodiments, the compound is (S)-3-fluoro-4-(3-methyl-6-(2-(1-methyl-1H-pyrazol-4-yl)morpholino)-4-oxo-2-(trifluoromethyl)-3,4-dihydropyrido[3,4-d]pyrimidin-8-yl)benzonitrile, or a pharmaceutically acceptable salt thereof. In some embodiments, the compound is (R)-3-fluoro-4-(3-methyl-6-(2-(1-methyl-1H-pyrazol-4-yl)morpholino)-4-oxo-2-(trifluoromethyl)-3,4-dihydropyrido[3,4-d]pyrimidin-8-yl)benzonitrile, or a pharmaceutically acceptable salt thereof.

In one aspect, the present invention relates to a compound selected from the group consisting of:

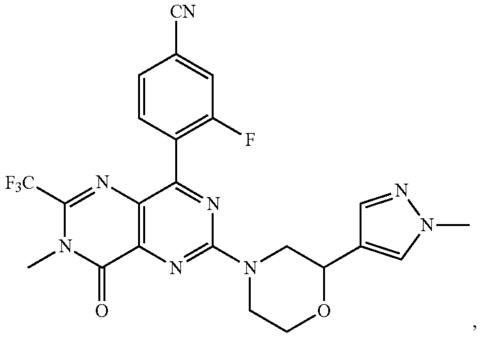

,

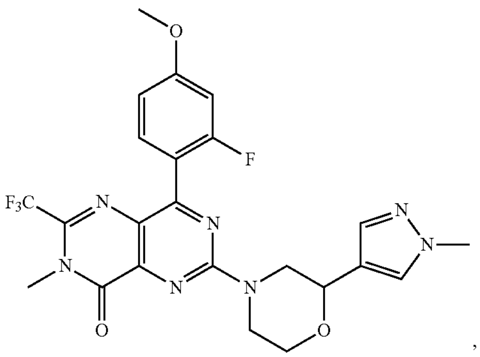

,

-continued
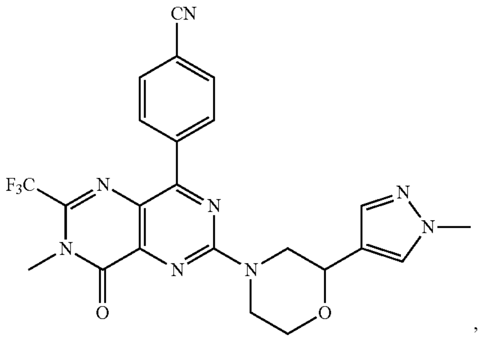
,
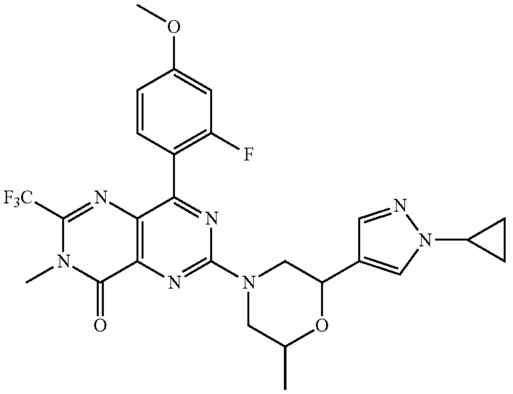
,
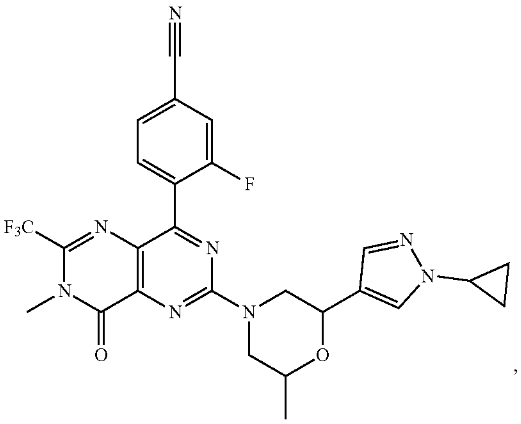
,
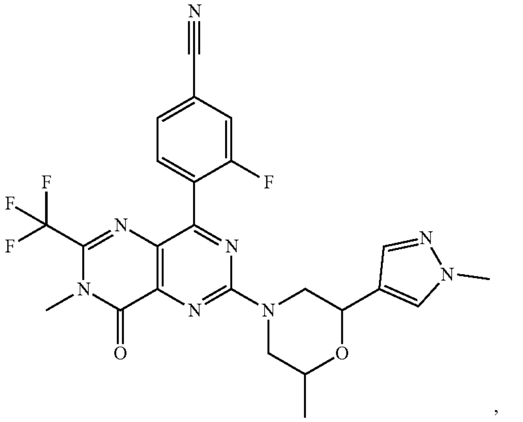
,
-continued
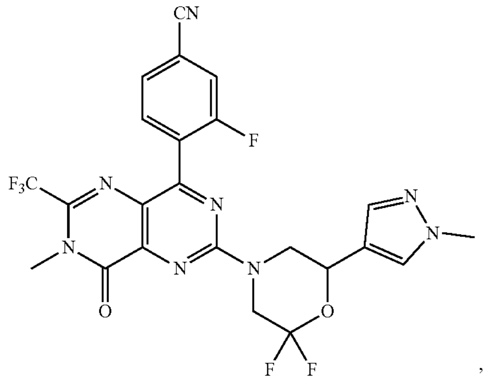
,
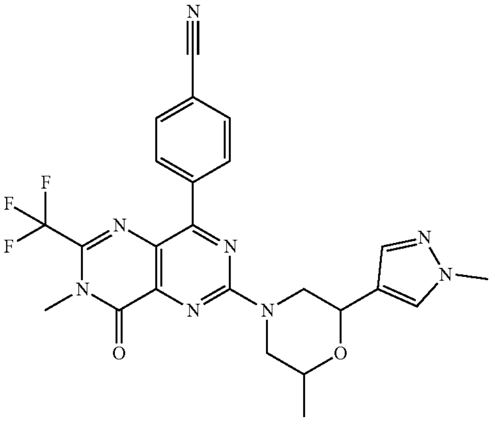
,
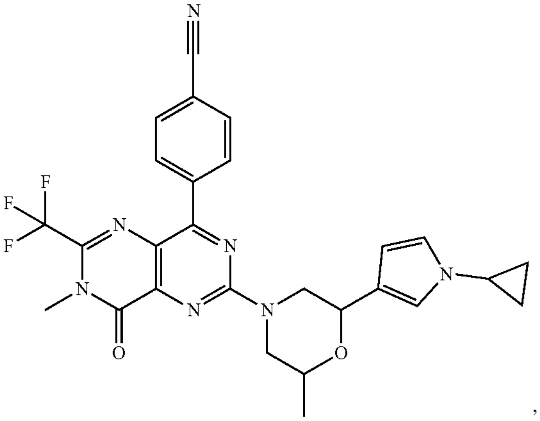
,
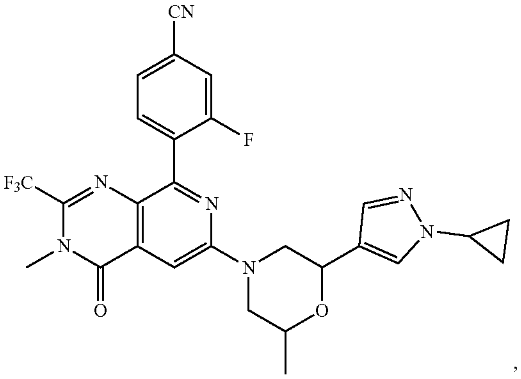
, -continued
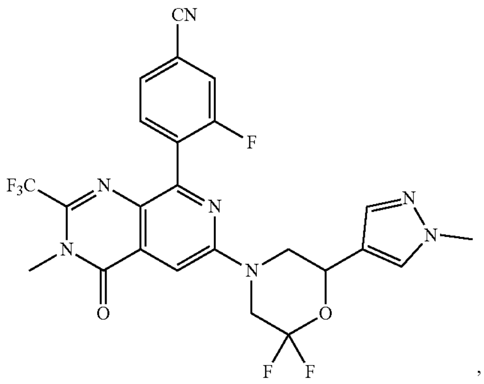
,
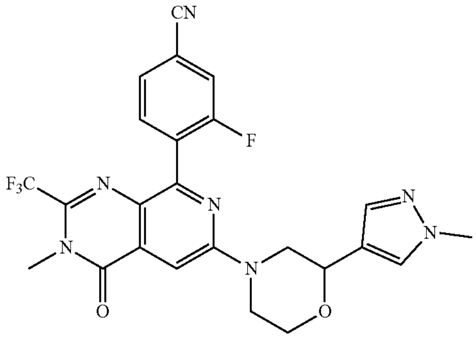
and
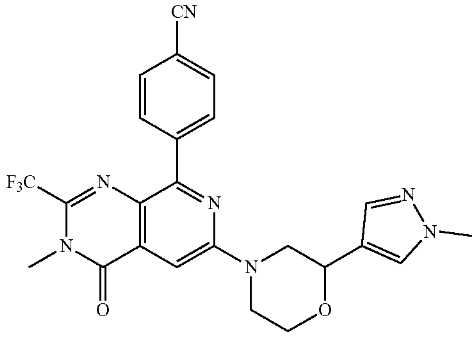
,
or a pharmaceutically acceptable salt thereof.
In one aspect, the present invention relates to a compound selected from the group consisting of:
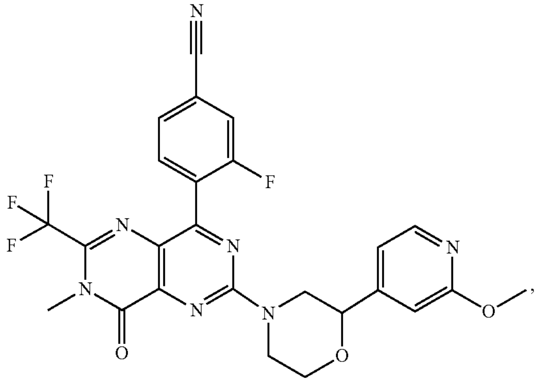
-continued
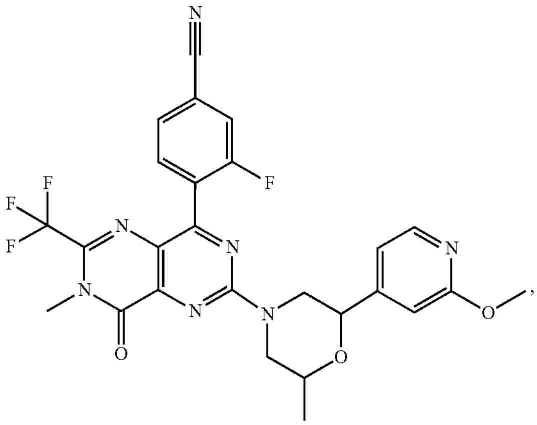
and
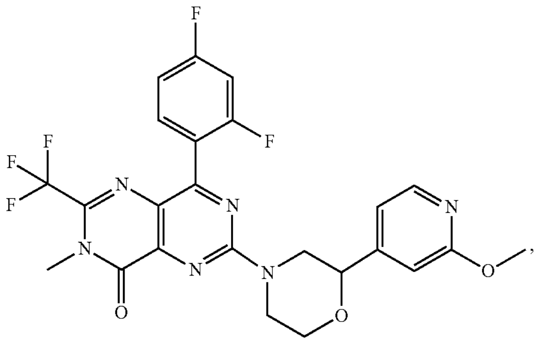
or a pharmaceutically acceptable salt thereof.
In one aspect, the present invention relates to a compound selected from the group consisting of:
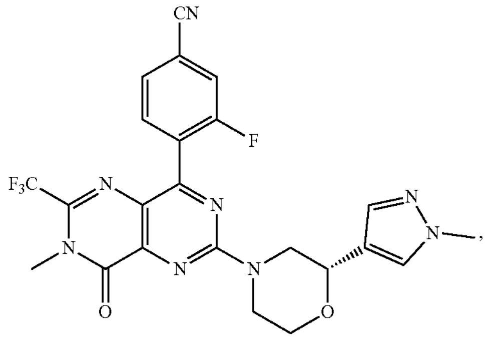
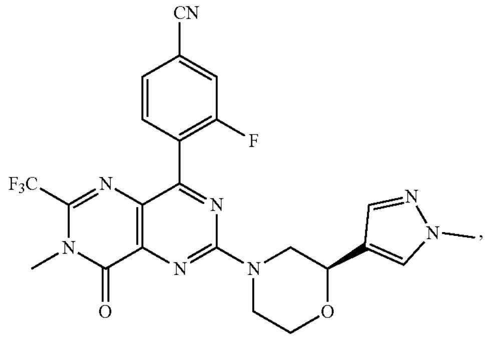

-continued
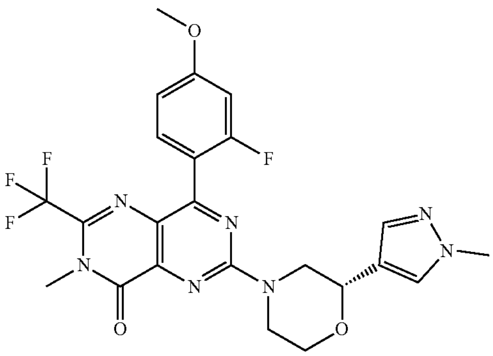,
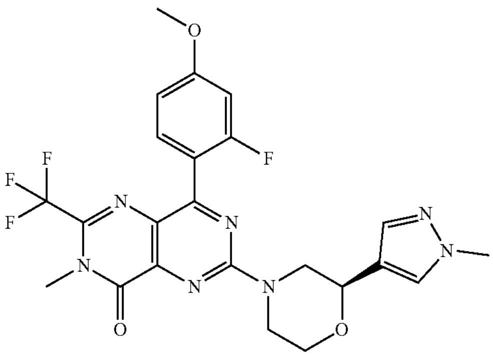,
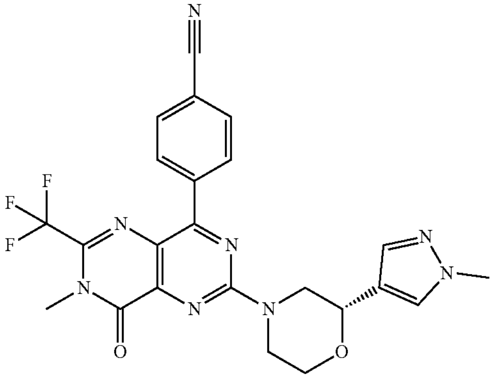,
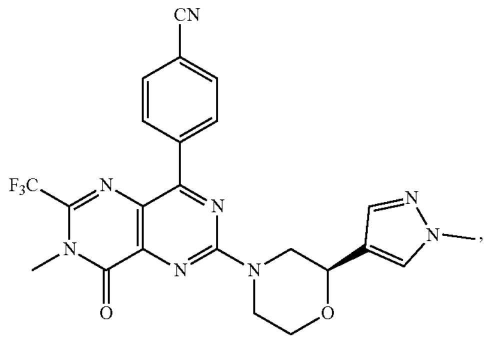,
-continued
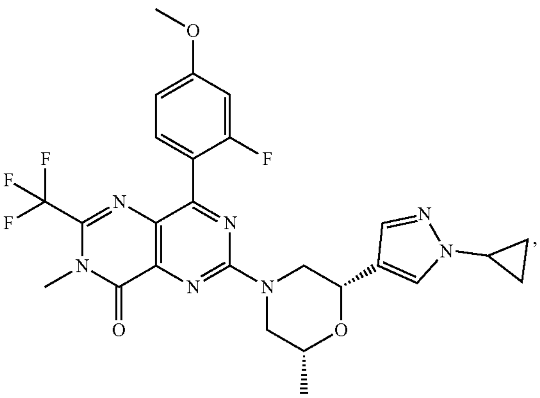,
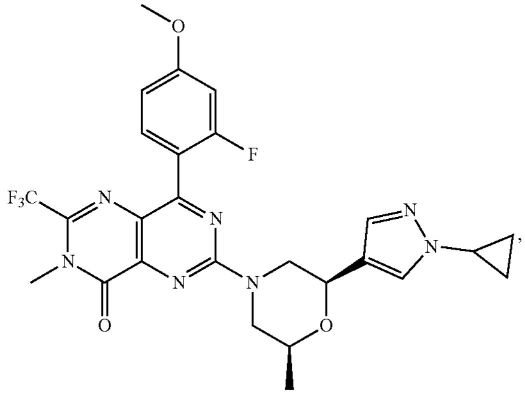,
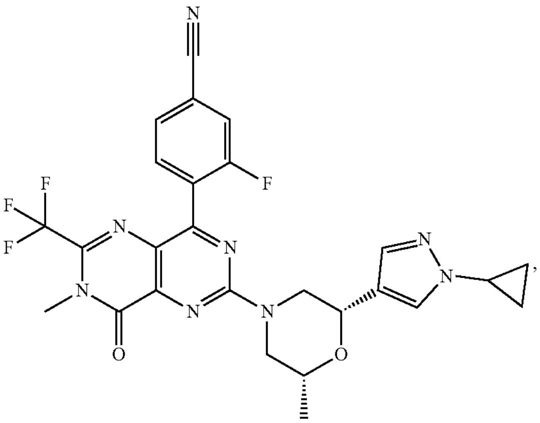,
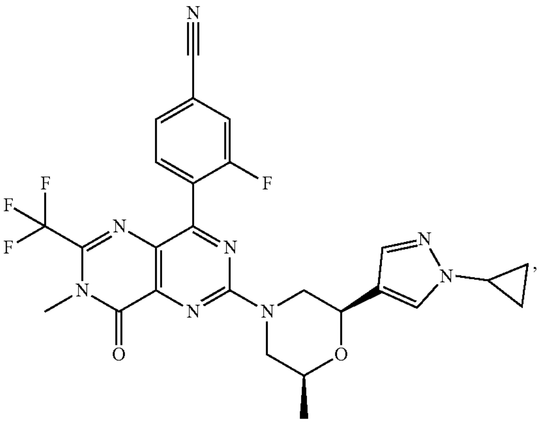, -continued
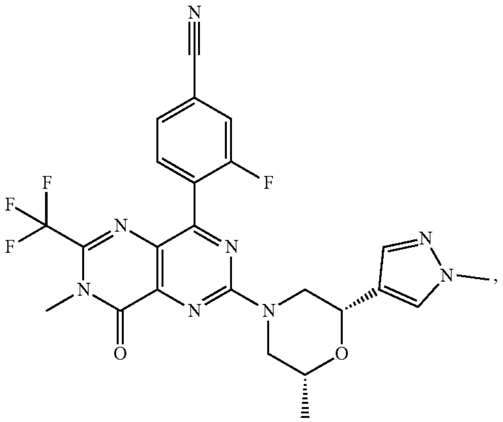
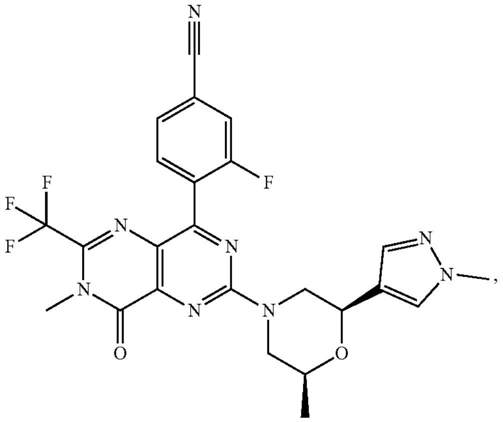
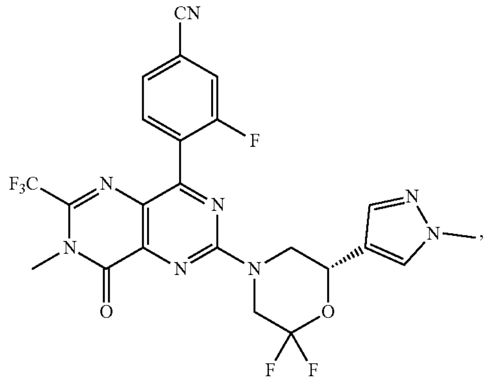
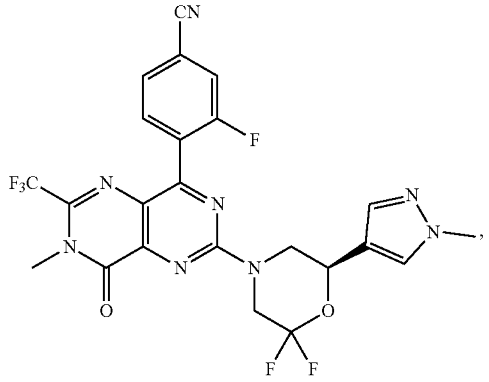
-continued
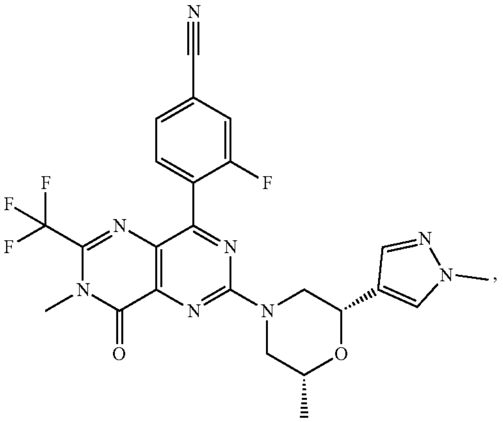
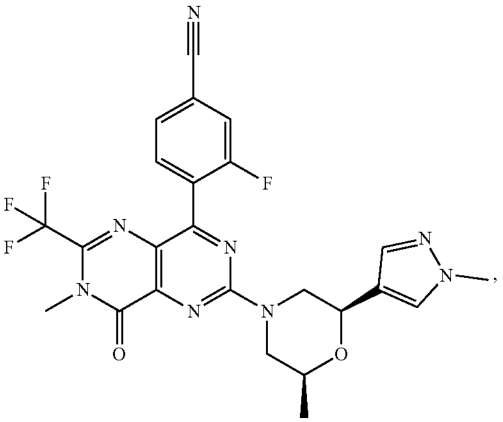
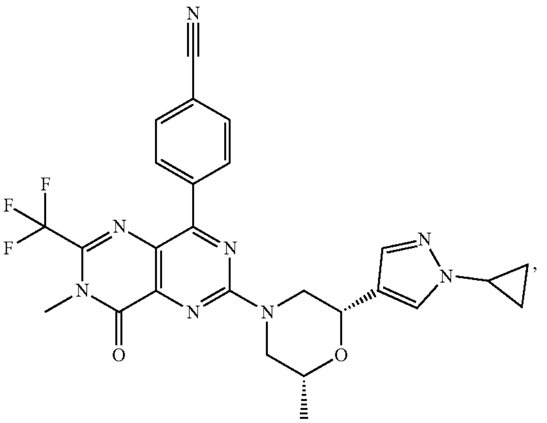
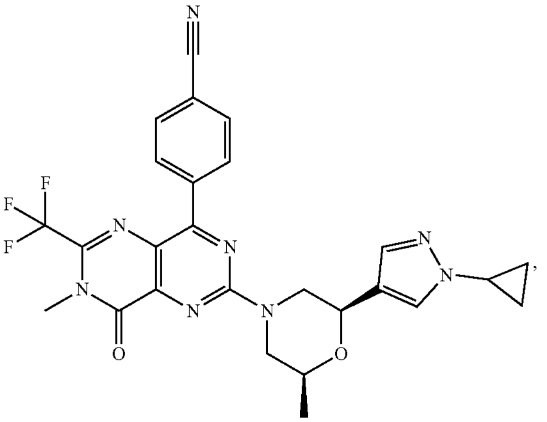

-continued
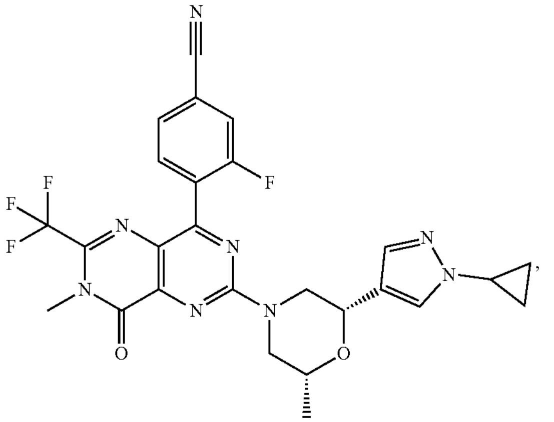
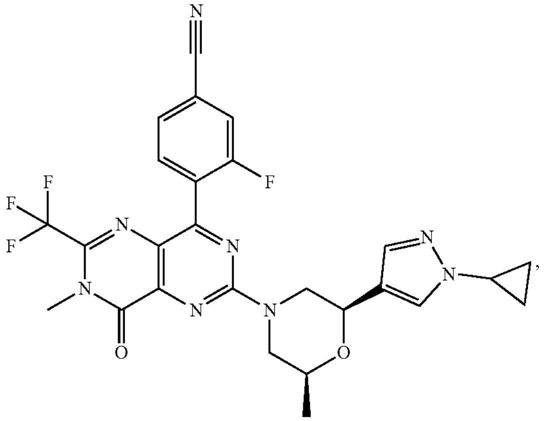
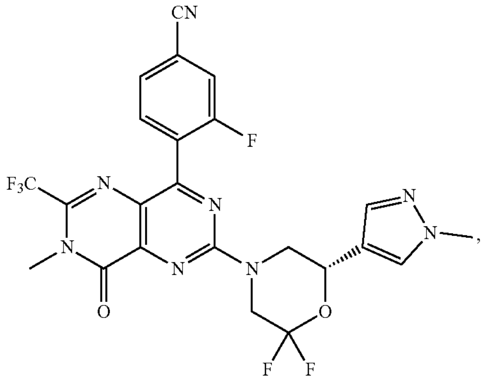
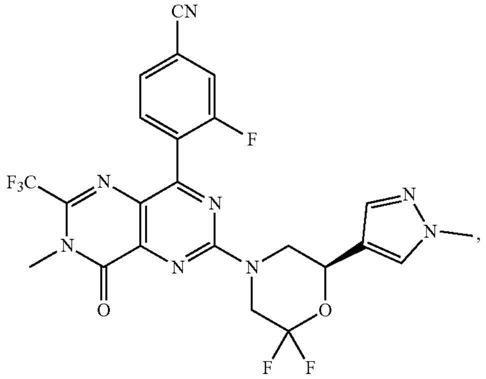
-continued
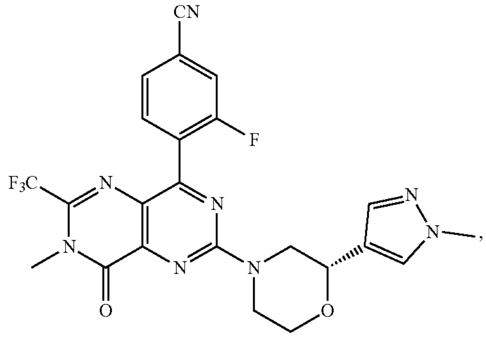
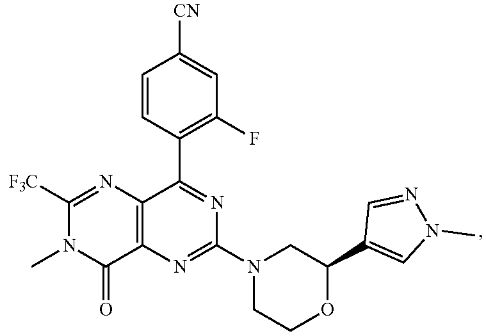
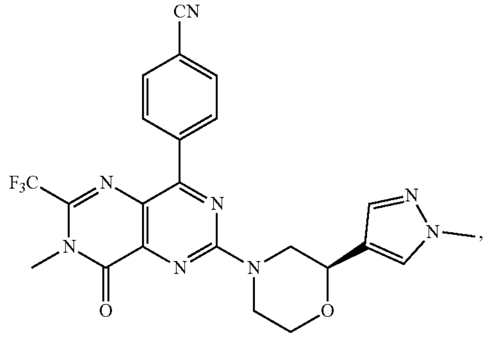
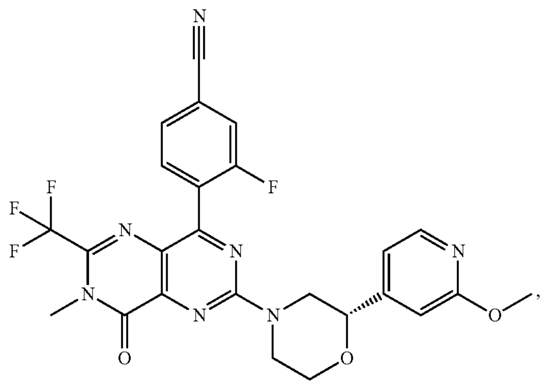

-continued
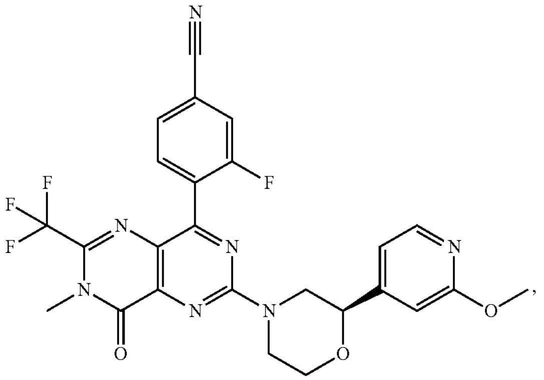
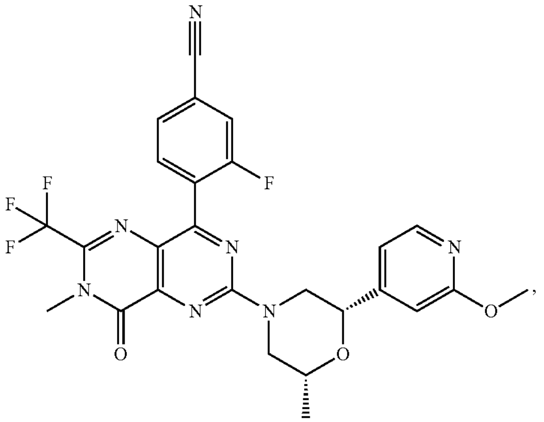
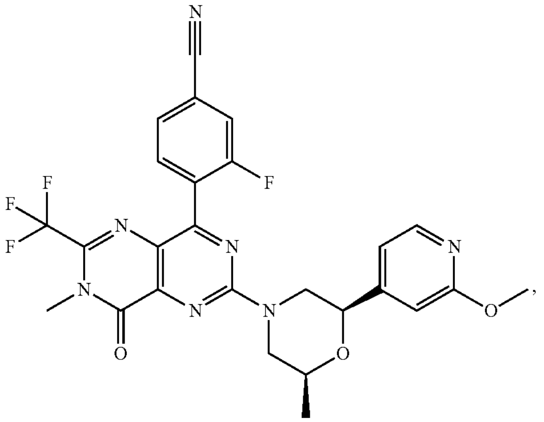
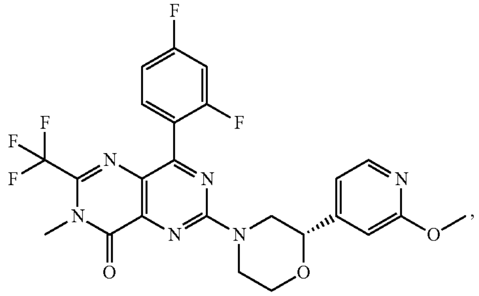
and
-continued
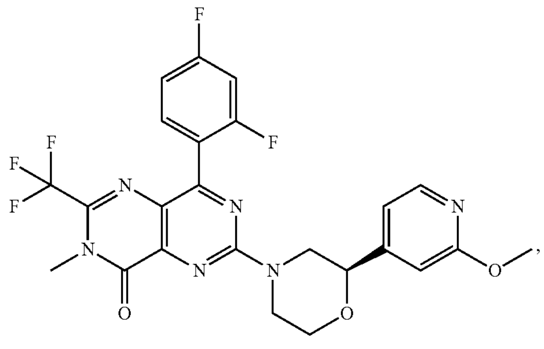
or a pharmaceutically acceptably salt thereof.
In one aspect, the present invention relates to a compound selected from:
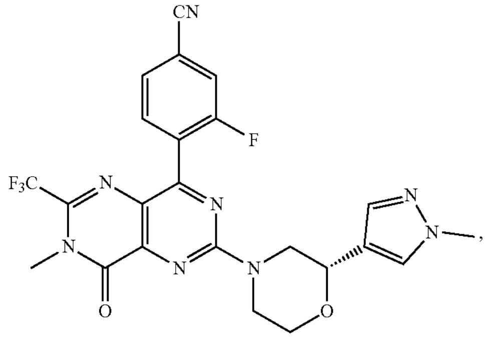
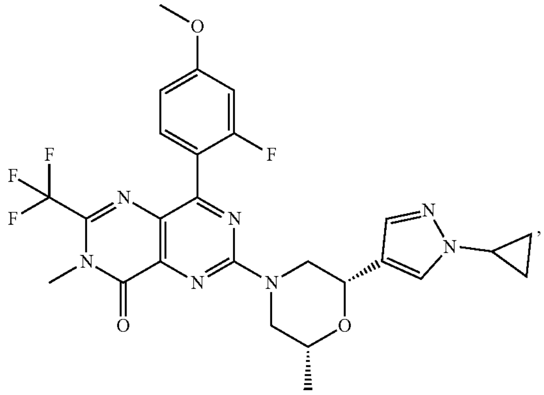
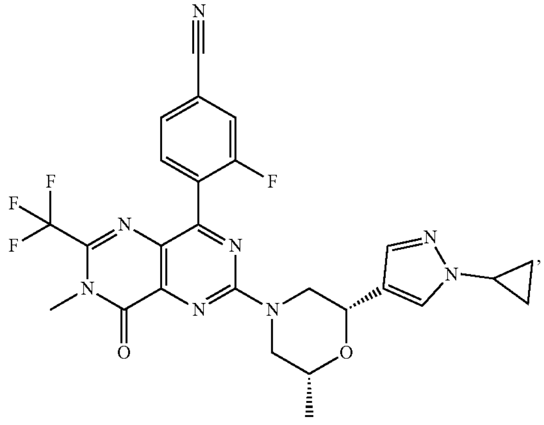

-continued
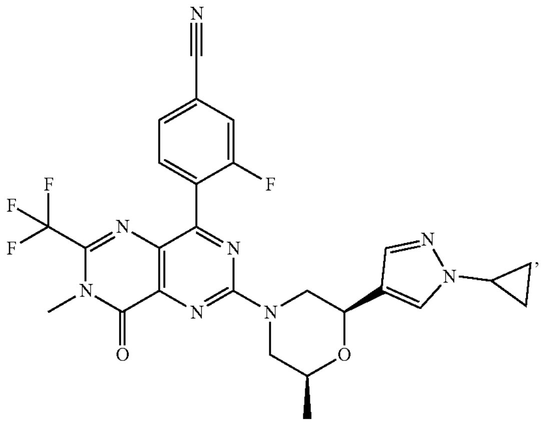
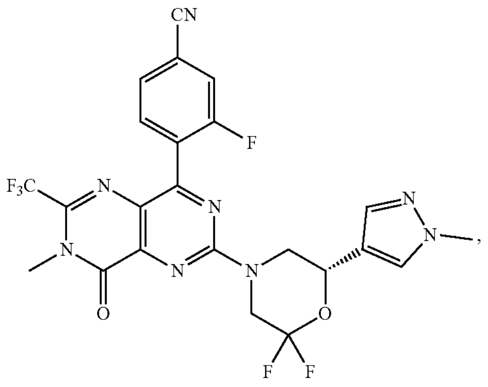
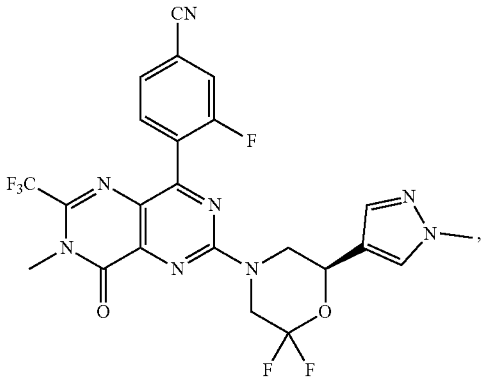
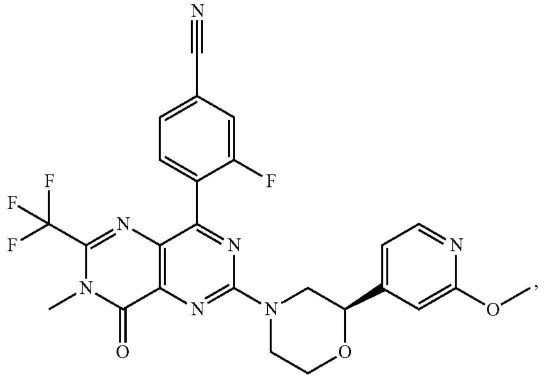
-continued
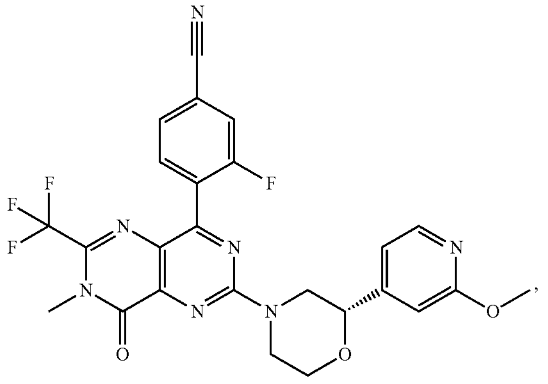
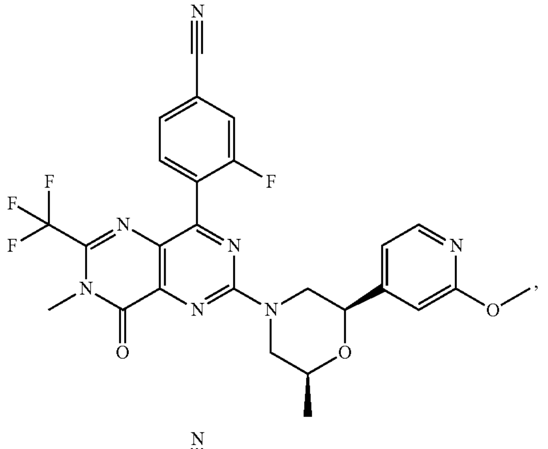
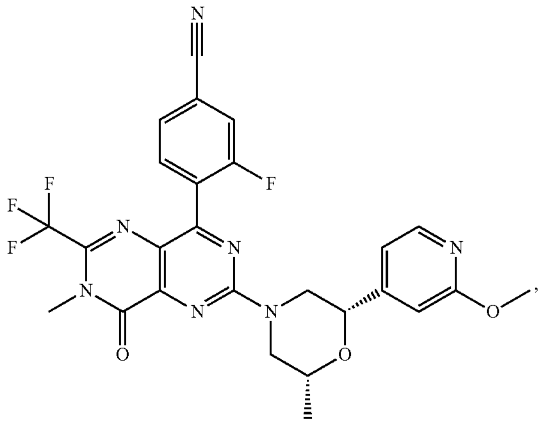
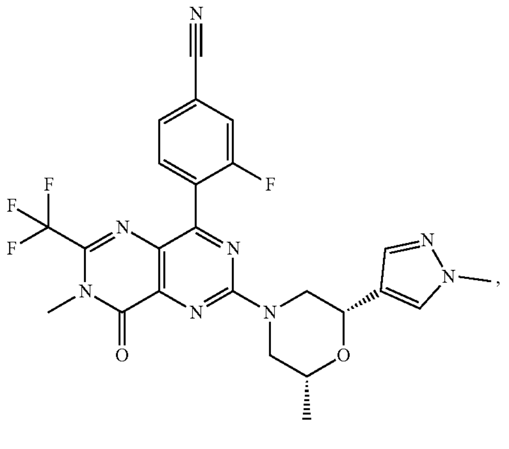

-continued
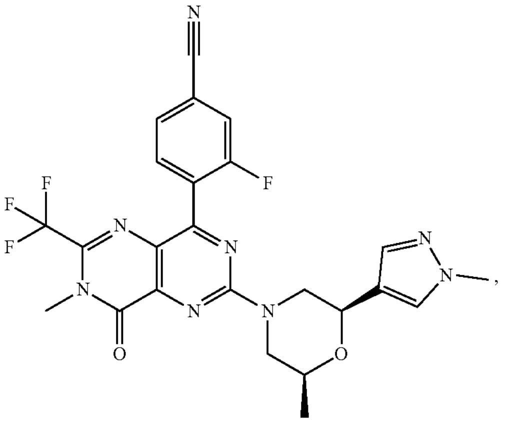
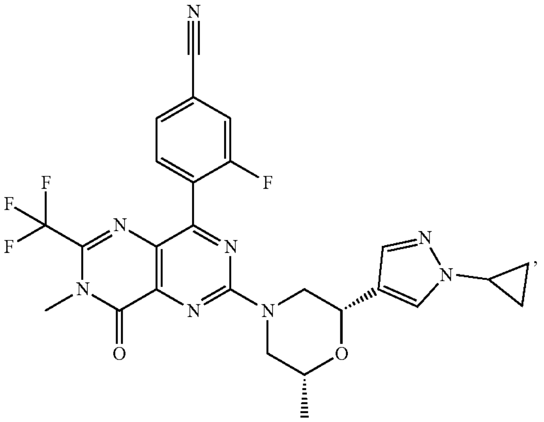
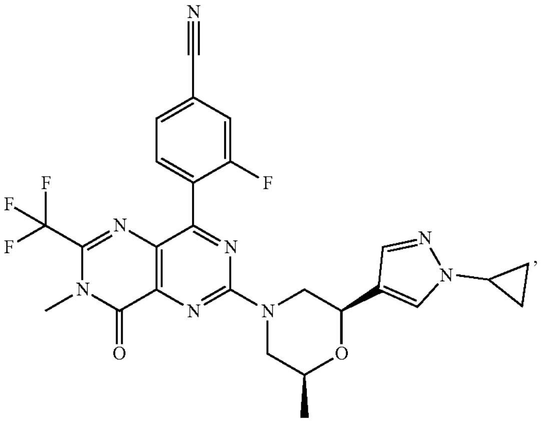
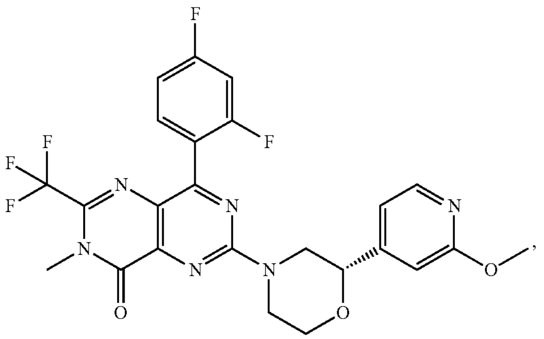
-continued
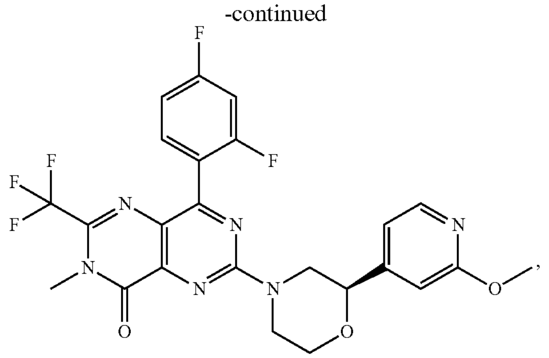
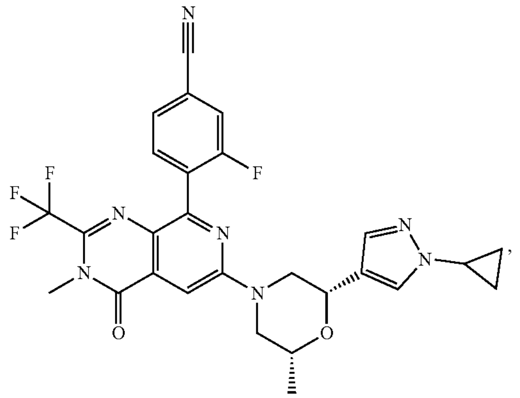
and
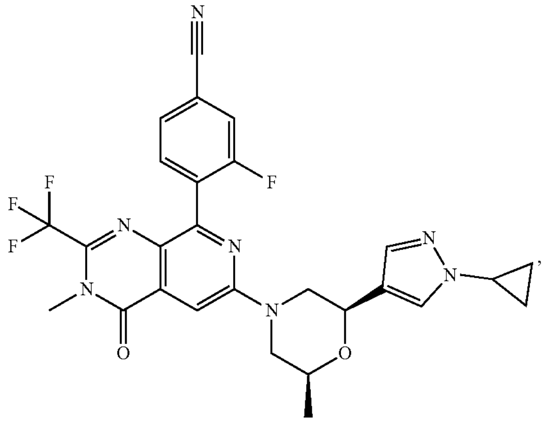
or a pharmaceutically acceptable salt thereof.
In some embodiments, the compound is
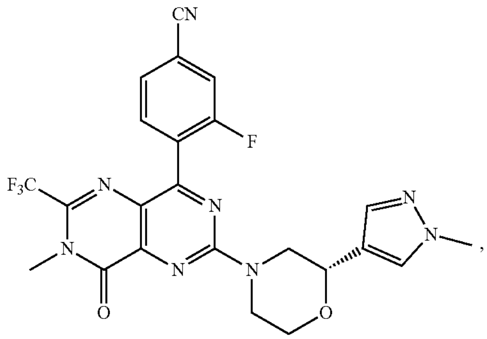
or a pharmaceutically acceptable salt thereof. In some embodiments, the compound is

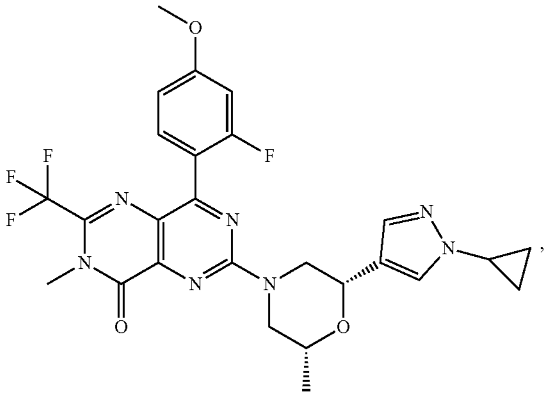

embodiments, the compound is

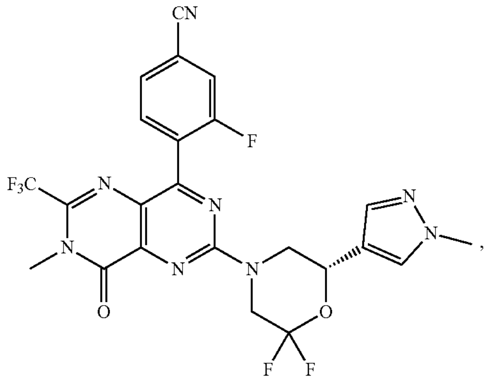

or a pharmaceutically acceptable salt thereof. In some embodiments, the compound is

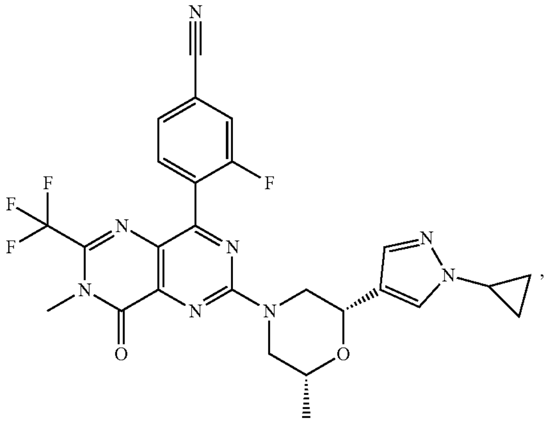

or a pharmaceutically acceptable salt thereof. In some embodiments, the compound is

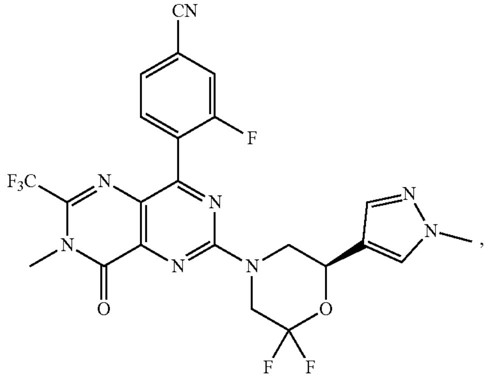

or a pharmaceutically acceptable salt thereof. In some embodiments, the compound is

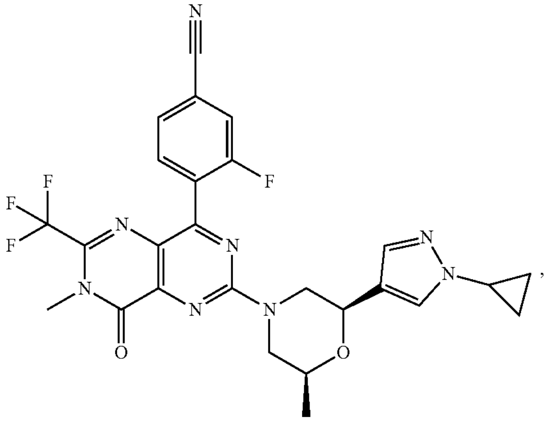

or a pharmaceutically acceptable salt thereof. In some embodiments, the compound is

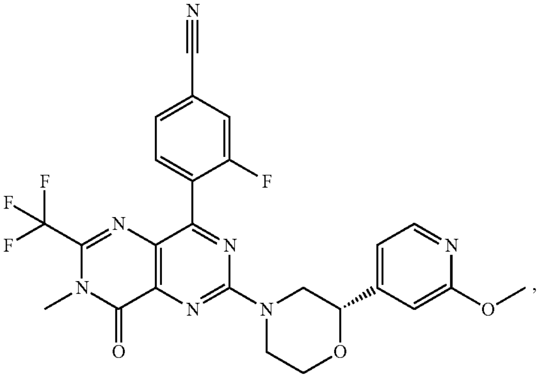

or a pharmaceutically acceptable salt thereof. In some embodiments, the compound is

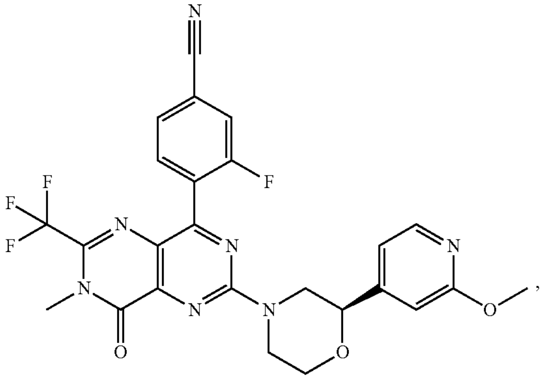

or a pharmaceutically acceptable salt thereof.

In some embodiments, the compound is

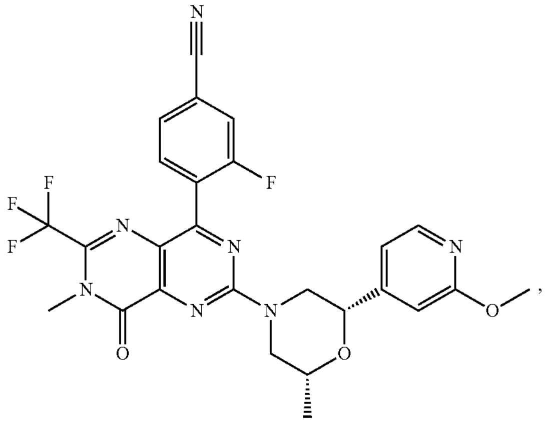

or a pharmaceutically acceptable salt thereof. In some embodiments, the compound is

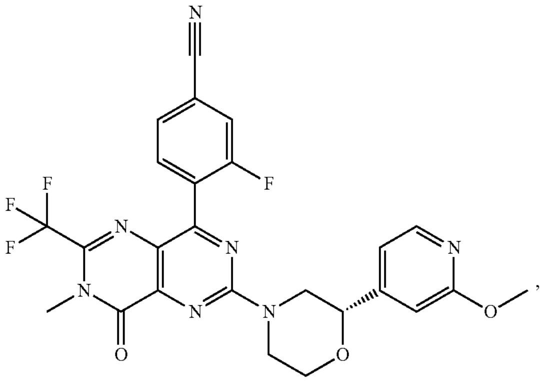

or a pharmaceutically acceptable salt thereof. In some embodiments, the compound is

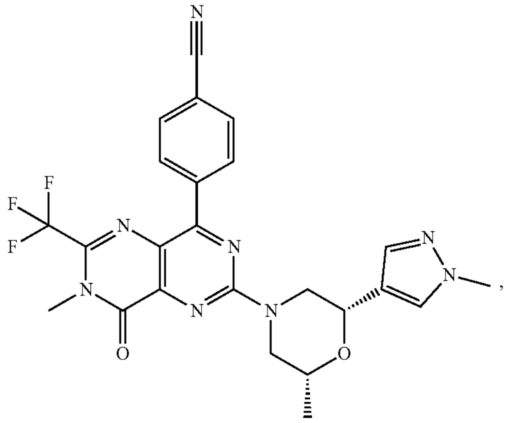

or a pharmaceutically acceptable salt thereof. In some embodiments, the compound is

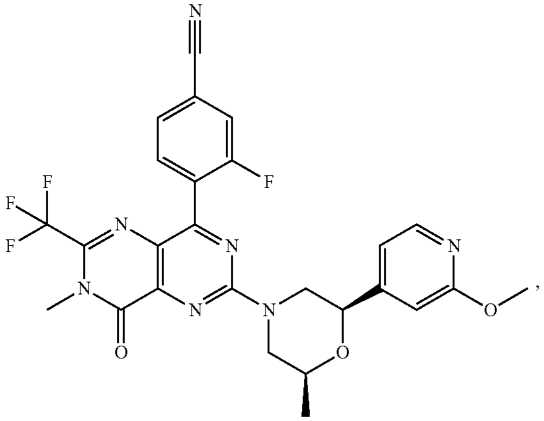

or a pharmaceutically acceptable salt thereof. In some embodiments, the compound is

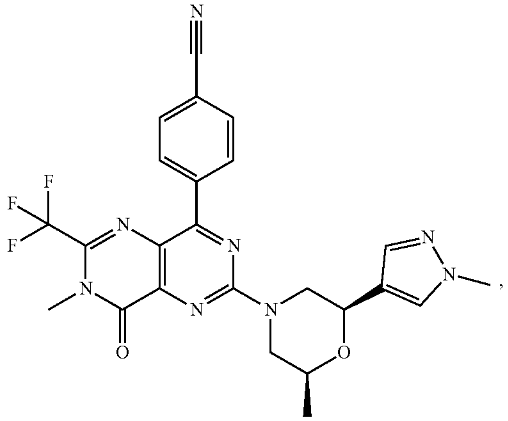

or a pharmaceutically acceptable salt thereof. In some embodiments, the compound is

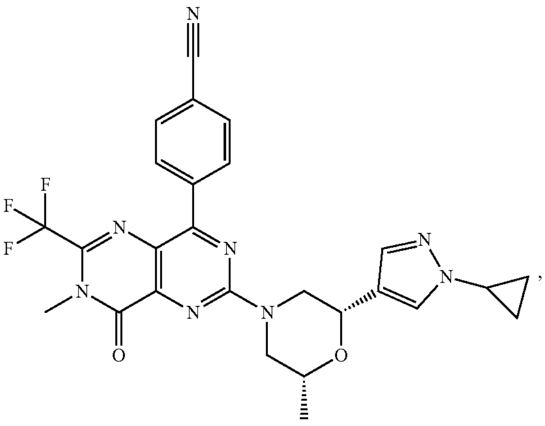
, or a pharmaceutically acceptable salt thereof. In some embodiments, the compound is

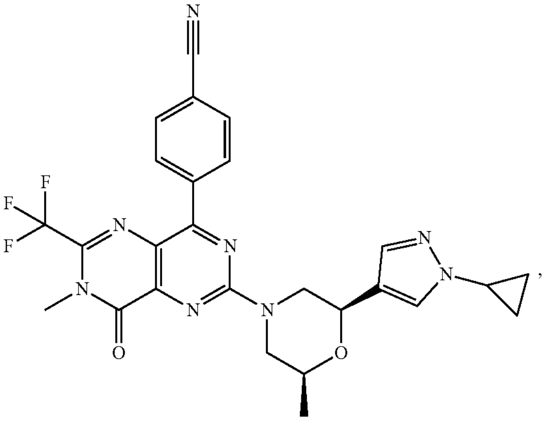
, or a pharmaceutically acceptable salt thereof. In some embodiments, the compound is

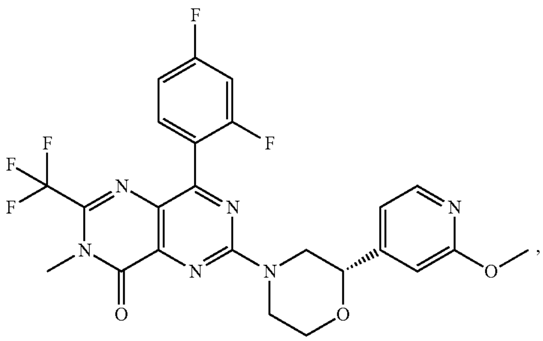
, or a pharmaceutically acceptable salt thereof. In some embodiments, the compound is

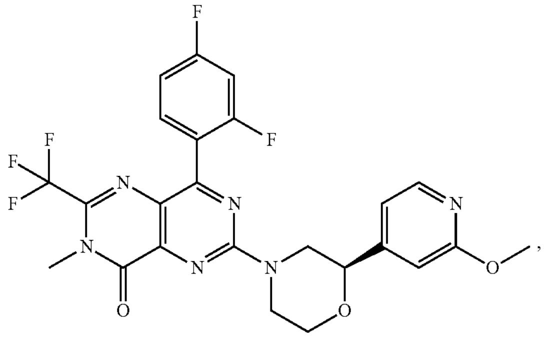
, or a pharmaceutically acceptable salt thereof. In some embodiments, the compound is

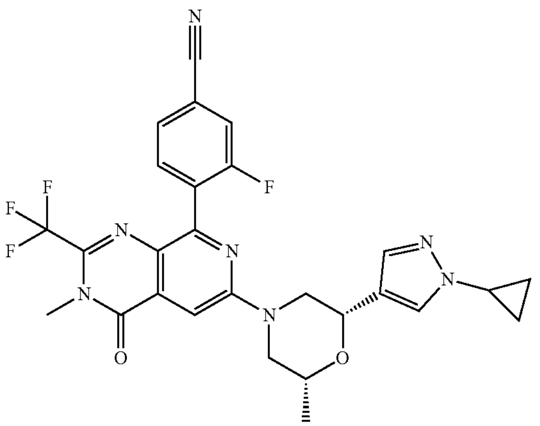
, or a pharmaceutically acceptable salt thereof. In some embodiments, the compound is

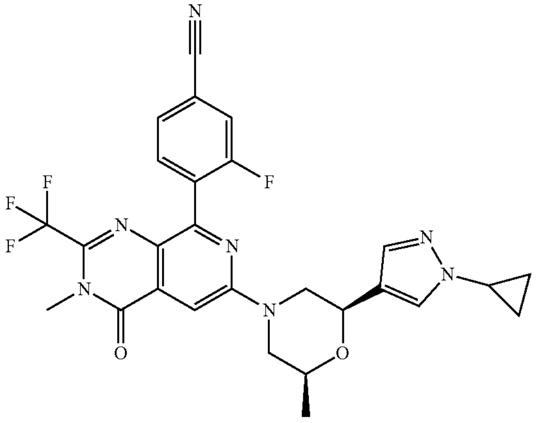
, or a pharmaceutically acceptable salt thereof.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone —enol pairs, amide —imidic acid pairs, lactam —lactim pairs, enamine —imine pairs, and annular forms where a proton can occupy two or more positions of a heterocyclic system, for example, 1H- and 3H-imidazole, 1H-, 2H- and 4H-1,2,4-triazole, 1H- and 2H- isoindole, and 1H- and 2H-pyrazole. Tautomeric forms can be in equilibrium or sterically locked into one form by appropriate substitution. Tautomeric forms can also include methyltropic tautomers, which result from the swapping of a single bond with an adjacent double bond together with the concomitant migration of a methyl group.

Compounds of the invention also include all isotopes of atoms occurring in the intermediates or final compounds. Isotopes include those atoms having the same atomic number but different mass numbers. In some embodiments, the compounds of the invention include one or more isotopes of atoms in an amount greater than the natural abundance of the isotope. For example, isotopes of hydrogen include tritium and deuterium. In some embodiments, a compound of the invention includes at least one deuterium atom in an amount that is greater than the natural abundance of deuterium (e.g., the compound is enriched in deuterium).

All compounds described herein, and pharmaceutically acceptable salts thereof, can be found together with other substances such as water and solvents (e.g., in the form of hydrates and solvates).

In one aspect, the present invention is directed to an intermediate compound, or a pharmaceutically acceptable salt thereof, which can be used in the synthesis of the compounds of the present invention. For example, said intermediate compound is in some embodiments one of the intermediate compounds, or a pharmaceutically acceptable salt thereof, of any one of examples 1 to 15 disclosed herein. In some embodiments the compound of the present invention is selected from any of the intermediate compounds, or a pharmaceutically acceptable salt thereof, disclosed in any one of examples 1 to 15 herein.

The compounds of the present invention may contain, for example, one or more asymmetric carbon atoms, and therefore may exist as stereoisomers, enantiomers and diastereomers. Accordingly, the scope of the instant invention is to be understood to encompass all possible stereoisomers of the illustrated compounds, including the stereoisomerically pure form and stereoisomeric mixtures of any chemical structures disclosed herein, unless the stereochemistry is specifically identified. If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated.

The term "stereoisomer" or "stereoisomerically pure" compound as used herein refers to one stereoisomer of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of the other enantiomer and diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

In some embodiments, the compound as defined herein is stereoisomerically pure.

Mixtures of stereoisomers may be resolved using standard techniques, such as chiral columns or chiral resolving agents, for example as outlined in the example section.

Pharmaceutical Composition

The present invention also relates to a pharmaceutical composition comprising, for example as an active ingredient, a pharmaceutically effective amount of a compound as disclosed herein. In some embodiments, said pharmaceutical composition comprises a therapeutically effective amount of a compound as disclosed herein or a pharmaceutically acceptable salt thereof, together with at least one pharmaceutically acceptable carrier, excipient and/or diluent.

In one aspect, the present invention relates to a pharmaceutical composition comprising a compound of Formula (I):

Formula (I)

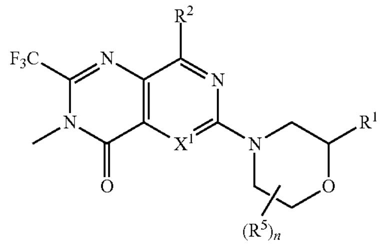

wherein $X^1$ is N or C(H);

$R^1$ is of Formula (II):

Formula (II)

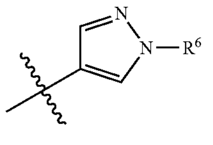

wherein $R^6$ is $C_{1-3}$ alkyl or cyclopropyl;

or $R^1$ is

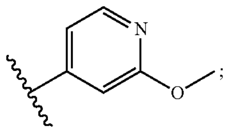

$R^2$ is selected from the group consisting of:

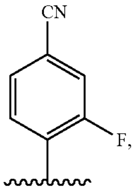
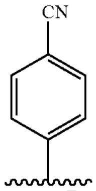
,
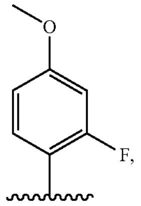
and
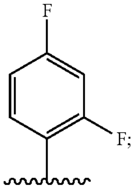 [SMILES: *c1ccc(F)cc1F]

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, with the proviso that when the compound is of Formula (VIII):

Formula (VIII)

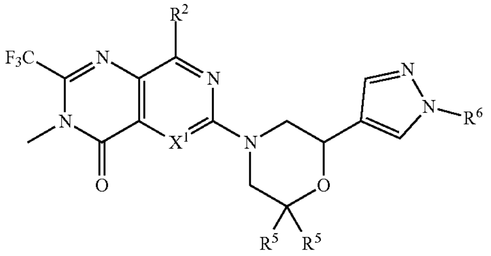

and $X^1$ is N, $R^5$ is C, alkanediyl and the two $R^5$ are linked together to form a 3-membered ring, $R^2$ is

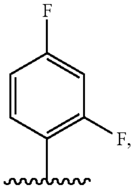

then $R^6$ is not methyl; and with the proviso that when the compound is of Formula (VIII) and $X^1$ is C(H) or N, one $R^5$ is H and the other $R^5$ is $CH_3$, $R^2$ is

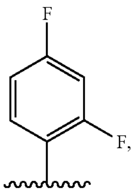

then $R^6$ is not cyclopropyl, or a pharmaceutically acceptable salt thereof, and one or more pharmaceutically acceptable carriers, excipients and/or diluents.

In one aspect, the present invention relates to a pharmaceutical composition comprising a compound of selected from:

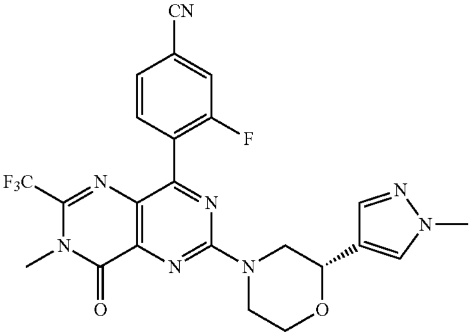
,

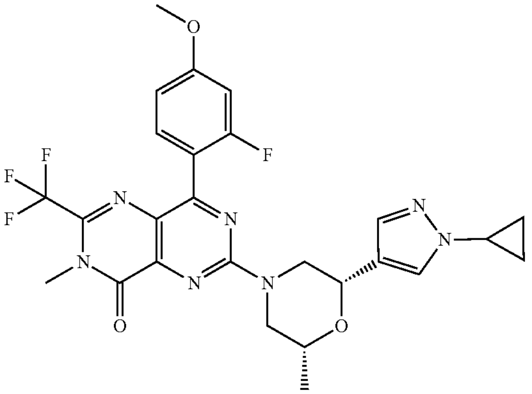
,

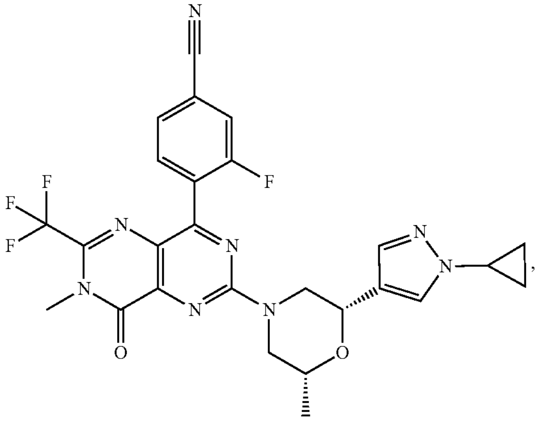
,

-continued
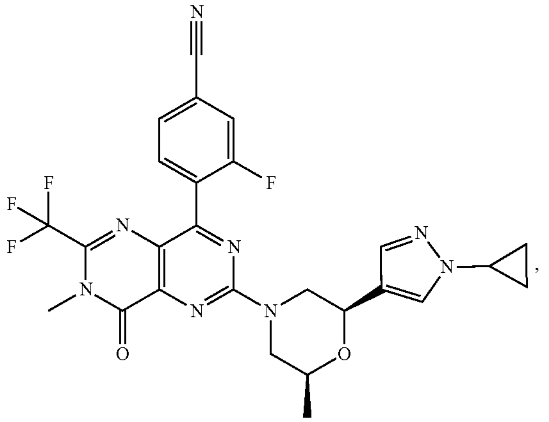
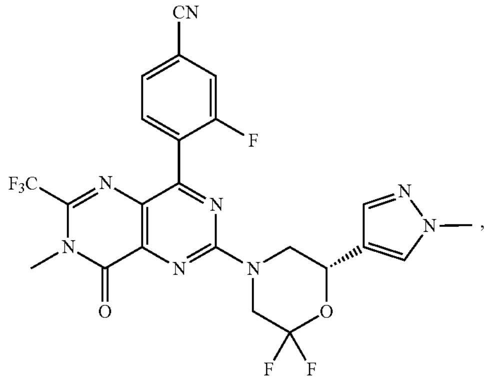
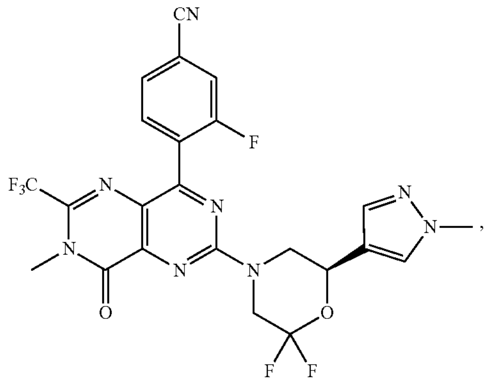
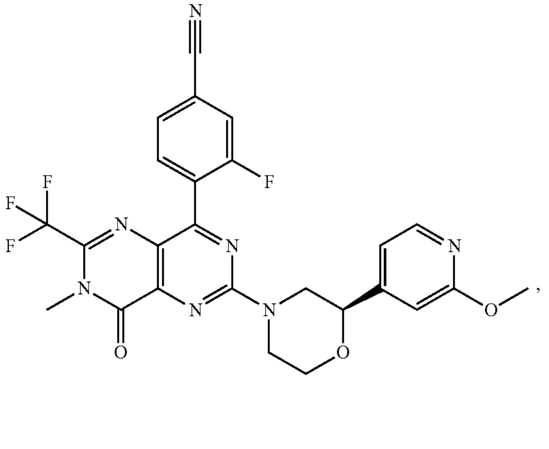
-continued
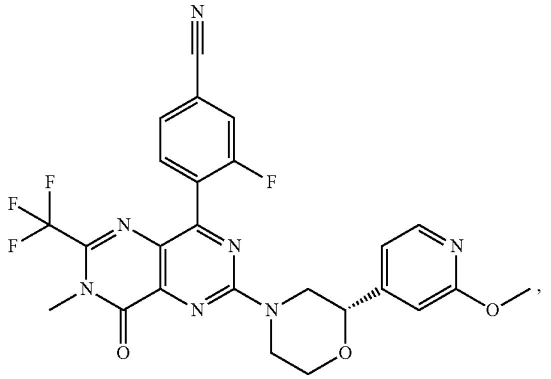
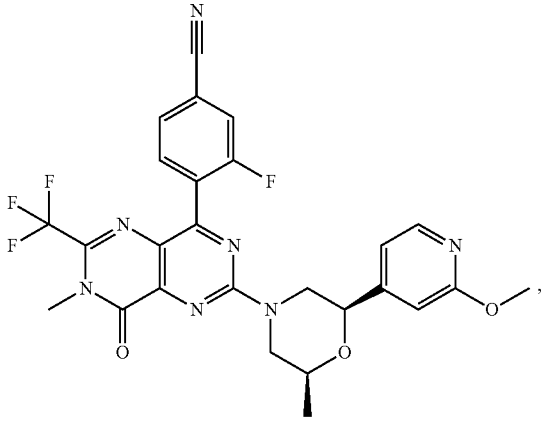
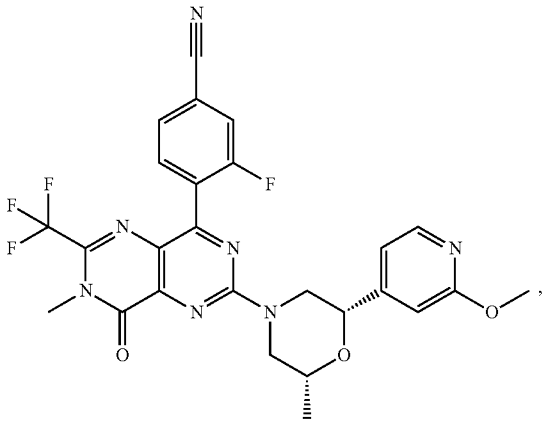
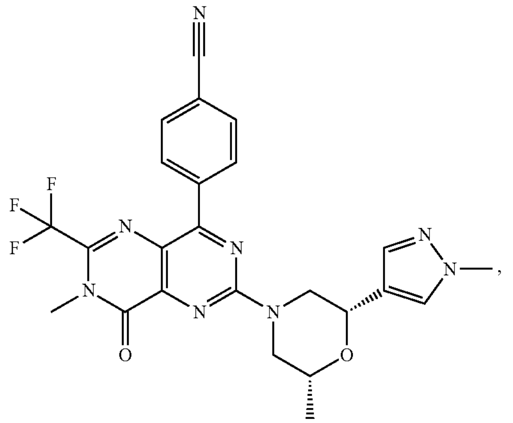

-continued

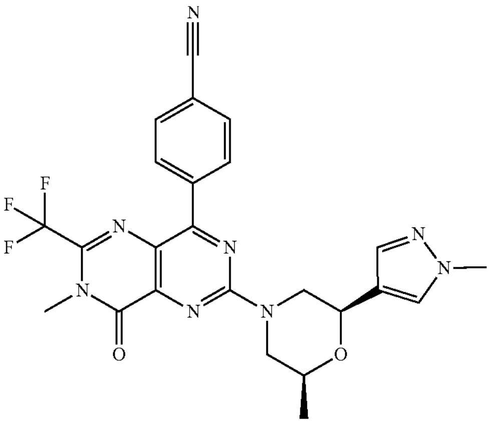

,

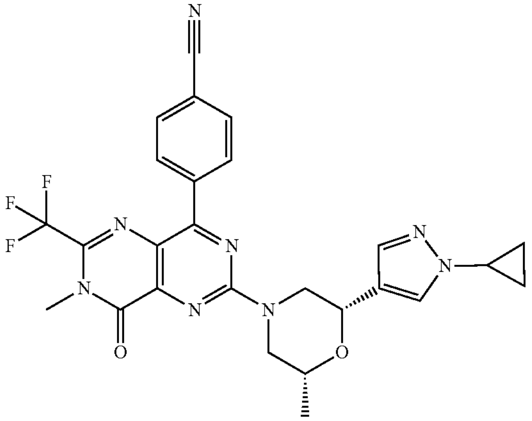

,

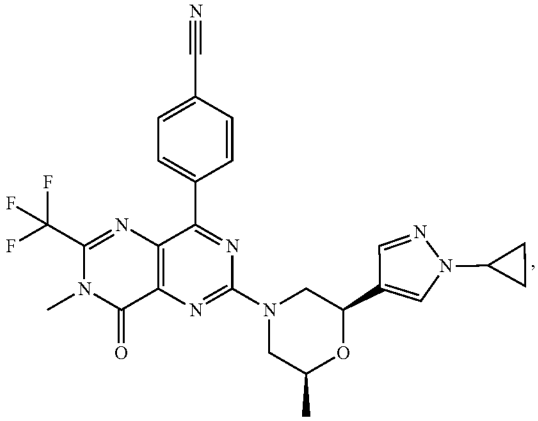

,

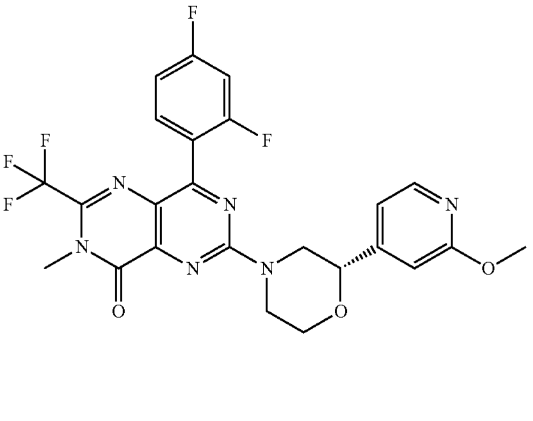

,

-continued

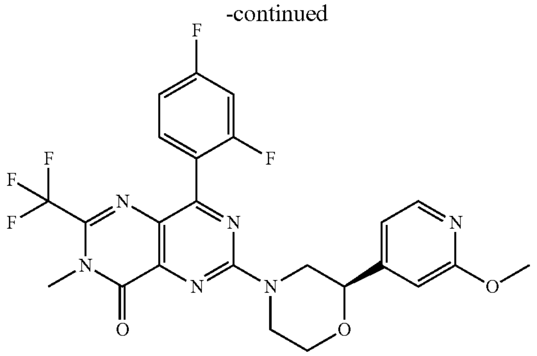

,

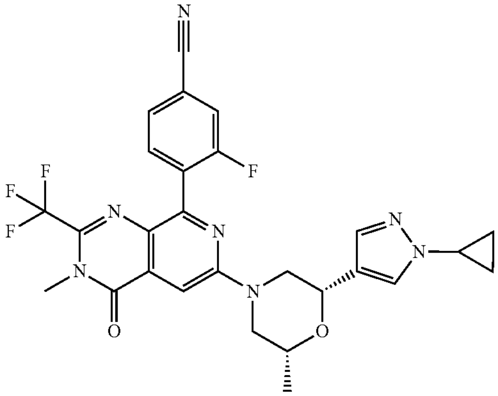

, and

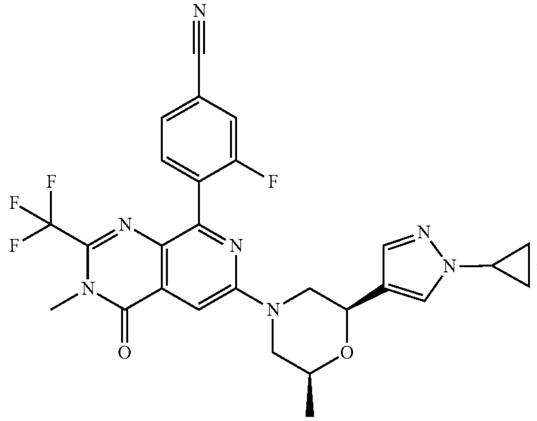

, or a pharmaceutically acceptable salt thereof, and one or more pharmaceutically acceptable carriers, excipients and/or diluents.

While a compound as disclosed herein for use in therapy may be administered in the form of the raw chemical compound, it is often preferred to introduce the active ingredient, optionally in the form of a pharmaceutically acceptable salt, in a pharmaceutical composition together with one or more adjuvants, excipients, carriers, buffers, diluents, and/or other customary pharmaceutical auxiliaries.

In some embodiments, the invention provides pharmaceutical compositions comprising a compound as disclosed herein or a pharmaceutically acceptable salt thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof. Examples of excipients and their use may be found in Remington's Pharmaceutical Sciences 20th Edition (Lippincott Williams & Wilkins, 2000).

A therapeutic amount or therapeutically effective amount or dose refers to that amount of active ingredient, i.e. the compounds or compositions as disclosed herein, which treats, alleviates, abates, or reduces the severity of symptoms of a disease in a subject, such as ameliorates one or more symptoms of the condition or the condition itself. A therapeutic amount of a compound as described herein may improve patient survival, increase survival time or rate, diminish symptoms, make an injury, disease, or condition (e.g, a neurodegenerative disease) more tolerable, slow the rate of degeneration or decline, or improve a patient's physical or mental well-being.

Therapeutic efficacy and toxicity, e.g. $ED_{50}$, may be determined by standard pharmacological procedures in cell cultures or experimental animals. The dose ratio between therapeutic and toxic effects is the therapeutic index and may be expressed by ratio between plasma levels resulting in therapeutic effects and plasma ratios resulting in toxic effects. Pharmaceutical compositions exhibiting large therapeutic indexes are preferred. In some embodiments, the therapeutically effective dose of a compound as disclosed herein is in the range of about 0.01 mg/kg to about 100 mg/kg bodyweight/day.

The dose administered must of course be carefully adjusted to the age, weight and condition of the individual being treated, as well as the route of administration, dosage form and regimen, and the result desired, and the exact dosage should of course be determined by the practitioner.

To administer refers to a method of delivering agents, compounds, or compositions to the desired site of biological action. These methods include, but are not limited to, enteral delivery, oral delivery, topical delivery, parenteral delivery, intravenous delivery, intradermal delivery, intramuscular delivery, intrathecal delivery, colonic delivery, rectal delivery, or intraperitoneal delivery.

In some embodiments, the compound of the present invention is suitable for use as a pharmaceutical agent. Hence, in some embodiments, the compound has suitable pharmacological activity, such as target efficacy, affinity and/or selectivity. In some embodiments, the compound has suitable Absorption, Distribution, Metabolism, Excretion, and Toxicity (ADMET) properties. For example, in some embodiments, the compound has acceptable levels of off-target effects, including low hERG channel (human Ether-á-go-go-Related Gene) inhibition, low off-target toxicity, genotoxicity, carcinogenicity, and/or hepatotoxicity. In some embodiments, the compound demonstrates suitable pharmacokinetics, such as bioavailability, half-life, and/or clearance. In some embodiments, the compound demonstrates suitable pharmacodynamics, such as efficacy and/or potency. In some embodiments, the compound demonstrates chemical stability and/or metabolic stability. Said parameters may be assessed by conventional in vitro tests, animal studies and/or clinical trials known by the skilled person. In some embodiments, the compound demonstrates suitable characteristics for oral formulation using pharmaceutically acceptable excipients. For example, the compound demonstrates suitable solubility in relevant media.

Biological Activity

As demonstrated in Example 16 compounds of the present invention are capable of modulating TREM2. Thus, in some embodiments, the compound of the present invention is a TREM2 modulator, such as a TREM2 agonist. The assay described in Example 16 may be used to assess and characterize a compound's ability to act as an agonist of TREM2. In some embodiments the compounds of the present invention are useful for the activation of TREM2. In some embodiments the compounds of the present invention activates TREM2. In some embodiments the compounds of the present invention enhances TREM2 activity. In some embodiments, a compound of the present invention induces phosphorylation of a kinase that interacts with the TREM2/DAP12 signalling complex, such as, but not limited to, Syk, ZAP70, PI3K, Erk, AKT and GSK3b. In some embodiments the compounds of the present invention enhances or activates TREM2 signalling through DAP12. In some embodiments the compounds of the present invention enhances or activates TREM2-induced phosphorylation levels of the Syk kinase. In some embodiments, a compound of the present invention induces or enhances phosphorylation of Syk if the level of Syk phosphorylation in a sample treated with the compound is increased by at least 10%, at least 20%, at least 30%, at least 40%, at least 50%, at least 60%, at least 70%, at least 80%, at least 90%, at least 100% or more as compared to a control value; such as is increased by at least 2-fold, 3-fold, 4-fold, 5-fold, 6-fold, 7-fold, 8-fold, 9-fold, 10-fold, or more as compared to a control value.

The potency of compounds of the present invention are in some embodiments expressed as $EC_{50}$ corresponding to the concentration of compound able to activate the phospho-Syk AlphaScreen signal to 50% of the maximal response. In some embodiments, the compounds of the present invention has an $EC_{50}$ value of less than 1000 nM, such as an $EC_{50}$ value between 100 nM and 1000 nM, such as an $EC_{50}$ value between 10 nM and 100 nM, such as an an EC50 value between 1 nM and 10 nM, such as an $EC_{50}$ value <1 nM. The $EC_{50}$ value may be determined as described in Example 16.

In some embodiments, the compounds of the present invention are capable of increasing the expression of one or more TREM2 regulated genes. In some embodiments the compounds of the present invention increases the expression of one or more TREM2 regulated genes. In some embodiments, the compounds of the present invention are capable or increasing one or more TREM2 regulated genes selected from the group consisting of CXCL10, CCL2, CST7 and TMEM119. In some embodiments the compounds of the present invention increases expression levels, such as brain expression levels, of one or more TREM2 regulated genes selected from the group consisting of CXCL10, CCL2, CST7 and TMEM119.

In some embodiments, a compound of the present invention increases expression levels, such as brain expression levels, if the level expression of the gene in a sample treated with the compound is increased by at least 10%, at least 20%, at least 30%, at least 40%, at least 50%, at least 60%, at least 70%, at least 80%, at least 90%, at least 100% or more as compared to a control value; such as is increased by at least 1.5-fold, 2-fold, 2.5-fold, 3-fold, 3.5-fold, 4-fold, 5-fold, or more as compared to a control value (e.g. untreated control/vehicle).

Medical Use

Being modulators of TREM2, the compounds of the present invention are of use in the treatment of diseases and disorders of a living body, including human. As used herein, the term "treatment" includes treatment, prevention, and/or alleviation or amelioration of one or more diseases and disorders or one or more symptoms of a disease or disorder. In one aspect, the compound as described herein is for use as a medicament.

In one aspect, the present invention relates to a compound, or a pharmaceutically acceptable salt thereof, as defined herein for use in the treatment of a condition associated with a loss of function of TREM2. In one aspect, the present invention relates to a compound, or a pharmaceutically acceptable salt thereof, as defined herein for use in the treatment of a condition associated with a mutation in TREM2.

In one aspect, the present invention relates to the compound, or a pharmaceutically acceptable salt thereof, as defined herein for use in the treatment of a neurodegenerative disease.

In some embodiments, a compound as described herein is used in treating a neurodegenerative disease that is characterized by a loss of function of TREM2. In some embodiments, a compound as described herein is used in treating a neurodegenerative disease that is characterized by a mutation in TREM2.

In one aspect, the present invention relates to a method for enhancing or increasing TREM2 activity in a subject in need thereof, such as in a subject having a neurodegenerative disease, said method comprising administering to the subject a compound, or a pharmaceutically acceptable salt thereof, as defined herein.

In one aspect, the present invention relates to method for one or more of i) enhancing or activating TREM2 signaling through DAP12, ii) inducing phosphorylation of a kinase that interacts with the TREM2/DAP12 signaling complex, such as, but not limited to, Syk, ZAP70, PI3K, Erk, AKT and GSK3b, iii) enhancing TREM2-induced phosphorylation levels of the Syk kinase, Iv) increasing the expression levels, such as brain expression levels, of one or more TREM2 regulated genes, and/or v) increasing the expression levels, such as brain expression levels, of one or more TREM2 regulated genes selected from the group consisting of CXCL10, CCL2, CST7 and TMEM119; in a subject in need thereof, such as in a subject having a neurodegenerative disease, said method comprising administering to the subject a compound, or a pharmaceutically acceptable salt thereof, as defined herein.

In some embodiments, the neurodegenerative disease is a tauopathy. Tautopathies depicts some neurodegenerative disorders characterized by tau deposits in the brain, with symptoms of dementia and parkinsonism. In some embodiments, the neurodegenerative disease is a tauopathy selected from the group consisting of Primary age related tauopathy (PART), globular glial tauopathy, Chronic traumatic encephalopathy (CTE), Progressive supranuclear palsy, Corticobasal degeneration, diffuse neurofibrillary tangles with calcification (DNTC), Frontotemporal dementia (FTD), and FTD with parkinsonism-17 (FTD with parkinsonism linked to chromosome 17; FTDP-17).

In some embodiments, the neurodegenerative disease is a neurodegenerative disorders associated with TDP-43 (TDP-43 proteinopathies or TDP-43-opathies). Inclusions of pathogenic deposits containing TAR DNA-binding protein 43 (TDP-43) are evident in the brain and spinal cord of patients that present across a spectrum of neurodegenerative diseases.

In some embodiments, the neurodegenerative disease is a TDP-43 proteinopathy selected from the group consisting of amyotrophic lateral sclerosis (ALS), sporadic amyotrophic lateral sclerosis (sALS), familial amyotrophic lateral sclerosis (fALS), frontotemporal lobar degeneration/disease (FTLD), Primary lateral sclerosis (PLS), progressive muscular atrophy (PMA), FTLD-tau, FTLD-FUS (bvFTLD), FTLD-TDP-43 or FTLD-U (types a, b and c), Facial onset sensory and motor neuronopathy (FOSMN), Limbic-predominant age-related TDP-43 encephalopathy (LATE), cerebral age-related TDP-43 with sclerosis (CARTS), Guam Parkinson-dementia complex (G-PDC) and ALS (G-ALS), Kii ALS/PDC, amyotrophic lateral sclerosis/parkinsonism-dementia complex of Guam (ALS-PDC), Multisystem proteinopathy (MSP; also referred to as inclusion body myopathy, IBM, associated with early-onset Paget disease of the bone and FTLD dementia), Perry disease, and disorders with concomitant TDP-43 pathology, including Alzheimer's disease (AD) and Chronic traumatic encephalopathy (CTE).

In some embodiments, the neurodegenerative disease is Multisystem proteinopathy (MSP). MSP is a dominantly inherited, pleiotropic, degenerative disorder of humans that can affect muscle, bone, and/or the central nervous system. MSP can manifest clinically as classical amyotrophic lateral sclerosis (ALS), frontotemporal dementia (FTD), inclusion body myopathy (IBM), Paget's disease of bone (PDB), or as a combination of these disorders (IBMPFD, IBMPFD/ALS).

In some embodiments, the neurodegenerative disease is a synucleinopathy. Synucleinopathies (also called $\alpha$-Synucleinopathies) are neurodegenerative diseases characterised by the abnormal accumulation of aggregates of alpha-synuclein protein in neurons, nerve fibres or glial cells.

In some embodiments, the neurodegenerative disease is a synucleinopathy selected from the group consisting of Parkinson's disease (PD), dementia with Lewy bodies (DLB), multiple system atrophy (MSA), neuroaxonal dystrophies, Alzheimer's Disease with Amygdalar Restricted Lewy Bodies (AD/ALB).

In some embodiments, the neurodegenerative disease is cognitive deficit and/or memory loss. In some embodiments, the neurodegenerative disease is dementia. In some embodiments, the neurodegenerative disease is dementia selected from the group consisting of Alzheimer's disease, Parkinson's disease dementia, Huntingtons disease dementia, vascular dementia, HIV dementia, frontotemporal dementia, dementia with lewy bodies, prion disease dementia, argyrophilic grain dementia, dementia pugilistica, Guadeloupean parkinsonism with dementia, neurofibrillary tangle-predominant dementia, tangle only dementia, Down's syndrome, semantic dementia, familial British dementia, familial Danish dementia, and other dementias caused by another medical condition such as brain tumors, subdural hematoma, endocrine disorders, nutritional deficiencies, infections, immune disorders, liver or kidney failure, metabolic disorders such as Kufs disease, some leukodystrophies, some neurological disorders such as epilepsy, and multiple sclerosis.

Disorders of peripheral nerves (peripheral neuropathy) are the most common neurological complications of systemic amyloidosis. In some embodiments, the neurodegenerative disease is peripheral amyloidosis (peripheral neuropathy in systemic amyloidosis).

In some embodiments, the neurodegenerative disease is a demyelinating disorder. In some embodiments, the neurodegenerative disease is a demyelinating disorder of the central nervous system, CNS. In some embodiments, the demyelinating disorder is a myelinoclastic or demyelinating disorder, such as selected from the group consisting of multiple sclerosis, neuromyelitis optica (Devic's disease) and idiopathic inflammatorydemyelinating diseases. In some embodiments, the demyelinating disorder is a leukodystrophic or dysmyelinating disorder, such as selected from the group consisting of CNS neuropathies such as vitamin B12 deficiency, central pontine myelinolysis, myelopathies such as tabes *dorsalis* (syphilitic myelopathy), leukoencephalopathies and leukodystrophies.

In some embodiments, the neurodegenerative disease is a demyelinating disorder of the peripheral nervous system, PNS. In some embodiments, the demyelinating disorder is selected from the group consisting of Guillain-Barre syndrome and its chronic counterpart, chronic inflammatory demyelinating polyneuropathy; Anti-MAG peripheral neuropathy; Charcot-Marie-Tooth disease and its counterpart Hereditary neuropathy with liability to pressure palsy; Copper deficiency-associated conditions (peripheral neuropathy, myelopathy, and rarely optic neuropathy); and Progressive inflammatory neuropathy.

In some embodiments, the neurodegenerative disease is Alzheimer's disease (AD). In some embodiments, the neurodegenerative disease is Alzheimer's disease (AD) with the R47H mutation. In some embodiments, the neurodegenerative disease is early Alzheimer's disease. In some embodiments, the neurodegenerative disease is Frontotemporal lobar degeneration (FTLD). In some embodiments, the neurodegenerative disease is frontotemporal dementia. In some embodiments, the neurodegenerative disease is Parkinson's disease. In some embodiments, the neurodegenerative disease is Nasu-Hakola disease (NHD). In some embodiments, the neurodegenerative disease is FTLD-like syndrome. In some embodiments, the neurodegenerative disease is Huntington disease. In some embodiments, the neurodegenerative disease is Amyotrophic lateral sclerosis (ALS). In some embodiments, the neurodegenerative disease is multiple sclerosis (MS). In some embodiments, the neurodegenerative disease is Guillain-Barre syndrome. In some embodiments, the neurodegenerative disease is chronic inflammatory demyelinating polyneuropathies. In some embodiments, the neurodegenerative disease is progressive subcortical gliosis. In some embodiments, the neurodegenerative disease is Charcot-Marie-Tooth disease. In some embodiments, the neurodegenerative disease is prion disease, such as prion protein cerebral amyloid angiopathy. In some embodiments, the neurodegenerative disease is stroke. In some embodiments, the neurodegenerative disease is cerebral amyloid angiopathy (CAA). In some embodiments the neurodegenerative disease is fragile X-associated tremor ataxia syndrome (FXTAS). In some embodiments the neurodegenerative disease is herpes simplex virus (HSV) encephalitis. In some embodiments the neurodegenerative disease is HIV-associated neurocognitive disorders (HAND). In some embodiments the neurodegenerative disease is progressive supranuclear palsy (PSP). In some embodiments the neurodegenerative disease is corticobasal degeneration. In some embodiments the neurodegenerative disease is Hallevorden-Spatz disease. In some embodiments the neurodegenerative disease is pallido-ponto-nigral degeneration. In some embodiments the neurodegenerative disease is postencephalitic parkinsonism. In some embodiments the neurodegenerative disease is subacute sclerosing panencephalitis (SSPE). In some embodiments the neurodegenerative disease is retinal degeneration (e.g., macular degeneration).

In some embodiments the neurodegenerative disease is a Leukoencephalopathy. Leukoencephalopathy (leukodystrophy-like diseases) is a term that describes all of the brain white matter diseases, whether their molecular cause is known or unknown. In some embodiments the neurodegenerative disease is a Leukoencephalopathy selected from the group consisting of Progressive multifocal leukoencephalopathy, Toxic leukoencephalopathy, Leukoencephalopathy with vanishing white matter, Leukoencephalopathy with neuroaxonal spheroids, Reversible posterior leukoencephalopathy syndrome, Megalencephalic leukoencephalopathy with subcortical cysts, and Hypertensive leukoencephalopathy. In some embodiments, the neurodegenerative disease is ALSP (Adult-onset leukoencephalopathy with axonal spheroids and pigmented glia).

In some embodiments the neurodegenerative disease is selected from the group consisting of cerebral autosomal dominant arteriopathy with subcortical infarcts or leukoencephalopathy; cerebral autosomal recessive arteriopathy with subcortical infarcts and leukoencephalopathy; and retinal vasculopathy with cerebral leukoencephalopathy (or cerebroretinal vasculopathy).

In some embodiments the neurodegenerative disease is a leukodystrophy. In some embodiments the neurodegenerative disease is vanishing white matter disease (VWM). Leukodystrophies are a group of rare, genetic disorders that affect the white matter of the brain. In some embodiments the neurodegenerative disease is a leukodystrophy selected from the group consisting of metachromatic leukodystrophy (MLD, also known as globoid cell leukodystrophy), Krabbe disease, Canavan disease, X-linked adrenoleukodystrophy, Alexander disease, hypomyelinating leukodystrophy type 7 (4H syndrome), Pelizaeus-Merzbacher disease, cerebrotendineous xanthomatosis and leukoendephalopathy with vanishing white matter. In some embodiments the neurodegenerative disease is adult-onset autosomal dominant leukodystrophy (ADLD). In some embodiments the neurodegenerative disease is X-linked adrenoleukodystrophy (X-ALD). In some embodiments the neurodegenerative disease is Nasu-Hakola disease also known as polycystic lipomembranous osteodysplasia with sclerosing leukoencephalopathy, PLOSL).

In some embodiments, the neurodegenerative disease is a transmissible spongiform encephalopathy (TSE), including Creutzfeldt-Jakob disease, Gerstmann-Straussler-Scheinker disease (GSS), kuru, and fatal familial insomnia.

In one aspect, the present invention relates to a method for treatment of a neurodegenerative disease comprising administering a compound, or a pharmaceutically acceptable salt thereof, as described herein to a subject in need thereof.

In one aspect, the present invention relates to a method for treatment of a neurodegenerative disease comprising one or more steps of administering a therapeutically effective amoubt of a compound, or a pharmaceutically acceptable salt thereof, as defined herein to a subject in need thereof.

In some embodiments, the subject is a mammal, such as a human.

In one aspect, the present invention relates to use of a compound, or a pharmaceutically acceptable salt thereof, as described herein for the manufacture of a medicament for treatment of a neurodegenerative disease.

In one aspect, the present invention relates to the compound, or a pharmaceutically acceptable salt thereof, as defined herein for use in the treatment of a disease or disorder associated with dysfunction of Colony stimulating factor 1 receptor (CSF1R, also known as macrophage colony-stimulating factor receptor/M-CSFR, or cluster of differentiation 115/CD115). In some embodiments the disease or disorder associated with dysfunction of CSF1R is a neurodegenerative disease associated with dysfunction of CSF1R.

In some embodiments the disease or disorder is caused by a heterozygous CSF1R mutation, a homozygous CSF1R mutation, a splice mutation in the csf1r gene, a missense mutation in the csf1r gene, a mutation in the catalytic kinase domain of CSF1R, a mutation in an immunoglobulin domain of CSF1R, a mutation in the ectodomain of CSF1R, a loss-of-function mutation in CSF1R. In some embodiments the disease or disorder result from a change (e.g. increase, decrease or cessation) in the activity of CSF1R and/or a decrease or cessation in the activity of CSF1R.

In some embodiments the neurodegenerative disease associated with dysfunction of CSF1R is a Leukoencephalopathy.

In some embodiments the neurodegenerative disease associated with dysfunction of CSF1R is selected from the group consisting of:

adult-onset leukoencephalopathy with axonal spheroids and pigmented glia (ALSP), CSF1R-related leukoencephalopathy, hereditary diffuse leukoencephalopathy with axonal spheroids (HDLS), pigmentary orthochromatic leukodystrophy (POLD), pediatric-onset leukoencephalopathy, congenital absence of microglia, brain abnormalities neurodegeneration and dysosteosclerosis (BANDDOS), and Cerebral autosomal dominant arteriopathy with subcortical infarcts and leukoencephalopathy (CADASIL).

In some embodiments the neurodegenerative disease is a condition associated with dysfunction of ATP-binding cassette transporter 1 (ABCD1).

In one aspect, the present invention relates to the compound, or a pharmaceutically acceptable salt thereof, as defined herein for use in the treatment of a lysosomal storage disorder (LSD). Most lysosomal storage disorders cause progressive neurodegeneration leading to early death.

In some embodiments the LSD is a lipidoses, such as a lipidoses selected from the group consisting of cholesteryl ester storage disease, fucosidosis, Schindler disease and Wolman disease.

In some embodiments the LSD is a sphingolipidoses, such as a sphingolipidoses selected from the group consisting of Fabry disease, Gaucher disease, Krabbe disease (globoid cell leukodystrophy), metachromatic leukodystrophy (MLD), Niemann-Pick disease (Types A, B and C), Sandhoff disease, Farmer disease, multiple sulfatase deficiency and Tay-Sachs disease.

In some embodiments the LSD is a mucopolysaccharidoses, such as a mucopolysaccharidoses selected from the group consinting of Hunter syndrome, Hurler syndomre, Hurler-Scheie syndrome, Scheie syndrome, Sanfilippo syndrome (A, B, C, D), Morquio syndrome, Maroteaux-Lamy syndrome, Sly syndrome and Natowicz syndrome.

In some embodiments the LSD is selected from the group consisting of Batten disease cyctinosis, Danon disease and Pompe disease.

In one aspect, the present invention relates to the compound, or a pharmaceutically acceptable salt thereof, as defined herein for use in the treatment of a disease or disorder of the bones and/or joints. In some embodiments said disease or disorder is selected from the group consisting of arthritis, rheumatoid arthritis, pyle disease, osteoporosis, osteopetrosis, osteosclerosis, skeletal dysplasia and dysosteoplasia.

In one aspect, the present invention relates to the compound, or a pharmaceutically acceptable salt thereof, as defined herein for use in the treatment of autism spectrum disorders, autism and Aspergers syndrome.

In one aspect, the present invention relates to the compound, or a pharmaceutically acceptable salt thereof, as defined herein for use in the treatment of traumatic brain injuries (TBI) and spinal cord injuries. Traumatic brain injuries (TBI), may also be known as intracranial injuries. Traumatic brain injuries occur when an external force traumatically injures the brain. Spinal cord injuries (SCI) include any injury to the spinal cord that is caused by trauma instead of disease. In some embodiments the TBI is chronic traumatic encephalopathy (CTE).

In one aspect, the present invention relates to the compound, or a pharmaceutically acceptable salt thereof, as defined herein for use in the treatment of muscular dystrophy such as myotonic dystrophy (DM) including Type 1 DM (DM1) and Type 2 DM (DM2).

In one aspect, the present invention relates to the compound, or a pharmaceutically acceptable salt thereof, as defined herein for use in the treatment of inflammation. In some embodiments said inflammation is selected from the group consisting of inclusion-body myositis, systemic lupus erythematosus (SLE), RA, gout, and certain bowel conditions including Inflammatory bowel disease (IBD).

A reduction in the functional levels of TREM2 results in dysregulation of lipid metabolism. In one aspect, the present invention relates to the compound, or a pharmaceutically acceptable salt thereof, as defined herein for use in the treatment of dysregulated lipid metabolism. In certain embodiments, the dysregulated lipid metabolism comprises increased intracellular and/or extracellular accumulation of one or more lipids. In some embodiments said dysregulated lipid metabolism is atherosclerosis.

In one aspect, the present invention relates to the compound, or a pharmaceutically acceptable salt thereof, as defined herein for use in the treatment of metabolic syndrome and conditions associated with metabolic syndrome, such as obesity, type 2 diabetes, atherosclerosis, alcoholic and non-alcoholic fatty liver disease, and alcoholic and non-alcoholic steatohepatitis, In one aspect, the present invention relates to the compound, or a pharmaceutically acceptable salt thereof, as defined herein for use in the treatment of Amyloidosis, including AL amyloidosis (immunoglobulin light chain amyloidosis), AA amyloidosis (secondary amyloidosis), familial amyloidosis, familial systemic amyloidosis, Wild-type amyloidosis (senile systemic amyloidosis) and Localized amyloidosis.

In some embodiments, the neurodegenerative disease is Alzheimer's disease. In some embodiments, the neurodegenerative disease is Nasu-Hakola disease. In some embodiments, the neurodegenerative disease is frontotemporal dementia. In some embodiments, the method comprises administering to the subject a compound as described herein, or a pharmaceutical composition comprising a compound as described herein.

The compounds of the present invention may be used to treat an animal patient belonging to any classification. Examples of such animals include mammals such as humans, rodents, dogs, cats, zoo animals and farm animals. In some embodiments, the subject referred to herein is a mammal, such as a human.

The term "compound," as used herein is meant to include all stereoisomers, geometric isomers, tautomers, and isotopes of the structures depicted, unless otherwise specified. Accordingly, the scope of the methods and uses herein is to be understood to encompass methods and uses employing all such forms.

Depending upon the particular condition, or disease, to be treated, additional therapeutic agents, which are normally administered to treat that condition, may be administered in combination with compounds and compositions of the present invention. As used herein, additional therapeutic agents that are normally administered to treat a particular disease, or condition, are known as "appropriate for the disease, or condition, being treated." In some embodiments, a provided combination, or composition thereof, is administered in combination with another therapeutic agent. In some embodiments, the present invention provides a method of treating a disclosed disease or condition comprising administering to a patient in need thereof an effective amount of a compound disclosed herein, or a pharmaceutically acceptable salt thereof, and co-administering simultaneously or sequentially an effective amount of one or more additional therapeutic agents. In some embodiments, the method includes co-administering one or more additional therapeutic agent. Examples of therapeutic agents the combinations of the present invention may also be combined with include, without limitation: treatments for Parkinson's disease, rheumatoid arthritis, Alzheimer's disease, Nasu-Hakola disease, frontotemporal dementia, multiple sclerosis, prion disease, or stroke. In some embodiments, the therapeutic agents the combinations of the present invention may also be combined with include, without limitation: treatments for a disease selected from the group consisting of a tauopathy, a TDP-43 proteinopathy, a synucleinopathy, dementia, amyloidosis, a demyelinating disorder of the CNS, a demyelinating disorder of the PNS, a Leukoencephalopathy, a leukodystrophy, a transmissible spongiform encephalopathy (TSE) and a lysosomal storage disorder (LSD). As used herein, the term "combination," "combined," and related terms refers to the simultaneous or sequential administration of therapeutic agents in accordance with the present invention. For example, a combination of the present invention may be administered with another therapeutic agent simultaneously or sequentially in separate unit dosage forms or together in a single unit dosage form.

In one aspect, the present invention relates to a method of treating a condition associated with a loss of function of TREM2 comprising administering to a subject a therapeutically effective amount of a compound selected from:

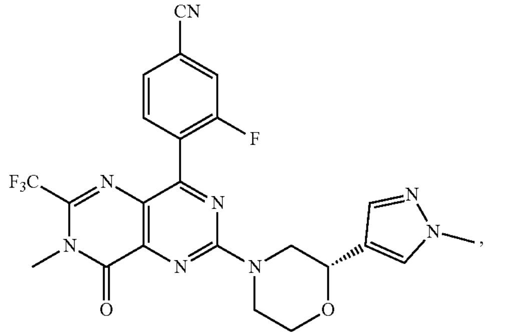 [SMILES: Cn1cc([C@H]2CN(c3nc(-c4ccc(C#N)cc4F)c4nc(C(F)(F)F)n(C)c(=O)c4n3)CCO2)cn1]

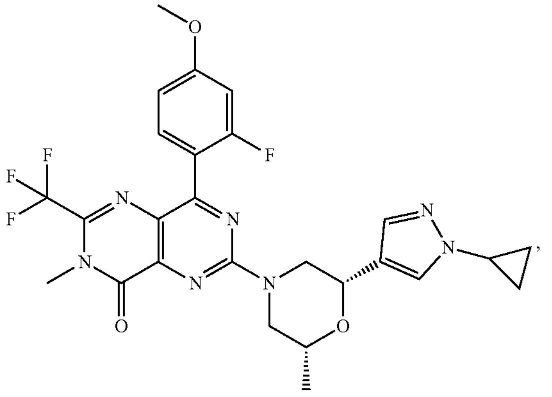 [SMILES: COc1ccc(-c2nc(N3C[C@@H](C)O[C@@H](c4cnn(C5CC5)c4)C3)nc3c(=O)n(C)c(C(F)(F)F)nc23)c(F)c1]

-continued

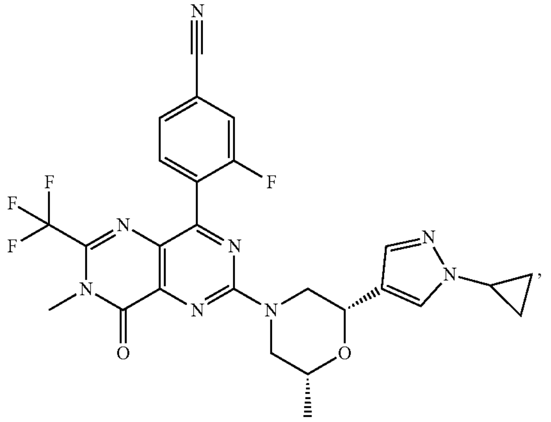

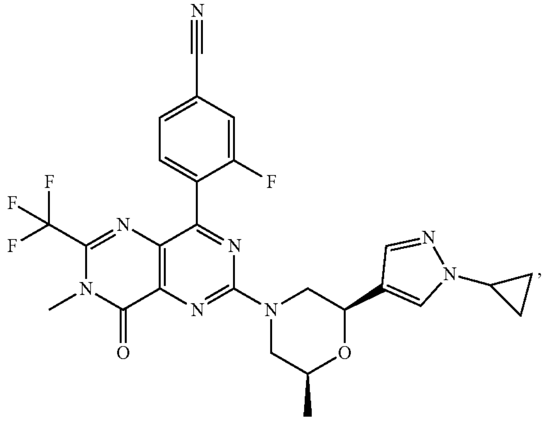

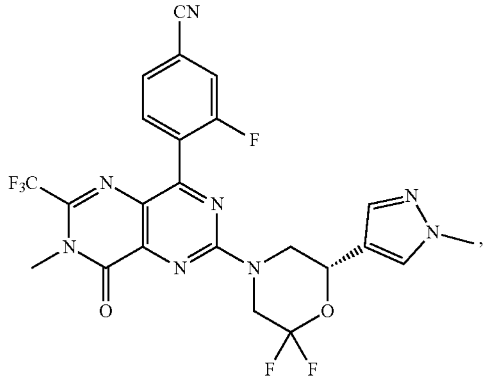 [SMILES: Cn1cc([C@H]2CN(c3nc(-c4ccc(C#N)cc4F)c4nc(C(F)(F)F)n(C)c(=O)c4n3)CC(F)(F)O2)cn1]

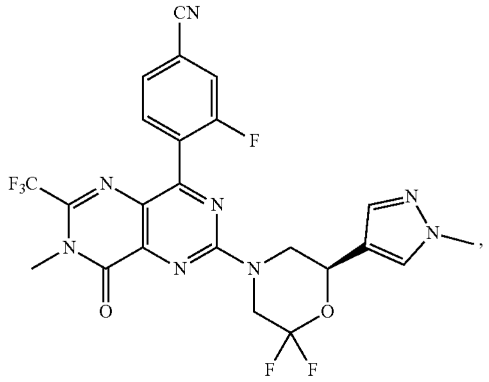 [SMILES: Cn1cc([C@@H]2CN(c3nc(-c4ccc(C#N)cc4F)c4nc(C(F)(F)F)n(C)c(=O)c4n3)CC(F)(F)O2)cn1]

-continued
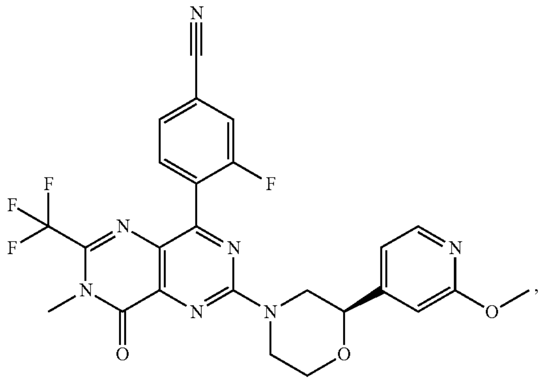 [SMILES: COc1cc([C@@H]2CN(c3nc(-c4ccc(C#N)cc4F)c4nc(C(F)(F)F)n(C)c(=O)c4n3)CCO2)ccn1]
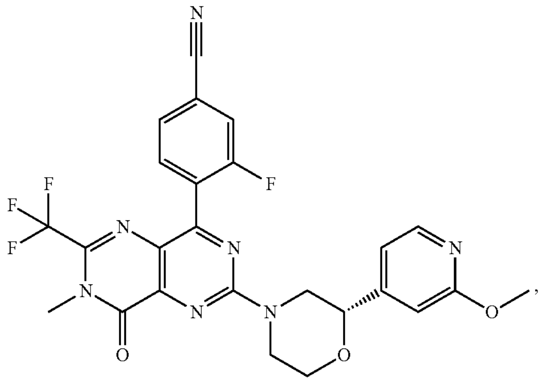 [SMILES: COc1cc([C@H]2CN(c3nc(-c4ccc(C#N)cc4F)c4nc(C(F)(F)F)n(C)c(=O)c4n3)CCO2)ccn1]
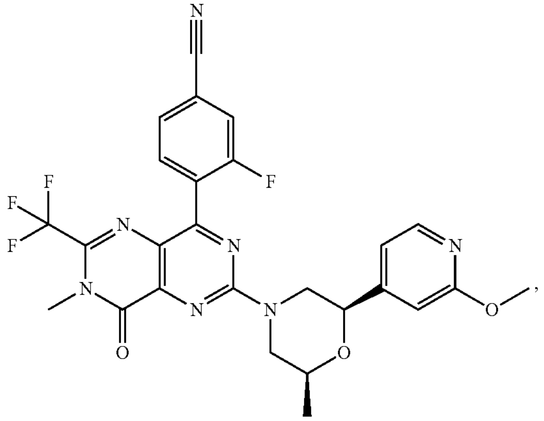 [SMILES: COc1cc([C@@H]2CN(c3nc(-c4ccc(C#N)cc4F)c4nc(C(F)(F)F)n(C)c(=O)c4n3)C[C@H](C)O2)ccn1]
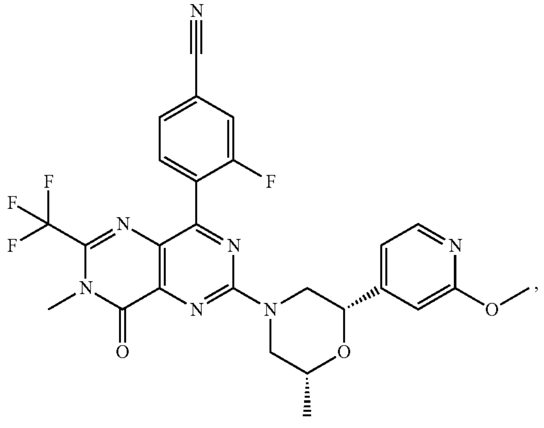 [SMILES: COc1cc([C@H]2CN(c3nc(-c4ccc(C#N)cc4F)c4nc(C(F)(F)F)n(C)c(=O)c4n3)C[C@@H](C)O2)ccn1]
-continued
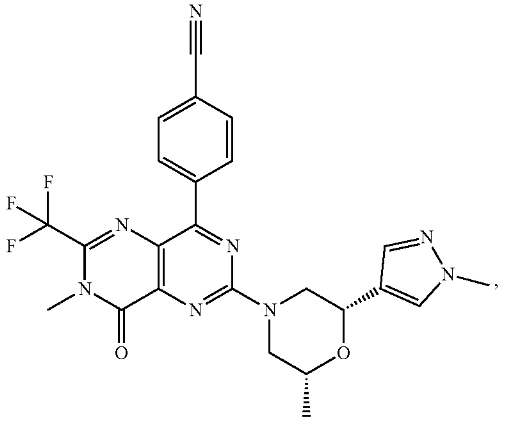 [SMILES: C[C@@H]1CN(c2nc(-c3ccc(C#N)cc3)c3nc(C(F)(F)F)n(C)c(=O)c3n2)C[C@H](c2cnn(C)c2)O1]
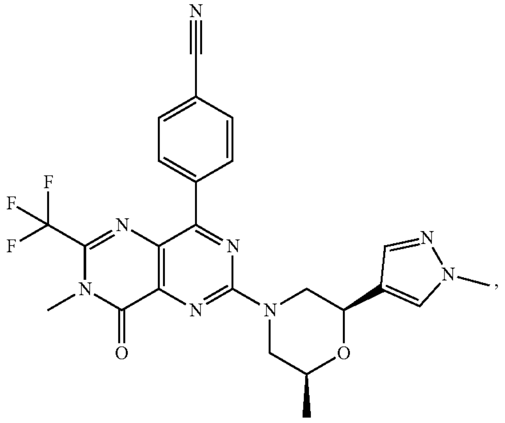 [SMILES: C[C@H]1CN(c2nc(-c3ccc(C#N)cc3)c3nc(C(F)(F)F)n(C)c(=O)c3n2)C[C@@H](c2cnn(C)c2)O1]
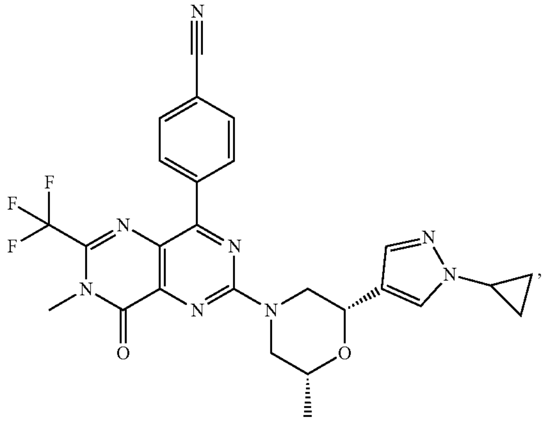 [SMILES: C[C@@H]1CN(c2nc(-c3ccc(C#N)cc3)c3nc(C(F)(F)F)n(C)c(=O)c3n2)C[C@H](c2cnn(C3CC3)c2)O1]
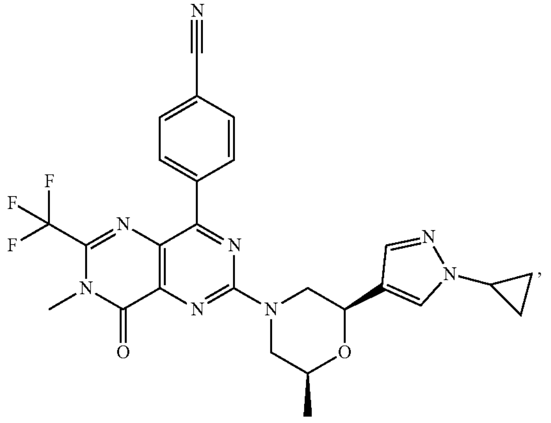

-continued

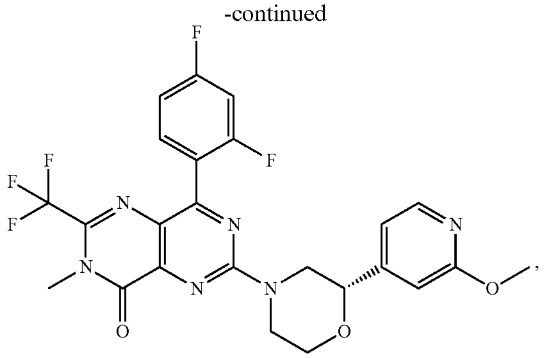

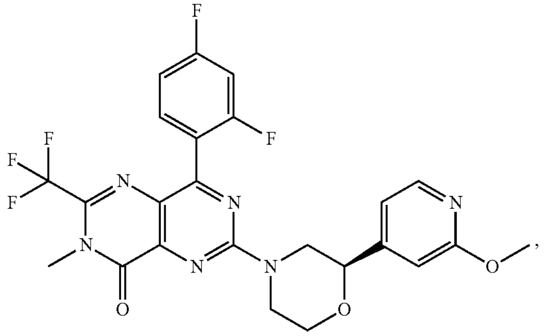 [SMILES: COc1cc([C@@H]2CN(c3nc(-c4ccc(F)cc4F)c4nc(C(F)(F)F)n(C)c(=O)c4n3)CCO2)ccn1]

,

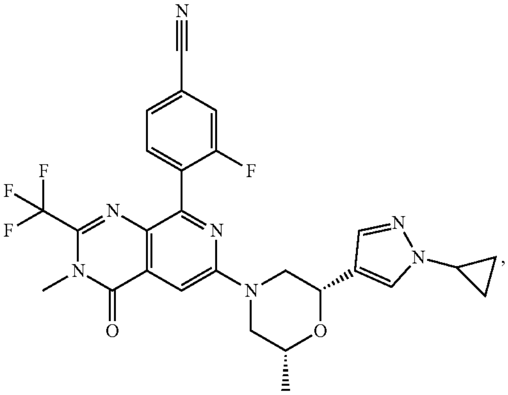 [SMILES: C[C@@H]1CN(c2cc3c(=O)n(C)c(C(F)(F)F)nc3c(-c3ccc(C#N)cc3F)n2)C[C@H](c2cnn(C3CC3)c2)O1]

, and

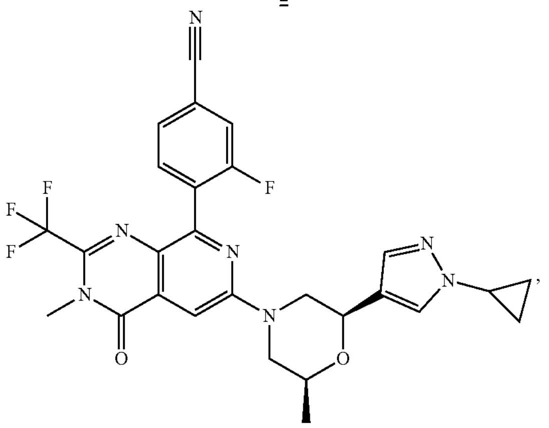

or a pharmaceutically acceptable salt thereof. In some embodiments, the condition is a neurodegenerative disease. In some embodiments, the neurodegenerative disease is Frontotemporal lobar degeneration (FTLD), frontotemporal dementia (FTD), Parkinson's disease, Nasu-Hakola disease, FTLD-like syndrome, Huntington disease, Amyotrophic lateral sclerosis, multiple sclerosis, Guillain-Barre syndrome, chronic inflammatory demyelinating polyneuropathies, Charcot-Marie-Tooth disease, prion disease and stroke. In some embodiments, the neurodegenerative disease is Alzheimer's Disease.

Methods of Manufacturing

Compounds of the present invention may be prepared according to any conventional methods of chemical synthesis known by the skilled person, e.g. those described in the working examples. The starting materials for the processes described in the present application are known or may readily be prepared by conventional methods known by the skilled artisan from commercially available chemicals. The end products of the reactions described herein may be isolated by conventional technique such as extraction, crystallisation, distillation, chromatography etc.

Generally, the compounds of the current invention may be synthesised according to the following schemes.

All starting materials are either commercially available or known in the art and may be synthesised by using known procedures. Starting materials may also be synthesised using the procedures disclosed herein. Reaction conditions such as reaction temperature, solvent and reagents for the Schemes in this section may be found in the experimental section herein.

When $X^1$ is N, the compounds of the invention may be synthesized according to scheme 1.

Scheme 1

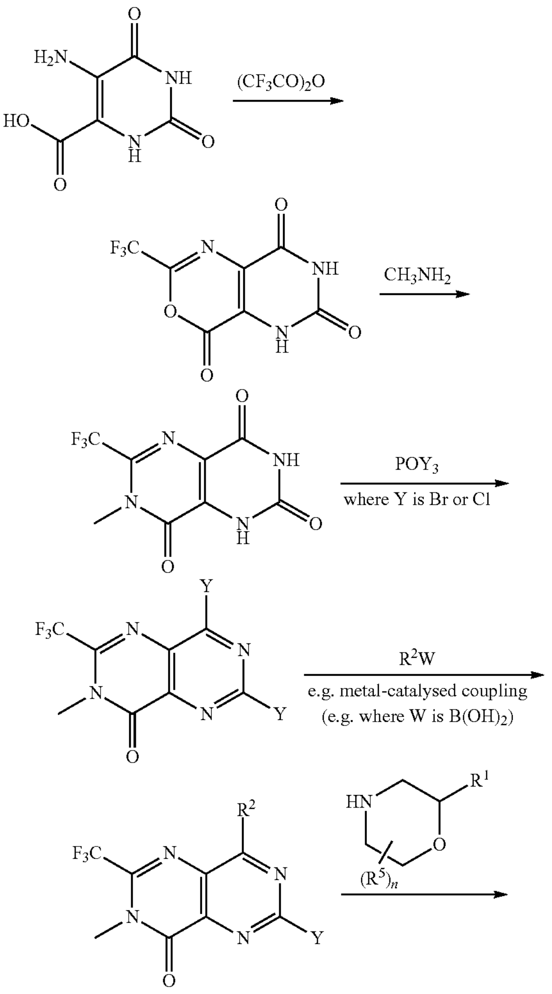

-continued

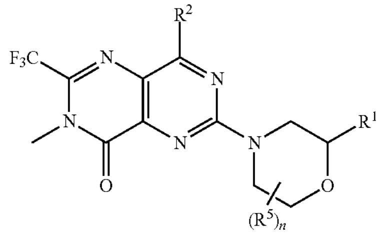

As shown in Scheme 1, $(CF_3CO)_20$ is condensed with 5-amino-2,6-dioxo-1,2,3,6-tetrahydropyrimidine-4-carboxylic acid to form a 2-substituted pyrimido[5,4-d][1,3]oxazine-4,6,8-trione. Addition and cyclisation with $CH_3NH_2$ affords the [1,3]diazino[5,4-d]pyrimidine-2,4,8-trione. Activation with $POCl_3$ or $POBr_3$ for example affords the 6,8-dihalo-pyrimido[5,4-d][1,3]diazin-4-one where Y is a Cl or Br leaving group. The $R^2$ substituent is added via cross-coupling reaction, for example where W is a boronic acid, boronate ester or other organometallic coupling reagent such as organomagnesium, organotin or organozinc reagent. The morpholine substituent may then subsequently be introduced via a nucleophilic displacement reaction.

When $X^1$ is C(H), the compounds of the invention may be synthesized according to scheme 2.

Scheme 2

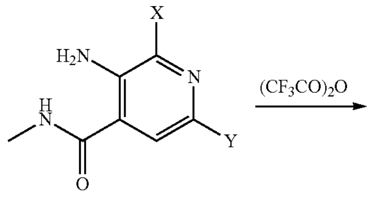

where Y and X are halogen

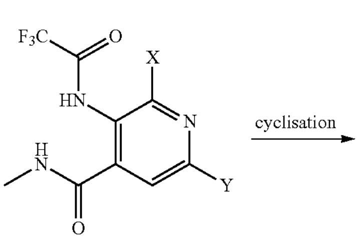

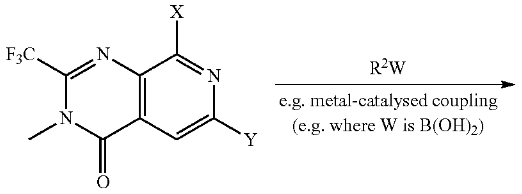

-continued

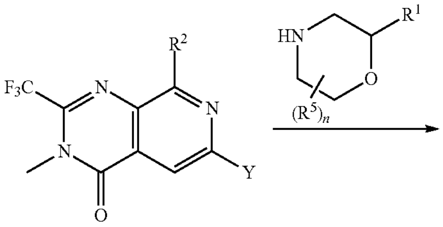

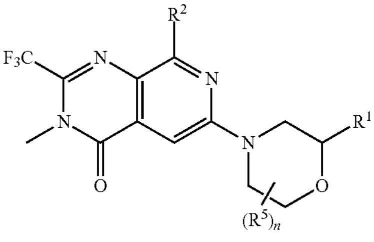

In Scheme 2, $(CF_3CO)_20$ is reacted with a 3-amino-2,6-dihalopyridyl-4-carboxamide. Cyclisation forms a 6,8-dihalo-2,3-disubstituted pyridopyrimidinone, the $R^2$ substituent is added via cross-coupling reaction, for example where W is a boronic acid, boronate ester or other organometallic coupling reagent such as organomagnesium, organotin or organozinc reagent. The morpholine substituent may then subsequently be introduced via a second metal-catalysed coupling.

Examples of the morpholine substituent

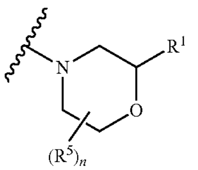

may be synthesised according to scheme 3A or scheme 3B below.

In Scheme 3A, wherein $R^5$ is H or $C_{1-3}$ alkyl and n is 1, a heterocyclic halomethylketone undergoes a nucleophilic substitution reaction with an aminoalcohol. Ketone reduction followed by acid-mediated cyclisation and then deprotection then affords the NH morpholine which is used as described in Schemes 1 and 2.

In Scheme 3B, wherein $R^5$ is F and n is 2, a heterocyclic aminoalcohol is acylated to form an amide. Base-mediated cyclisation gives a cyclic lactam which is then reduced to afford the NH morpholine which is used as described in Schemes 1 and 2.

Scheme 3A

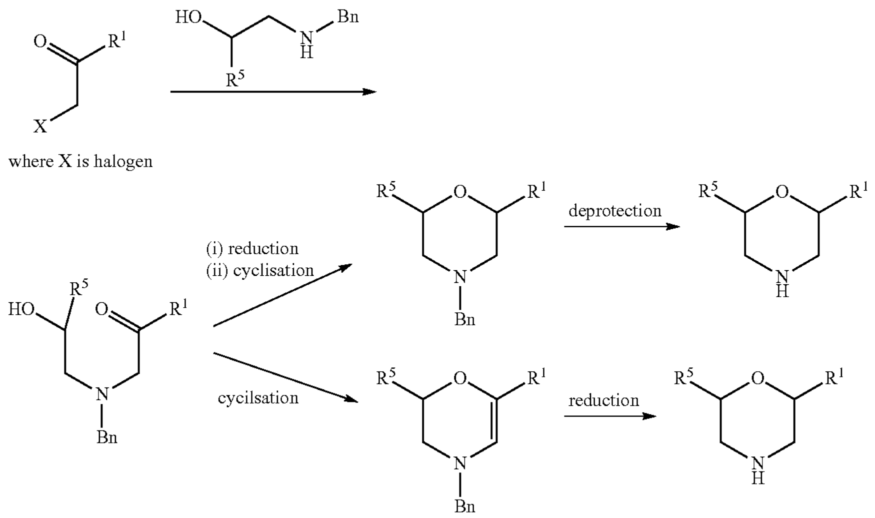

Scheme 3B

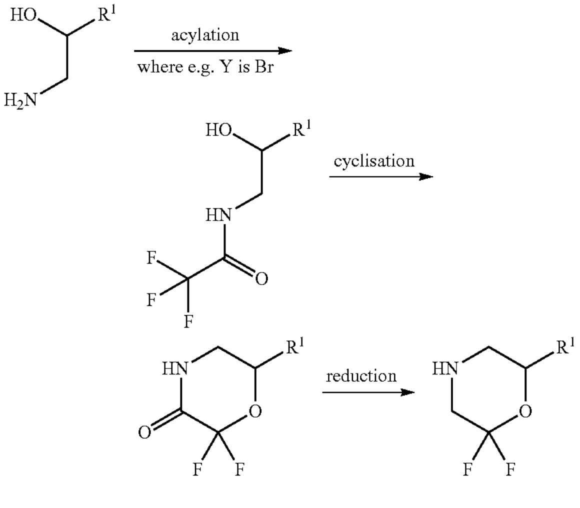

Thus, in one aspect, the present invention relates to a method for synthesizing a compound of Formula (I) comprising one or more of the steps described above. In one aspect, the present invention relates to a method for manufacturing a compound of Formula (I) as defined herein, said method comprising the step of reacting a compound of Formula (SI):

Formula (SI)

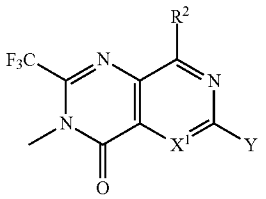

wherein $X^1$ and $R^2$ are as defined herein and Y is Br or Cl, with a compound of Formula (SII):

Formula (SII)

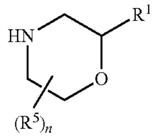

wherein $R^1$, $R^5$, and n are as defined herein, to generate the compound of Formula (I).

Items

1. A compound of Formula (I):

Formula (I)

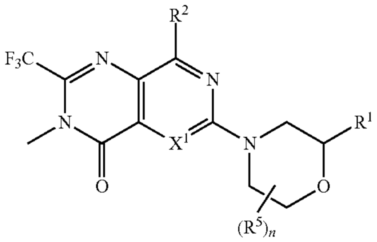

wherein $X^1$ is N or C(H);

$R^1$ is of Formula (II):

Formula (II)

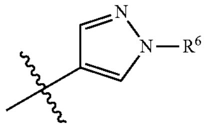

wherein $R^6$ is $C_{1-3}$ alkyl or cyclopropyl; or

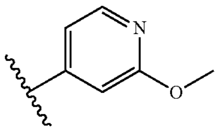

;

$R^2$ is selected from the group consisting of:

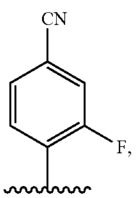

,

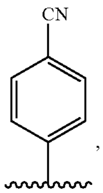

,

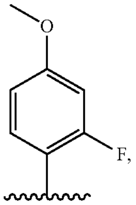

, and

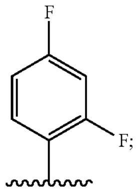 [SMILES: *c1ccc(F)cc1F]

;

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, or a pharmaceutically acceptable salt thereof.

2. A compound of Formula (1):

Formula (I)

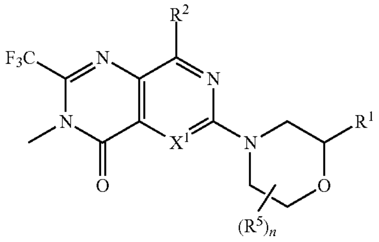

wherein $X^1$ is N or C(H);

$R^1$ is of Formula (II):

Formula (II)

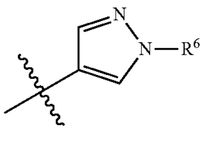

wherein $R^6$ is $C_{1-3}$ alkyl or cyclopropyl; or

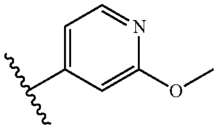

;

$R^2$ is of Formula (XII):

Formula (XII)

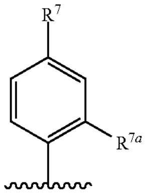

wherein $R^7$ is —CN, —$OC_{1-3}$ alkyl or F; and $R^{7a}$ is F or H;

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, or a pharmaceutically acceptable salt thereof.

3. The compound according to any one of items 1 or 2, wherein the compound is of Formula (Ia):

Formula (Ia)

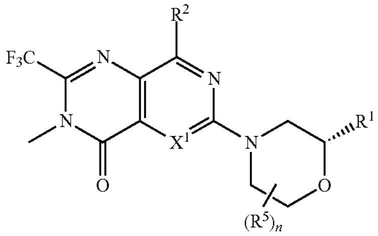

or a pharmaceutically acceptable salt thereof.

4. The compound according to any one of items 1 to 3, wherein the compound is of Formula (Ib):

Formula (Ib)

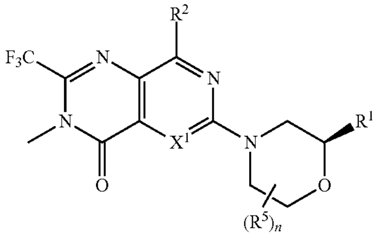

or a pharmaceutically acceptable salt thereof.

5. The compound according to item 1, wherein the compound is of Formula (III):

Formula (III)

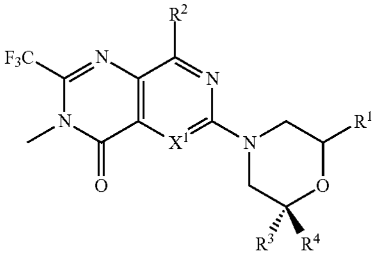

wherein $X^1$ is N or C(H);

$R^1$ is of Formula (II):

Formula (II)

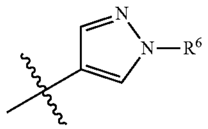

wherein $R^6$ is $C_{1-3}$ alkyl or cyclopropyl;

or

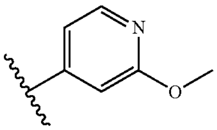;

$R^2$ is selected from the group consisting of:

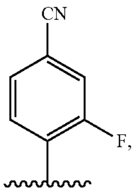, 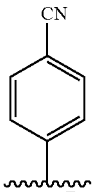, 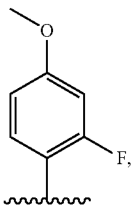, and 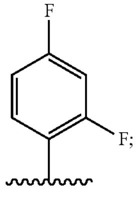 [SMILES: *c1ccc(F)cc1F];

$R^3$ is selected from the group consisting of H, F and $C_{1-3}$ alkyl; and $R^4$ is selected from the group consisting of H, F and $C_{1-3}$ alkyl;

or $R^3$ and $R^4$ are $C_{1-3}$ alkanediyl, $R^3$ and $R^4$ are linked together to form a 3- to 6-membered ring, or a pharmaceutically acceptable salt thereof.

6. The compound according to item 5, wherein the compound is of Formula (IIIa):

Formula (IIIa)

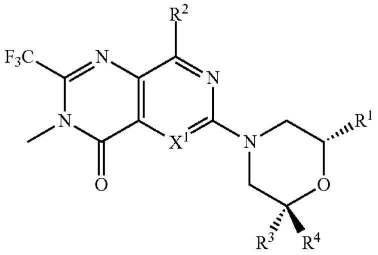

or a pharmaceutically acceptable salt thereof.

7. The compound according to item 5, wherein the compound is of Formula (IIIb):

Formula (IIIb)

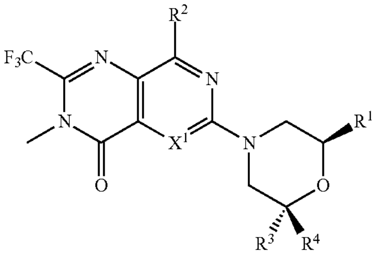

or a pharmaceutically acceptable salt thereof.

8. The compound according to item 1, wherein the compound is of Formula (IV):

Formula (IV)

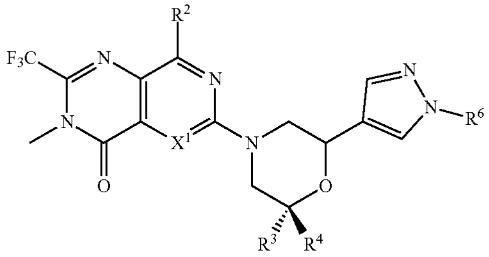

wherein $X^1$ is N or C(H);

wherein $R^6$ is $C_{1-3}$ alkyl or cyclopropyl;

$R^2$ is selected from the group consisting of:

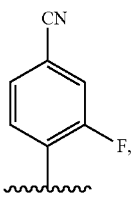, 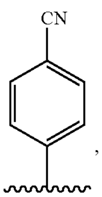, 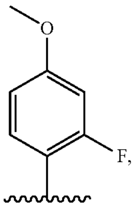, and

-continued

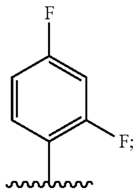

$R^3$ is selected from the group consisting of H, F and $C_{1-3}$ alkyl; and $R^4$ is selected from the group consisting of H, F and $C_{1-3}$ alkyl;

or $R^3$ and $R^4$ are $C_{1-3}$ alkanediyl, $R^3$ and $R^4$ are linked together to form a 3- to 6-membered ring, or a pharmaceutically acceptable salt thereof.

9. The compound according to item 8, wherein the compound is of Formula (IVa):

Formula (IVa)

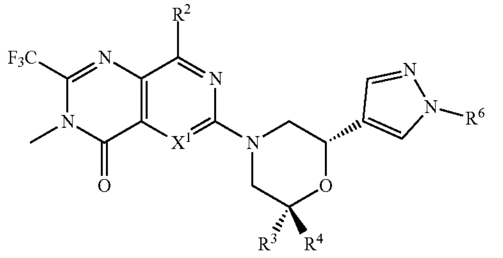

or a pharmaceutically acceptable salt thereof.

10. The compound according to item 8, wherein the compound is of Formula (IVb):

Formula (IVb)

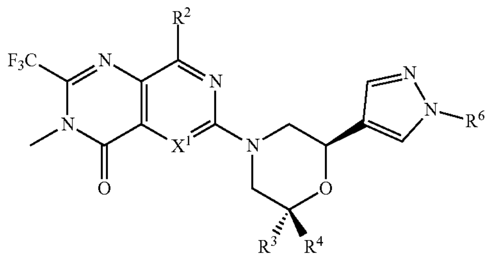

or a pharmaceutically acceptable salt thereof.

11. The compound according to item 1, wherein the compound is of Formula (X):

Formula (X)

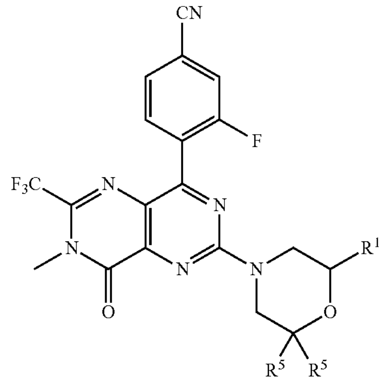

or a pharmaceutically acceptable salt thereof, wherein $R^1$ is of Formula (II):

Formula (II)

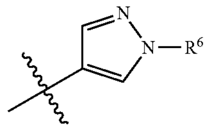

wherein $R^6$ is $C_{1-3}$ alkyl or cyclopropyl;

or

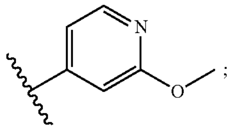 [SMILES: *c1ccnc(OC)c1]

and each $R^5$ is individually selected from the group consisting of H, F and $C_{1-3}$ alkyl.

12. The compound according to item 1, wherein the compound is of Formula (XI):

Formula (XI)

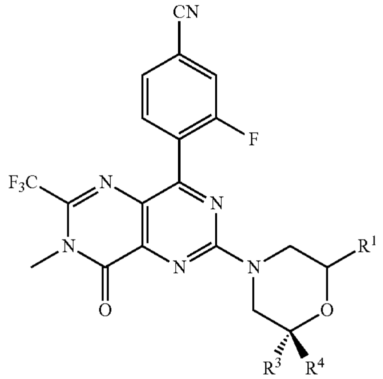

or a pharmaceutically acceptable salt thereof, wherein $R^1$ is of Formula (II):

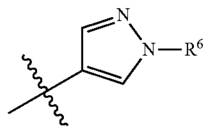

Formula (II)

wherein $R^6$ is $C_{1-3}$ alkyl or cyclopropyl;

or

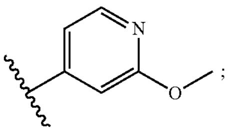 [SMILES: *c1ccnc(OC)c1]

$R^3$ is H, F or $C_{1-3}$ alkyl; and $R^4$ is H, F or $C_{1-3}$ alkyl.

13. The compound according to item 1, wherein the compound is of Formula (V):

Formula (V)

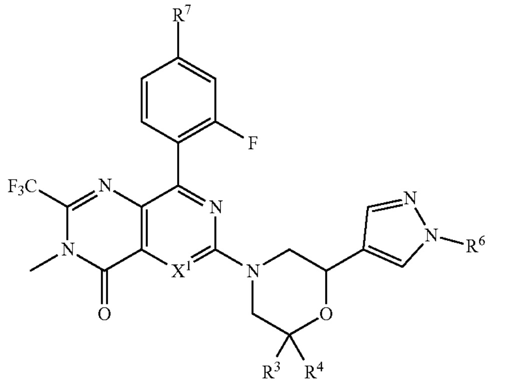

wherein $X^1$ is N or C(H);

$R^6$ is $C_{1-3}$ alkyl or cyclopropyl;

$R^7$ is —CN, —$OC_{1-3}$ alkyl or F;

$R^3$ is selected from the group consisting of H, F and $C_{1-3}$ alkyl; and $R^4$ is selected from the group consisting of H, F and $C_{1-3}$ alkyl;

or a pharmaceutically acceptable salt thereof.

14. The compound according to any one of the preceding items, with the proviso that when $R^2$ is

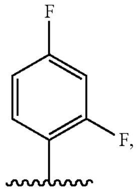

then $R^1$ is

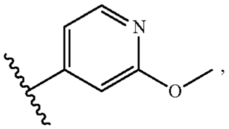 [SMILES: *c1ccnc(OC)c1]

or a pharmaceutically acceptable salt thereof.

15. The compound according to any one of the preceding items, with the proviso that when $R^2$ is

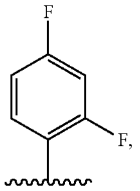

then n is 0, or a pharmaceutically acceptable salt thereof.

16. The compound according to any one of the preceding items, with the proviso that when $R^2$ is

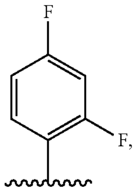

then $R^3$ and $R^4$ are H, or a pharmaceutically acceptable salt thereof.

17. The compound according to any one of the preceding items, wherein $X^1$ is N, or a pharmaceutically acceptable salt thereof.

18. The compound according to any one of the preceding items, wherein $X^1$ is C(H), or a pharmaceutically acceptable salt thereof.

19. The compound according to any one of the preceding items, wherein $R^1$ is of Formula (II):

Formula (II)

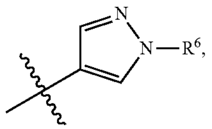

wherein $R^6$ is $C_{1-3}$ alkyl or cyclopropyl, or a pharmaceutically acceptable salt thereof.

20. The compound according to any one of the preceding items, wherein $R^6$ is —$C_{1-3}$ alkyl, or a pharmaceutically acceptable salt thereof.

21. The compound according to any one of the preceding items, wherein $R^6$ is —$CH_3$, or a pharmaceutically acceptable salt thereof.

22. The compound according to any one of the preceding items, wherein $R^6$ is —$CH_2CH_3$, or a pharmaceutically acceptable salt thereof.

23. The compound according to any one of the preceding items, wherein $R^6$ is $—CH_2CH_2CH_3$, or a pharmaceutically acceptable salt thereof.

24. The compound according to any one of the preceding items, wherein $R^6$ is cyclopropyl, or a pharmaceutically acceptable salt thereof.

25. The compound according to any one of the preceding items, wherein $R^1$ is

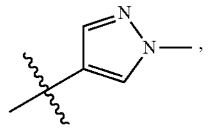 [SMILES: *c1cnn(C)c1]

or a pharmaceutically acceptable salt thereof.

26. The compound according to any one of the preceding items, wherein $R^1$ is

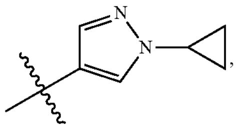 [SMILES: *c1cnn(C2CC2)c1]

or a pharmaceutically acceptable salt thereof.

27. The compound according to any one of the preceding items, wherein $R^1$ is

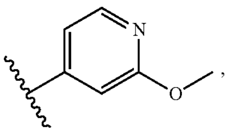 [SMILES: *c1ccnc(OC)c1]

or a pharmaceutically acceptable salt thereof.

28. The compound according to any one of the preceding items, wherein $R^7$ is —CN, or a pharmaceutically acceptable salt thereof.

29. The compound according to any one of the preceding items, wherein $R^7$ is $—OC_{1-3}$ alkyl, or a pharmaceutically acceptable salt thereof.

30. The compound according to any one of the preceding items, wherein $R^7$ is $—OCH_3$, or a pharmaceutically acceptable salt thereof.

31. The compound according to any one of the preceding items, wherein $R^{7a}$ is F.

32. The compound according to any one of the preceding items, wherein $R^2$ is of Formula (XII) and $R^7$ is —CN.

33. The compound according to any one of the preceding items, wherein $R^2$ is of Formula (XII), $R^7$ is $—OC_{1-3}$ alkyl, and $R^{7a}$ is F.

34. The compound according to any one of the preceding items, wherein $R^2$ is

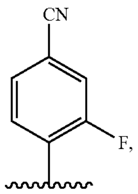 [SMILES: *c1ccc(C#N)cc1F] 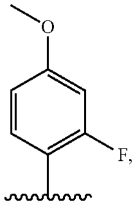 or 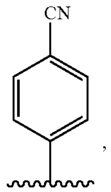

or a pharmaceutically acceptable salt thereof

35. The compound according to any one of the preceding items, wherein $R^2$ is

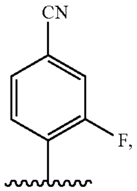

or a pharmaceutically acceptable salt thereof.

36. The compound according to any one of the preceding items, wherein $R^2$ is

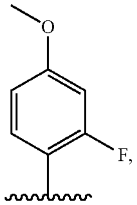 [SMILES: *c1ccc(OC)cc1F]

or a pharmaceutically acceptable salt thereof.

37. The compound according to any one of the preceding items, wherein $R^2$ is

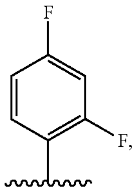

or a pharmaceutically acceptable salt thereof.

38. The compound according to any one of the preceding items, wherein $R^2$ is

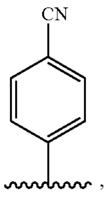

or a pharmaceutically acceptable salt thereof.

39. The compound according to any one of the preceding items, wherein n is 0, 1 or 2, and $R^5$ is individually H, F or $C_{1-3}$ alkyl, or a pharmaceutically acceptable salt thereof.
40. The compound according to any one of the preceding items, wherein n is 0, 1 or 2, and $R^5$ is individually F or $C_{1-3}$ alkyl, or a pharmaceutically acceptable salt thereof.
41. The compound according to any one of the preceding items, wherein $R^5$ is H, or a pharmaceutically acceptable salt thereof.
42. The compound according to any one of the preceding items, wherein $R^5$ is individually F or $C_{1-3}$ alkyl.
43. The compound according to any one of the preceding items, wherein $R^5$ is F, or a pharmaceutically acceptable salt thereof.
44. The compound according to any one of the preceding items, wherein $R^5$ is $C_{1-3}$ alkyl, or a pharmaceutically acceptable salt thereof.
45. The compound according to any one of the preceding items, wherein $R^5$ is $CH_3$, or a pharmaceutically acceptable salt thereof.
46. The compound according to any one of the preceding items, wherein n is 0, or a pharmaceutically acceptable salt thereof.
47. The compound according to any one of the preceding items, wherein n is 1, or a pharmaceutically acceptable salt thereof.
48. The compound according to any one of the preceding items, wherein n is 2, or a pharmaceutically acceptable salt thereof.
49. The compound according to any one of the preceding items, wherein $R^3$ is H, F or $C_{1-3}$ alkyl, and $R^4$ is H, F or $C_{1-3}$ alkyl, or a pharmaceutically acceptable salt thereof.
50. The compound according to any one of the preceding items, wherein $R^3$ is H, or a pharmaceutically acceptable salt thereof.
51. The compound according to any one of the preceding items, wherein $R^3$ is F, or a pharmaceutically acceptable salt thereof.
52. The compound according to any one of the preceding items, wherein $R^3$ is $C_{1-3}$ alkyl, or a pharmaceutically acceptable salt thereof.
53. The compound according to any one of the preceding items, wherein $R^3$ is $CH_3$, or a pharmaceutically acceptable salt thereof.
54. The compound according to any one of the preceding items, wherein $R^4$ is H, or a pharmaceutically acceptable salt thereof.
55. The compound according to any one of the preceding items, wherein $R^4$ is F, or a pharmaceutically acceptable salt thereof.
56. The compound according to any one of the preceding items, wherein $R^4$ is $C_{1-3}$ alkyl, or a pharmaceutically acceptable salt thereof.
57. The compound according to any one of the preceding items, wherein $R^4$ is $CH_3$, or a pharmaceutically acceptable salt thereof.
58. The compound according to any one of the preceding items, wherein $R^3$ and $R^4$ are identical, or a pharmaceutically acceptable salt thereof.
59. The compound according to any one of the preceding items, wherein $R^3$ and $R^4$ are different, or a pharmaceutically acceptable salt thereof.
60. The compound according to any one of the preceding items, wherein $R^3$ is $C_{1-3}$ alkyl and $R^4$ is $C_{1-3}$ alkyl, or a pharmaceutically acceptable salt thereof.
61. The compound according to any one of the preceding items, wherein $R^3$ is $CH_3$ and $R^4$ is $CH_3$, or a pharmaceutically acceptable salt thereof.
62. The compound according to any one of the preceding items, wherein $R^3$ is $CH_3$ and $R^4$ is H, or a pharmaceutically acceptable salt thereof.
63. The compound according to any one of the preceding items, wherein $R^3$ is H and $R^4$ is H, or a pharmaceutically acceptable salt thereof.
64. The compound according to any one of the preceding items, wherein $R^3$ is H and $R^4$ is $CH_3$, or a pharmaceutically acceptable salt thereof.
65. The compound according to any one of the preceding items, wherein $R^3$ is F and $R^4$ is F, or a pharmaceutically acceptable salt thereof.
66. The compound according to any one of the preceding items, wherein $X^1$ is N; $R^3$ is H; and $R^4$ is H, or a pharmaceutically acceptable salt thereof.
67. The compound according to any one of the preceding items, wherein $X^1$ is C(H); $R^3$ is H; and $R^4$ is H, or a pharmaceutically acceptable salt thereof.
68. The compound according to any one of the preceding items, wherein $X^1$ is N; $R^3$ is F; and $R^4$ is F, or a pharmaceutically acceptable salt thereof.
69. The compound according to any one of the preceding items, $X^1$ is C(H); $R^3$ is F; and $R^4$ is F, or a pharmaceutically acceptable salt thereof.
70. The compound according to any one of the preceding items, wherein $X^1$ is N; $R^3$ is $CH_3$; and $R^4$ is H, or a pharmaceutically acceptable salt thereof.
71. The compound according to any one of the preceding items, $X^1$ is C(H); $R^3$ is $CH_3$; and $R^4$ is H, or a pharmaceutically acceptable salt thereof.
72. The compound according to any one of the preceding items, wherein the compound is of Formula (III) and $X^1$ is N; $R^3$ is H; and $R^4$ is H, or a pharmaceutically acceptable salt thereof.
73. The compound according to any one of the preceding items, wherein the compound is of Formula (III) and $X^1$ is C(H); $R^3$ is H; and $R^4$ is H, or a pharmaceutically acceptable salt thereof.
74. The compound according to any one of the preceding items, wherein the compound is of Formula (III) and $X^1$ is N; $R^3$ is F; and $R^4$ is F, or a pharmaceutically acceptable salt thereof.
75. The compound according to any one of the preceding items, wherein the compound is of Formula (III) and $X^1$ is C(H); $R^3$ is F; and $R^4$ is F, or a pharmaceutically acceptable salt thereof.
76. The compound according to any one of the preceding items, wherein the compound is of Formula (III) and $X^1$ is N; $R^3$ is $CH_3$; and $R^4$ is H, or a pharmaceutically acceptable salt thereof.
77. The compound according to any one of the preceding items, wherein the compound is of Formula (III) and $X^1$ is C(H); $R^3$ is $CH_3$; and $R^4$ is H, or a pharmaceutically acceptable salt thereof.
78. The compound according to any one of the preceding items, wherein $X^1$ is N; $R^6$ is $CH_3$; $R^3$ is H; and $R^4$ is H, or a pharmaceutically acceptable salt thereof.
79. The compound according to any one of the preceding items, $X^1$ is C(H); $R^6$ is $CH_3$; $R^3$ is H; and $R^4$ is H, or a pharmaceutically acceptable salt thereof.

80. The compound according to any one of the preceding items, $X^1$ is N; $R^6$ is $CH_3$; $R^3$ is F; and $R^4$ is F, or a pharmaceutically acceptable salt thereof.
81. The compound according to any one of the preceding items, wherein $X^1$ is C(H); $R^6$ is $CH_3$; $R^3$ is F; and $R^4$ is F, or a pharmaceutically acceptable salt thereof.
82. The compound according to any one of the preceding items, $X^1$ is N; $R^6$ is cyclopropyl; $R^3$ is $CH_3$; and $R^4$ is H, or a pharmaceutically acceptable salt thereof.
83. The compound according to any one of the preceding items, $X^1$ is C(H); $R^6$ is cyclopropyl; $R^3$ is $CH_3$; and $R^4$ is H, or a pharmaceutically acceptable salt thereof.
84. The compound according to any one of the preceding items, $X^1$ is N; $R^6$ is $CH_3$; $R^3$ is $CH_3$; and $R^4$ is H, or a pharmaceutically acceptable salt thereof.
85. The compound according to any one of the preceding items, wherein $X^1$ is N; $R^6$ is cyclopropyl; $R^3$ is H; and $R^4$ is $CH_3$, or a pharmaceutically acceptable salt thereof.
86. The compound according to any one of the preceding items, wherein $X^1$ is C(H); $R^6$ is cyclopropyl; $R^3$ is H; and $R^4$ is $CH_3$, or a pharmaceutically acceptable salt thereof.
87. The compound according to any one of the preceding items, wherein $X^1$ is N; $R^6$ is $CH_3$; $R^3$ is H; and $R^4$ is $CH_3$, or a pharmaceutically acceptable salt thereof.
88. The compound according to any one of the preceding items, wherein the compound is of Formula (IV) and $X^1$ is N; $R^6$ is $CH_3$; $R^3$ is H; and $R^4$ is H, or a pharmaceutically acceptable salt thereof.
89. The compound according to any one of the preceding items, wherein the compound is of Formula (IV) and $X^1$ is C(H); $R^6$ is $CH_3$; $R^3$ is H; and $R^4$ is H, or a pharmaceutically acceptable salt thereof.
90. The compound according to any one of the preceding items, wherein the compound is of Formula (IV) and $X^1$ is N; $R^6$ is $CH_3$; $R^3$ is F; and $R^4$ is F, or a pharmaceutically acceptable salt thereof.
91. The compound according to any one of the preceding items, wherein the compound is of Formula (IV) and $X^1$ is C(H); $R^6$ is $CH_3$; $R^3$ is F; and $R^4$ is F, or a pharmaceutically acceptable salt thereof.
92. The compound according to any one of the preceding items, wherein the compound is of Formula (IV) and $X^1$ is N; $R^6$ is cyclopropyl; $R^3$ is $CH_3$; and $R^4$ is H, or a pharmaceutically acceptable salt thereof.
93. The compound according to any one of the preceding items, wherein the compound is of Formula (IV) and $X^1$ is C(H); $R^6$ is cyclopropyl; $R^3$ is $CH_3$; and $R^4$ is H, or a pharmaceutically acceptable salt thereof.
94. The compound according to any one of the preceding items, wherein the compound is of Formula (IV) and $X^1$ is N; $R^6$ is $CH_3$; $R^3$ is $CH_3$; and $R^4$ is H, or a pharmaceutically acceptable salt thereof.
95. The compound according to any one of the preceding items, wherein the compound is of Formula (IVa) and $X^1$ is N; $R^6$ is $CH_3$; $R^3$ is H; and $R^4$ is H, or a pharmaceutically acceptable salt thereof.
96. The compound according to any one of the preceding items, wherein the compound is of Formula (IVa) and $X^1$ is C(H); $R^6$ is $CH_3$; $R^3$ is H; and $R^4$ is H, or a pharmaceutically acceptable salt thereof.
97. The compound according to any one of the preceding items, wherein the compound is of Formula (IVa) and $X^1$ is N; $R^6$ is $CH_3$; $R^3$ is F; and $R^4$ is F, or a pharmaceutically acceptable salt thereof.
98. The compound according to any one of the preceding items, wherein the compound is of Formula (IVa) and $X^1$ is C(H); $R^6$ is $CH_3$; $R^3$ is F; and $R^4$ is F, or a pharmaceutically acceptable salt thereof.
99. The compound according to any one of the preceding items, wherein the compound is of Formula (IVa) and $X^1$ is N; $R^6$ is cyclopropyl; $R^3$ is $CH_3$; and $R^4$ is H, or a pharmaceutically acceptable salt thereof.
100. The compound according to any one of the preceding items, wherein the compound is of Formula (IVa) and $X^1$ is C(H); $R^6$ is cyclopropyl; $R^3$ is $CH_3$; and $R^4$ is H, or a pharmaceutically acceptable salt thereof.
101. The compound according to any one of the preceding items, wherein the compound is of Formula (IVa) and $X^1$ is N; $R^6$ is $CH_3$; $R^3$ is $CH_3$; and $R^4$ is H, or a pharmaceutically acceptable salt thereof.
102. The compound according to any one of the preceding items, wherein the compound is of Formula (IVb) and $X^1$ is N; $R^6$ is $CH_3$; $R^3$ is H; and $R^4$ is H, or a pharmaceutically acceptable salt thereof.
103. The compound according to any one of the preceding items, wherein the compound is of Formula (IVb) and $X^1$ is C(H); $R^6$ is $CH_3$; $R^3$ is H; and $R^4$ is H, or a pharmaceutically acceptable salt thereof.
104. The compound according to any one of the preceding items, wherein the compound is of Formula (IVb) and $X^1$ is N; $R^6$ is $CH_3$; $R^3$ is F; and $R^4$ is F, or a pharmaceutically acceptable salt thereof.
105. The compound according to any one of the preceding items, wherein the compound is of Formula (IVb) and $X^1$ is C(H); $R^6$ is $CH_3$; $R^3$ is F; and $R^4$ is F, or a pharmaceutically acceptable salt thereof.
106. The compound according to any one of the preceding items, wherein the compound is of Formula (IVb) and $X^1$ is N; $R^6$ is cyclopropyl; $R^3$ is H; and $R^4$ is $CH_3$, or a pharmaceutically acceptable salt thereof.
107. The compound according to any one of the preceding items, wherein the compound is of Formula (IVb) and $X^1$ is C(H); $R^6$ is cyclopropyl; $R^3$ is H; and $R^4$ is $CH_3$, or a pharmaceutically acceptable salt thereof.
108. The compound according to any one of the preceding items, wherein the compound is of Formula (IVb) and $X^1$ is N; $R^6$ is $CH_3$; $R^3$ is H; and $R^4$ is $CH_3$, or a pharmaceutically acceptable salt thereof.
109. The compound according to any one of the preceding items, wherein $R^3$ is $C_{1-3}$ alkanediyl, $R^4$ is $C_{1-3}$ alkanediyl, and $R^3$ and $R^4$ are linked together to form a ring, or a pharmaceutically acceptable salt thereof.
110. The compound according to any one of the preceding items, wherein $R^3$ is $-CH_2-$, $R^4$ is $-CH_2-$, and $R^3$ and $R^4$ are linked together to form a ring, or a pharmaceutically acceptable salt thereof.
111. The compound according to any one of the preceding items, wherein when $X^1$ is N, n is 2 and the two $R^5$ are C, alkanediyl, linked together to form a 3-membered ring, $R^2$ is

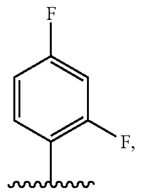

and $R^1$ is of Formula (II), then $R^6$ is not methyl,

112. The compound according to any one of the preceding items, with the proviso that when the compound is of Formula (VIII):

Formula (VIII)

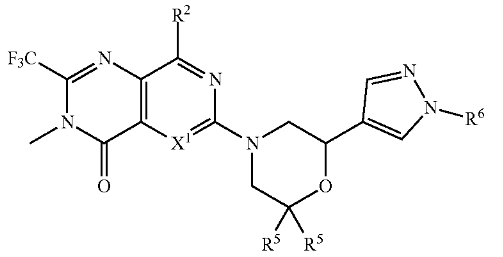

$X^1$ is N, $R^5$ is C, alkanediyl, and the two $R^5$ are linked together to form a 3-membered ring, $R^2$ is

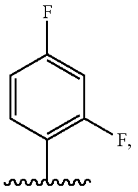

then $R^6$ is not methyl.

113. The compound according to any one of the preceding items, with the proviso that when the compound is of Formula (IX):

Formula (IX)

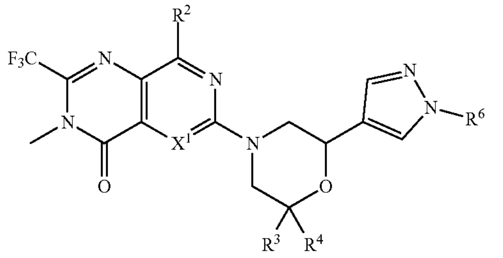

$X^1$ is N, $R^3$ and $R^4$ are C, alkanediyl, linked together to form a 3-membered ring, $R^2$ is

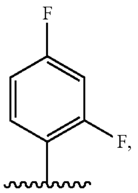

then $R^6$ is not methyl.

114. The compound according to any one of the preceding items, wherein the compound is not 8-(2,4-difluorophenyl)-3-methyl-6-(5-(1-methyl-1H-pyrazol-4-yl)-4-oxa-7-azaspiro[2.5]octan-7-yl)-2-(trifluoromethyl)pyrimido[5,4-d]pyrimidin-4(3H)-one, or a pharmaceutically acceptable salt thereof.

115. The compound according to any one of the preceding items, wherein the compound is not (R)-8-(2,4-difluorophenyl)-3-methyl-6-(5-(1-methyl-1H-pyrazol-4-yl)-4-oxa-7-azaspiro[2.5]octan-7-yl)-2-(trifluoromethyl)pyrimido[5,4-d]pyrimidin-4(3H)-one, or a pharmaceutically acceptable salt thereof.

116. The compound according to any one of the preceding items, wherein the compound is not (S)-8-(2,4-difluorophenyl)-3-methyl-6-(5-(1-methyl-1H-pyrazol-4-yl)-4-oxa-7-azaspiro[2.5]octan-7-yl)-2-(trifluoromethyl)pyrimido[5,4-d]pyrimidin-4(3H)-one, or a pharmaceutically acceptable salt thereof.

117. The compound according to any one of the preceding items, with the proviso that when n is 1, $R^5$ is $CH_3$, $R^2$ is

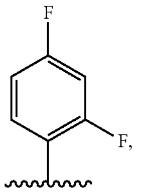

and $R^1$ is of Formula (II), then $R^6$ is not cyclopropyl.

118. The compound according to any one of the preceding items, with the proviso that when the compound is of Formula (VIII):

Formula (VIII)

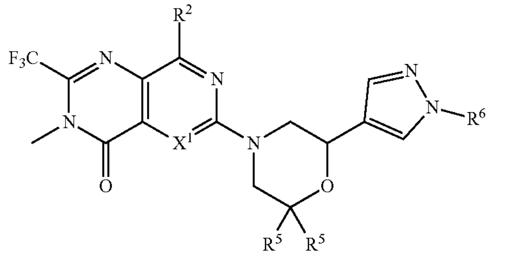

$X^1$ is N or C(H), one $R^5$ is H and the other $R^5$ is $CH_3$, $R^2$ is

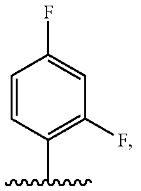

then $R^6$ is not cyclopropyl.

119. The compound according to any one of the preceding items, with the proviso that when the compound is of Formula (IX):

Formula (IX)

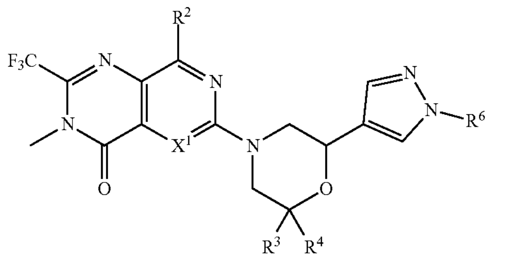

$X^1$ is N or C(H), $R^3$ is H, $R^4$ is $CH_3$, $R^2$ is

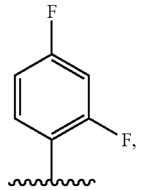

then $R^6$ is not cyclopropyl.

120. The compound according to any one of the preceding items, wherein when $X^1$ is C(H), n is 1, $R^5$ is $CH_3$, $R^2$ is

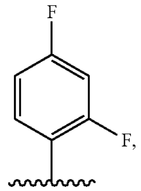

and $R^1$ is of Formula (II), then $R^6$ is not cyclopropyl.

121. The compound according to any one of the preceding items, with the proviso that when the compound is of Formula (VIII):

Formula (VIII)

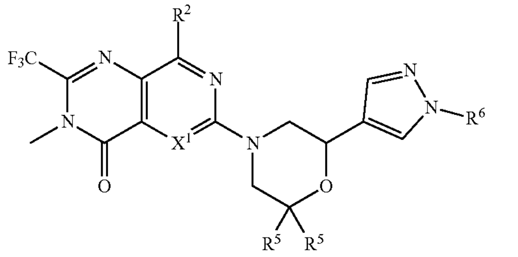

$X^1$ is C(H), one $R^5$ is H and the other $R^5$ is $CH_3$, $R^2$ is

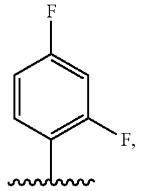

then $R^6$ is not cyclopropyl.

122. The compound according to any one of the preceding items, with the proviso that when the compound is of Formula (IX):

Formula (IX)

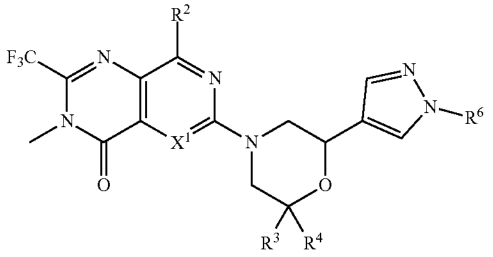

$X^1$ is C(H), $R^3$ is H, $R^4$ is $CH_3$, $R^2$ is

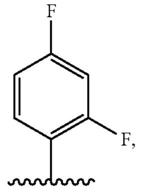

then $R^6$ is not cyclopropyl.

123. The compound according to any one of the preceding items, wherein the compound is not 6-(2-(1-cyclopropyl-1H-pyrazol-4-yl)-6-methylmorpholino)-8-(2,4-difluorophenyl)-3-methyl-2-(trifluoromethyl)pyrido[3,4-d]pyrimidin-4(3H)-one, or a pharmaceutically acceptable salt thereof.

124. The compound according to any one of the preceding items, wherein the compound is not not 6-((2R,6S)-2-(1-cyclopropyl-1H-pyrazol-4-yl)-6-methylmorpholino)-8-(2,4-difluorophenyl)-3-methyl-2-(trifluoromethyl)pyrido[3,4-d]pyrimidin-4(3H)-one, or a pharmaceutically acceptable salt thereof.

125. The compound according to any one of the preceding items, wherein the compound is not 6-((2S,6R)-2-(1-cyclopropyl-1H-pyrazol-4-yl)-6-methylmorpholino)-8-(2,4-difluorophenyl)-3-methyl-2-(trifluoromethyl) pyrido[3,4-d]pyrimidin-4(3H)-one, or a pharmaceutically acceptable salt thereof. 126. The compound according to any one of the preceding items, with the proviso that when $X^1$ is N, n is 1, $R^5$ is $CH_3$, $R^2$ is

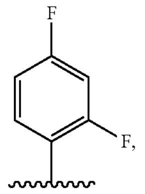

and $R^1$ is of Formula (II), then $R^6$ is not cyclopropyl.

127. The compound according to any one of the preceding items, with the proviso that when the compound is of Formula (VIII):

Formula (VIII)

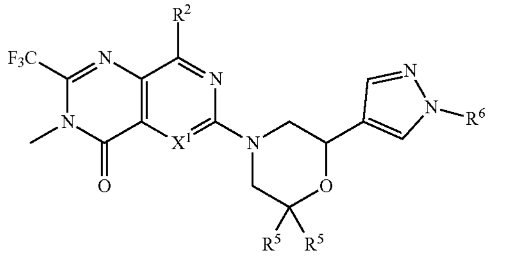

$X^1$ is N, one $R^5$ is H and the other $R^5$ is $CH_3$, $R^2$ is

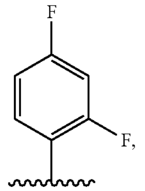

then $R^6$ is not cyclopropyl.

128. The compound according to any one of the preceding items, with the proviso that when the compound is of Formula (IX):

Formula (IX)

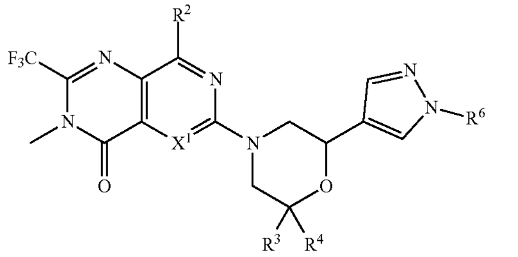

$X^1$ is N, $R^3$ is H, $R^4$ is $CH_3$, $R^2$ is

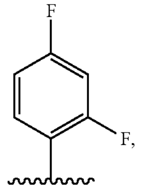

then $R^6$ is not cyclopropyl.

129. The compound according to any one of the preceding items, wherein the compound is not 6-[2-(1-cyclopropyl-1H-pyrazol-4-yl)-6-methyl-4-morpholinyl]-8-(2,4-difluorophenyl)-3-methyl-2-(trifluoromethyl)-pyrimido[5,4-d]pyrimidin-4(3H)-one, or a pharmaceutically acceptable salt thereof.

130. The compound according to any one of the preceding items, wherein the compound is not 6-[(2R,6S)-2-(1-cyclopropyl-1H-pyrazol-4-yl)-6-methyl-4-morpholinyl]-8-(2,4-difluorophenyl)-3-methyl-2-(trifluoromethyl)-pyrimido[5,4-d]pyrimidin-4(3H)-one, or a pharmaceutically acceptable salt thereof.

131. The compound according to any one of the preceding items, wherein the compound is not 6-[(2S,6R)-2-(1-cyclopropyl-1H-pyrazol-4-yl)-6-methyl-4-morpholinyl]-8-(2,4-difluorophenyl)-3-methyl-2-(trifluoromethyl)-pyrimido[5,4-d]pyrimidin-4(3H)-one, or a pharmaceutically acceptable salt thereof.

132. The compound according to item 1, wherein the compound is selected from the group consisting of:

3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile:

8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one;

4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile;

6-(2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one;

6-(3-((1-cyclopropyl-1H-pyrazol-4-yl)methyl)azetidin-1-yl)-8-(2,4-difluorophenyl)-3-methyl-2-(trifluoromethyl)pyrimido[5,4-d]pyrimidin-4(3H)-one;

3-fluoro-4-(7-methyl-2-(2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile;

4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile;

3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile;

3-fluoro-4-(2-(2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile;

4-(7-methyl-2-(2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile;

4-(2-(2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile;

8-(2,4-difluorophenyl)-6-(2-(2-methoxypyridin-4-yl)morpholino)-3-methyl-2-(trifluoromethyl)pyrimido[5,4-d]pyrimidin-4(3H)-one;

4-(6-(2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile;
4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile;
3-fluoro-4-(3-methyl-6-(2-(1-methyl-1H-pyrazol-4-yl)morpholino)-4-oxo-2-(trifluoromethyl)-3,4-dihydropyrido[3,4-d]pyrimidin-8-yl)benzonitrile,
or a pharmaceutically acceptable salt thereof.

133. The compound according to item 1, wherein the compound is selected from the group consisting of:
(S)-3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile;
(R)-3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile;
(S)-8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one;
(R)-8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one;
(S)-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile;
(R)-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile;
6-((2S,6R)-2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one;
6-((2R,6S)-2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one;
4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile;
4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile;
3-fluoro-4-(7-methyl-2-((2R,6S)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile;
3-fluoro-4-(7-methyl-2-((2S,6R)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile;
(S)-4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile;
(R)-4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile;
(S)-3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile;
(R)-3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile;
3-fluoro-4-(2-((2S,6R)-2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile;
3-fluoro-4-(2-((2R,6S)-2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile;
4-(7-methyl-2-((2R,6S)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile;
4-(7-methyl-2-((2S,6R)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile;
4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile;
4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile;
(S)-8-(2,4-difluorophenyl)-6-(2-(2-methoxypyridin-4-yl)morpholino)-3-methyl-2-(trifluoromethyl)pyrimido[5,4-d]pyrimidin-4(3H)-one;
(R)-8-(2,4-difluorophenyl)-6-(2-(2-methoxypyridin-4-yl)morpholino)-3-methyl-2-(trifluoromethyl)pyrimido[5,4-d]pyrimidin-4(3H)-one;
4-(6-((2R,6S)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile;
4-(6-((2S,6R)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile;
(S)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile;
(R)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile;
(S)-3-fluoro-4-(3-methyl-6-(2-(1-methyl-1H-pyrazol-4-yl)morpholino)-4-oxo-2-(trifluoromethyl)-3,4-dihydropyrido[3,4-d]pyrimidin-8-yl)benzonitrile;
(R)-3-fluoro-4-(3-methyl-6-(2-(1-methyl-1H-pyrazol-4-yl)morpholino)-4-oxo-2-(trifluoromethyl)-3,4-dihydropyrido[3,4-d]pyrimidin-8-yl)benzonitrile, or a pharmaceutically acceptable salt thereof.

134. The compound according to any one of the preceding items, or a pharmaceutically acceptable salt thereof, wherein the compound is a TREM2 modulator, such as a TREM2 activator, such as a TREM2 agonist.

135. The compound according to any one of the preceding items, or a pharmaceutically acceptable salt thereof, wherein the compound enhances or activates TREM2 signaling through DAP12; and/or wherein the compound induces phosphorylation of a kinase that interacts with the TREM2/DAP12 signaling complex, such as, but not limited to, Syk, ZAP70, PI3K, Erk, AKT and GSK3b; and/or wherein the compound enhances TREM2-induced phosphorylation levels of the Syk kinase.

136. The compound according to any one of the preceding items, or a pharmaceutically acceptable salt thereof, wherein the compound increases the expression of one or more TREM2 regulated genes, such as wherein the compound increases the expression of one or more TREM2 regulated genes selected from the group consisting of CXCL10, CCL2, CST7 and TMEM119.

137. A pharmaceutical composition comprising a compound according to any one of the preceding items, or a pharmaceutically acceptable salt thereof, and one or more pharmaceutically acceptable carriers, excipients and/or diluents.

138. The compound according to any one of items 1 to 136, or a pharmaceutically acceptable salt thereof, or the pharmaceutical composition according to item 137, for use as a medicament.

139. The compound according to any one of items 1 to 136, or a pharmaceutically acceptable salt thereof, or the pharmaceutical composition according to item 137, for use in the treatment of a condition associated with a loss of function of TREM2, such as for use in the treatment of a condition associated with a mutation of TREM2.

140. The compound according to any one of items 1 to 136, or a pharmaceutically acceptable salt thereof, or the pharmaceutical composition according to item 137, for use in the treatment of a neurodegenerative disease.

141. The compound according to any one of items 1 to 136, or a pharmaceutically acceptable salt thereof, or the pharmaceutical composition according to item 137, for use in in the treatment of neurodegenerative disease selected from the group consisting of a tauopathy, a TDP-43 proteinopathy, a synucleinopathy, dementia, amyloidosis, a demyelinating disorder of the CNS, a demyelinating disorder of the PNS, a Leukoencephalopathy, a leukodystrophy, a transmissible spongiform encephalopathy (TSE) and a lysosomal storage disorder (LSD).

142. The compound according to any one of items 1 to 136, or a pharmaceutically acceptable salt thereof, or the pharmaceutical composition according to item 137, for use in the treatment of a neurodegenerative disease selected from the group consisting of Alzheimer's disease, Frontotemporal lobar degeneration (FTLD), frontotemporal dementia (FTD), Parkinson's disease, Nasu-Hakola disease, FTLD-like syndrome, Huntington disease, Amyotrophic lateral sclerosis, multiple sclerosis, Guillain-Barre syndrome, chronic inflammatory demyelinating polyneuropathies, Charcot-Marie-Tooth disease, prion disease and stroke.

143. The compound according to any one of items 1 to 136, or a pharmaceutically acceptable salt thereof, or the pharmaceutical composition according to item 137, for use in the treatment of a disease selected from the group consisting of arthritis, rheumatoid arthritis, pyle disease, osteoporosis, osteopetrosis, osteosclerosis, skeletal dysplasia, dysosteoplasia, autism spectrum disorders, autism and Aspergers syndrome, traumatic brain injuries (TBI), spinal cord injuries, muscular dystrophy, myotonic dystrophy, inclusion-body myositis, systemic lupus erythematosus (SLE), RA, gout, bowel conditions, Inflammatory bowel disease (IBD), metabolic syndrome, obesity, type 2 diabetes, atherosclerosis, alcoholic and non-alcoholic fatty liver disease, alcoholic and non-alcoholic steatohepatitis, Amyloidosis.

144. The compound according to any one of items 1 to 136, or a pharmaceutically acceptable salt thereof, or the pharmaceutical composition according to item 137, for use according to any one of items 138 to 144, wherein said compound is administered in an amount of about 0.01 mg/kg to about 100 mg/kg bodyweight/day.

145. The compound according to any one of items 1 to 136, or a pharmaceutically acceptable salt thereof, or the pharmaceutical composition according to item 137, for use according to any one of items 138 to 144, wherein said compound is administered via enteral delivery, oral delivery, topical delivery, parenteral delivery, intravenous delivery, intradermal delivery, intramuscular delivery, intrathecal delivery, colonic delivery, rectal delivery, or intraperitoneal delivery.

146. A method for treatment of a condition associated with a loss of function of TREM2, such as a neurodegenerative disease, said method comprising administering a therapeutically effective amount of a compound according to any one of items 1 to 136, or a pharmaceutically acceptable salt thereof, or the pharmaceutical composition according to item 137, to a subject in need thereof.

147. Use of a compound according to any one of items 1 to 136, or a pharmaceutically acceptable salt thereof, or the pharmaceutical composition according to item 137, for the manufacture of a medicament for the treatment of a condition associated with a loss of function of TREM2, such as a neurodegenerative disease.

148. A method of enhancing or increasing TREM2 activity, such as a method of one or more of i) enhancing or activating TREM2 signaling through DAP12, ii) inducing phosphorylation of a kinase that interacts with the TREM2/DAP12 signaling complex, such as, but not limited to, Syk, ZAP70, PI3K, Erk, AKT and GSK3b, iii) enhancing TREM2-induced phosphorylation levels of the Syk kinase, Iv) increasing the expression levels, such as brain expression levels, of one or more TREM2 regulated genes, and/or v) increasing the expression levels, such as brain expression levels, of one or more TREM2 regulated genes selected from the group consisting of CXCL10, CCL2, CST7 and TMEM119; in a subject in need thereof, such as in a subject having a neurodegenerative disease, said method comprising administering to the subject a compound, or a pharmaceutically acceptable salt thereof, according to any one of items 1 to 136.

149. A compound of Formula (I):

Formula (I)

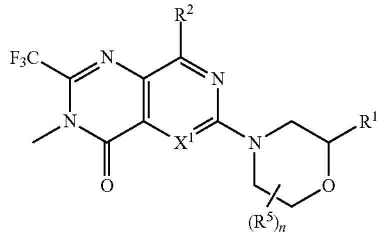

wherein $X^1$ is N or C(H);

$R^1$ is of Formula (II):

Formula (II)

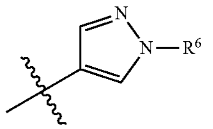

wherein $R^6$ is $C_{1-3}$ alkyl or cyclopropyl;

or

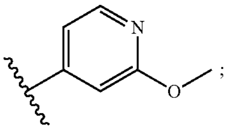 [SMILES: *c1ccnc(OC)c1]

$R^2$ is selected from the group consisting of:

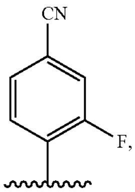

,

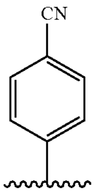

,

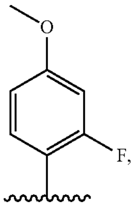

and

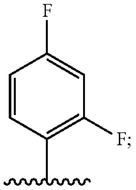 [SMILES: *c1ccc(F)cc1F]

$R^5$ is individually selected from the group consisting of H, F and $C_{1-3}$ alkyl; and n is 0, 1 or 2;

or n is 2 and $R^5$ is $C_{1-3}$ alkanediyl, and the two $R^5$ are linked together to form a 3- to 6-membered ring, with the proviso that when the compound is of Formula (VIII):

Formula (VIII)

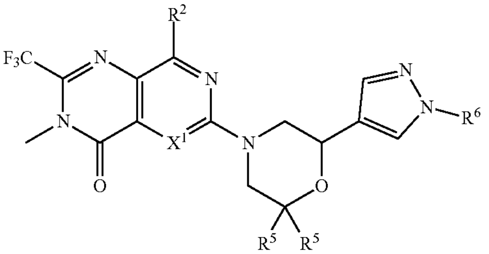

and $X^1$ is N, $R^5$ is C, alkanediyl and the two $R^5$ are linked together to form a 3-membered ring, $R^2$ is

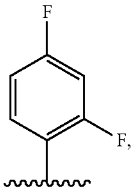

then $R^6$ is not methyl; and with the proviso that when the compound is of Formula (VIII) and $X^1$ is C(H) or N, $R^3$ is H, $R^4$ is $CH_3$, $R^2$ is

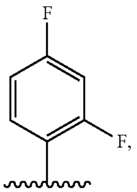

then $R^6$ is not cyclopropyl, or a pharmaceutically acceptable salt thereof.

150. A compound selected from:

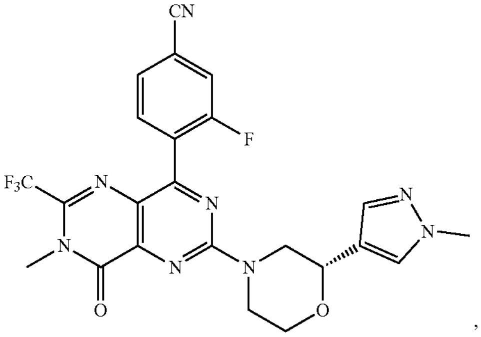 [SMILES: Cn1cc([C@H]2CN(c3nc(-c4ccc(C#N)cc4F)c4nc(C(F)(F)F)n(C)c(=O)c4n3)CCO2)cn1]

,

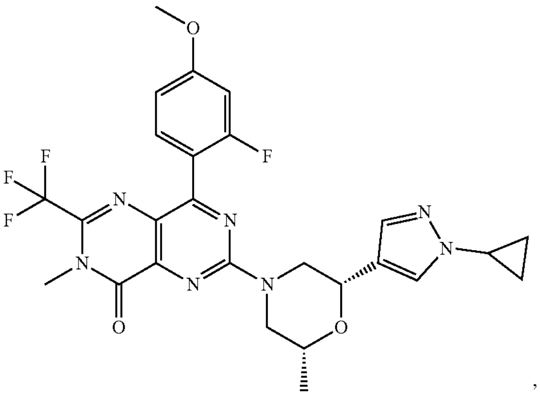

,

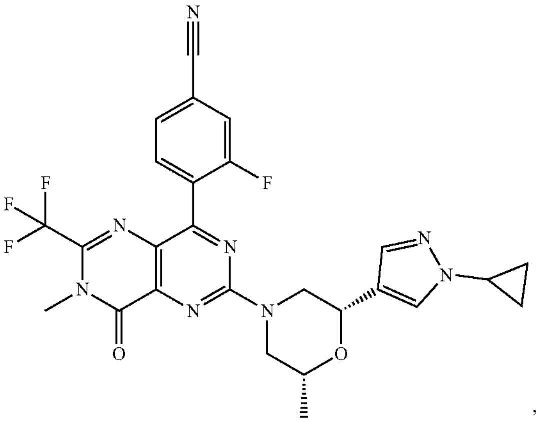

,

-continued
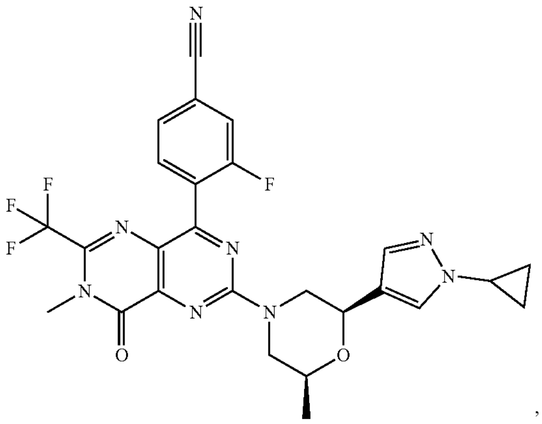
,
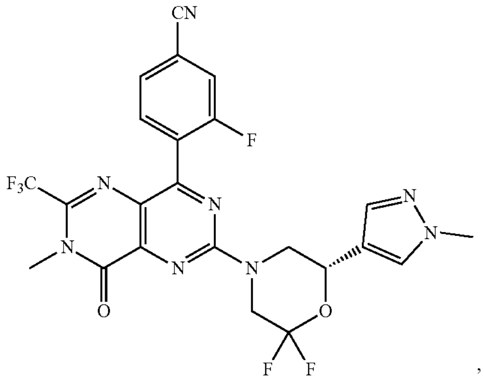
,
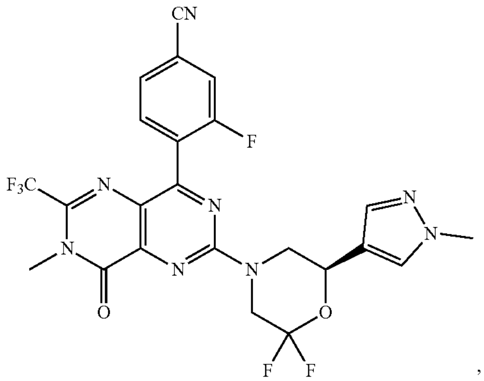
,
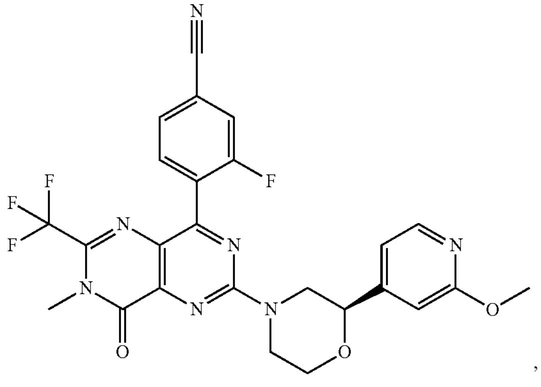
,
-continued
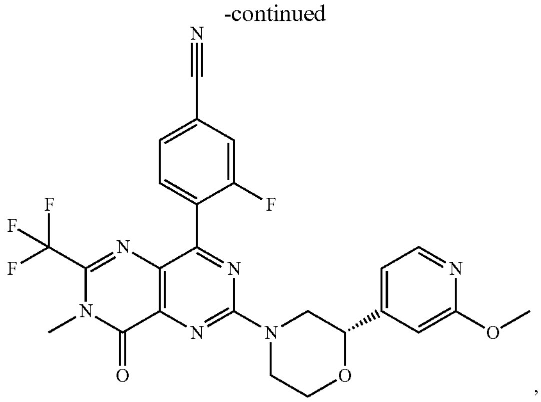
,
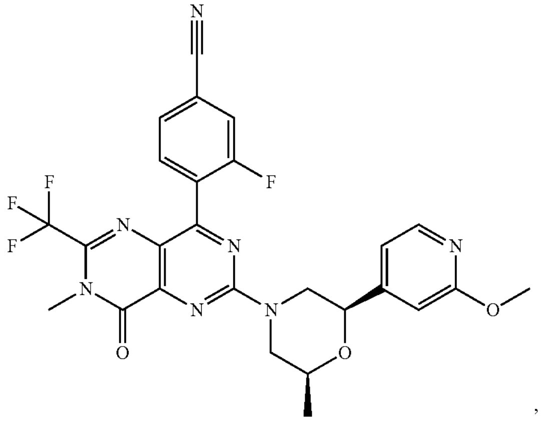
,
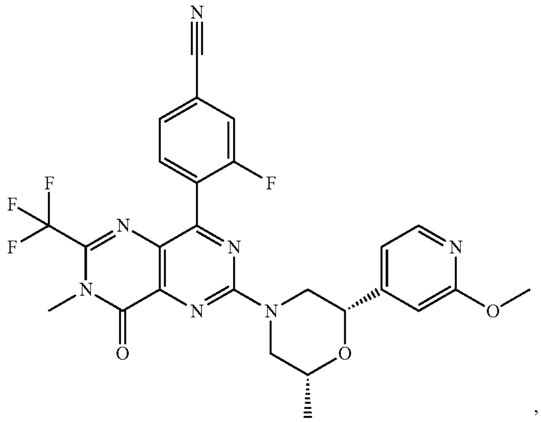
,
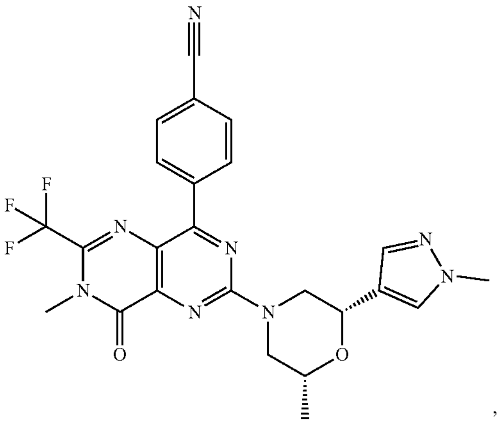
, -continued
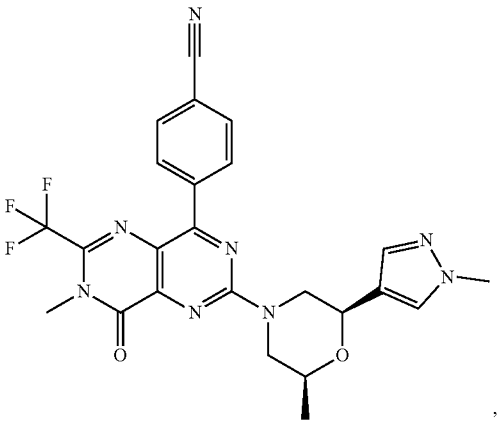
,
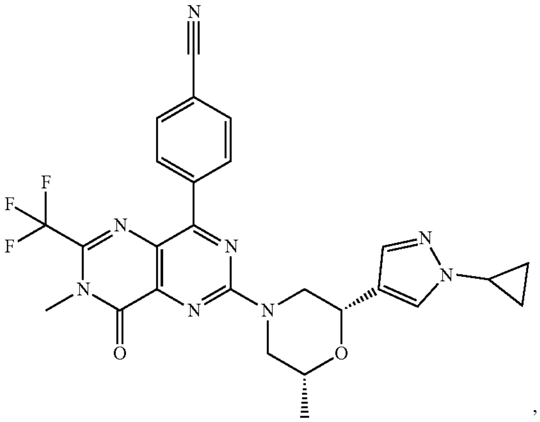
,
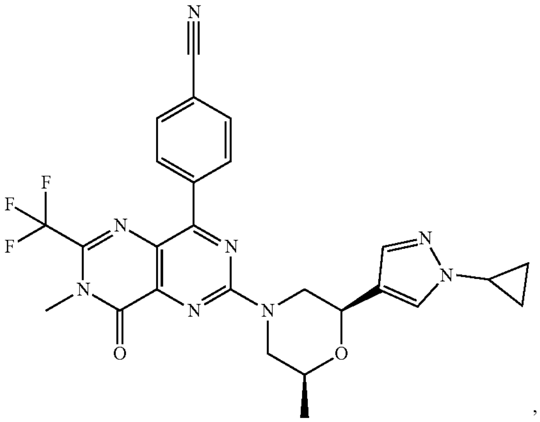
,
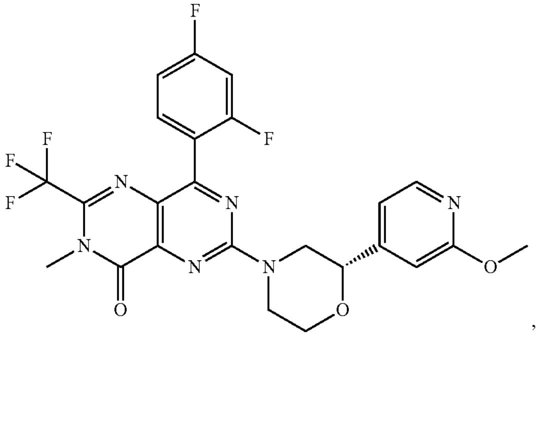
,
-continued
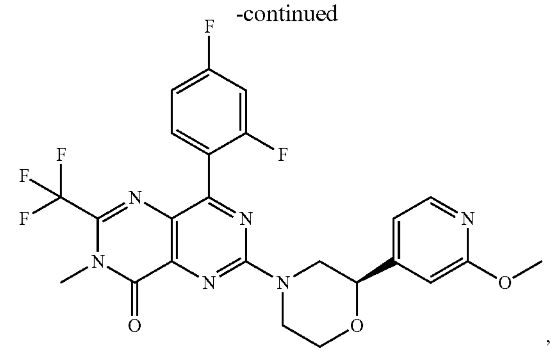
,
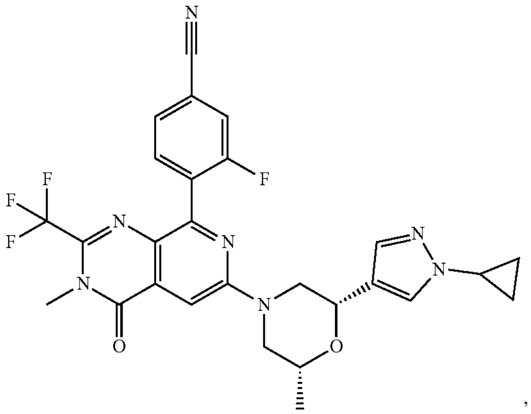
, and
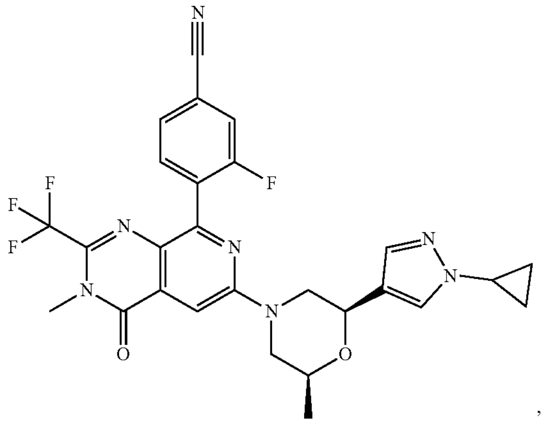
,
or a pharmaceutically acceptable salt thereof.
151. A pharmaceutical composition comprising a compound of item 150, or a pharmaceutically acceptable salt thereof, and one or more pharmaceutically acceptable carriers, excipients and/or diluents.
152. The compound of item 150, wherein the compound is:

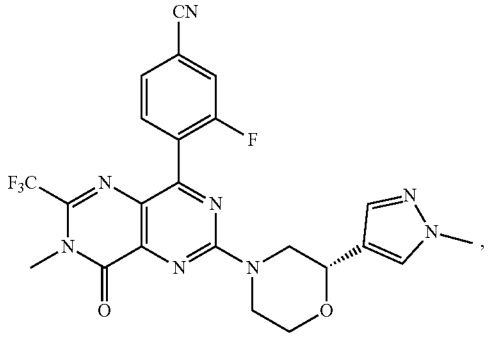

or a pharmaceutically acceptable salt thereof.

153. A pharmaceutical composition comprising a compound of item 152, or a pharmaceutically acceptable salt thereof, and one or more pharmaceutically acceptable carriers, excipients and/or diluents.

154. The compound of item 150, wherein the compound is:

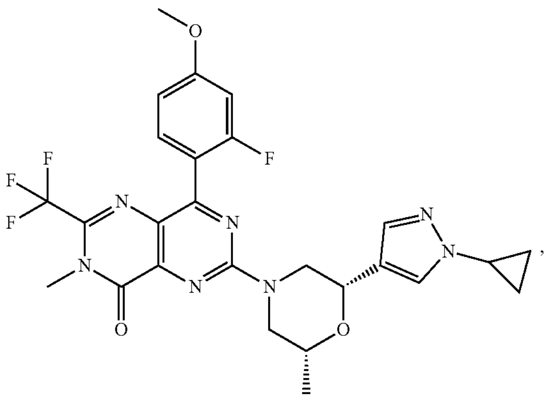 [SMILES: COc1ccc(-c2nc(N3C[C@@H](C)O[C@@H](c4cnn(C5CC5)c4)C3)nc3c(=O)n(C)c(C(F)(F)F)nc23)c(F)c1]

or a pharmaceutically acceptable salt thereof.

155. A pharmaceutical composition comprising a compound of item 154, or a pharmaceutically acceptable salt thereof, and one or more pharmaceutically acceptable carriers, excipients and/or diluents.

156. The compound of item 150, wherein the compound is:

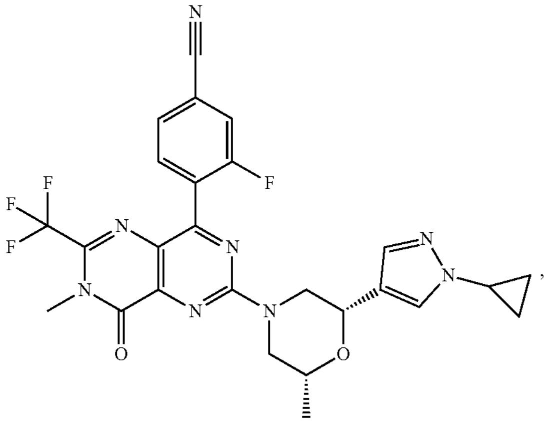

or a pharmaceutically acceptable salt thereof.

157. A pharmaceutical composition comprising a compound of item 156, or a pharmaceutically acceptable salt thereof, and one or more pharmaceutically acceptable carriers, excipients and/or diluents.

158. The compound of item 150, wherein the compound is:

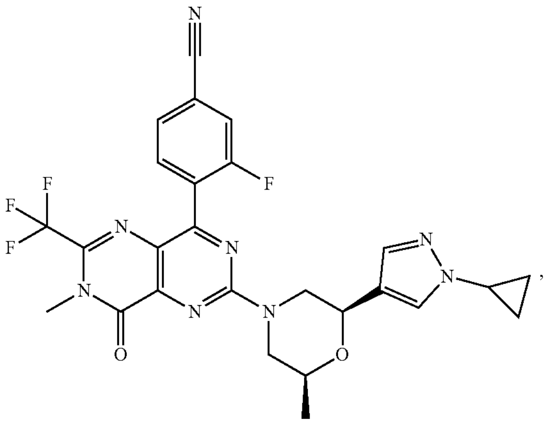

or a pharmaceutically acceptable salt thereof.

159. A pharmaceutical composition comprising a compound of item 158, or a pharmaceutically acceptable salt thereof, and one or more pharmaceutically acceptable carriers, excipients and/or diluents.

160. The compound of item 150, wherein the compound is:

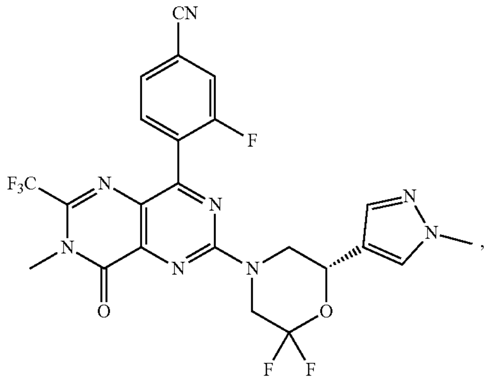 [SMILES: Cn1cc([C@H]2CN(c3nc(-c4ccc(C#N)cc4F)c4nc(C(F)(F)F)n(C)c(=O)c4n3)CC(F)(F)O2)cn1]

or a pharmaceutically acceptable salt thereof.

161. A pharmaceutical composition comprising a compound of item 160, or a pharmaceutically acceptable salt thereof, and one or more pharmaceutically acceptable carriers, excipients and/or diluents.

162. The compound of item 150, wherein the compound is:

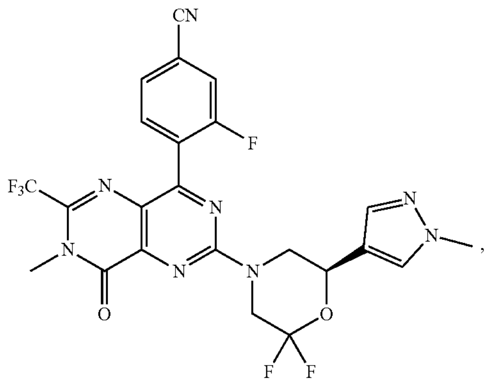 [SMILES: Cn1cc([C@@H]2CN(c3nc(-c4ccc(C#N)cc4F)c4nc(C(F)(F)F)n(C)c(=O)c4n3)CC(F)(F)O2)cn1]

or a pharmaceutically acceptable salt thereof.

163. A pharmaceutical composition comprising a compound of item 162, or a pharmaceutically acceptable salt thereof, and one or more pharmaceutically acceptable carriers, excipients and/or diluents.

164. The compound of item 150, wherein the compound is:

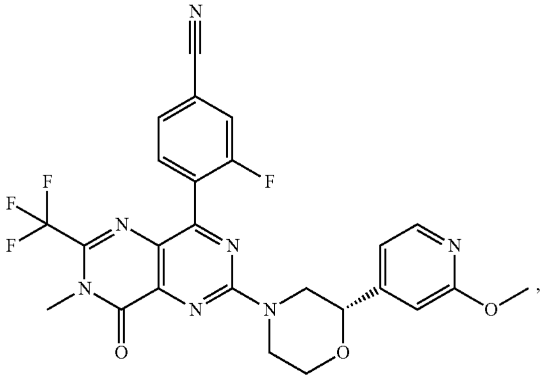 [SMILES: COc1cc([C@H]2CN(c3nc(-c4ccc(C#N)cc4F)c4nc(C(F)(F)F)n(C)c(=O)c4n3)CCO2)ccn1]

or a pharmaceutically acceptable salt thereof.

165. A pharmaceutical composition comprising a compound of item 164, or a pharmaceutically acceptable salt thereof, and one or more pharmaceutically acceptable carriers, excipients and/or diluents.

166. The compound of item 150, wherein the compound is:

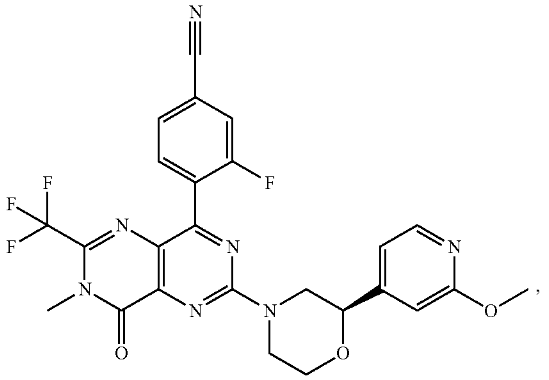 [SMILES: COc1cc([C@@H]2CN(c3nc(-c4ccc(C#N)cc4F)c4nc(C(F)(F)F)n(C)c(=O)c4n3)CCO2)ccn1]

or a pharmaceutically acceptable salt thereof.

167. A pharmaceutical composition comprising a compound of item 166, or a pharmaceutically acceptable salt thereof, and one or more pharmaceutically acceptable carriers, excipients and/or diluents.

168. The compound of item 150, wherein the compound is:

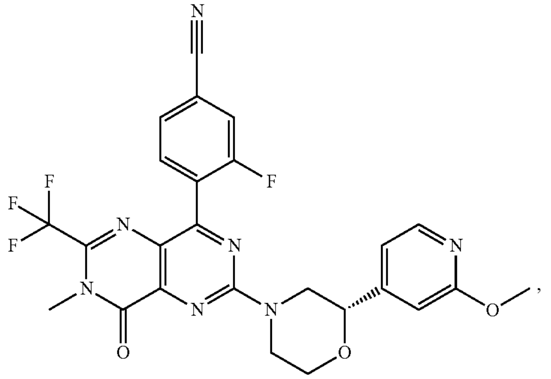 [SMILES: COc1cc([C@H]2CN(c3nc(-c4ccc(C#N)cc4F)c4nc(C(F)(F)F)n(C)c(=O)c4n3)CCO2)ccn1]

or a pharmaceutically acceptable salt thereof.

169. A pharmaceutical composition comprising a compound of item 168, or a pharmaceutically acceptable salt thereof, and one or more pharmaceutically acceptable carriers, excipients and/or diluents.

170. The compound of item 150, wherein the compound is:

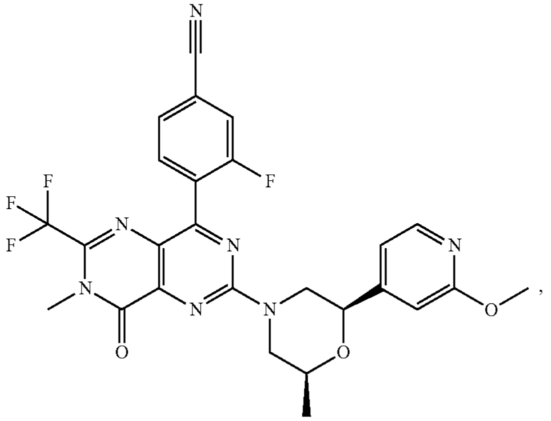

or a pharmaceutically acceptable salt thereof.

171. A pharmaceutical composition comprising a compound of item 170, or a pharmaceutically acceptable salt thereof, and one or more pharmaceutically acceptable carriers, excipients and/or diluents.

172. The compound of item 150, wherein the compound is:

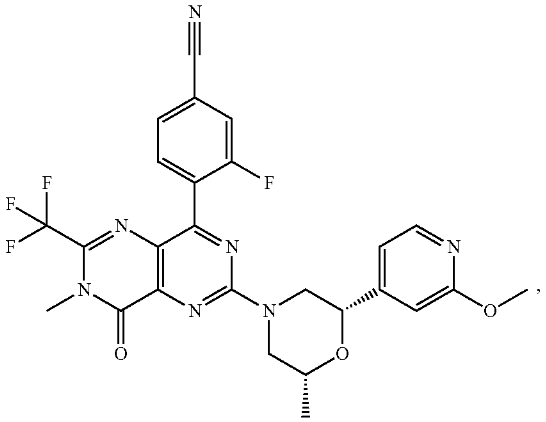 [SMILES: COc1cc([C@H]2CN(c3nc(-c4ccc(C#N)cc4F)c4nc(C(F)(F)F)n(C)c(=O)c4n3)C[C@@H](C)O2)ccn1]

or a pharmaceutically acceptable salt thereof.

173. A pharmaceutical composition comprising a compound of item 172, or a pharmaceutically acceptable salt thereof, and one or more pharmaceutically acceptable carriers, excipients and/or diluents.

174. The compound of item 150, wherein the compound is:

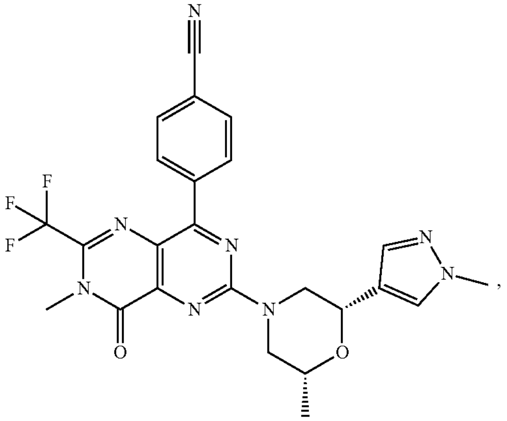 [SMILES: C[C@@H]1CN(c2nc(-c3ccc(C#N)cc3)c3nc(C(F)(F)F)n(C)c(=O)c3n2)C[C@H](c2cnn(C)c2)O1]

or a pharmaceutically acceptable salt thereof.

175. A pharmaceutical composition comprising a compound of item 174, or a pharmaceutically acceptable salt thereof, and one or more pharmaceutically acceptable carriers, excipients and/or diluents.

176. The compound of item 150, wherein the compound is:

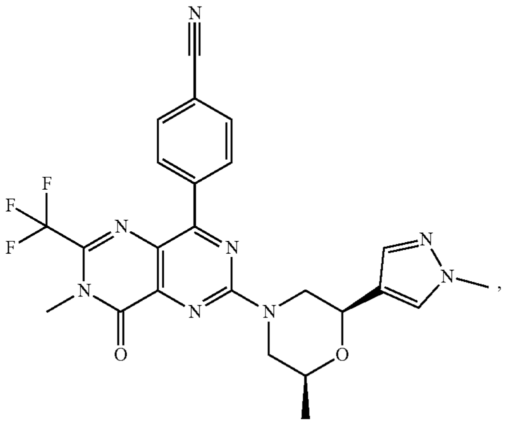 [SMILES: C[C@H]1CN(c2nc(-c3ccc(C#N)cc3)c3nc(C(F)(F)F)n(C)c(=O)c3n2)C[C@@H](c2cnn(C)c2)O1]

or a pharmaceutically acceptable salt thereof.

177. A pharmaceutical composition comprising a compound of item 176, or a pharmaceutically acceptable salt thereof, and one or more pharmaceutically acceptable carriers, excipients and/or diluents.

178. The compound of item 150, wherein the compound is:

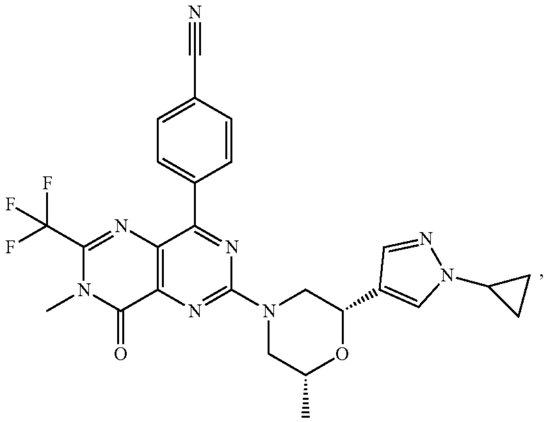

or a pharmaceutically acceptable salt thereof.

179. A pharmaceutical composition comprising a compound of item 178, or a pharmaceutically acceptable salt thereof, and one or more pharmaceutically acceptable carriers, excipients and/or diluents.

180. The compound of item 150, wherein the compound is:

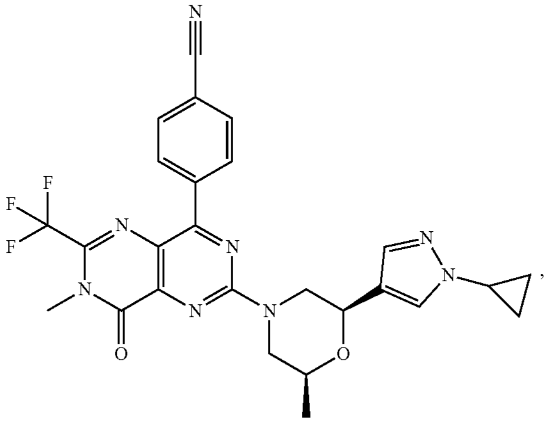

or a pharmaceutically acceptable salt thereof.

181. A pharmaceutical composition comprising a compound of item 180, or a pharmaceutically acceptable salt thereof, and one or more pharmaceutically acceptable carriers, excipients and/or diluents.

182. The compound of item 150, wherein the compound is:

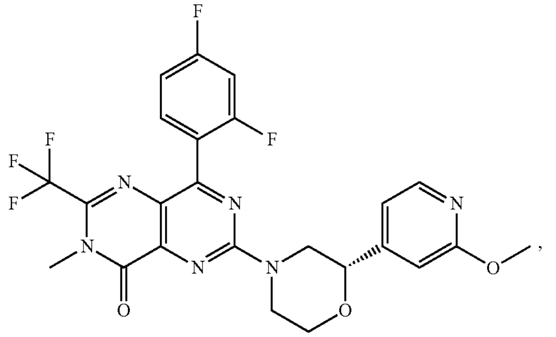 [SMILES: COc1cc([C@H]2CN(c3nc(-c4ccc(F)cc4F)c4nc(C(F)(F)F)n(C)c(=O)c4n3)CCO2)ccn1]

or a pharmaceutically acceptable salt thereof.

183. A pharmaceutical composition comprising a compound of item 182, or a pharmaceutically acceptable salt thereof, and one or more pharmaceutically acceptable carriers, excipients and/or diluents.

184. The compound of item 150, wherein the compound is:

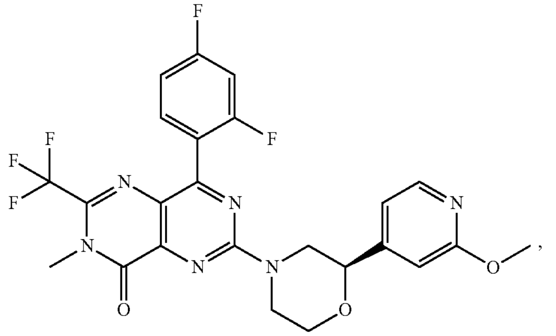 [SMILES: COc1cc([C@@H]2CN(c3nc(-c4ccc(F)cc4F)c4nc(C(F)(F)F)n(C)c(=O)c4n3)CCO2)ccn1]

or a pharmaceutically acceptable salt thereof.

185. A pharmaceutical composition comprising a compound of item 184, or a pharmaceutically acceptable salt thereof, and one or more pharmaceutically acceptable carriers, excipients and/or diluents.

186. The compound of item 150, wherein the compound is:

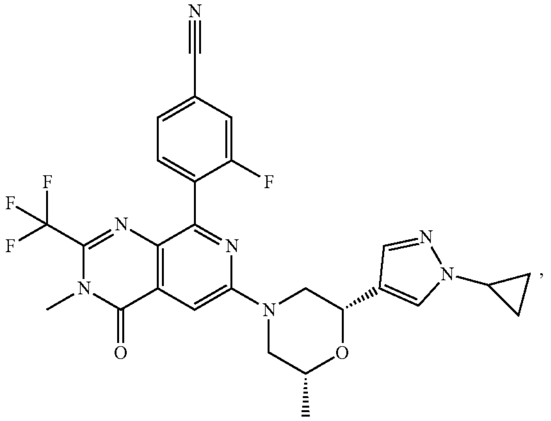

or a pharmaceutically acceptable salt thereof.

187. A pharmaceutical composition comprising a compound of item 186, or a pharmaceutically acceptable salt thereof, and one or more pharmaceutically acceptable carriers, excipients and/or diluents.

188. The compound of item 150, wherein the compound is:

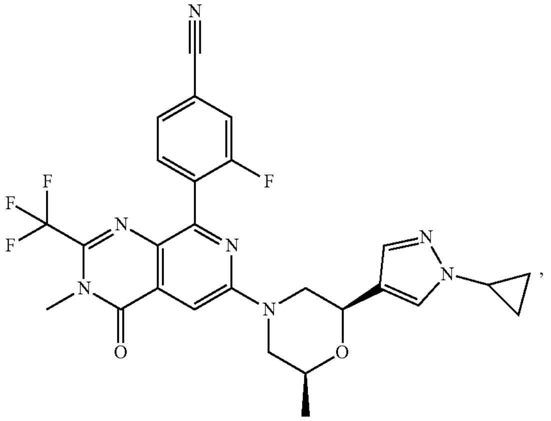

or a pharmaceutically acceptable salt thereof.

189. A pharmaceutical composition comprising a compound of item 188, or a pharmaceutically acceptable salt thereof, and one or more pharmaceutically acceptable carriers, excipients and/or diluents.

190. A method of treating a condition associated with a loss of function of TREM2 comprising administering to a subject a therapeutically effective amount of a compound of item 150, or a pharmaceutically acceptable salt thereof.

191. The method of item 190, wherein the condition is a neurodegenerative disease.

192. The method of item 191, wherein the neurodegenerative disease is Frontotemporal lobar degeneration (FTLD), frontotemporal dementia (FTD), Parkinson's disease, Nasu-Hakola disease, FTLD-like syndrome, Huntington disease, Amyotrophic lateral sclerosis, multiple sclerosis, Guillain-Barre syndrome, chronic inflammatory demyelinating polyneuropathies, Charcot-Marie-Tooth disease, prion disease, stroke, and traumatic brain injuries (TBI).

193. The method of item 191, wherein the neurodegenerative disease is Alzheimer's Disease.

EXAMPLES

Certain compounds of the Examples were obtained as a mixture of stereoisomers and were subsequently separated by chiral prep HPLC. In some of the Examples, the assignment of stereochemistry is arbitrary (noted in these Examples). Thus, in said Examples, the stereochemistry of the compounds obtained after the chiral prep HPLC are annotated based on the order. For example, in Example 5, two stereoisomers are obtained. These are annotated "5A", which is peak 1, and "5B", which is peak 2. The structure has been arbitrarily assigned to 4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile for 5A and (4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile for 5B. However, since the assignment of stereochemistry is arbitrary, it is possible that the stereochemistry is different. Importantly, the numbering (for example 5A for peak 1 in Example 5) is maintained in the biological evaluation.

Abbreviations

DCM Dichloromethane
HPLC High performance liquid chromatography
MeOH Methanol
THF: Tetrahydrofuran
DMF: N,N-dimethylformamide
TFA: Trifluoroacetic Acid
DIPEA N,N-Diisopropylethylamine
EtOAc Ethyl acetate
NBS N-bromo succinimide
$NH_4OAc$ Ammonium acetate
DMAP 4-Dimethylaminopyridine
$Me_2NH_2$, HCl Methylamine hydrochloride
HATU 1-[Bis(dimethylamino)methylene]-1H-1,2,3-triazolo[4,5-b]pyridinium 3-oxid hexafluorophosphate
rt: room temperature
LCMS Liquid chromatography-mass spectrometry
NMR: Nuclear magnetic resonance
° C. Degree Celsius
mg milligrams
g gram(s)
Rt Retention time
h Hour
mmol millimole
mL millilitre
aq. Aqueous
m/z mass divided by charge
MS Mass spectra
n-BuLi n-butyllithium
sat. saturated
eq. equivalent
min. minutes
mm millimeter
SM Starting material
TMSOTf Trimethylsilyl trifluoromethanesulfonate
DCE Dichloroethane
LAH Lithium aluminum Hydride
SFC Supercritical fluid chromatography
NP Normal Phase
Bn Benzyl

LCMS conditions

Condition A

LCMS Column-Acquity BEH C18 (50×2.1 mm, 1.7u), Initially (90% [0.05% HCOOH in water]and 10% [0.05% HCOOH in $CH_3CN$: water (90:10)]is held up to 0.75 min, then to 50% [0.05% HCOOH in water]and 50% [0.05% HCOOH in $CH_3CN$: water (90:10)]in 1.00 min, then to 2% [0.05% HCOOH in water]and 98% [0.05% HCOOH in $CH_3CN$: water (90:10)]in 2.00 min held this mobile phase composition up to 2.25 min and finally back to initial condition in 2.60 min and held up to 3.00 min). Flow: 0.60 ml/min.

Condition B

Column-Xbridge C18 (4.6×50 mm, 5 u) mobile phase: 90% [10 mM Ammonium Acetate in Water]and 10% [$CH_3CN$]to 70% [10 mM Ammonium Acetate in Water]and 30% [$CH_3CN$]in 1.5 min, further to 10% [10 mM Ammonium Acetate in Water]and 90% [$CH_3CN$]in 3.00 min, held this mobile phase composition up to 4.00 min and finally back to initial condition in 5.00 min. Flow=1.20 ml/min

Condition C

LCMS Column-Acquity BEH C8 (50×2.1 mm, 1.7u), Initially (95% [0.05% HCOOH in water]and 5% [0.05% HCOOH in CH3CN: water (90:10)]is held up to 0.75 min, then to 75% [0.05% HCOOH in water]and 25% [0.05% HCOOH in CH3CN: water (90:10)]in 1.50 min, then to 5% [0.05% HCOOH in water]and 95% [0.05% HCOOH in CH3CN: water (90:10)]in 3.00 min held this mobile phase composition up to 4.00 min and finally back to initial condition in 4.50 min and held up to 5.10 min). Flow: 0.80 ml/min.

Condition D

Column-Xbridge C18 column (3.5 µm, 50×3 mm), (initially 95% [5 mM NH4OAc in water]and 5% [5 mM NH4OAc in ACN: Water (90:10)]held for 0.75 min, then to 70% [5 mM NH4OAc in water]and 30% [5 mM NH4OAc in ACN: Water (90:10)]in 1.00 min, and finally 2% [5 mM NH4OAc in water]and 98% [5 mM NH4OAc in ACN: Water (90:10)]in 2.00 min, held this mobile phase composition up to 2.50 min and finally back to initial condition in 2.75 min and held this composition up to 3.0 min). Flow: 1.20 ml/min.

Condition E

Column-YMC Triart C18 (33×2.1 mm, 3u), (initially 98% [0.05% HCOOH in water]and 2% [0.05% HCOOH in ACN: Water (90:10)]held for 0.75 min, then to 90% [0.05% HCOOH in water]and 10% [0.05% HCOOH in ACN: Water (90:10)]in 1.0 min, further to 2% [0.05% HCOOH in water] and 98% [0.05% HCOOH in ACN: Water (90:10)]in 2.00 min, held this mobile phase composition up to 2.50 min and finally back to initial condition in 4.90 min and held this composition up to 3.0 min). Flow: 1.0 ml/min.

Reverse Phase Prep-Purification method

Prep-A

Preparative HPLC was done on Waters auto purification instrument. Column name: LONG-YMC, C18(20×250 mm), 5 μm operating at ambient temperature and flow rate of 16 mL/min. Mobile phase: A=Acetonitrile, B=10 mM Ammonium Acetate in water; Gradient Profile: Mobile phase initial composition of 30% A and 70% B, then 45% A and 55% B in 3 min, then to 78% A and 22% B in 18 min., then to 100% A and 0% B in 19 min., held this composition up to 21.5 min. for column washing, then returned to initial composition in 22 min. and held till 24 min.

Prep-B

Preparative HPLC was done on Waters auto purification instrument. Column name: YMC-Actus C18 (250×20 mm, 5p) operating at ambient temperature and flow rate of 16 mL/min. Mobile phase: A=20Mm Ammonium bicarbonate in water, B=Acetonitrile; Gradient Profile: Mobile phase initial composition of 60% A and 40% B, then 40% A and 60% B in 3 min, then to 20% A and 80% B in 20 min., then to 5% A and 95% B in 21 min., held this composition up to 22 min. for column washing, then returned to initial composition in 23 min. and held till 25 min.

Chiral Separation method

SFC method-1: Chiral separation was done by running sample in Waters Thar SFC-80 instrument equipped with UV Detector 40D by using CHIRALPAK-IG (30.0 mm×250 mm), 5p Column operating at 35° C. temperature, maintaining flow rate of 70 ml/min, using 60% CO2 in super critical state & 40% of (100% MeOH) as Mobile phase, run this isocratic mixture upto 10.0 minutes and also maintained the isobaric condition of 110 bar at 220 nm wavelength.

SFC method-2

Purification of sample was carried out on PIC SOLUTIONS-175 instrument equipped with Knauer 40D Detector by using Chiralpak IG (30.0 mm×250 mm), 5μ Column operating at 35° C. temperature, maintaining flow rate of 100 ml/min, using 60% CO2 in super critical state & 40% of 100% MeOH as Mobile phase. Run this isocratic mixture up to 15.0 minutes and maintained the isobaric condition of 100 bar at 230 nm wavelength.

Normal Phase Chiral Prep Methods

NP Chiral Method-1

Chiral separation was done on Agilent 1200 series instrument. Column name: CHIRALPAK IG (250×30 mm) 5p. Operating at ambient temperature and flow rate is 27.0 mL/min. Mobile phase was mixture of 70% Hexane, 15% DCM, 15% EtOH, held this isocratic mixture run up to 30 min with wavelength of 318 nm.

NP Chiral Method-2

Chiral separation was done on Agilent 1200 series instrument. Column name: CHIRALPAK IC (250×20 mm) 5p. Operating at ambient temperature and flow rate is 18.0 mL/min. Mobile phase was mixture of 80% Hexane, 10% DCM and 10% EtOH held this isocratic mixture run up to 22 min with wavelength of 316 nm.

Synthesis of 2-(1-methyl-1H-pyrazol-4-yl)morpholine (as HCl salt): (Intermediate I-1)

Step-1

Preparation of 2-chloro-1-(1-methyl-1H-pyrazol-4-yl)ethan-1-one

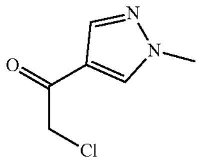

To a stirred solution of 4-bromo-1-methyl-1H-pyrazole (10 g, 62.22 mmol) in dry THF (100 mL) at −78° C. was added n-BuLi (40 mL, 93.22 mmol; 2.3 M in hexane) slowly under argon atmosphere and reaction was continued for at −78° C. for 1 h. A solution of 2-chloro-N-methoxy-N-methylacetamide (13 g, 93.2 mmol) in THF (40 mL) was added to the reaction mixture dropwise and it was continued for further at same temperature for 1 h.

After completion, reaction mixture was quenched with saturated aqueous ammonium chloride solution at −78° C. and extracted with ethyl acetate. Combined organic layer was dried over $Na_2SO_4$ and concentrated into vacuo. The crude product was triturated with ether-pentane mixture to afford 2-chloro-1-(1-methyl-1H-pyrazol-4-yl)ethan-1-one (3.5 g, 35.5% yield) as off-white solid.

1H NMR (400 MHz, DMSO D6) δ 8.46 (s, 1H), 7.99 (s, 1H), 4.81 (s, 2H), 3.88 (s, 3H).

LCMS Condition A: Rt=1.48 min. m/z 159.02 [M+H]P.

Step-2

Preparation of 2-(benzyl(2-hydroxyethyl)amino)-1-(1-methyl-1H-pyrazol-4-yl)ethan-1-one

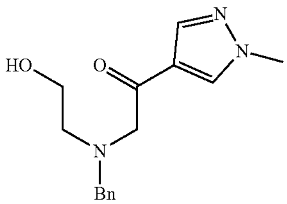 [SMILES: Cn1cc(C(=O)CN(CCO)Cc2ccccc2)cn1]

To a stirred solution of 2-chloro-1-(1-methyl-1H-pyrazol-4-yl)ethan-1-one (5.0 g, 31.6 mmol) in acetonitrile (50 mL) was added 2-(benzylamino)ethen-1-ol (5.75 g, 38.3 mmol) and potassium carbonate (8.8 g, 63.2) and heated the reaction mixture at 60° C. for 16 h. After completion excess solvent was removed under reduced pressure and the residue was diluted with cold water and followed by extracted with ethyl acetate. Combined organic layer was dried over sodium sulphate and concentrated under reduced pressure.

The crude was purified by column chromatography (silica gel; 40-60% ethyl acetate-hexane) to afford 2-(benzyl(2-hydroxyethyl)amino)-1-(1-methyl-1H-pyrazol-4-yl)ethan-1-one (6 g, 69.5% yield) as yellow oil.

1H NMR (400 MHz, DMSO D6) δ 8.38 (s, 1H), 7.92 (s, 1H), 7.56-7.27 (m, 5H), 4.44 (t, J=5.04 Hz, 1H), 3.85 (s, 3H), 3.76 (s, 1H), 3.71 (s, 3H), 3.51-3.48 (m, 2H), 2.61 (t, J=6.32 Hz, 2H),

LCMS Condition A: Rt=0.46 min. m/z 274.3 $[M+H]^+$.

Step-3

Preparation of 2-(benzyl(2-hydroxyethyl)amino)-1-(1-methyl-1H-pyrazol-4-yl)ethan-1-ol

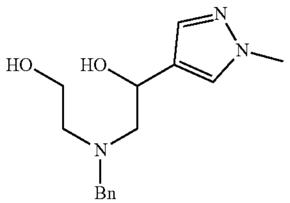 [SMILES: Cn1cc(C(O)CN(CCO)Cc2ccccc2)cn1]

To a stirred solution of 2-(benzyl(2-hydroxyethyl)amino)-1-(1-methyl-1H-pyrazol-4-yl)ethan-1-one (5 g, 18.32 mmol) was in dry methanol and cooled the reaction mixture at 0° C. $NaBH_4$ (1.4 g, 3.67 mmol) was added to it portion-wise for 10 min and reaction was kept stirring for 15 min at 0° C. Reaction was then warm to room temperature for 2 h. The reaction mixture was quenched with cold water and followed by extracted with dichloromethane. Combined organic layer was dried over sodium sulphate and concentrated under reduced pressure. The crude mass was purified by column chromatography (silica gel; 10% methanol-DCM) to afford 2-(benzyl(2-hydroxyethyl)amino)-1-(1-methyl-1H-pyrazol-4-yl)ethan-1-ol (3 g, 59.5% yield) as yellow sticky oil.

1H NMR (400 MHz, DMSO D6) δ 7.47 (s, 1H), 7.35-7.29 (m, 5H), 7.26 (s, 1H). 4.76 (d, J=3.52 Hz, 1H), 4.62-4.58 (m, 1H), 4.38 (t, J=5.36 Hz, 1H), 3.75 (s, 3H), 3.69 (d, J=9.08 Hz, 2H), 3.48-3.4 (m, 2H), 2.63-2.54 (m, 3H).

LCMS Condition A: Rt=0.39 min. m/z 276.3 $[M+H]^+$.

Step-4

Preparation of 4-benzyl-2-(1-methyl-1H-pyrazol-4-yl)morpholine (as HCl salt)

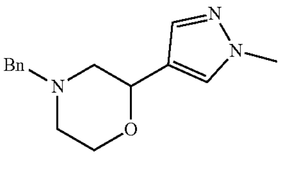 [SMILES: Cn1cc(C2CN(Cc3ccccc3)CCO2)cn1]

A mixture of 2-(benzyl(2-hydroxyethyl)amino)-1-(1-methyl-1H-pyrazol-4-yl)ethan-1-ol (2 g, 7.27 mmol) and aqueous HCl (6N, 20 mL) was heated at reflux for 2 h. The reaction mixture was evaporated under reduced pressure and the residue was washed with ether and dried under vacuum to afford 4-benzyl-2-(1-methyl-1H-pyrazol-4-yl)morpholine (1.7 g, 90.8% yield; HCl salt) as yellow sticky solid.

This material was forwarded for the next step without further purification.

1H NMR (400 MHz, DMSO D6) δ 7.76 (s, 1H), 7.68-7.63 (m, 2H), 7.46-7.43 (m, 3H), 7.41 (s, 1H), 4.95 (d, J=10.0 Hz, 1H), 4.34 (s, 2H), 4.08-4.0 (m, 2H), 3.78 (s, 3H), 3.32 (d, J=11.8 Hz, 1H), 3.21 (d, J=12.12 Hz, 1H), 3.15-3.07 (m, 2H).

LCMS Condition A: Rt=0.40 min. m/z 258.3 $[M+H]^+$.

Step-5

Preparation of 2-(1-methyl-1H-pyrazol-4-yl)morpholine (as HCl salt)

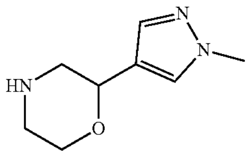

An ethanolic (50 mL) solution of 4-benzyl-2-(1-methyl-1H-pyrazol-4-yl)morpholine (2 g, 7.8 mmol) was taken in a par-autoclave vessel (100 mL) and purged it with argon. $Pd(OH)_2$ (0.5 g; 10% w/w) was added to it and reaction mixture was hydrogenated (30 psi) for 18 h at rt. The reaction mixture was filtered through a pad of celite and washed with ethanol. Evaporation of the solvent under reduced pressure afforded 2-(1-methyl-1H-pyrazol-4-yl) morpholine (1.2 g, 92.2% yield; HCl salt) as gummy liquid. 1H NMR (400 MHz, DMSO D6) δ 9.54 (brs, 1H), 7.75 (s, 1H), 7.45 (s, 1H), 4.71 (d, J=10.8 Hz, 1H), 4.00-3.97 (m, 1H), 3.89-3.87 (m, 1H), 3.80 (s, 3H), 3.32 (brs, 1H), 3.21-3.16 (m, 1H), 3.02 (brs, 2H).

LCMS Condition A: Rt=0.70 min. m/z 168.1 $[M+H]^+$.

Synthesis of (S)-2-(1-methyl-1H-pyrazol-4-yl)morpholine (as HCl salt) Intermediate I-1A) and (R)-2-(1-methyl-1H-pyrazol-4-yl)morpholine (as HCl salt) (Intermediate 1-1B)

I-1A (Peak1)

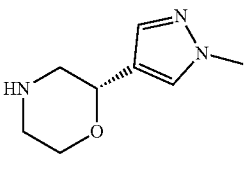

and

I-1B (Peak2)

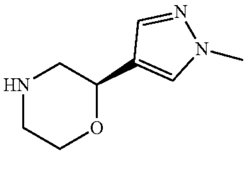

Chiral separation of 2-(1-methyl-1H-pyrazol-4-yl)morpholine (3 g, 0.086 mmol) was done by SFC (SFC method-1) to afford (S)-2-(1-methyl-1H-pyrazol-4-yl)morpholine (intermediate I-1A, 730 mg, 24.3% yield; eluted first, assigned as Peak1 as light yellow gum and (R)-2-(1-methyl-1H-pyrazol- 4-yl)morpholine (intermediate 1-1B, 762 mg, 25.4% yield eluted later, assigned as Peak2 as light yellow gum.

Intermediate I-1A: 1H NMR (400 MHz, DMSO-d6) δ 9.54 (brs, 1H), 7.75 (s, 1H), 7.45 (s, 1H), 4.71(d, J=10.8 Hz, 1H), 4.00-3.97 (m, 1H), 3.89-3.87 (m, 1H), 3.80 (s, 3H), 3.32 (brs, 1H), 3.21-3.16 (m, 1H), 3.02 (brs, 2H).

LCMS Condition A: Rt=0.70 min. m/z 168.1 $[M+H]^+$.

Intermediate 1-1B: 1H NMR (400 MHz, DMSO-d6) δ 9.54 (brs, 1H), 7.75 (s, 1H), 7.45 (s, 1H), 4.71(d, J=10.8 Hz, 1H), 4.00-3.97 (m, 1H), 3.89-3.87 (m, 1H), 3.80 (s, 3H), 3.32 (brs, 1H), 3.21-3.16 (m, 1H), 3.02 (brs, 2H).

LCMS Condition A: Rt=0.70 min. m/z 168.1 $[M+H]^+$.

Analytical chiral HPLC: CHIRALPAK AD-H (4.6×250 mm), 5p Mobile Phase: 0.5% DEA in EtOH Flow Rate: 4.0 ml/min. Solubility: MeOH, Rt=2.4 min for Peak1 and Rt=3.02 min for Peak2.

Preparation of 2-methyl-6-(1-methyl-1H-pyrazol-4-yl)morpholine (as HCl salt) (Intermediate 1-2)

Step-1

Preparation of 2-(benzyl(2-hydroxypropyl)amino)-1-(1-methyl-1H-pyrazol-4-yl)ethan-1-one

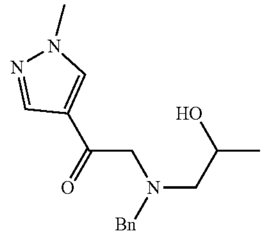 [SMILES: CC(O)CN(CC(=O)c1cnn(C)c1)Cc1ccccc1]

To a suspension of 2-chloro-1-(1-methyl-1H-pyrazol-4-yl)ethan-1-one (4 g, 25.3 mmol, intermediate I-1, Step-1) in acetonitrile (50 mL) was added 1-(benzylamino)propan-2-ol (5.2 g, 30.3 mmol) and potassium carbonate (7 g, 50.2 mmol) and it was stirred at rt for 16 h. After completion excess solvent was removed under reduced pressure and the residue was with cold water and followed by extracted with ethyl acetate. Combined organic layer was dried over sodium sulphate and concentrated under reduced pressure.

The crude was purified by column chromatography (silica gel; 40-60% ethyl acetate-hexane) to afford 2-(benzyl(2-hydroxypropyl)amino)-1-(1-methyl-1H-pyrazol-4-yl)ethan-1-one (2.6 g, 36% yield) as yellow oil.

LCMS Condition B: Rt=2.94 min. m/z 288.2 $[M+H]^+$.

Step-2

Preparation of 4-benzyl-2-methyl-6-(1-methyl-1H-pyrazol-4-yl)-3,4-dihydro-2H-1,4-oxazine

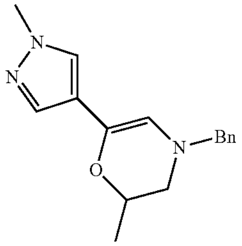 [SMILES: CC1CN(Cc2ccccc2)C=C(c2cnn(C)c2)O1]

To a stirred solution of 2-(benzyl(2-hydroxypropyl)amino)-1-(1-methyl-1H-pyrazol-4-yl)ethan-1-one (500 mg, 1.73 mmol) in DCE (10 mL) was added TMSOTf (7.5 mL) at 0° C. The resulting mixture was heated at 70° C. for 3 h. After completion of reaction, the reaction mixture was quenched with aqueous $NaHCO_3$ solution and extracted with dichloromethane. Combined organic layer was dried over sodium sulphate and concentrated into vacuo and purified by column chromatography (silica gel; 0-5% methanol in dichloromethane) to afford 4-benzyl-2-methyl-6-(1-methyl-1H-pyrazol-4-yl)-3,4-dihydro-2H-1,4-oxazine (250 mg, 80% yield) as yellow sticky oil.

LCMS Condition B: Rt=2.16 min. m/z 270.24 $[M+H]^+$.

Step-3

Preparation of 2-methyl-6-(1-methyl-1H-pyrazol-4-y)morpholine

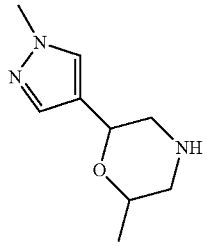

To a stirred solution of 4-benzyl-2-methyl-6-(1-methyl-1H-pyrazol-4-yl)-3,4-dihydro-2H-1,4-oxazine (1.3 g, 4.80 mmol) in methanol (20 mL) was added ammonium formate (1.5 g, 24.04 mmol) and $Pd(OH)_2$ (3.36 g, 10% on carbon) under nitrogen atmosphere. Resulting mixture was heated to 80° C. for 1 h. Reaction mixture was filtered through a pad of celite bed, washed with methanol and concentrated. The crude residue was quenched with sodium bicarbonate solution, extracted with 10% methanol-dichloromethane mixture, dried over sodium sulphate and concentrated. Crude mass was purified by combi flash chromatography (silica gel: 10% methanol-dichloromethane) to afford 2-methyl-6-(1-methyl-1H-pyrazol-4-yl)morpholine (600 mg, 69% yield) as gum.

LCMS Condition B: Rt=0.73 min. m/z 182.2 $[M+H]^+$.

Synthesis of 2-(1-cyclopropyl-1H-pyrazol-4-yl)-6-methylmorpholine (Intermediate 1-3)

Step-1

Preparation of 4-bromo-1-cyclopropyl-1H-pyrazole

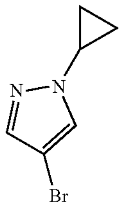

To a stirred solution of 4-bromo-1H-pyrazole (10 g, 68.02 mmol) in dichloroethane (200 mL) were added cyclopropyl boronic acid (11.7 g, 137.93 mmol), 2,2-bipyridyl (11.7 g, 74.83 mmol) and sodium carbonate (15.9 g, 149.66 mmol) under oxygen atmosphere. Finally, copper acetate (13.6 g, 74.83 mmol) was added to the reaction mixture. Resulting mixture was heated to 65° C. for 16 h. Reaction mixture was filtered through a pad of celite bed, washed with methanol and concentrated under reduced pressure. The crude residue was extracted with ethyl acetate, washed with brine, dried over sodium sulphate and concentrated. Crude product was purified by combi-flash chromatography (silica gel; 10% ethyl acetate-hexane) to afford 4-bromo-1-cyclopropyl-1H-pyrazole (6.5 g, 51% yield) as colourless liquid.

LCMS Condition C: Rt=1.86 min. m/z 187.1 [M+H]P.

Step-2

Preparation of 1-cyclopropyl-4-(1-ethoxyvinyl)-1H-pyrazole

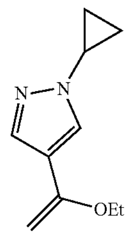

To a stirred solution of 4-bromo-1-cyclopropyl-1H-pyrazole (5 g, 26.73 mmol) in toluene (100 mL) was added tributyl(1-ethoxyvinyl)stannane (9.9 mL, 29.42 mmol). Resulting mixture was degassed with argon and $Pd(PPh_3)_4$ (1.54 g, 1.33 mmol) was added under inert atmosphere. Resulting mixture was heated to 110° C. for 16 h. Reaction mixture was filtered through a short pad of celite and washed with ethyl acetate. Combined layer was concentrated to get 1-cyclopropyl-4-(1-ethoxyvinyl)-1H-pyrazole (4.5 g, crude). The crude product was carried forward for the next step without further purification.

Step-3

Preparation of 2-bromo-1-(1-cyclopropyl-1H-pyrazol-4-yl)ethan-1-one

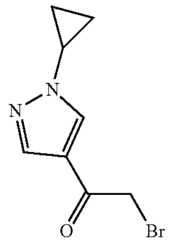 [SMILES: O=C(CBr)c1cnn(C2CC2)c1]

To a stirred solution of 1-cyclopropyl-4-(1-ethoxyvinyl)-1H-pyrazole (4.5 g, crude) in THF (120 mL) and water (50 mL) at 0° C. was added NBS (10 g, 62.5 mmol). Resulting reaction mixture was stirred at room temperature for 3 h. Reaction mixture was extracted with ethyl acetate, washed brine, dried over anhydrous sodium sulphate, filtered and concentrated under reduced pressure. Crude mass was purified by column chromatography (silica gel; 25-40% ethyl acetate-hexane) to afford 2-bromo-1-(1-cyclopropyl-1H-pyrazol-4-yl)ethan-1-one (1.5 g, 23.4% yield) as white solid.

LCMS Condition C: Rt=1.74 min. m/z 229.1 $[M+H]^+$.

Step-4

Preparation of 2-(benzyl(2-hydroxypropyl)amino)-1-(1-cyclopropyl-1H-pyrazol-4-yl)ethan-1-one

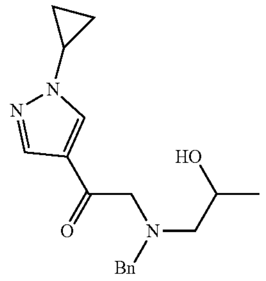 [SMILES: CC(O)CN(CC(=O)c1cnn(C2CC2)c1)Cc1ccccc1]

To a stirred solution of 2-bromo-1-(1-cyclopropyl-1H-pyrazol-4-yl)ethan-1-one (1.5 g, 6.55 mmol) in $CH_3CN$ (30 mL) were added $K_2CO_3$ (1.8 g, 13.0 mmol) and 1-(benzylamino)propan-2-ol (1.18 g, 7.20 mmol) at rt. Resulting reaction mixture was stirred at rt for 6 h. Reaction mixture was quenched with water and extracted with ethyl acetate. The combined organic layer was washed with water, brine, dried over anhydrous sodium sulphate, filtered and concentrated under reduced pressure. Crude mass was purified by combi-flash chromatography (silica gel, 50-80% ethyl acetate-hexane) to afford 2-(benzyl(2-hydroxypropyl)amino)-1-(1-cyclopropyl-1H-pyrazol-4-yl)ethan-1-one (1.7 g, 82% yield) as yellow gum.

LCMS Condition A: Rt=4.35 min. m/z 314.1 $[M+H]^+$.

Step-5

Preparation of 1-(benzyl(2-(1-cyclopropyl-1H-pyrazol-4-yl)-2-hydroxyethyl)amino)propan-2-ol

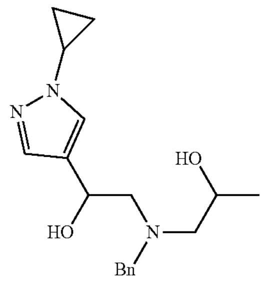 [SMILES: CC(O)CN(Cc1ccccc1)CC(O)c1cnn(C2CC2)c1]

To a stirred solution of 2-(benzyl(2-hydroxypropyl)amino)-1-(1-cyclopropyl-1H-pyrazol-4-yl)ethan-1-one (1.7 g, 5.4 mmol) in MeOH (20 mL) at 0° C. was added $NaBH_4$ (310 mg, 8.1 mmol) was added portion wise. The resulting mixture was stirred at rt for 1 h. Reaction mixture was quenched with ice cold water and extracted with dichloromethane. The combined organic layers were washed with brine, dried over anhydrous sodium sulphate, filtered and concentrated under reduced pressure. Crude mass was purified by column chromatography (silica-gel; 10-20% methanol-dichloromethane) to afford 1-(benzyl(2-(1-cyclopropyl-1H-pyrazol-4-yl)-2-hydroxyethyl)amino)propan-2-ol (1.5 g, 88% yield) as yellow gum.

LCMS Condition A: Rt=1.37 min. m/z 316.3 $[M+H]^+$.

Step-6

Preparation of 4-benzyl-2-(1-cyclopropyl-1H-pyrazol-4-yl)-6-methylmorpholine

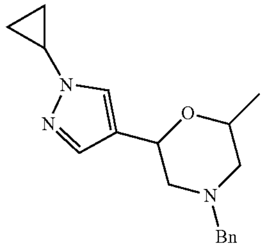 [SMILES: CC1CN(Cc2ccccc2)CC(c2cnn(C3CC3)c2)O1]

To a stirred solution of 1-(benzyl(2-(1-cyclopropyl-1H-pyrazol-4-yl)-2-hydroxyethyl)amino)propan-2-ol (1.5 g, 4.7 mmol) in 1,4-dioxane (5 mL) was added 4 M HCl-1,4-Dioxane solution (5 mL) at room temperature. Resulting mixture was heated at 110° C. for 4 h. The reaction mixture cooled to room temperature and poured into the ice cold water, neutralised with sodium bicarbonate, extracted with 10% methanol-dichloromethane, dried over sodium sulphate and concentrated to afford 4-benzyl-2-(1-cyclopropyl-1H-pyrazol-4-yl)-6-methylmorpholine (1 g, 71% yield) as a gum.

LCMS Condition A: Rt=2.09 min. m/z 298.3 $[M+H]^+$.

Step-7

Preparation of 2-(1-cyclopropyl-1H-pyrazol-4-yl)-6-methylmorpholine

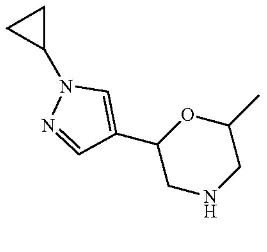

To a stirred solution of 4-benzyl-2-(1-cyclopropyl-1H-pyrazol-4-yl)-6-methylmorpholine (1 g, 3.35 mmol) in methanol (20 mL) was added ammonium formate (1.1 g, 17.82 mmol) and $Pd(OH)_2$ (300 mg, 20% on carbon) under nitrogen atmosphere. Resulting mixture was heated to 80° C. for 1 h. Reaction mixture was filtered through a pad of celite bed, washed with methanol and concentrated. The crude residue was quenched with sodium bicarbonate solution, extracted with 10% methanol/dichloromethane mixture, dried over sodium sulphate and concentrated. Crude mass was purified by combi flash chromatography (silica gel: 10% methanol-dichloromethane) to afford 2-(1-cyclopropyl-1H-pyrazol-4-yl)-6-methylmorpholine (500 mg, 71% yield) as gum.

LCMS Condition A: Rt=0.53 min. m/z 208.23 $[M+H]^+$.

Synthesis of (2R,6S)-2-(1-cyclopropyl-1H-pyrazol-4-yl)-6-methylmorpholine (Intermediate I-3A) and (2S,6R)-2-(1-cyclopropyl-1H-pyrazol-4-yl)-6-methylmorpholine (Intermediate I-3B)

I-3A (Peak1)

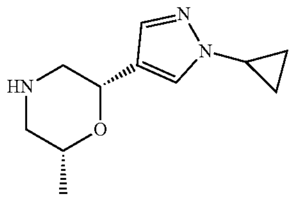

and

I-3B (Peak2)

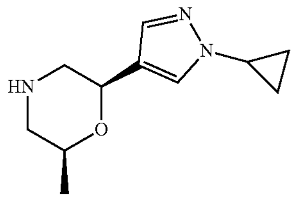

Chiral separation of 2-(1-cyclopropyl-1H-pyrazol-4-yl)-6-methylmorpholine (1 g) was done by SFC (SFC method-1) to afford (2S,6R)-2-(1-cyclopropyl-1H-pyrazol-4-yl)-6-methylmorpholine (I-3A: 300 mg, 31% yield; eluted first, assigned as Peak1 as light yellow gum and (2R,6S)-2-(1-cyclopropyl-1H-pyrazol-4-yl)-6-methylmorpholine (1-3B, 320 mg, 33% yield eluted later, assigned as Peak2 as light yellow gum. Absolute stereochemistry not determined and assigned arbitrarily.

Intermediate I-3A: 1H NMR (400 MHz, DMSO-d6) δ 7.66 (s, 1H), 7.32 (s, 1H), 4.29 (d, J=8.4 Hz, 1H), 3.64-3.53 (m, 2H), 2.80-2.76 (m, 2H), 2.67 (brs, 1H), 2.32-2.26 (m, 1H) 1.06-0.94 (m, 7H).

LCMS Condition A: Rt=0.53 min. m/z 208.23 $[M+H]^+$.

Intermediate 1-3B: 1H NMR (400 MHz, DMSO-d6) δ 7.66 (s, 1H), 7.32 (s, 1H), 4.29 (d, J=8.4 Hz, 1H), 3.64-3.53 (m, 2H), 2.80-2.76 (m, 2H), 2.67 (brs, 1H), 2.32-2.26 (m, 1H) 1.06-0.94 (m, 7H).

LCMS Condition A: Rt=0.53 min. m/z 208.23 $[M+H]^+$.

Analytical chiral HPLC (SFC): CHIRALPAK IG (4.6×250 mm), 5p Mobile Phase: 0.5% IPA in MeOH Flow Rate: 4.0 ml/min. Solubility: MeOH, Rt=1.97 min for Peak1 and Rt=3.28 min for Peak2.

Preparation of 2,2-difluoro-6-(1-methyl-1H-pyrazol-4-yl)morpholine; (Intermediate 1-4)

Step-1

Preparation of 1-(1-methyl-1H-pyrazol-4-yl)-2-nitroethan-1-ol

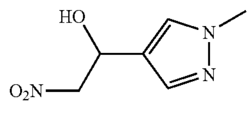

To a stirred solution of 1-methyl-1H-pyrazole-4-carbaldehyde (10 gm, 90.43 mmol) in nitromethane (100 mL) was added triethyl amine (26 mL, 180 mmol) at 0° C. Resulting mixture was stirred at rt for 6 h. The reaction mixture was evaporated under reduced pressure and purified by column chromatography (silica gel, 20-70% ethyl acetate in Hexane) to afford 1-(1-methyl-1H-pyrazol-4-yl)-2-nitroethan-1-ol (8.0 g, 50% yield) as brown gum.

LCMS Condition A: Rt=1.18 min. m/z 172.1 $[M+H]^+$.

Step-2

Preparation of 2-amino-1-(1-methyl-1H-pyrazol-4-y)ethan-1-ol

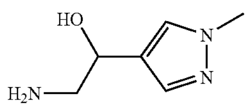

To a stirred solution of 1-(1-methyl-1H-pyrazol-4-yl)-2-nitroethan-1-ol (3.2 g, 18.7 mmol) in methanol (64 mL) ware added glacial acetic acid (0.2 mL) and Pd/C (1.6 g, 10% on charcoal) under nitrogen atmosphere. Finally, under vacuum condition the reaction mixture was charged with hydrogen gas pressure. The resulting reaction mixture was stirred at rt for 16 h. The reaction was filtered through a pad of celite bed, washed with methanol and concentrated under reduced pressure to afford 2-amino-1-(1-methyl-1H-pyrazol-4-yl)ethan-1-ol (2.4 g, 70% yield) as gummy liquid.

LCMS Condition A: Rt=0.19 min. m/z 142.1 $[M+H]^+$.

Step-3

Preparation of 2-bromo-2,2-difluoro-N-(2-hydroxy-2-(1-methyl-1H-pyrazol-4-yl)ethyl)acetamide

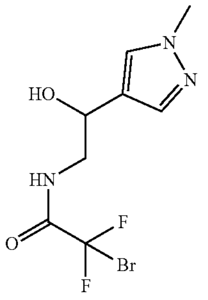 [SMILES: Cn1cc(C(O)CNC(=O)C(F)(F)Br)cn1]

To a stirred solution of 2-amino-1-(1-methyl-1H-pyrazol-4-yl)ethan-1-ol (2.4 g, 17.0 mmol) in DMF (20 mL) was added ethyl-2-bromo-2,2-difluoro acetate (3.43 g, 17.0 mmol). Resulting mixture was stirred at rt for 16 h. Reaction was quenched with crushed ice and extracted with 10% methanol-DCM (100 mL). Combined organic layer was washed with brine, dried over sodium sulphate, filtered and evaporated under reduced pressure. Crude product was purified by combi-flash chromatography (silica gel; 0-10% MeOH-dichloromethane) to get 2-bromo-2,2-difluoro-N-(2-hydroxy-2-(1-methyl-1H-pyrazol-4-yl)ethyl)acetamide (1.1 g, 31% yield) as white solid.

LCMS Condition A: Rt=1.80 min. m/z 298.0 $[M+H]^+$.

Step-4 Preparation of 2,2-difluoro-6-(1-methyl-1H-pyrazol-4-yl)morpholin-3-one

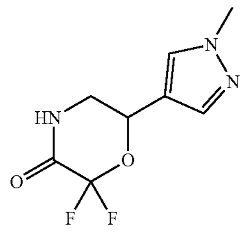

To a stirred solution of 2-bromo-2,2-difluoro-N-(2-hydroxy-2-(1-methyl-1H-pyrazol-4-yl)ethyl)acetamide (1.1 g, 3.69 mmol) in THF (40 mL) under ice cold condition, sodium tert butoxide (9.2 mL, 2.0 M in THF, 18.45 mmol) was added. The reaction was stirred at room temperature for 16 h. Crude 1H-NMR indicated 60% of desired product and 40% of SM. Again, sodium tert butoxide (9.2 mL, 2.0 M in THF, 18.45 mmol) was added and stirred further 18 h. Reaction was quenched with sat $NH_4Cl$ and separated the organic layer, dried over sodium sulphate, filtered, and evaporated under reduced pressure. Crude product was triturated with ethyl acetate to afford 2,2-difluoro-6-(1-methyl-1H-pyrazol-4-yl)morpholin-3-one (300 mg, 41% yield) as white solid. 1H NMR (400 MHz, DMSO-d6) δ 7.76 (s, 1H), 7.56 (s, 1H), 5.49-5.45 (m, 1H), 3.88 (s, 3H), 3.84-3.73 (m, 1H), 3.54-3.51 (m, 1H).

LCMS Condition A: Rt=1.30 min. m/z 218.2 $[M+H]^+$.

Step-5

Preparation of 2,2-difluoro-6-(1-methyl-1H-pyrazol-4-yl)morpholine

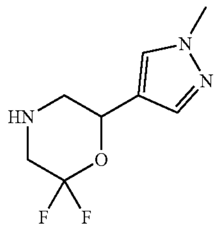

To a stirred solution of 2,2-difluoro-6-(1-methyl-1H-pyrazol-4-yl)morpholin-3-one (1 g, 4.58 mmol) in THF (20 mL), LAH (7 mL, 1M in THF, 6.88 mmol) at 0° C. Resulting mixture was stirred at rt for 3 h. The reaction mixture was quenched with ice cold sodium sulphate solution and extracted with 20% Methanol/DCM (40 mL). Combined organic layers were washed with brine, dried over sodium sulphate, filtered, and evaporated under reduced pressure. The crude was purified by combi-flash chromatography (silica gel; 10% MeOH-DCM) to afford 2,2-difluoro-6-(1-methyl-1H-pyrazol-4-yl)morpholine (160 mg, crude) as gummy liquid.

LCMS Condition A: Rt=1.57 min. m/z 204.17 $[M+H]^+$.

Synthesis of 2-(2-methoxypyridin-4-yl)morpholine (Intermediate 1-5)

Step-1

Preparation of 4-(1-ethoxyvinyl)-2-methoxypyridine

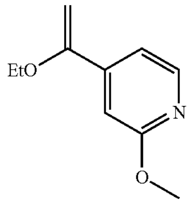

To a stirred solution of 4-bromo-2-methoxypyridine (2.0 g, 10.63 mmol) in toluene (20 mL) was added tributyl(1-ethoxyvinyl)stannane (3.9 mL, 10.63 mmol) Resulting mixture was degassed with argon and $Pd(PPh_3)_4$(614 mg, 0.53 mmol) was added under inert atmosphere. Resulting mixture was heated to 110° C. for 16 h. Reaction mixture was filtered through a short pad of celite and washed with ethyl acetate. Combined filtrate was concentrated under reduced pressure to afford 4-(1-ethoxyvinyl)-2-methoxypyridine (1.6 g, crude) as black liquid. The crude material was used in the next step without further purification.

LCMS Condition A: Rt=2.21 min. m/z 180.1 $[M+H]^+$.

Step-2

Preparation of 2-bromo-1-(2-methoxypyridin-4-yl)ethan-1-one

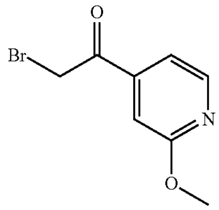

To a stirred solution of 4-(1-ethoxyvinyl)-2-methoxypyridine (1.6 g, crude) in THF (15 mL) and water (10 mL) at 0° C. was added NBS (1.6 g, 8.8 mmol). The resulting solution was stirred at rt for 1 h. Reaction mixture was quenched with water and extracted with ethyl acetate. The combined organic layers were washed with water, brine, dried over anhydrous sodium sulphate, filtered and concentrated under reduced pressure. Crude mass was purified by column chromatography (silica gel; 25-40% ethyl acetate-hexane) to afford 2-bromo-1-(2-methoxypyridin-4-yl)ethan-1-one (1.2 g, 24.3% yield) as colorless liquid.

LCMS Condition A: Rt=1.87 min. m/z 230.1 $[M+H]^+$.

Step-3

Preparation of 2-(benzyl(2-hydroxyethyl)amino)-1-(2-methoxypyridin-4-yl)ethan-1-one

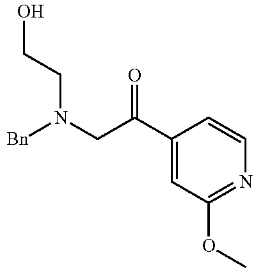 [SMILES: COc1cc(C(=O)CN(CCO)Cc2ccccc2)ccn1]

To a stirred solution of 2-bromo-1-(2-methoxypyridin-4-yl)ethan-1-one (500 mg, 2.17 mmol) in acetonitrile (10 mL) were added potassium carbonate (450 mg, 3.26 mmol) and 2-(benzylamino)ethan-1-ol (328 mg, 2.17 mmol). Resulting mixture was stirred at rt for 3 h. Reaction mixture was quenched with water and extracted with ethyl acetate. The combined organic layer was washed with water, brine, dried over anhydrous sodium sulphate, filtered and concentrated under reduced pressure. Crude mass was purified by column chromatography (silica gel; 50-80% ethyl acetate in hexane) to afford 2-(benzyl(2-hydroxyethyl)amino)-1-(2-methoxypyridin-4-yl)ethan-1-one (500 mg, 76% yield) as yellow liquid.

LCMS Condition E: Rt=1.62 min. m/z 301.2 $[M+H]^+$.

Step-4

Preparation of 2-(benzyl(2-hydroxyethyl)amino)-1-(2-methoxypyridin-4-yl)ethan-1-ol

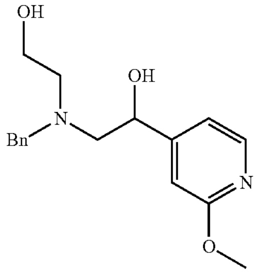 [SMILES: COc1cc(C(O)CN(CCO)Cc2ccccc2)ccn1]

To a stirred solution of 2-(benzyl(2-hydroxyethyl)amino)-1-(2-methoxypyridin-4-yl)ethan-1-one (300 mg, 0.99 mmol) in methanol (10 mL) sodium borohydride (56 mg, 1.49 mmol) was added portion wise at 0° C. Resulting mixture was stirred at 0° C. for 0.5 h and then at rt for 2 h. Reaction mixture was quenched with ice cold water and extracted with dichloromethane. Combined organic layer was washed with water, brine, dried over anhydrous sodium sulphate, filtered and concentrated under reduced pressure. Crude mass was triturated with diethyl ether to afford 2-(benzyl(2-hydroxyethyl)amino)-1-(2-methoxypyridin-4-yl)ethan-1-ol (280 mg, 86% yield) as colorless sticky liquid.

LCMS Condition A: Rt=1.55 min. m/z 303.2 $[M+H]^+$.

Step-5

Preparation of 4-benzyl-2-(2-methoxypyridin-4-yl)morpholine

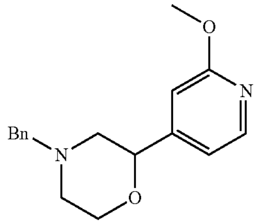 [SMILES: COc1cc(C2CN(Cc3ccccc3)CCO2)ccn1]

To a stirred solution of 2-(benzyl(2-hydroxyethyl)amino)-1-(2-methoxypyridin-4-yl)ethan-1-ol (250 mg, 0.87 mmol) in THF (10 mL), was added NaH (100 mg, 2.48 mmol) under argon atmosphere at 0° C. The reaction mixture was stirred for 10 min at rt and tosyl imidazole (275 mg, 1.24 mmol) was added. Reaction mixture was stirred at rt for 16 h. Reaction mixture was quenched with ice cold water and extracted with dichloromethane. Combined organic layer was washed with water, brine, dried over anhydrous sodium sulphate, filtered and concentrated under reduced pressure. Crude mass was purified by chromatography (silica gel; 5-10% MeOH-DCM) to afford 4-benzyl-2-(2-methoxypyridin-4-yl)morpholine (100 mg, 40% yield) as colorless sticky liquid.

LCMS Condition A: Rt=1.62 min. m/z 285.2 $[M+H]^+$.

Step-6

Preparation of 2-(2-methoxypyridin-4-yl)morpholine

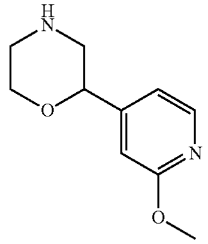

To a stirred solution of 4-benzyl-2-(2-methoxypyridin-4-yl)morpholine (100 mg, 0.35 mmol) in methanol (5 mL) was added ammonium formate (63 mg, 1.75 mmol) and $Pd(OH)_2$ (50 mg, 20% on carbon) under nitrogen atmosphere. Resulting mixture was heated to 80° C. for 1 h. Reaction mixture was filtered through a pad of celite bed, washed with methanol and concentrated. The crude residue was quenched with sodium bicarbonate solution, extracted with 10% methanol-dichloromethane mixture, dried over sodium sulphate and concentrated. Crude mass was purified by combi flash chromatography (silica gel: 10% MeOH-DCM) to afford 2-(2-methoxypyridin-4-yl)morpholine (35 mg, 51% yield) as gum.

LCMS Condition A: Rt=2.09 min. m/z 298.3 $[M+H]^+$.

Synthesis of 2-(2-methoxypyridin-4-yl)-6-methylmorpholine (Intermediate 1-6): Step-1

Preparation of 2-(benzyl(2-hydroxypropyl)amino)-1-(2-methoxypyridin-4-yl)ethan-1-one

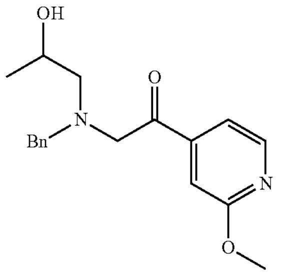 [SMILES: COc1cc(C(=O)CN(Cc2ccccc2)CC(C)O)ccn1]

To a stirred solution of 2-bromo-1-(2-methoxypyridin-4-yl)ethan-1-one (700 mg, 3.04 mmol, Step-2; 1-5) in acetonitrile (10 mL) were added potassium carbonate (630 mg, 4.56 mmol) and 1-(benzylamino)propan-2-ol (502 mg, 3.04 mmol). Resulting mixture was stirred at rt for 3 h. Reaction mixture was quenched with water and extracted with ethyl acetate. The combined organic layer was washed with water, brine, dried over anhydrous sodium sulphate, filtered and concentrated under reduced pressure. Crude mass was purified by combi-flash chromatography (50-80% ethyl acetate in hexane) to afford 2-(benzyl(2-hydroxypropyl)amino)-1-(2-methoxypyridin-4-yl)ethan-1-one (700 mg, 73% yield) as yellow liquid.

LCMS Condition A: Rt=1.59 min. m/z 315.31 $[M+H]^+$.

Step-2

Preparation of 4-benzyl-6-(2-methoxypyridin-4-yl)-2-methyl-3,4-dihydro-2H-1,4-oxazine

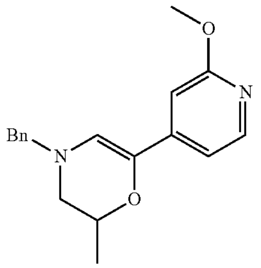 [SMILES: COc1cc(C2=CN(Cc3ccccc3)CC(C)O2)ccn1]

To a stirred solution of 2-(benzyl(2-hydroxypropyl)amino)-1-(2-methoxypyridin-4-yl)ethan-1-one (500 mg, 1.62 mmol) in DCE (10 mL) was added TMSOTf (8.5 mL) at 0° C. The resulting mixture was heated at 70° C. for 4 h. After completion of reaction, the reaction mixture was quenched with aqueous $NaHCO_3$ solution and extracted with dichloromethane. Combined organic layer was dried over sodium sulphate and concentrated into vacuo and purified by column chromatography (silica gel; 0-5% MeOH-DCM) to afford 4-benzyl-6-(2-methoxypyridin-4-yl)-2-methyl-3,4-dihydro-2H-1,4-oxazine (350 mg, 75% yield) as yellow sticky oil.

LCMS Condition A: Rt=1.67 min. m/z 297.3 $[M+H]^+$.

Step-3

Preparation of 2-2-methoxypyridin-4-yl)-6-methylmorpholine

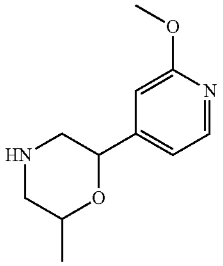

To a stirred solution of 4-benzyl-6-(2-methoxypyridin-4-yl)-2-methyl-3,4-dihydro-2H-1,4-oxazine (200 mg, 0.68 mmol) in methanol (10 mL) was added ammonium formate (212 mg, 3.37 mmol) and $Pd(OH)_2$ (191 mg, 20% on carbon) under nitrogen atmosphere. Resulting mixture was refluxed at 70° C. for 2 h. Reaction mixture was filtered through a pad of celite bed, washed with methanol and concentrated. The crude residue was quenched with sodium bicarbonate solution, extracted with 10% methanol-dichloromethane mixture, dried over sodium sulphate and concentrated. Crude mass was purified by combi flash chromatography (silica gel: 10% MeOH-DCM) to afford 2-(2-methoxypyridin-4-yl)-6-methylmorpholine (100 mg, 70% yield) as gum.

LCMS Condition A: Rt=0.66 min. m/z 209.17 $[M+H]^+$.

Synthesis of 4-(2-chloro-7-methyl-8-oxo-6-(trifluoromethyl)-7,8-dihydropyrimido[5,4-d]pyrimidin-4-yl)-3-fluorobenzonitrile(Intermediate 1-7): Step-1

Preparation of 2-(trifluoromethyl)-4H-pyrimido[5,4-d][1,3]oxazine-4,6,8(5H,7H)-trione

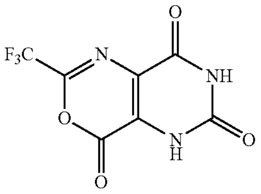 [SMILES: O=c1[nH]c(=O)c2nc(C(F)(F)F)oc(=O)c2[nH]1]

To a stirred solution of 5-amino-2,6-dioxo-1,2,3,6-tetrahydropyrimidine-4-carboxylic acid (50 g, 292.21 mmol) was added trifuoroacetic anhydride (490 mL, 3.5 mol) in drop wise at 0° C. Resulting mixture was heated at 120° C. for 16 h under autoclave. It was cooled to ambient temperature and concentrated under reduced pressure. The crude product was triturated with DCM and dried to afford 2-(trifluoromethyl)-4H-pyrimido[5,4-d][1,3]oxazine-4,6,8(5H, 7H)-trione (50 g, 68.63% yield) as brown solid. 1H NMR (400 MHz, DMSO-D6) δ 12.24 (s, 1H), 12.03 (s, 1H).

Step-2

Preparation of 7-methyl-6-(trifluoromethyl)-1,7-dihydropyrimido[5,4-d]pyrimidine-2,4,8(3H)-trione

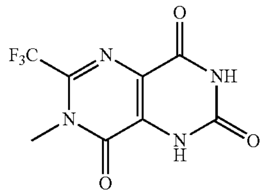 [SMILES: Cn1c(C(F)(F)F)nc2c(=O)[nH]c(=O)[nH]c2c1=O]

To a stirred solution of 2-(trifluoromethyl)-4H-pyrimido[5,4-d][1,3]oxazine-4,6,8(5H,7H)-trione (50 g, 202 mmol) in acetic acid (1.1 L) was added sodium acetate (16 g, 202 mmol) followed by added $MeNH_2$, HCl (134 g, 2.02 mol) at rt. Resulting mixture was heated at 120° C. for 16 h. The mixture was cooled to rt and concentrated under reduced pressure. The residue was diluted with water and precipitate thus formed was collected and dried. It was then triturated with diethyl ether, ethyl acetate successively and dried under high vacuum to afford 7-methyl-6-(trifluoromethyl)-1,7-dihydropyrimido[5,4-d]pyrimidine-2,4,8(3H)-trione (25 g, 48% yield) as light brown solid.

LCMS Condition A: Rt=1.14 min. m/z 262.1 $[M+H]^+$

Step-3

Preparation of 6,8-dichloro-3-methyl-2-(trifluoromethyl)pyrimido[5,4-d]pyrimidin-4(3H)-one

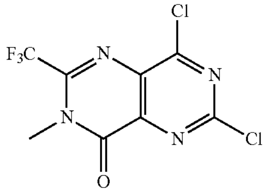 [SMILES: Cn1c(C(F)(F)F)nc2c(Cl)nc(Cl)nc2c1=O]

To a stirred solution of 7-methyl-6-(trifluoromethyl)-1,7-dihydropyrimido[5,4-d]pyrimidine-2,4,8(3H)-trione (10 g, 38 mmol) in $POCl_3$ (160 mL, 1.7 mol), DIPEA (26 mL, 152 mmol) was added drop wise at 0° C. Resultant mixture was stirred at rt for 15 min and then heated to 100° C. for 16 h. The mixture was cooled to rt and concentrated under reduced pressure. The residue was cooled to 0° C., quenched with saturated aqueous $NaHCO_3$ solution and extracted with ethyl acetate. The combined organic part was washed with brine, dried over anhydrous sodium sulphate, filtered and concentrated under reduced pressure. Crude mass was purified by column chromatography (silica gel; 50% ethyl acetate-hexane) to afford 6,8-dichloro-3-methyl-2-(trifluoromethyl)pyrimido[5,4-d]pyrimidin-4(3H)-one (7 g, 61% yield) as yellow solid.

LCMS Condition A: Rt=3.26 min. m/z 299.0 $[M+H]^+$.

Step-4

Preparation of 4-(2-chloro-7-methyl-8-oxo-6-(trifluoromethyl)-7,8-dihydropyrimido[5,4-d]pyrimidin-4-yl)-3-fluorobenzonitrile

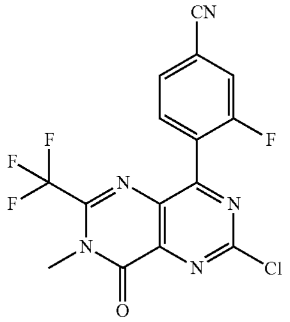 [SMILES: Cn1c(C(F)(F)F)nc2c(-c3ccc(C#N)cc3F)nc(Cl)nc2c1=O]

To a stirred solution of 6,8-dichloro-3-methyl-2-(trifluoromethyl)pyrimido[5,4-d]pyrimidin-4(3H)-one (500 mg, 1.67 mmol) and 3-fluoro-4-(4,4,5,5-tetramethyl-1,3,2-dioxaborolan-2-yl)benzonitrile (620 mg, 2.5 mmol) in toluene (6 mL) and water (2 mL) was added 2M aqueous sodium carbonate (710 mg, 6.70 mmol; 2M solution in water) solution and degassed with argon. PdCl2(dppf) (136 mg, 0.16 mmol) was added under inert atmosphere. The resulting mixture was stirred for 3 h. Reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (silica gel; 35% ethyl acetate-hexane) to afford 4-(2-chloro-7-methyl-8-oxo-6-(trifluoromethyl)-7,8-dihydropyrimido[5,4-d]pyrimidin-4-yl)-3-fluorobenzonitrile (250 mg, 39% yield) as white solid.

LCMS condition A: Rt=3.21 min m/z 384.13 $[M+H]^+$

The below intermediates 1-8 to 1-10 ware synthesized by using similar procedures described for Intermediate 1-7 (Step 4)

| Structure | Name | SM1 | SM2 | Intermediate Number |
|---|---|---|---|---|
| 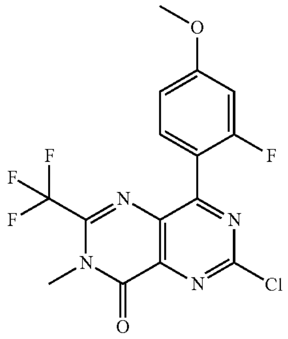 [SMILES: COc1ccc(-c2nc(Cl)nc3c(=O)n(C)c(C(F)(F)F)nc23)c(F)c1] | 6-chloro-8-(2-fluoro-4-methoxyphenyl)-3-methyl-2-(trifluoromethyl)pyrimido[5,4-d]pyrimidin-4(3H)-one | 6,8-dichloro-3-methyl-2-(trifluoromethyl)pyrimido[5,4-d]pyrimidin-4(3H)-one | 2-fluoro-4-methoxyphenyl)boronic acid | 1-8 |
| 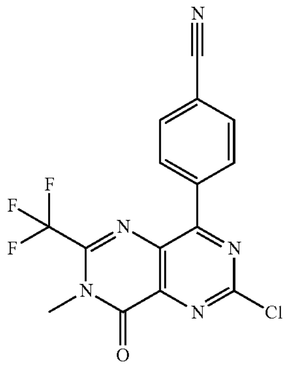 [SMILES: Cn1c(C(F)(F)F)nc2c(-c3ccc(C#N)cc3)nc(Cl)nc2c1=O] | 4-(2-chloro-7-methyl-8-oxo-6-(trifluoromethyl)-7,8-dihydropyrimido[5,4-d]pyrimidin-4-yl)benzonitrile | 6,8-dichloro-3-methyl-2-(trifluoromethyl)pyrimido[5,4-d]pyrimidin-4(3H)-one | (4-cyanophenyl)boronic acid | 1-9 |

-continued

| Structure | Name | SM1 | SM2 | Inter-mediate Number |
|---|---|---|---|---|
| 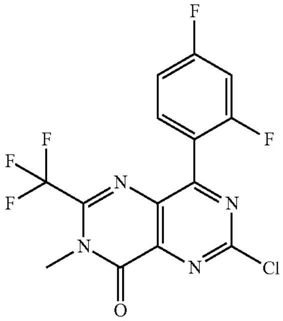 [SMILES: Cn1c(C(F)(F)F)nc2c(-c3ccc(F)cc3F)nc(Cl)nc2c1=O] | 6-chloro-8-(2,4-difluorophenyl)-3-methyl-2-(trifluoromethyl) pyrimido[5,4-d]pyrimidin-4(3H)-one | 6,8-dichloro-3-methyl-2-(trifluoromethyl) pyrimido[5,4-d]pyrimidin-4(3H)-one | (2,4-difluorophenyl) boronic acid | 1-10 |

The following table describes analytical data analysis and yield information of intermediates 1-8 to 1-10

| Intermediate Number | LCMS/NMR | Description | Yield % |
|---|---|---|---|
| I-8 | Condition A: Rt = 2.10 min. m/z 389.1 [M + H]$^+$ | White solid | 43.0 |
| I-9 | Condition A: Rt = 2.12 min. m/z 366.1 [M + H]$^+$ | White solid | 45.0 |
| I-10 | Condition A: Rt = 2.22 min. m/z 377.1 [M + H]$^+$ | White solid | 43.0 |

Synthesis of 4-(6-chloro-3-methyl-4-oxo-2-(trifluoromethyl)-3,4-dihydropyrido[3,4-d]pyrimidin-8-yl)-3-fluorobenzonitrile (Intermediate I-11)

Step-1

Preparation of 5-amino-2-chloro-N-methylisonicotinamide

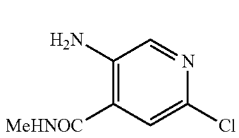

To a stirred solution of 5-amino-2-chloroisonicotinic acid (20 g, 116.3 mmol) in DMF (250 mL) at 0° C. was added $MeNH_2$·HCl (9.4 g, 139.5 mmol) followed by HATU (53 g, 139.5 mmol) and DIPEA (70.8 mL, 406.9 mmol). Resulting mixture was stirred at rt for 16 h. After completion, reaction mixture was quenched with water, extracted with ethyl acetate, washed with brine, dried over sodium sulphate, filtered and concentrated under reduced pressure. Crude product was purified by combi-flash chromatography (silica gel; 50-60% ethyl acetate-hexane) to get 5-amino-2-chloro-N-methylisonicotinamide (18 g, 83.72% yield) as pale-yellow solid.

1H NMR (400 MHz, DMSO-d6) δ 8.59 (s, 1H), 7.91 (s, 1H), 7.45 (s, 1H), 6.54 (s, 2H), 2.72 (s, 3H).

LCMS Condition A: Rt=1.92 min. m/z 186.2 [M+H]$^+$.

Step-2

Preparation of 3-amino-2-bromo-6-chloro-N-methylisonicotinamide

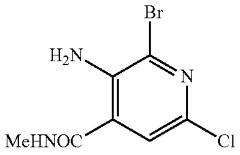

To a stirred solution of 5-amino-2-chloro-N-methylisonicotinamide (17 g, 91.8 mmol) in DMF (100 mL) was added NBS (16.3 g, 91.9 mmol) at 0° C. Resulting mixture was heated at 80° C. for 2 h. Reaction mixture was quenched with crushed ice, extracted with ethyl acetate, washed with brine, dried over sodium sulphate, filtered and evaporated under reduced pressure. Crude product was purified by combi-flash chromatography (silica gel; 25-30% ethyl acetate-hexane) to get (11 g, 45.2% yield) as pale-yellow solid. 1H NMR (400 MHz, DMSO-d6) δ 8.76 (s, 1H), 7.62 (s, 1H), 6.52 (s, 2H), 2.74 (s, 3H).

LCMS Condition D: Rt=2.78 min. m/z 266.2 [M+H]$^+$.

Step-3

Preparation of 2-bromo-6-chloro-N-methyl-3-(2,2,2-trifluoroacetamido)isonicotinamide

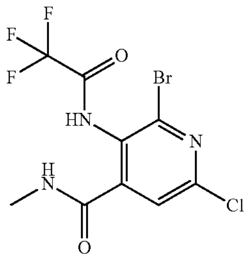 [SMILES: CNC(=O)c1cc(Cl)nc(Br)c1NC(=O)C(F)(F)F]

To a stirred solution of 3-amino-2-bromo-6-chloro-N-methyipyridine-4-carboxamide (3.8 g, 14.36 mmol) in THF (30.0 mL) were added pyridine (3.47 ml, 43.09 mmol) and DMAP (350 mg, 2.87 mmol) successively. Finally, the reaction mixture cooled to 0° C. and trifluoro acetic anhydride (6.03 mL, 43.09 mmol) was added dropwise to the reaction mixture. Then it was stirred at rt for 2 h. The reaction mixture was quenched with cold water, extracted with ethyl acetate, washed with brine, dried over sodium sulphate, filtered and concentrated under reduced pressure. Crude product was purified by combi-flash chromatography (silica gel; 30-40% ethyl acetate-hexane) to get 2-bromo-6-chloro-N-methyl-3-(2,2,2-trifluoroacetamido)isonicotinamide (2.6 g, 50%) as grey solid mass.

LCMS Condition A: Rt=2.21 min. m/z 362.1 $[M+H]^+$.

Step-4

Preparation of 8-bromo-6-chloro-3-methyl-2-(trifluoromethyl)pyrido[3,4-d]pyrimidin-4(3H)-one

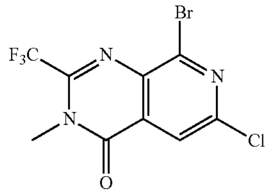 [SMILES: Cn1c(C(F)(F)F)nc2c(Br)nc(Cl)cc2c1=O]

To a stirred mixture of 2-bromo-6-chloro-N-methyl-3-(2,2-trifluoroacetamido)isonicotinamide (2.2 g, 6.10 mmol) in acetic acid (30 mL) was added sodium acetate (750 mg, 9.15 mmol). Resulting mixture was heated at 120° C. for 16 h. The reaction mixture was evaporated to dryness and quenched with sat. sodium bicarbonate solution and extracted with 10% MeOH-DCM mixture. Combined organic layer was dried over sodium sulphate, filtered and concentrated under reduced pressure. Crude mass was purified by combi flash chromatography (silica gel; 30-40% ethyl acetate-hexane) to afford 8-bromo-6-chloro-3-methyl-2-(trifluoromethyl)pyrido[3,4-d]pyrimidin-4(3H)-one (1.2 g, 57% yield) as brown solid.

LCMS Condition A: Rt=1.89 min. m/z 342.27 $[M+H]^+$.

Step-5

Preparation of 4-(6-chloro-3-methyl-4-oxo-2-(trifluoromethyl)-3,4-dihydropyrido[3,4-d]pyrimidin-8-yl)-3-fluorobenzonitrile

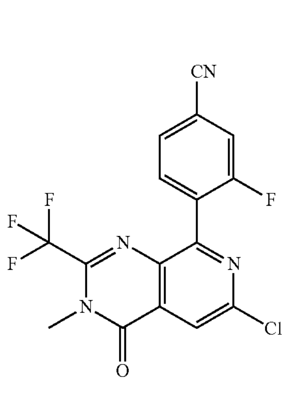 [SMILES: Cn1c(C(F)(F)F)nc2c(-c3ccc(C#N)cc3F)nc(Cl)cc2c1=O]

To a stirred solution of 8-bromo-6-chloro-3-methyl-2-(trifluoromethyl)pyrido[3,4-d]pyrimidin-4(3H)-one (500 mg, 1.46 mmol) and corresponding 3-fluoro-4-(4,4,5,5-tetramethyl-1,3,2-dioxaborolan-2-yl)benzonitrile (541 mg, 2.19 mmol) in dioxane (15 mL) and water (5 mL) was added sodium carbonate (464 mg, 4.38 mmol) and degassed with argon. PdCl2(dppf).DCM (120 mg, 0.14 mmol) was added under inert atmosphere. The resulting mixture was heated at 90° C. for 3 h. Reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (35% ethyl acetate-hexane) to afford 4-(6-chloro-3-methyl-4-oxo-2-(trifluoromethyl)-3,4-dihydropyrido[3,4-d]pyrimidin-8-yl)-3-fluorobenzonitrile (270 mg, 60% yield) as white solid.

LCMS Condition A: Rt=3.38 min. m/z 383.08 $[M+H]^+$.

Examples 1-12

Example 1: (S)-3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile

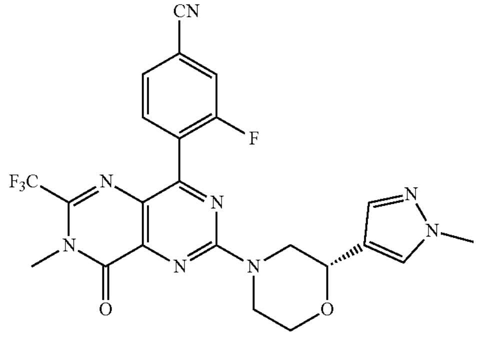 [SMILES: Cn1cc([C@H]2CN(c3nc(-c4ccc(C#N)cc4F)c4nc(C(F)(F)F)n(C)c(=O)c4n3)CCO2)cn1]

To a stirred solution of 4-(2-chloro-7-methyl-8-oxo-6-(trifluoromethyl)-7,8-dihydropyrimido[5,4-d]pyrimidin-4-yl)-3-fluorobenzonitrile (40 mg, 0.1 mmol)) in DMSO (4 mL) was added (S)-2-(1-methyl-1H-pyrazol-4-yl)morpholine (I-1A, 18 mg, 0.1 mmol) and followed by DIPEA (0.1 mL, 0.4 mmol) at rt and stirred for 1 h. Reaction mixture was directly submitted for reverse phase preparative HPLC (Prep-A) to afford (S)-3-fluoro-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile (30 mg, 55% yield) as yellow solid.

$^1H$ NMR (400 MHz, DMSO-$d_6$) b 8.06 (d, J=9.6 Hz, 1H), 7.88-7.85 (m, 2H), 7.76 (s, 1H), 7.46 (s, 1H), 4.66-5.51 (m, 3H), 4.01 (m, 1H), 3.81 (s, 3H), 3.66 (t, J=11.6 Hz, 1H), 3.56 (s, 3H), 3.32-3.23 (m, 2H).

LCMS condition A: Rt=2.87 min. m/z 515.38 $[M+H]^+$

Example 2 to Example 4 were synthesised by using chirally pure amine and Examples 5-12 ware synthesised by using racemate amine with similar protocols as described for Example 1.

| Example # | Structure | Name | SM1 | SM2 | Purification method (Prep-HPLC) |
|---|---|---|---|---|---|
| 2 | 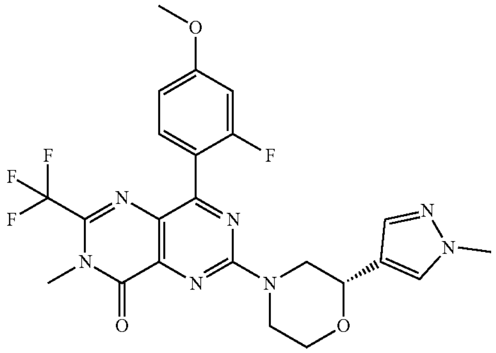 [SMILES: COc1ccc(-c2nc(N3CCO[C@@H](c4cnn(C)c4)C3)nc3c(=O)n(C)c(C(F)(F)F)nc23)c(F)c1] | (S)-8-(2-fluoro-4-methoxyphenyl)-3-methyl-6-(2-(1-methyl-1H-pyrazol-4-yl)morpholino)-2-(trifluoromethyl)pyrimido[5,4-d]pyrimidin-4(3H)-one | I-8 | I-1A | Prep-A |
| 3 | 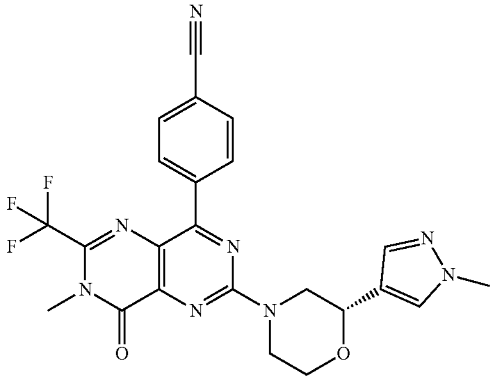 [SMILES: Cn1cc([C@H]2CN(c3nc(-c4ccc(C#N)cc4)c4nc(C(F)(F)F)n(C)c(=O)c4n3)CCO2)cn1] | (S)-4-(7-methyl-2-(2-(1-methyl-1H-pyrazol-4-yl)morpholino)-8-oxo-6-(trifluoromethyl)-7,8-dihydropyrimido[5,4-d]pyrimidin-4-yl)benzonitrile | I-9 | I-1A | Prep-A |
| 4 | 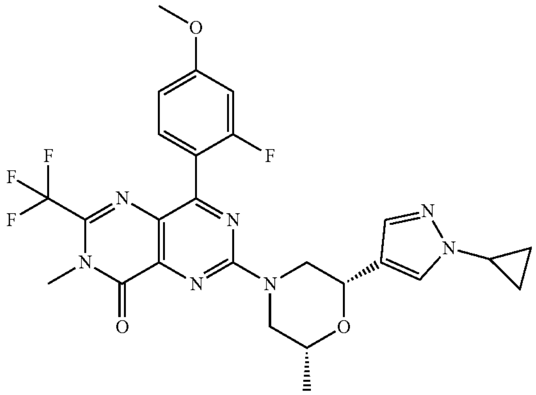 [SMILES: COc1ccc(-c2nc(N3C[C@@H](C)O[C@@H](c4cnn(C5CC5)c4)C3)nc3c(=O)n(C)c(C(F)(F)F)nc23)c(F)c1] | 6-((2S,6R)-2-(1-cyclopropyl-1H-pyrazol-4-yl)-6-methylmorpholino)-8-(2-fluoro-4-methoxyphenyl)-3-methyl-2-(trifluoromethyl)pyrimido[5,4-d]pyrimidin-4(3H)-one Stereochemistry assigned arbitrarily | I-8 | I-3A | Prep-A |
| 5 | 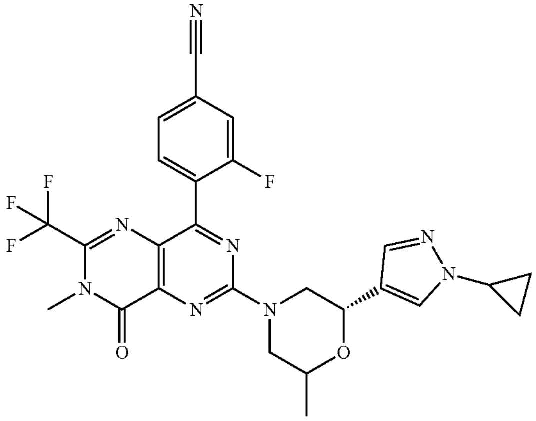 [SMILES: CC1CN(c2nc(-c3ccc(C#N)cc3F)c3nc(C(F)(F)F)n(C)c(=O)c3n2)C[C@H](c2cnn(C3CC3)c2)O1] | 6-(3-((1-cyclopropyl-1H-pyrazol-4-yl)methyl)azetidin-1-yl)-8-(2,4-difluorophenyl)-3-methyl-2-(trifluoromethyl)pyrimido[5,4-d]pyrimidin-4(3H)-one | I-7 | I-3 | Prep-A |

-continued

| Example # | Structure | Name | SM1 | SM2 | Purification method (Prep-HPLC) |
| --- | --- | --- | --- | --- | --- |
| 6 | 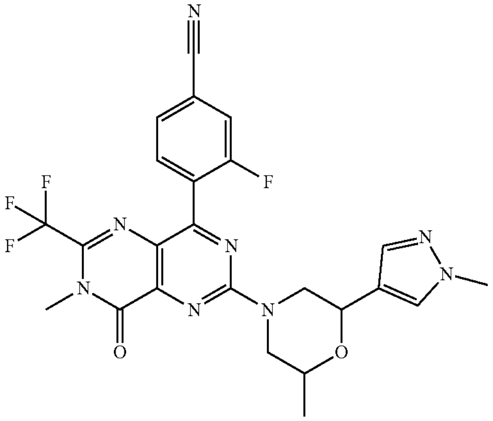 [SMILES: CC1CN(c2nc(-c3ccc(C#N)cc3F)c3nc(C(F)(F)F)n(C)c(=O)c3n2)CC(c2cnn(C)c2)O1] | 3-fluoro-4-(7-methyl-2-(2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile | I-7 | I-2 | Prep-A |
| 7 | 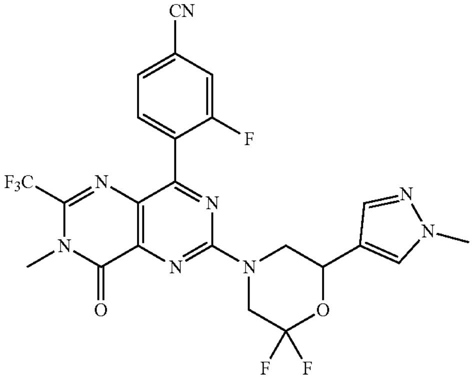 [SMILES: Cn1cc(C2CN(c3nc(-c4ccc(C#N)cc4F)c4nc(C(F)(F)F)n(C)c(=O)c4n3)CC(F)(F)O2)cn1] | 4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile | I-7 | I-4 | Prep-A |
| 8 | 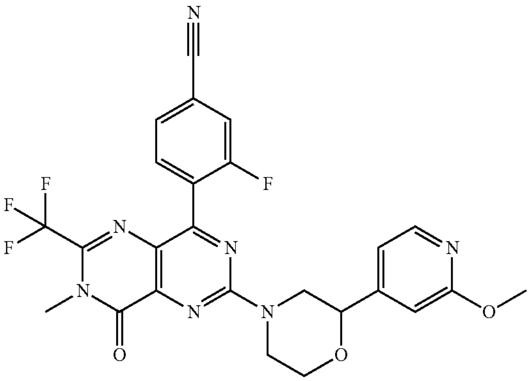 [SMILES: COc1cc(C2CN(c3nc(-c4ccc(C#N)cc4F)c4nc(C(F)(F)F)n(C)c(=O)c4n3)CCO2)ccn1] | 3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile | I-7 | I-5 | Prep-A |

-continued

| Example # | Structure | Name | SM1 | SM2 | Purification method (Prep-HPLC) |
|---|---|---|---|---|---|
| 9 | 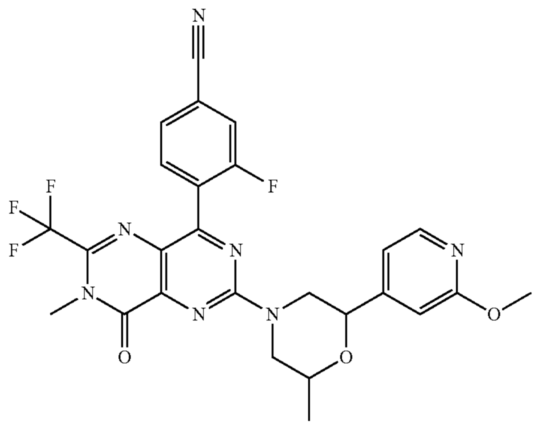 [SMILES: COc1cc(C2CN(c3nc(-c4ccc(C#N)cc4F)c4nc(C(F)(F)F)n(C)c(=O)c4n3)CC(C)O2)ccn1] | 3-fluoro-4-(2-(2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile | I-7 | I-6 | Prep-A |
| 10 | 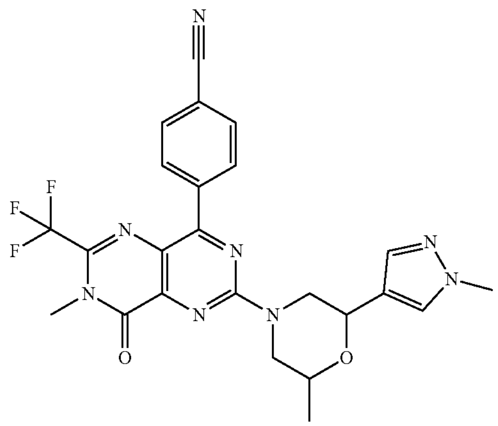 [SMILES: CC1CN(c2nc(-c3ccc(C#N)cc3)c3nc(C(F)(F)F)n(C)c(=O)c3n2)CC(c2cnn(C)c2)O1] | 4-(7-methyl-2-(2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile | I-9 | I-2 | Prep-A |
| 11 | 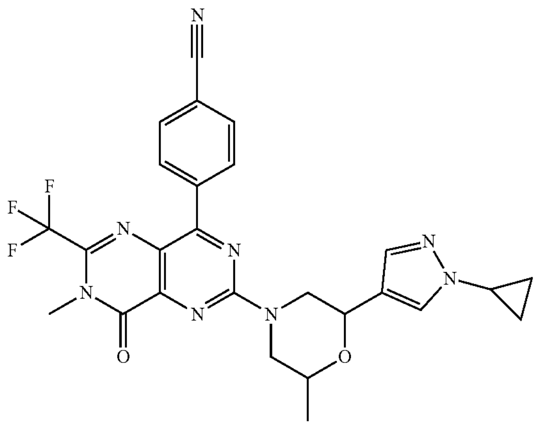 [SMILES: CC1CN(c2nc(-c3ccc(C#N)cc3)c3nc(C(F)(F)F)n(C)c(=O)c3n2)CC(c2cnn(C3CC3)c2)O1] | 4-(2-(2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile | I-9 | I-3 | Prep-A |

-continued

| Example # | Structure | Name | SM1 | SM2 | Purification method (Prep-HPLC) |
|---|---|---|---|---|---|
| 12 | 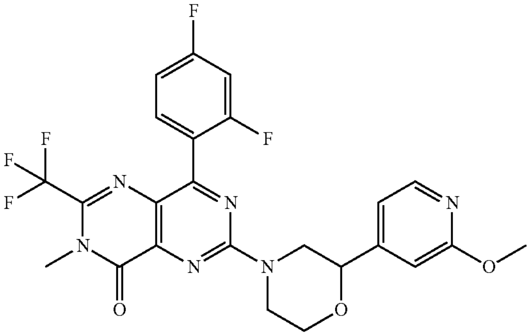 [SMILES: COc1cc(C2CN(c3nc(-c4ccc(F)cc4F)c4nc(C(F)(F)F)n(C)c(=O)c4n3)CCO2)ccn1] | 8-(2,4-difluorophenyl)-6-(2-(2-methoxypyridin-4-yl)morpholino)-3-methyl-2-(trifluoromethyl)pyrimido[5,4-d]pyrimidin-4(3H)-one | I-10 | I-5 | Prep-A |

| Target# | 1H-NMR | LCMS | Description | Yield % |
|---|---|---|---|---|
| 2 | $^1$H NMR (400 MHz, DMSO-$d_6$) δ 7.76 (s, 1H), 7.65 (t, J = 8.4 Hz, 1H), 7.46 (s, 1H), 7.02-6.93 (m, 2H), 4.71-4.68 (m, 1H), 4.61-4.58 (m, 1H), 4.53-4.50 (m, 1H), 4.00 (d, J = 12.4 Hz, 1H), 3.85 (s, 3H), 3.81 (s, 3H), 3.68-3.62 (m, 1H), 3.56 (s, 3H), 3.33-3.23 (m, 2H). | Condition A: Rt = 1.89 min. m/z 520.42 $[M + H]^+$ | Yellow solid | 35.0 |
| 3 | $^1$H NMR (400 MHz, DMSO-$d_6$) δ 8.38 (d, J = 7.6 Hz, 2H), 8.03 (d, J = 8.0 Hz, 2H), 7.77 (s, 1H), 7.48 (s, 1H), 4.72-4.64 (m, 2H), 4.54-4.52 (m, 1H), 4.05-4.02 (m, 1H) 3.82 (s, 3H), 3.70-3.65 (m, 1H), 3.58 (s, 3H), 3.30-3.24 (m, 2H). | Condition A: Rt = 2.85 min. m/z 497.40 $[M + H]^+$ | Yellow solid | 28.0 |
| 4 | $^1$H NMR (400 MHz, DMSO-$d_6$) δ 7.86 (s, 1H), 7.64 (t, J = 8.0 Hz, 1H), 7.47 (s, 1H), 7.01-6.93 (m, 2H), 4.73-4.72 (m, 2H), 4.51 (d, J = 10.4 Hz, 1H), 3.85 (s, 3H), 3.71-3.70 (m, 2H), 3.56 (s, 3H), 3.14-3.08 (m, 1H), 2.84-2.78 (m, 1H), 1.22-1.21 (m, 3H), 1.02-0.99 (m, 2H), 0.94-0.93 (m, 2H). | Condition A: Rt = 3.08 min. m/z 560.43 $[M + H]^+$ | Yellow solid | 34.0 |
| 5 | $^1$H-NMR (400 MHz, DMSO-$d_6$): δ 8.06 (d, J = 8.8 Hz, 1H), 7.88 (m, 3H), 7.47 (s, 1H), 4.77-4.70 (m, 2H), 4.52 (d, J = 10.8 Hz, 1H), 3.73-3.69 (m, 2H), 3.56 (s, 3H), 3.13 (t, J = 11.2 Hz, 1H), 2.83 (d, J = 12.0 Hz, 1H), 1.23-1.20 (m, 3H), 1.02-0.99 (m, 2H), 0.94-0.93 (m, 2H). | Condition A: Rt = 3.03 min. m/z 555.36 $[M + H]^+$ | Yellow solid | 56.0 |
| 6 | $^1$H NMR (400 MHz, DMSO-$d_6$) δ 8.06 (d, J = 9.6 Hz, 1H), 7.88-7.85 (m, 2H), 7.77 (s, 1H), 7.47 (s, 1H), 4.70-4.66 (m, 2H), 4.54 (d, J = 9.6 Hz, 1H), 3.81 (s, 3H), 3.76 (brs, 1H), 3.56 (s, 3H), 3.11 (t, J = 12.0 Hz, 1H), 2.84 (t, J = 11.2 Hz, 1H), 1.23-1.22 (m, 3H). | Condition A: Rt = 2.73 min. m/z 529.2 $[M + H]^+$ | Yellow solid | 47.0 |
| 7 | $^1$H NMR (400 MHz, DMSO-$d_6$) δ 8.08 (d, J = 9.6 Hz, 1H), 7.93-7.90 (m, 3H), 7.60 (s, 1H), 5.32-5.28 (m, 1H), 4.99 (d, J = 11.6 Hz, 1H), 4.75 (d, J = 9.6 Hz, 1H), 3.90-3.85 (m, 4H), 3.65-3.57 (m, 4H). | Condition A: Rt = 2.95 min. m/z 551.42 $[M + H]^+$ | Yellow solid | 21.0 |
| 8 | $^1$H NMR (400 MHz, DMSO-$d_6$) δ 8.18 (s, 1H), 8.10 (d, J = 10.4 Hz, 1H), 7.90 (s, 2H), 7.04 (s, 1H), 6.85 (s, 1H), 4.75-4.72 (m, 1H), 4.62 (d, J = 9.6 Hz, 2H), 4.16-4.14 (m, 1H), 3.85 (s, 3H), 3.76-3.71 (m, 1H), 3.57 (s, 3H), 3.32-3.26 (m, 1H), 3.13-3.07 (m, 1H). | Condition A: Rt = 3.37 min. m/z 542.38 $[M + H]^+$ | Yellow solid | 34.0 |
| 9 | $^1$H NMR (400 MHz, DMSO-$d_6$) δ 8.19 (s, 1H), 8.07 (d, J = 9.6 Hz, 1H), 7.90-7.89 (m, 2H), 7.05 (d, J = 5.2 Hz, 1H), 6.86 (s, 1H), 4.78-4.66 (m, 3H), 3.86-3.85 (m, 4H), 3.57 (s, 3H), 2.96-2.86 (m, 2H). 1.29-1.23 (m, 3H). | Condition A: Rt = 3.08 min. m/z 556.41 $[M + H]^+$ | Yellow solid | 32.0 |
| 10 | $^1$H NMR (400 MHz, DMSO-$d_6$) δ 8.38 (s, 2H), 8.03 (d, J = 7.6 Hz, 2H), 7.78 (s, 1H), 7.49 (s, 1H), 4.82-4.75 (m, 2H), 4.57-4.54 (m, 1H), 3.83 (s, 3H), 3.76-3.75 (m, 1H), 3.58 | Condition A: Rt = 2.92 min. m/z 511.35 $[M + H]^+$ | Yellow solid | 42.0 |

-continued

| Target# | 1H-NMR | LCMS | Description | Yield % |
|---|---|---|---|---|
| | (s, 3H), 3.15-3.09 (m, 1H), 2.87-2.81(m, 1H), 1.24 (d, J = 5.6 Hz, 3H). | | | |
| 11 | $^{1}$H NMR (400 MHz, DMSO-$d_6$) δ 8.38 (d, J = 5.6 Hz 2H), 8.05 (d, J = 7.6 Hz, 2H), 7.88 (s, 1H), 7.49 (s, 1H), 4.81-4.78 (m, 2H), 4.55-4.53 (m, 1H), 3.75-3.68 (m, 2H), 3.58 (s, 3H), 3.18-3.12 (m, 1H), 2.87-2.81 (m, 1H), 1.22 (d, J = 9.6 Hz, 3H), 1.03-0.99 (m, 2H), 0.95-0.92 (m, 2H). | Condition A: Rt = 3.04 min. m/z 537.40 $[M + H]^+$ | Yellow solid | 37.0 |
| 12 | $^{1}$H NMR (400 MHz, DMSO-$d_6$) δ 8.18 (d, J = 4.4 Hz, 1H), 7.81-7.75 (m, 1H), 7.48-7.43 (m, 1H), 7.31-7.27 (m, 1H), 7.05 (d, J = 4.4 Hz, 1H), 6.86 (s, 1H), 4.77-4.74 (m, 1H), 4.64-4.62 (m, 2H), 4.16-4.13 (m, 1H), 3.85 (s, 3H), 3.76-3.70 (m, 1H), 3.57 (s, 3H), 3.31-3.27 (m, 1H), 3.11-3.06 (m, 1H). | Condition A: Rt = 3.15 min. m/z 535.72 $[M + H]^+$ | Yellow solid | 38.0 |

Example 5A: Peak-1

4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile Example 5B: Peak-2

4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile Example 5A

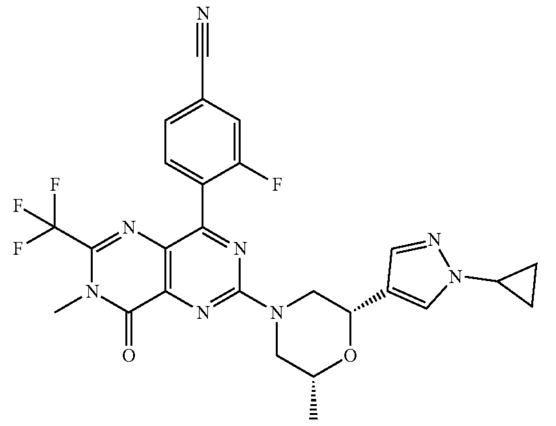

Example 5B

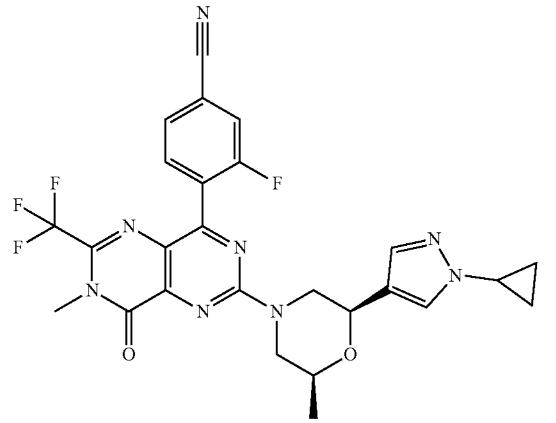

Chiral separation of 4-(2-(2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile (Example 5, 100 mg) by normal phase chiral prep HPLC (NP Chiral Method-1) afforded Example 5A, 4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile (42 mg, 42% yield; eluted first, assigned as Peak 1 with arbitrary assignment of absolute stereochemistry) as yellow solid and Example 5B, 4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)-3-fluorobenzonitrile (35 mg, 34% yield; eluted later, assigned as Peak 2 with arbitrary assignment of absolute stereochemistry) as yellow solid.

Example 5A (Peak 1):1H-NMR (400 MHz, DMSO-$d_6$): δ 8.06 (d, J=8.8 Hz, 1H), 7.88 (m, 3H), 7.47 (s, 1H), 4.77-4.70 (m, 2H), 4.52 (d, J=10.8 Hz, 1H), 3.73-3.69 (m, 2H), 3.56 (s, 3H), 3.13 (t, J=11.2 Hz, 1H), 2.83 (d, J=12.0 Hz, 1H), 1.23-1.20 (m, 3H), 1.02-0.99 (m, 2H), 0.94-0.93 (m, 2H).

LCMS Condition A: Rt=3.03 min. m/z 555.36 $[M+H]^+$

Example 5B (Peak 2):1H-NMR (400 MHz, DMSO-$d_6$): δ 8.06 (d, J=8.8 Hz, 1H), 7.88 (m, 3H), 7.47 (s, 1H), 4.77-4.70 (m, 2H), 4.52 (d, J=10.8 Hz, 1H), 3.73-3.69 (m, 2H), 3.56 (s, 3H), 3.13 (t, J=11.2 Hz, 1H), 2.83 (d, J=12.0 Hz, 1H), 1.23-1.20 (m, 3H), 1.02-0.99 (m, 2H), 0.94-0.93 (m, 2H).

LCMS Condition A: Rt=3.03 min.m/z 555.36 $[M+H]^+$

Analytical chiral HPLC: Chiralpak IG (4.6×250 mm), 5 μ ARD/K/Mobile Phase: Hexane/DCM/EtOH/IPAmine: 60/20/20/0.1 Flow Rate: 1.0 ml/min Solubility: MeOH; Rt=8.90 m for Peak 1 and Rt=10.17 m for Peak 2

The following table describes information regarding separation of enantiomers Examples 6(A-B) to 12(A-B) as described for Example 5A and 5B. Absolute stereochemistry was not determined and was assigned arbitrarily.

| Ex. # | Structure | Name | SM | Chiral Separation method |
|---|---|---|---|---|
| Ex. 6A (Peak-1) | 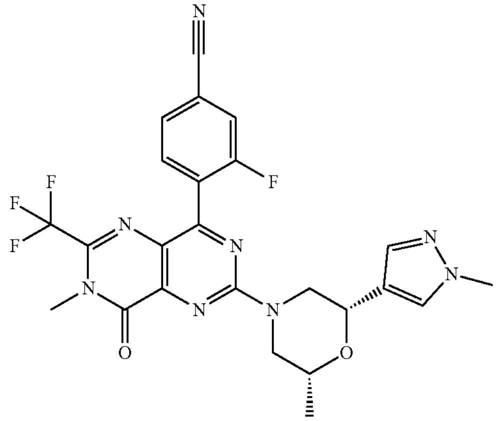 [SMILES: C[C@@H]1CN(c2nc(-c3ccc(C#N)cc3F)c3nc(C(F)(F)F)n(C)c(=O)c3n2)C[C@H](c2cnn(C)c2)O1] | 3-fluoro-4-(7-methyl-2-((2S,6R)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile | 6 | NP Chiral Method-1 |
| Ex. 6B (Peak-2) | 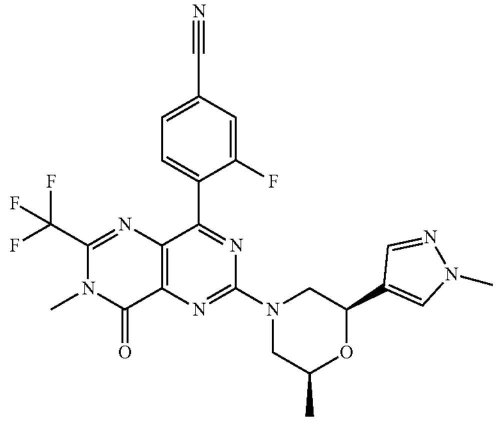 [SMILES: C[C@H]1CN(c2nc(-c3ccc(C#N)cc3F)c3nc(C(F)(F)F)n(C)c(=O)c3n2)C[C@@H](c2cnn(C)c2)O1] | 3-fluoro-4-(7-methyl-2-((2R,6S)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile | 6 | NP Chiral Method-1 |
| Ex. 7A (Peak-1) | 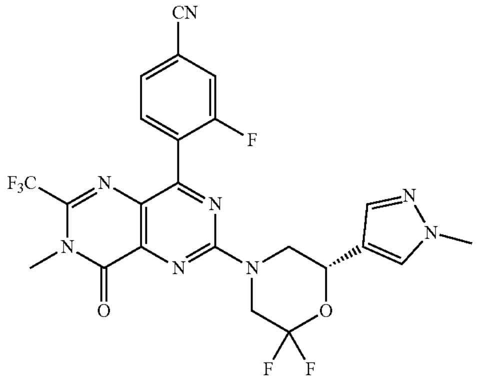 [SMILES: Cn1cc([C@H]2CN(c3nc(-c4ccc(C#N)cc4F)c4nc(C(F)(F)F)n(C)c(=O)c4n3)CC(F)(F)O2)cn1] | (S)-4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile | 7 | NP Chiral Method-1 |

-continued

| Ex. # | Structure | Name | SM | Chiral Separation method |
|---|---|---|---|---|
| Ex. 7B (Peak-2) | 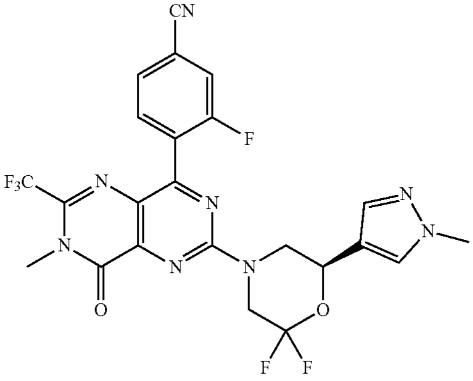 [SMILES: Cn1cc([C@@H]2CN(c3nc(-c4ccc(C#N)cc4F)c4nc(C(F)(F)F)n(C)c(=O)c4n3)CC(F)(F)O2)cn1] | (R)-4-(2-(2,2-difluoro-6-(1-methyl-1H-pyrazol-4-yl)morpholino)-7-methyl-8-oxo-6-(trifluoromethyl)-7,8-dihydropyrimido[5,4-d]pyrimidin-4-yl)-3-fluorobenzonitrile | 7 | NP Chiral Method-1 |
| Ex. 8A (Peak-1) | 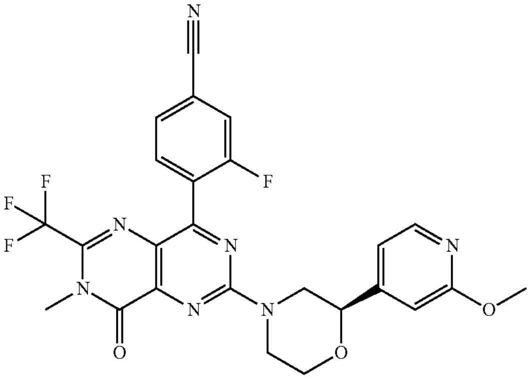 [SMILES: COc1cc([C@@H]2CN(c3nc(-c4ccc(C#N)cc4F)c4nc(C(F)(F)F)n(C)c(=O)c4n3)CCO2)ccn1] | (R)-3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile | 8 | NP Chiral Method-2 |
| Ex. 8B (Peak-2) | 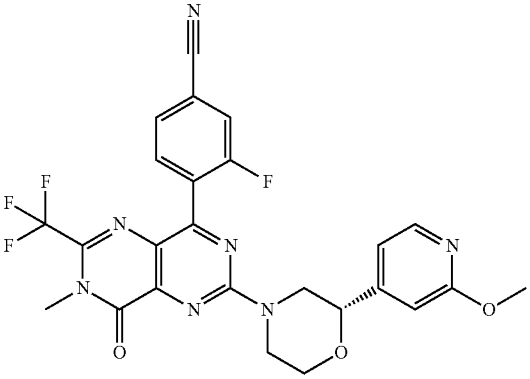 [SMILES: COc1cc([C@H]2CN(c3nc(-c4ccc(C#N)cc4F)c4nc(C(F)(F)F)n(C)c(=O)c4n3)CCO2)ccn1] | (S)-3-fluoro-4-(2-(2-(2-methoxypyridin-4-yl)morpholino)-7-methyl-8-oxo-6-(trifluoromethyl)-7,8-dihydropyrimido[5,4-d]pyrimidin-4-yl)benzonitrile | 8 | NP Chiral Method-2 |
| Ex. 9A (Peak-1) | 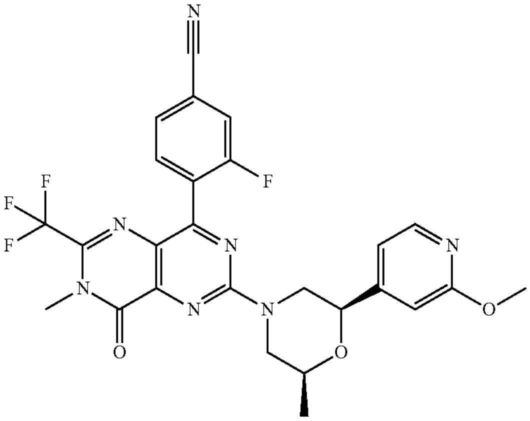 [SMILES: COc1cc([C@@H]2CN(c3nc(-c4ccc(C#N)cc4F)c4nc(C(F)(F)F)n(C)c(=O)c4n3)C[C@H](C)O2)ccn1] | 3-fluoro-4-(2-((2R,6S)-2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile | 9 | NP Chiral Method-2 |

-continued

| Ex. # | Structure | Name | SM | Chiral Separation method |
| --- | --- | --- | --- | --- |
| Ex. 9B (Peak-2) | 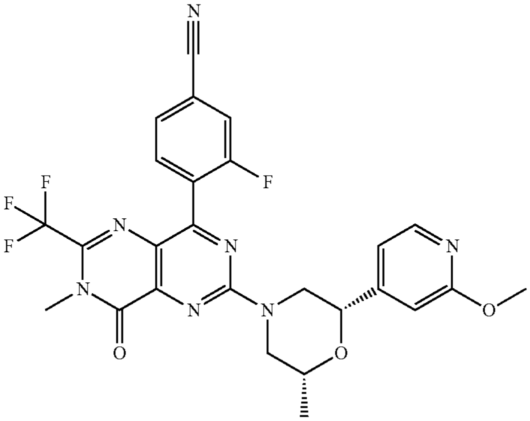 [SMILES: COc1cc([C@H]2CN(c3nc(-c4ccc(C#N)cc4F)c4nc(C(F)(F)F)n(C)c(=O)c4n3)C[C@@H](C)O2)ccn1] | 3-fluoro-4-(2-((2S,6R)-2-(2-methoxypyridin-4-yl)-6-methylmorpholino)-7-methyl-8-oxo-6-(trifluoromethyl)-7,8-dihydropyrimido[5,4-d]pyrimidin-4-yl)benzonitrile | 9 | NP Chiral Method-2 |
| Ex. 10A (Peak-1) | 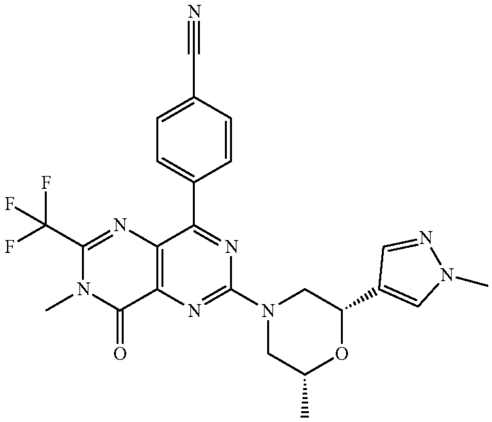 [SMILES: C[C@@H]1CN(c2nc(-c3ccc(C#N)cc3)c3nc(C(F)(F)F)n(C)c(=O)c3n2)C[C@H](c2cnn(C)c2)O1] | 4-(7-methyl-2-((2S,6R)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile | 10 | NP Chiral Method-1 |
| Ex. 10B (Peak-2) | 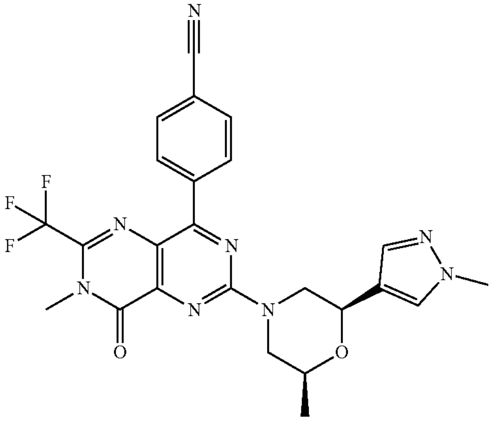 [SMILES: C[C@H]1CN(c2nc(-c3ccc(C#N)cc3)c3nc(C(F)(F)F)n(C)c(=O)c3n2)C[C@@H](c2cnn(C)c2)O1] | 4-(7-methyl-2-((2R,6S)-2-methyl-6-(1-methyl-1H-pyrazol-4-yl)morpholino)-8-oxo-6-(trifluoromethyl)-7,8-dihydropyrimido[5,4-d]pyrimidin-4-yl)benzonitrile | 10 | NP Chiral Method-1 |

-continued

| Ex. # | Structure | Name | SM | Chiral Separation method |
|---|---|---|---|---|
| Ex. 11A (Peak-1) | 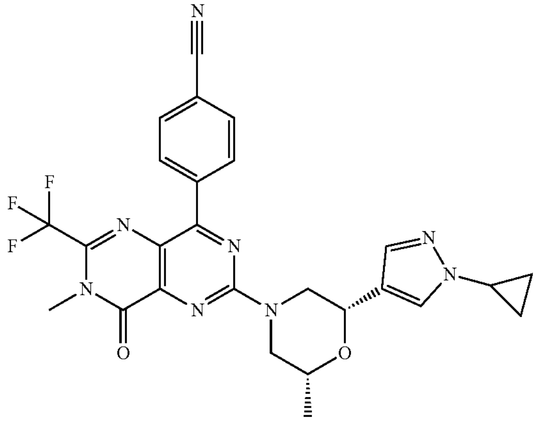 [SMILES: C[C@@H]1CN(c2nc(-c3ccc(C#N)cc3)c3nc(C(F)(F)F)n(C)c(=O)c3n2)C[C@H](c2cnn(C3CC3)c2)O1] | 4-(2-((2S,6R)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile | 11 | NP Chiral Method-1 |
| Ex. 11B (Peak-2) | 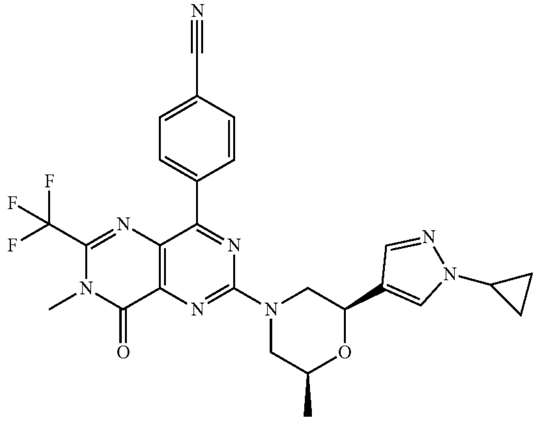 [SMILES: C[C@H]1CN(c2nc(-c3ccc(C#N)cc3)c3nc(C(F)(F)F)n(C)c(=O)c3n2)C[C@@H](c2cnn(C3CC3)c2)O1] | 4-(2-((2R,6S)-2-(1-cyclopropyl-1H-pyrazol-4-yl)-6-methylmorpholino)-7-methyl-8-oxo-6-(trifluoromethyl)-7,8-dihydropyrimido[5,4-d]pyrimidin-4-yl)benzonitrile | 11 | NP Chiral Method-1 |
| Ex. 12A (Peak-1) | 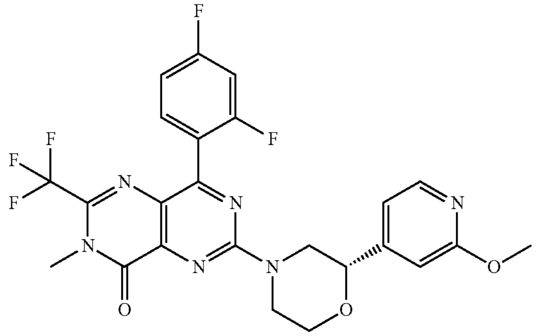 [SMILES: COc1cc([C@H]2CN(c3nc(-c4ccc(F)cc4F)c4nc(C(F)(F)F)n(C)c(=O)c4n3)CCO2)ccn1] | (S)-8-(2,4-difluorophenyl)-6-(2-(2-methoxypyridin-4-yl)morpholino)-3-methyl-2-(trifluoromethyl)pyrimido[5,4-d]pyrimidin-4(3H)-one | 12 | NP Chiral Method-1 |
| Ex. 12B (Peak-2) | 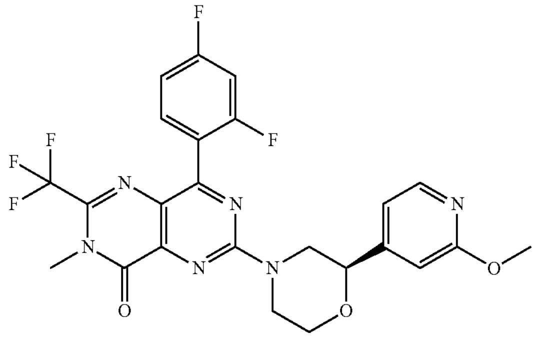 [SMILES: COc1cc([C@@H]2CN(c3nc(-c4ccc(F)cc4F)c4nc(C(F)(F)F)n(C)c(=O)c4n3)CCO2)ccn1] | (R)-8-(2,4-difluorophenyl)-6-(2-(2-methoxypyridin-4-yl)morpholino)-3-methyl-2-(trifluoromethyl)pyrimido[5,4-d]pyrimidin-4(3H)-one | 12 | NP Chiral Method-1 |

The following table describes analytical data analysis and yield information of examples 5(A-B) to 12(A-B).

| Ex # | 1H-NMR | LCMS | Chiral separation specification | Description | Yield % |
|---|---|---|---|---|---|
| Ex. 6A (Peak-1) | $^1$H NMR (400 MHz, DMSO-$d_6$) δ 8.06 (d, J = 9.6 Hz, 1H), 7.88-7.85 (m, 2H), 7.77 (s, 1H), 7.47 (s, 1H), 4.70-4.66 (m, 2H), 4.54 (d, J = 9.6 Hz, 1H), 3.81 (s, 3H), 3.76 (brs, 1H), 3.56 (s, 3H), 3.11 (t, J = 12.0 Hz, 1H), 2.84 (t, J = 11.2 Hz, 1H), 1.23-1.22 (m, 3H). | Condition A: Rt = 2.73 min. m/z 529.2 [M + H]$^+$ | Chiralpak IG (4.6 × 250 mm),5μ ARD/K/Mobile Phase: Hexane/EA/EtOH/ IPAmine: 50/25/25/0.1 Flow Rate: 1.0 ml/min Solubility: MeOH; Rt = 6.52 min for Peak 1 and Rt = 7.42 min | Yellow solid | 35.0 |
| Ex. 6B (Peak-2) | $^1$H NMR (400 MHz, DMSO-$d_6$) δ 8.06 (d, J = 9.6 Hz, 1H), 7.88-7.85 (m, 2H), 7.77 (s, 1H), 7.47 (s, 1H), 4.70-4.66 (m, 2H), 4.54 (d, J = 9.6 Hz, 1H), 3.81 (s, 3H), 3.76 (brs, 1H), 3.56 (s, 3H), 3.11 (t, J = 12.0 Hz, 1H), 2.84 (t, J = 11.2 Hz, 1H), 1.23-1.22 (m, 3H). | Condition A: Rt = 2.73 min. m/z 529.2 [M + H]$^+$ | for Peak 2 | Yellow solid | 35.0 |
| Ex. 7A (Peak-1) | $^1$H NMR (400 MHz, DMSO-$d_6$) δ 8.08 (d, J = 9.6 Hz, 1H), 7.93-7.90 (m, 3H), 7.60 (s, 1H), 5.32-5.28 (m, 1H), 4.99 (d, J = 11.6 Hz, 1H), 4.75 (d, J = 9.6 Hz, 1H), 3.90-3.85 (m, 4H), 3.65-3.57 (m, 4H). | Condition A: Rt = 2.95 min. m/z 551.42 [M + H]$^+$ | Chiralpak IG (4.6 × 250 mm), 5μ ARD/K/Mobile Phase: Hexane/EA/EtOH/ IPAmine: 60/20/20/0.1 Flow Rate: 1.0 ml/min Solubility: MeOH; | Yellow solid | 22.0 |
| Ex. 7B (Peak-2) | $^1$H NMR (400 MHz, DMSO-$d_6$) δ 8.08 (d, J = 9.6 Hz, 1H), 7.93-7.90 (m, 3H), 7.60 (s, 1H), 5.32-5.28 (m, 1H), 4.99 (d, J = 11.6 Hz, 1H), 4.75 (d, J = 9.6 Hz, 1H), 3.90-3.85 (m, 4H), 3.65-3.57 (m, 4H). | Condition A: Rt = 2.95 min. m/z 551.42 [M + H]$^+$ | Rt = 8.56 min for Peak 1 and Rt = 9.21 min for Peak 2 | Yellow solid | 14.0 |
| Ex. 8A (Peak-1) | $^1$H NMR (400 MHz, DMSO-$d_6$) δ 8.18 (s, 1H), 8.10 (d, J = 10.4 Hz, 1H), 7.90 (s, 2H), 7.04 (s, 1H), 6.85 (s, 1H), 4.75-4.72 (m, 1H), 4.62 (d, J = 9.6 Hz, 2H), 4.16-4.14 (m, 1H), 3.85 (s, 3H), 3.76-3.71 (m, 1H), 3.57 (s, 3H), 3.32-3.26 (m, 1H), 3.13-3.07 (m, 1H). | Condition A: Rt = 3.37 min. m/z 542.21 [M + H]$^+$ | Chiralpak IC (250 × 4.6) mm, 5μ M.P.-Hexane/DCM/ EtOH/IPAmine: 60/20/20/0.1 Flow Rate - 1.0 ml/min Solubility: MeOH; Rt = 7.42 min for Peak 1 and Rt = 8.36 min | Yellow solid | 39.0 |
| Ex. 8B (Peak-2) | $^1$H NMR (400 MHz, DMSO-$d_6$) δ 8.18 (s, 1H), 8.10 (d, J = 10.4 Hz, 1H), 7.90 (s, 2H), 7.04 (s, 1H), 6.85 (s, 1H), 4.75-4.72 (m, 1H), 4.62 (d, J = 9.6 Hz, 2H), 4.16-4.14 (m, 1H), 3.85 (s, 3H), 3.76-3.71 (m, 1H), 3.57 (s, 3H), 3.32-3.26 (m, 1H), 3.13-3.07 (m, 1H). | Condition A: Rt = 3.37 min. m/z 542.21 [M + H]$^+$ | for Peak 2 | Yellow solid | 40.0 |
| Ex. 9A (Peak-1) | $^1$H NMR (400 MHz, DMSO-$d_6$) δ 8.19 (s, 1H), 8.07 (d, J = 9.6 Hz, 1H), 7.90-7.89 (m, 2H), 7.05 (d, J = 5.2 Hz, 1H), 6.86 (s, 1H), 4.78-4.66 (m, 3H), 3.86-3.85 (m, 4H), 3.57 (s, 3H), 2.96-2.86 (m, 2H). 1.29-1.23 (m, 3H). | Condition A: Rt = 3.08 min. m/z 556.41 [M + H]$^+$ | Chiralpak IC (250 × 4.6) mm, 5μ M.P.- Hexane/DCM/ EtOH/IPAmine: 60/20/20/0.1 Flow Rate - 1.0 ml/min Solubility: MeOH; | Yellow solid | 38.0 |
| Ex. 9B (Peak-2) | $^1$H NMR (400 MHz, DMSO-$d_6$) δ 8.19 (s, 1H), 8.07 (d, J = 9.6 Hz, 1H), 7.90-7.89 (m, 2H), 7.05 (d, J = 5.2 Hz, 1H), 6.86 (s, 1H), 4.78-4.66 (m, 3H), 3.86-3.85 (m, 4H), 3.57 (s, 3H), 2.96-2.86 (m, 2H). 1.29-1.23 (m, 3H). | Condition A: Rt = 3.08 min. m/z 556.41 [M + H]$^+$ | Rt = 6.27 min for Peak 1 and Rt = 6.92 min for Peak 2 | Yellow solid | 36.0 |

-continued

| Ex # | 1H-NMR | LCMS | Chiral separation specification | Description | Yield % |
|---|---|---|---|---|---|
| Ex. 10A (Peak-1) | $^1H$ NMR (400 MHz, DMSO-$d_6$) δ 8.38 (s, 2H), 8.03 (d, J = 7.6 Hz, 2H), 7.78 (s, 1H), 7.49 (s, 1H), 4.82-4.75 (m, 2H), 4.57-4.54 (m, 1H), 3.83 (s, 3H), 3.76-3.75 (m, 1H), 3.58 (s, 3H), 3.15-3.09 (m, 1H), 2.87-2.81(m, 1H), 1.24 (d, J = 5.6 Hz, 3H). | Condition A: Rt = 2.89 min. m/z 511.39 $[M + H]^+$ | Chiralpak IG (4.6 × 250 mm), 5μ ARD/K/Mobile Phase: Hexane/DCM/EtOH/ IPAmine: 50/25/25/0.1 Flow Rate: 1.0 ml/min Solubility: MeOH; Rt = 5.80 min for Peak | Yellow solid | 40.0 |
| Ex. 10B (Peak-2) | $^1H$ NMR (400 MHz, DMSO-$d_6$) δ 8.38 (s, 2H), 8.03 (d, J = 7.6 Hz, 2H), 7.78 (s, 1H), 7.49 (s, 1H), 4.82-4.75 (m, 2H), 4.57-4.54 (m, 1H), 3.83 (s, 3H), 3.76-3.75 (m, 1H), 3.58 (s, 3H), 3.15-3.09 (m, 1H), 2.87-2.81(m, 1H), 1.24 (d, J = 5.6 Hz, 3H). | Condition A: Rt = 2.89 min. m/z 511.39 $[M + H]^+$ | 1 and Rt = 6.34 min for Peak 2 | Yellow solid | 41.0 |
| Ex. 11A (Peak-1) | $^1H$ NMR (400 MHz, DMSO-$d_6$) δ 8.38 (d, J = 5.6 Hz, 2H), 8.05 (d, J = 7.6 Hz, 2H), 7.88 (s, 1H), 7.49 (s, 1H), 4.81-4.78 (m, 2H), 4.55-4.53 (m, 1H), 3.75-3.68 (m, 2H), 3.58 (s, 3H), 3.18-3.12 (m, 1H), 2.87-2.81 (m, 1H), 1.22 (d, J = 9.6 Hz, 3H), 1.03-0.99 (m, 2H), 0.95-0.92 (m, 2H). | Condition A: Rt = 3.04 min. m/z 537.40 $[M + H]^+$ | Chiralpak IG (4.6 × 250 mm), 5μ ARD/K/Mobile Phase: Hexane/EA/EtOH/ IPAmine: 50/25/25/0.1 Flow Rate: 1.0 ml/min Solubility: MeOH; Rt = 9.84 min for Peak 1 and Rt = 11.42 min | Yellow solid | 35.0 |
| Ex. 11B (Peak-2) | $^1H$ NMR (400 MHz, DMSO-$d_6$) δ 8.38 (d, J = 5.6 Hz, 2H), 8.05 (d, J = 7.6 Hz, 2H), 7.88 (s, 1H), 7.49 (s, 1H), 4.81-4.78 (m, 2H), 4.55-4.53 (m, 1H), 3.75-3.68 (m, 2H), 3.58 (s, 3H), 3.18-3.12 (m, 1H), 2.87-2.81 (m, 1H), 1.22 (d, J = 9.6 Hz, 3H), 1.03-0.99 (m, 2H), 0.95-0.92 (m, 2H). | Condition A: Rt = 3.04 min. m/z 537.40 $[M + H]^+$ | for Peak 2 | Yellow solid | 37.0 |
| Ex. 12A (Peak-1) | $^1H$ NMR (400 MHz, DMSO-$d_6$) δ 8.18 (d, J = 4.4 Hz, 1H), 7.81-7.75 (m, 1H), 7.48-7.43 (m, 1H), 7.31-7.27 (m, 1H), 7.05 (d, J = 4.4 Hz, 1H), 6.86 (s, 1H), 4.77-4.74 (m, 1H), 4.64-4.62 (m, 2H), 4.16-4.13 (m, 1H), 3.85 (s, 3H), 3.76-3.70 (m, 1H), 3.57 (s, 3H), 3.31-3.27 (m, 1H), 3.11-3.06 (m, 1H). | Condition A: Rt = 3.15 min. m/z 535.72 $[M + H]^+$ | Chiralpak IG (4.6 × 250 mm), 5μ ARD/K/Mobile Phase: Hexane/EA/EtOH/ IPAmine: 50/25/25/0.1 Flow Rate: 1.0 ml/min Solubility: MeOH; Rt = 4.62 min for Peak 1 and Rt = 5.20 min for Peak 2 | Yellow solid | 23.0 |
| Ex. 12B (Peak-2) | $^1H$ NMR (400 MHz, DMSO-$d_6$) δ 8.18 (d, J = 4.4 Hz, 1H), 7.81-7.75 (m, 1H), 7.48-7.43 (m, 1H), 7.31-7.27 (m, 1H), 7.05 (d, J = 4.4 Hz, 1H), 6.86 (s, 1H), 4.77-4.74 (m, 1H), 4.64-4.62 (m, 2H), 4.16-4.13 (m, 1H), 3.85 (s, 3H), 3.76-3.70 (m, 1H), 3.57 (s, 3H), 3.31-3.27 (m, 1H), 3.11-3.06 (m, 1H). | Condition A: Rt = 3.15 min. m/z 535.72 $[M + H]^+$ | | Yellow solid | 31.0 |

Example 13

Example 13A: Peak-1

4-(6-((2S,6R)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile Example 13B: Peak-2

4-(6-((2R,6S)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile Step-1

Preparation of 4-(6-(2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile

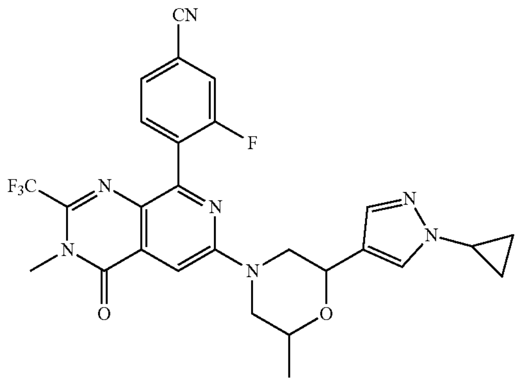 [SMILES: CC1CN(c2cc3c(=O)n(C)c(C(F)(F)F)nc3c(-c3ccc(C#N)cc3F)n2)CC(c2cnn(C3CC3)c2)O1]

To a stirred solution of 4-(6-chloro-3-methyl-4-oxo-2-(trifluoromethyl)-3,4-dihydropyrido[3,4-d]pyrimidin-8-yl)-3-fluorobenzonitrile (130 mg, 0.34 mmol) and 2-(1-cyclopropyl-1H-pyrazol-4-yl)-6-methylmorpholine (77 mg, 0.37 mmol) in toluene (4 mL) degassed with argon was added caesium carbonate (221 mg, 0.68 mmol) and RuPhos (15 mg, 0.03 mmol) and RuPhos-Pd-G3 (28 mg, 0.03 mmol). The resulting mixture was heated at 80° C. for 3 h. Reaction mixture was diluted with DCM, filtered through a short pad of celite and washed with ethyl acetate. Combined organic layer was washed with water, brine, dried over anhydrous sodium sulphate, filtered and concentrated under reduced pressure. Crude was purified by Prep-HPLC (Prep-A) to afford 4-(6-(2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile (40 mg; 21% yield) as yellow solid.

1H-NMR (400 MHz, DMSO-$d_6$): δ 8.00 (d, J=8.8 Hz, 1H), 7.84-7.77 (m, 3H), 7.47 (s, 2H), 4.58-4.54 (m, 1H), 4.46-4.37 (m, 2H), 3.79-3.65 (m, 2H), 3.56 (s, 3H), 2.98-2.88 (m, 1H), 2.72-2.68 (m, 1H), 1.22-1.15 (m, 3H), 1.03-0.99 (m, 2H), 0.94-0.92 (m, 2H).

LCMS condition A: Rt=3.16 min. m/z 554.46 $[M+H]^+$

Step-2

Preparation of 4-(6-((2S,6R)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile (Example 13A) and 4-(6-((2R,6S)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile (Example 13B)

Example 13A

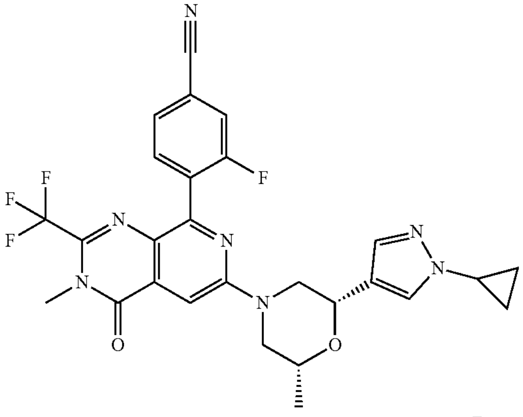

and

Example 13B

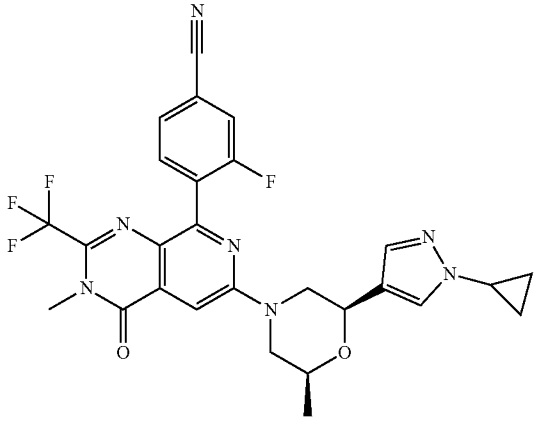

Chiral separation of 4-(6-(2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile (35 mg) by normal phase chiral prep HPLC (NP Chiral Method-1) afforded Example 13A, 4-(6-((2S,6R)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile (12 mg, 33% yield; eluted first, assigned as Peak 1 with arbitrary assignment of stereochemistry) as off-white solid and Example 13B, 4-(6-((2R,6S)-2-(1-cyclopropyl-1H-pyrazol-4-yl)-6-methylmorpholino)-3-methyl-4-oxo-2-(trifluoromethyl)-3,4-dihydropyrido[3,4-d]pyrimidin-8-yl)-3-fluorobenzonitrile (13 mg, 34% yield; eluted later, assigned as Peak 2 with arbitrary assignment of stereochemistry) as off-white solid.

Example 13A (Peak 1): 1H-NMR (400 MHz, DMSO-$d_6$): δ 8.00 (d, J=8.8 Hz, 1H), 7.84-7.77 (m, 3H), 7.47 (s, 2H), 4.58-4.54 (m, 1H), 4.46-4.37 (m, 2H), 3.79-3.65 (m, 2H), 3.56 (s, 3H), 2.98-2.88 (m, 1H), 2.72-2.68 (m, 1H), 1.22-1.15 (m, 3H), 1.03-0.99 (m, 2H), 0.94-0.92 (m, 2H).

LCMS condition A: Rt=3.16 min. m/z 554.46 $[M+H]^+$

Example 13B (Peak 2): 1H-NMR (400 MHz, DMSO-$d_6$): δ 8.00 (d, J=8.8 Hz, 1H), 7.84-7.77 (m, 3H), 7.47 (s, 2H), 4.58-4.54 (m, 1H), 4.46-4.37 (m, 2H), 3.79-3.65 (m, 2H), 3.56 (s, 3H), 2.98-2.88 (m, 1H), 2.72-2.68 (m, 1H), 1.22-1.15 (m, 3H), 1.03-0.99 (m, 2H), 0.94-0.92 (m, 2H).

LCMS condition A: Rt=3.16 min. m/z 554.46 $[M+H]^+$

Analytical chiral HPLC: Chiralpak IG (4.6×250 mm), 5 μ ARD/K/Mobile Phase: Hexane/EA/EtOH/IPAmine: 50/25/25/0.1 Flow Rate: 1.0 ml/min; Solubility: MeOH; Rt=5.80 min for Peak 1 and Rt=6.82 min for Peak 2

Example 14

Example 14A: Peak-1

(S)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile Example 14B: Peak-2

(R)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile Step-1

Preparation of 4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile

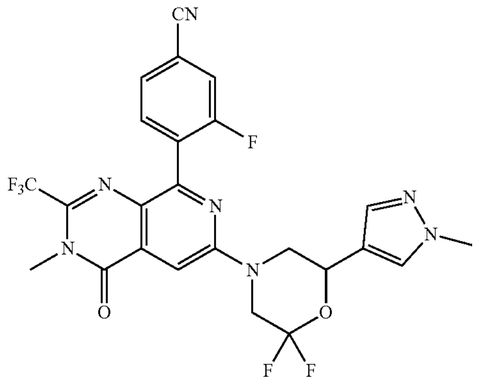

4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile (30 mg, % yield; yellow solid) was synthesized by using similar protocol mentioned Example 13A and 13B (Step-1) using 4-(6-chloro-3-methyl-4-oxo-2-(trifluoromethyl)-3,4-dihydropyrido[3,4-d]pyrimidin-8-yl)-3-fluorobenzonitrile and 2,2-difluoro-6-(1-methyl-1H-pyrazol-4-yl)morpholine.

$^1$H NMR (400 MHz, DMSO-$d_6$) b 8.01 (d, J=9.6 Hz, 1H), 7.91 (s, 1H), 7.86-7.81 (m, 2H), 7.62 (s, 1H), 7.60 (s, 1H), 5.33-5.30 (m, 1H), 4.81 (d, J=14.0 Hz, 1H), 4.53 (d, J=13.2 Hz, 1H), 3.84 (s, 3H), 3.80-3.71 (m, 1H), 3.75 (s, 3H), 3.50-3.44 (m, 1H).

LCMS condition A: Rt=3.05 min. m/z 550.43 $[M+H]^+$

Step-2

Preparation of (S)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile (Example 14A) and (R)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile (Example 14B)

Example 14A

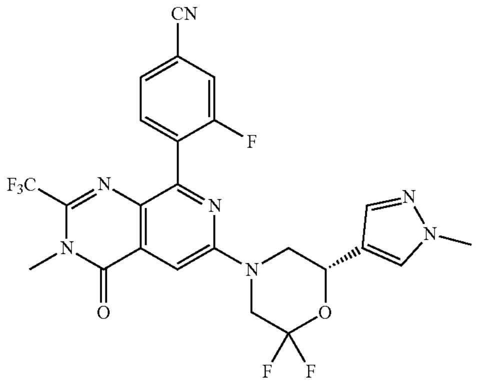

and

Example 14B

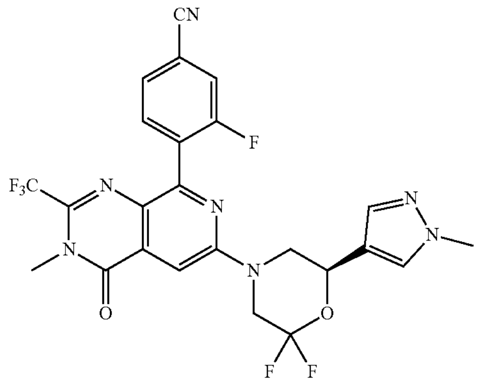

Chiral separation of 4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile (35 mg) by normal phase chiral prep HPLC (NP Chiral Method-1) afforded Example 14A, (R)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile (15 mg, 33% yield; eluted first, assigned as Peak 1 with arbitrary assignment of stereochemistry) as yellow solid and Example 14B, (S)-4-(6-(2,2-difluoro-6-(1-methyl-1H-pyrazol-4-yl)morpholino)-3-methyl-4-oxo-2-(trifluoromethyl)-3,4-dihydropyrido[3,4-d]pyrimidin-8-yl)-3-fluorobenzonitrile (13 mg, 28% yield; eluted later, assigned as Peak 2 with arbitrary assignment of stereochemistry) as yellow solid.

Example 14A (Peak 1): $^1$H NMR (400 MHz, DMSO-$d_6$) b 8.01 (d, J=9.6 Hz, 1H), 7.91 (s, 1H), 7.86-7.81 (m, 2H), 7.62 (s, 1H), 7.60 (s, 1H), 5.33-5.30 (m, 1H), 4.81 (d, J=14.0

Hz, 1H), 4.53 (d, J=13.2 Hz, 1H), 3.84 (s, 3H), 3.80-3.71 (m, 1H), 3.75 (s, 3H), 3.50-3.44 (m, 1H).

LCMS Condition A: Rt=3.05 min. m/z 550.43 $[M+H]^+$,

Example 14B (Peak 2): $^1$H NMR (400 MHz, DMSO-$d_6$) b 8.01 (d, J=9.6 Hz, 1H), 7.91 (s, 1H), 7.86-7.81 (m, 2H), 7.62 (s, 1H), 7.60 (s, 1H), 5.33-5.30 (m, 1H), 4.81 (d, J=14.0 Hz, 1H), 4.53 (d, J=13.2 Hz, 1H), 3.84 (s, 3H), 3.80-3.71 (m, 1H), 3.75 (s, 3H), 3.50-3.44 (m, 1H).

LCMS Condition A: Rt=3.05 min. m/z 550.43 $[M+H]^+$

Analytical chiral HPLC: Chiralpak OD-H (4.6×250 mm), 5 μ ARD/K/Mobile Phase: Hexane/EtOH/IPAmine: 50/50//0.1 Flow Rate: 1.0 ml/min Solubility: MeOH; Rt=11.13 min for Peak 1 and Rt=15.30 min for Peak 2.

Example 15

(S)-3-fluoro-4-(3-methyl-6-(2-(1-methyl-1H-pyrazol-4-yl)morpholino)-4-oxo-2-(trifluoromethyl)-3,4-dihydro-pyrido[3,4-d]pyrimidin-8-yl)benzonitrile

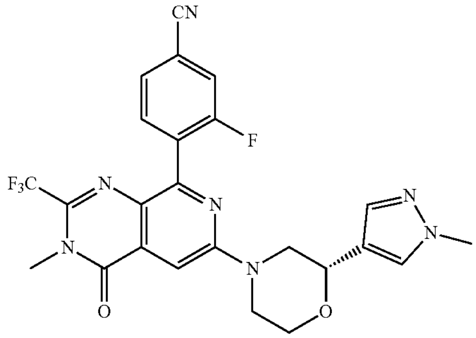

(S)-3-fluoro-4-(3-methyl-6-(2-(1-methyl-1H-pyrazol-4-yl) morpholino)-4-oxo-2-(trifluoromethyl)-3,4-dihydro-pyrido[3,4-d]pyrimidin-8-yl)benzonitrile (107 mg, 66% yield; yellow solid) was synthesized by using the similar protocol as Example 13A and 13B (Step-1) using 4-(6-chloro-3-methyl-4-oxo-2-(trifluoromethyl)-3,4-dihydro-pyrido[3,4-d]pyrimidin-8-yl)-3-fluorobenzonitrile and (S)-2-(1-methyl-1H-pyrazol-4-yl)morpholine. 1H NMR (400 MHz, MeOD) b 7.77 (t, J=7.6 Hz, 1H), 7.67-7.65 (m, 3H), 7.52 (s, 1H), 7.46 (s, 1H), 4.64-4.61 (m, 1H), 4.45 (d, J=12.8 Hz, 1H), 4.26 (d, J=12.8 Hz, 1H), 4.07 (d, J=11.6 Hz, 1H), 3.87 (s, 3H), 3.84-3.78 (m, 1H), 3.66 (s, 3H), 3.24-3.18 (m, 1H), 3.16-3.10 (m, 1H).

LCMS Condition A: Rt=2.97 min. m/z 514.39 $[M+H]^+$

Example 16—Biological evaluation

Human TREM2, in vitro Measurement of Triggering Receptor Expressed on Myeloid Cells 2 activity using cellular phosphorylation of Spleen Tyrosine Kinase ("Syk") Assay Cell line:

HEK-293 cells were co-transfected with separate plasmids encoding TREM2 and DAP12 to generate a stable cell line. After antibiotic selection, functional clone pool analysis and two successive limiting dilutions, the final clone "HEK293/DAP12+TREM2" underwent a qPCR analysis and a pharmacological validation.

Assay

TREM2 signaling through DAP12 was monitored in the HEK293/DAP12+TREM2 stable cell line by measuring the phosphorylation levels of the Syk kinase using the commercially available AlphaLISA SureFire Ultra p-SYK (Tyr525/526) Assay Kit (PerkinElmer #ALSU-PSYK), based on the Perkin Elmer AlphaScreen/AlphaLISA technology.

Compounds are transferred to the test plate and tested in full dose response, 8 concentrations in quadruplicate data points. Compound serial dilutions were performed at Cybi-Felix instrument in 100% DMSO and the dose response curves were assembled in automated fashion in 384MPT at Hamilton STARlet instrument. All the stock solutions were prepared at 20 mM in 100% DMSO. For compounds testing, the starting concentration was 100 μM, dilution steps 1:6. A different concentration's range was adapted for compound's activity based on the preliminary results. Finally, a 384MPT reformatted for all compounds at 8 concentrations, quadruplicates, was used as "mother to child" process with a CyBi®-Well dispenser in which 1 μL of each compound was moved into a destination plate pre-filled with 65.6 μL of EMEM cell culture medium (BIOWHITTAKER_cat.BE12-125F), thus obtaining 3× concentrated compounds working solution. In columns 1-2 and 23-24 the control wells were added. In particular, dose response curves of a reference control agonist were included in column 1 and 24 as reference control agonist (Reference control agonists used include Human TREM2 polyclonal Antibody AF1828: R&D Systems; Human TREM2 monoclonal Antibody MAB1828: R&D Systems). The dose response curves were tested starting at 30 μM, dilution step 1:6. Both "source" compound plate and "destination" compound plate were barcoded and a relationship between the two plates was thus generated.

HEK293/DAP12+TREM2 cells were cultured in EMEM medium supplemented with IX Penicillin/Streptomycin (BIOWHITTAKER_cat.DE17-602E), ULTRAGLUTAMINE I 200 mM, 10% Fetal Bovine Serum plus antibiotics referred to as "HEK293 Culture Medium". The day before the experiment, cells were detached by gentle wash with DPBS, followed by 5 min incubation at 37° C. with Trypsin solution. Cells were then diluted in HEK293 Culture Medium without antibiotics, counted and seeded into 384-well poly-D-Lysine coated microplates black/clear bottom (GREINER 781946) at a density of 10,000 cells/well in 25 μL/well by the use of a MATRIX WellMate dispenser. Plates were placed into a humidified cell culture incubator at 37° C. with 5% $CO_2$ until the experimental day. 20-24 hours after seeding mature medium was removed and replaced with 10 μL/well of EMEM cell medium supplemented with 0.1% Pluronic F-68 non-ionic surfactant (Thermofisher, 24040032), referred to as "Assay Buffer", using the CyBi®-Well instrument. Then 5 μL/well of Assay Buffer containing 3× concentrated test compounds or the reference control agonist (in 0.5% final DMSO concentration) were added to the cells with the CyBi®-Well instrument. Cell plates were incubated for 30 min into a humidified cell culture incubator at 37° C. with 5% $C_{O2}$,then the medium was removed by manually discard. 20 μL/well of lysis buffer were dispensed using the CyBi®-Well instrument and plates were incubated for 10 min at room temperature on a plate shaker (350 rpm). Then, 10 μL/well of lysate were transferred to the Alpha plates. The CyBi®-Well instrument was used to dispense 5 μL/well of AlphaLISA Acceptor Bead Solution in IX Immunoassay buffer (Perkin Elmer ALOOOF). Then the plates were sealed with Heat sealing foil, shaked for 2 minutes (350 rpm) and incubated for 1 hour at room temperature. Following the incubation with the AlphaLISA Acceptor Bead Solution, the CyBi®-Well instrument was used to dispense 5 μL/well of AlphaLISA Donor Bead Solution in IX Immunoassay buffer. The plates were sealed with Heat sealing foil, shaked for 2 minutes (350 rpm) and then incubated for 1 hour at room temperature. At the end of the incubation an AlphaLISA signal was acquired from the donor and acceptor beads using the Pherastar FSX instrument, a high throughput multi-modal microplate reader calibrated to the plate type with the AlphaLISA mirror and filter-set in 384-well mode, 680-615 nanometer excitation wavelength. The total integration time was 0.60 seconds with a 0.30 second excitation time and a gain of 3600.

Data analysis was performed with Genedata Screener@software and reported compounds activity as % effect in relation to the normalization standards. The AlphaScreen Signal was normalized versus Neutral Controls (Assay buffer plus 0.5% DMSO final conc.) and Stimulator Controls ($EC_{100}$ of the reference control agonist in Assay buffer plus 0.5% DMSO final conc.) in order to obtain the Activity[%]for each well. The normalization places the compound activity values on an equivalent scale and makes them comparable across plates or different compound batches. Therefore, the compound activity values were scaled (based on the two references) to a common range (two-point normalization). The following equation was used by the software to normalize the signal values to the desired signal range:

$$N(x) = CR + \left[\left((x - <cr>)/(<sr> - <cr>)\right) \cdot (SR - CR)\right]$$

where: x is the signal value of a well; <cr > is the median of the signal values for the Central Reference wells of a plate (median of Neutral Controls); <sr > is the median of the signal values for the Scale Reference wells of a plate (median of Stimulator Controls); CR is the desired median normalized value for the Central Reference (0) and SR is the desired median normalized value for the Scale Reference (100).

The final equation to calculate the Activity % can be simplified as follow:

$$\%\ Activity = 100 \cdot \left(x - <NeutralControls>\right)/\left(<StimulatorControls> - <NeutralControls>\right)$$

where full activation corresponds to % Activity=100.

The fitting of the dose-response curve of each test compound is performed in the Analyzer module of the Screener software on the normalized values and applying the "smart fit" strategy. This strategy allowed an automatic selection between the "Constant Fit" and the "Hill Fit" model calculating which fit model best matched the experimental data. The Constant Fit was applied when no change of activity was detected across the measured concentrations, and the corresponding compounds were further classified as "inactive". The Hill Fit was applied when the observed activity significantly changed with the compound concentration. In case of Hill Fit, Hill equation was used to determine the concentration at which activity reaches 50% of maximum level, i.e., $AC_{50}$.

$$Y = S_0 + \left((S_{inf} - S_0)/\left(1 + \left(10^{LogAC50}/10^X\right)^n\right)\right)$$

where X is Log10 of compound concentration.

The equation has four parameters:

Zero Activity (SO) —Activity level at zero concentration of test compound;

Infinite Activity ($S_{inf}$) —Activity level at infinite concentration of test compound;

$AC_{50}$-Concentration at which activity reaches 50% of maximum level. This term corresponds to $EC_{50}$ in this assay;

Hill coefficient (n) —Measure of the slope at $AC_{50}$

The potency of the test compounds was expressed as $EC_{50}$ corresponding to the test compound concentration able to activate the phospho-Syk AlphaScreen signal to 50% of the maximal response.

The $EC_{50}$ values measured in this assay for the exemplified compounds and other TREM2 modulating compounds are set out in the table below:

| Example | $EC_{50}$ | $E_{max}$ |
|---|---|---|
| 1 | A | ++ |
| 2 | B | ++ |
| 3 | B | + |
| 4 | A | ++ |
| 5A | A | +++ |
| 5B | B | +++ |
| 6A | B | ++ |
| 6B | B | ++ |
| 7A | A | +++ |
| 7B | B | ++ |
| 8A | C | ++ |
| 8B | A | ++ |
| 9A | A | ++ |
| 9B | A | ++ |
| 10A | A | ++ |
| 10B | B | ++ |
| 11A | A | ++ |
| 11B | B | ++ |
| 12A | A | ++ |
| 12B | C | ++ |
| 13A | A | ++ |
| 13B | B | ++ |
| 14A | B | ++ |
| 14B | C | ++ |
| 15 | B | ++ |
| 6-((2S,6R)-2-(1-cyclopropyl-1H-pyrazol-4-yl)-6-methylmorpholino)-8-(2,4-difluorophenyl)-2,3-dimethylpyrimido[5,4-d]pyrimidin-4(3H)-one (reference compound) | B | ++ |
| 6-((2S,6R)-2-(1-cyclopropyl-1H-pyrazol-4-yl)-6-methylmorpholino)-8-(2,4-difluorophenyl)-3-methylpyrimido[5,4-d]pyrimidin-4(3H)-one (reference compound) | C | ++ |

wherein "A "denotes an $EC_{50}$ value <1 nM, "B" denotes an $EC_{50}$ value between 1 nM and 10 nM, "C" denotes an $EC_{50}$ value between 10 and 100 nM. Regarding $E_{max}$ values, "+" denotes <75% , "++" denotes 75-110% and "+++" denotes >110% maximal response relative to the maximal response of the reference agonist (8-(4-chloro-2-fluorophenyl)-2,3-dimethyl-6-[(2S)-2-(1-methyl-1H-pyrazol-4-yl)morpholin-4-yl]-3H,4H-[1,3]diazino[5,4-d]pyrimidin-4-one).

REFERENCES

Colonna, M. et al. (2016) Nat Rev Neurosc; 17, 201-207

Deczkowska, A. et al. (2020) Perspective, 181, 6, 1207-1217

Hammond, T. R. (2019) Immunity, 50, 4 5955-974

Suarez-Calvet, M. et al. (2016) EMBO Mol Med, 8, 466-476

Yamazaki, K. et al. (2015) Clinical psychopharmacology and neuroscience: the official scientific journal of the Korean College of Neuropsychopharmacology, 13(3), 324-326

Paloneva BM, J. et al. (2001) Neurology, 56 (11) 1552-1558;

Ulrich J.D. et al. (2017) Neuron., 19; 94(2):237-248)

Atagi, Y. et al. (2015) J Biol Chem., 290(43), 26043-50

Kleinberger, G. et al (2014) Sci Transl Med., 2, 6 (243):243

The invention claimed is:
1. A compound selected from:
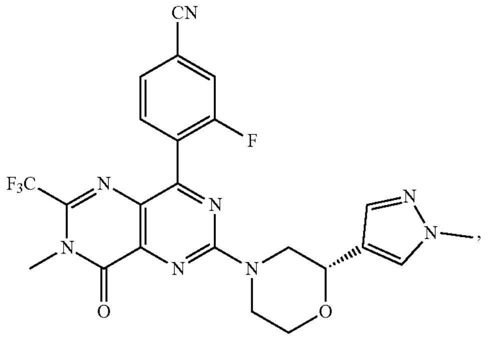 [SMILES: Cn1cc([C@H]2CN(c3nc(-c4ccc(C#N)cc4F)c4nc(C(F)(F)F)n(C)c(=O)c4n3)CCO2)cn1]
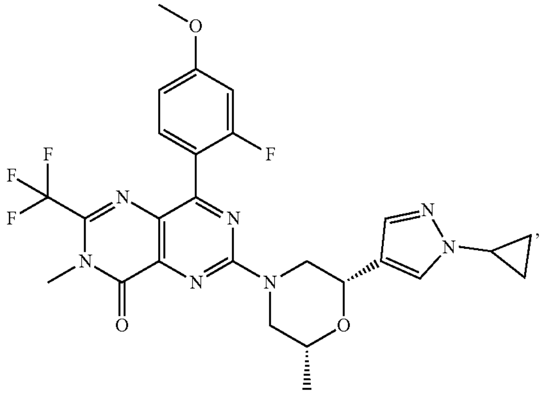
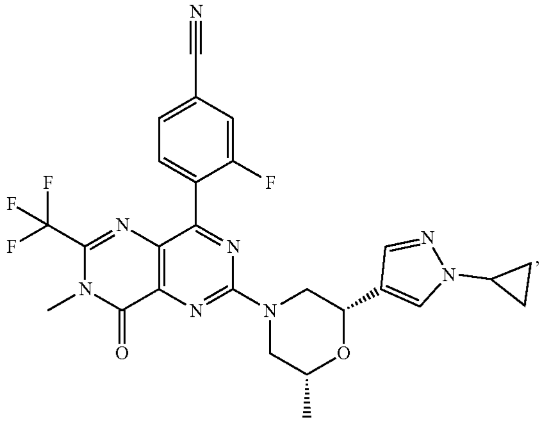
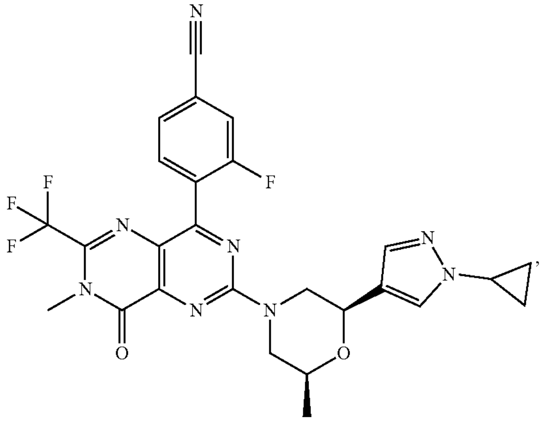
-continued
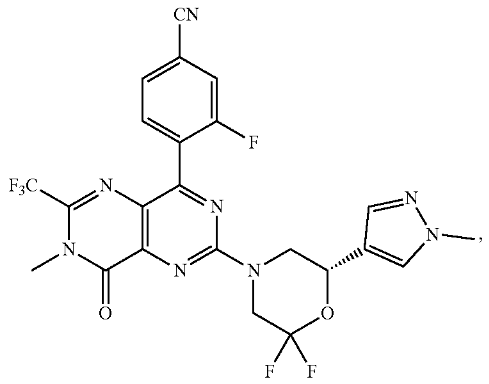 [SMILES: Cn1cc([C@H]2CN(c3nc(-c4ccc(C#N)cc4F)c4nc(C(F)(F)F)n(C)c(=O)c4n3)CC(F)(F)O2)cn1]
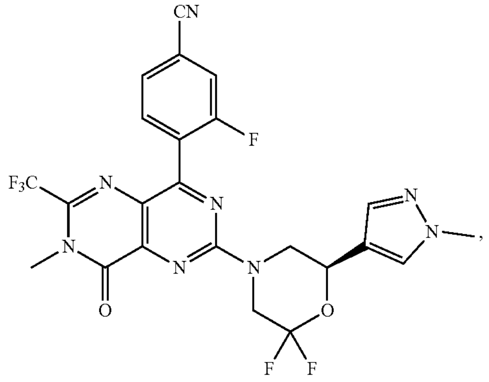
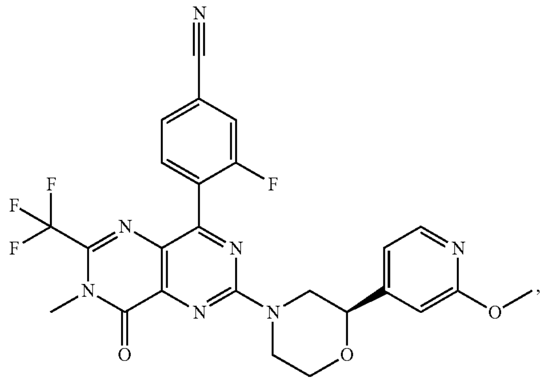
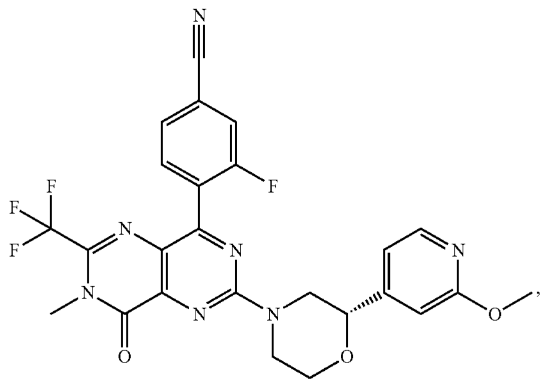

-continued
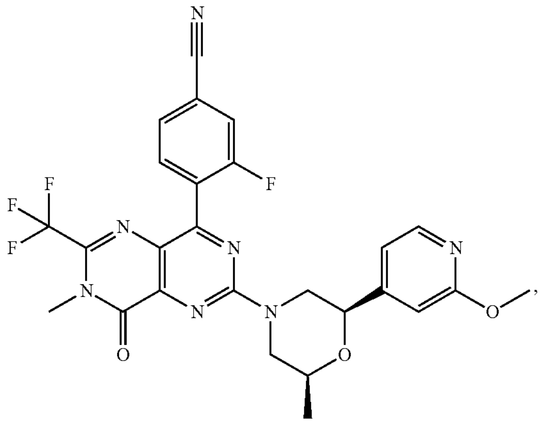
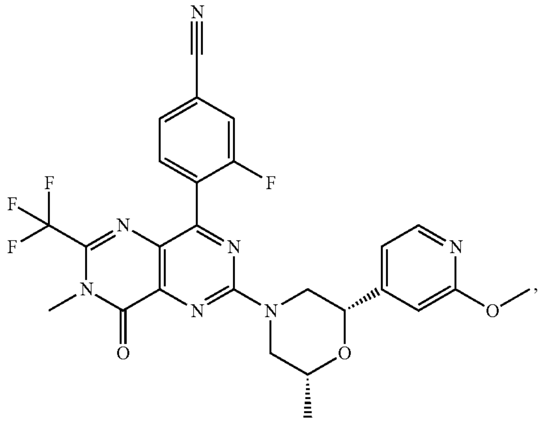
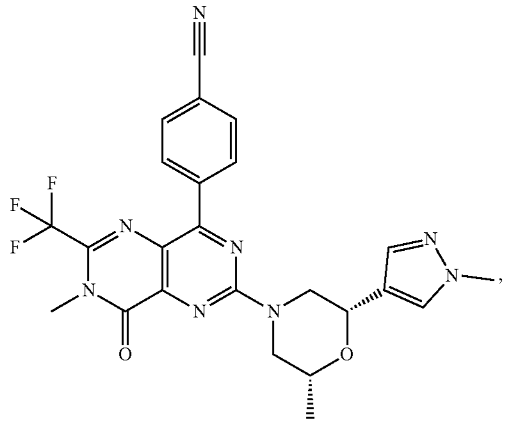
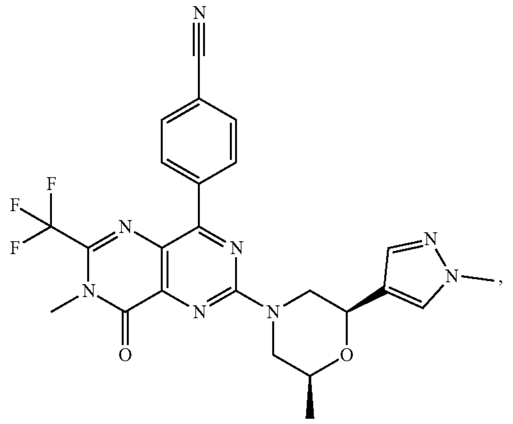
-continued
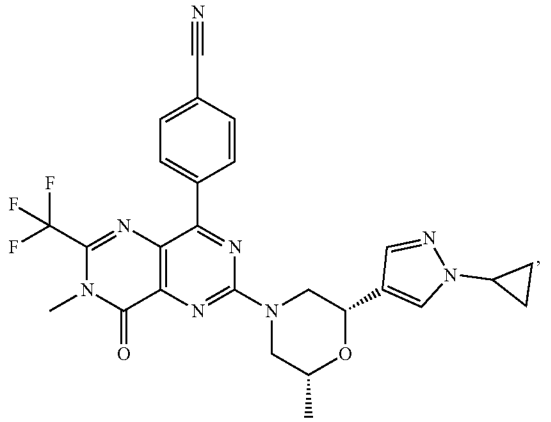
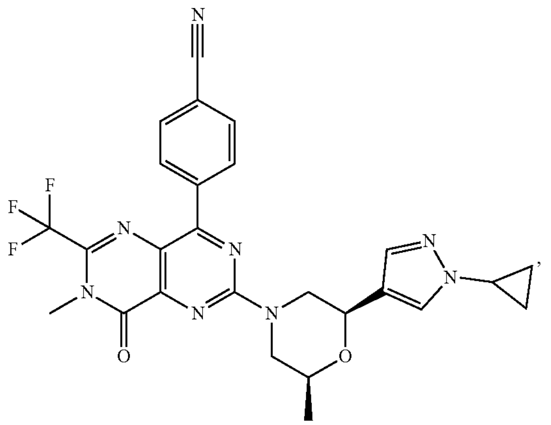
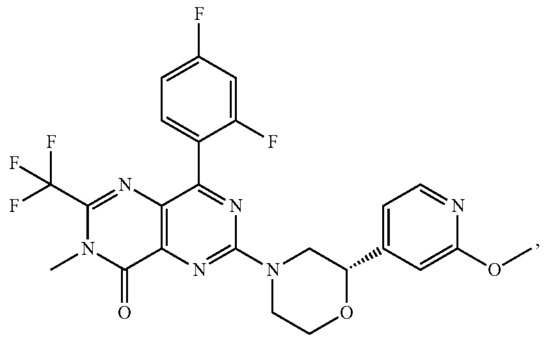
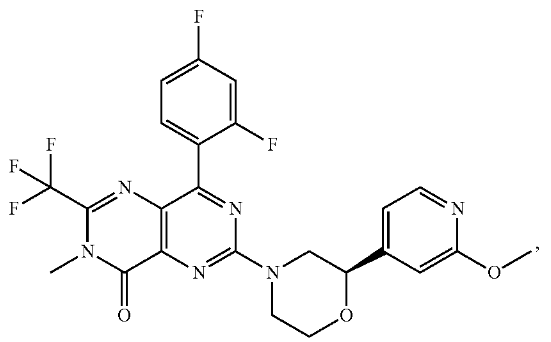

-continued

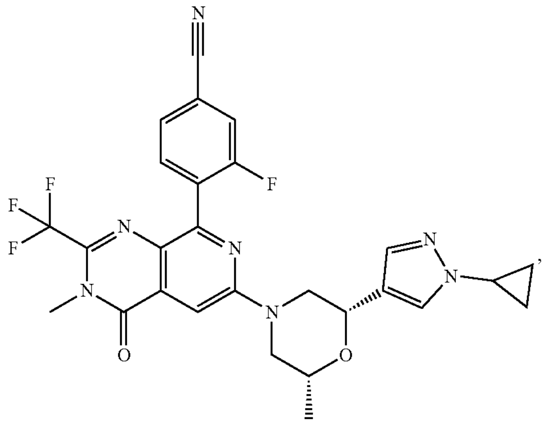

, and

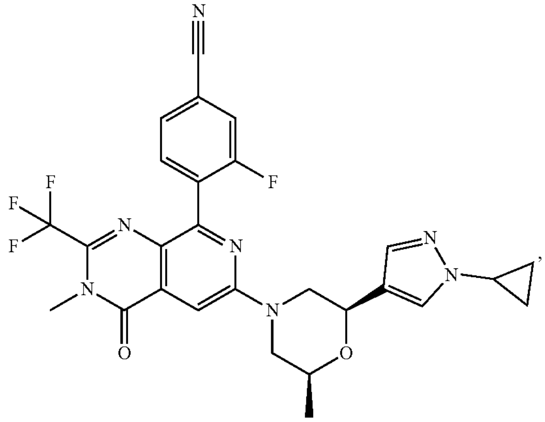

, or a pharmaceutically acceptable salt thereof.

2. The compound of claim 1, wherein the compound is:

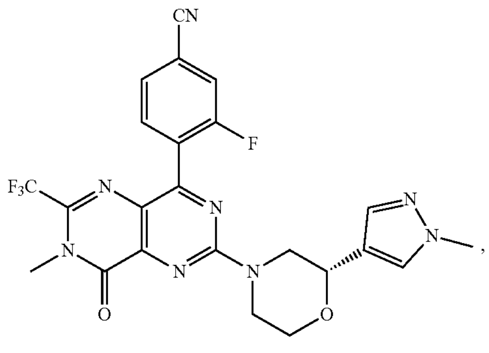

, or a pharmaceutically acceptable salt thereof.

3. The compound of claim 1, wherein the compound is:

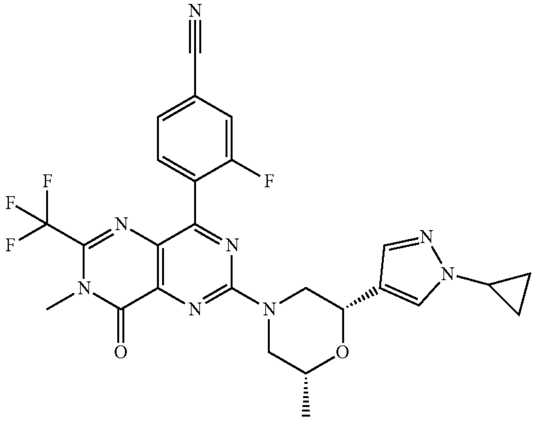

, or a pharmaceutically acceptable salt thereof.

4. The compound of claim 1, wherein the compound is:

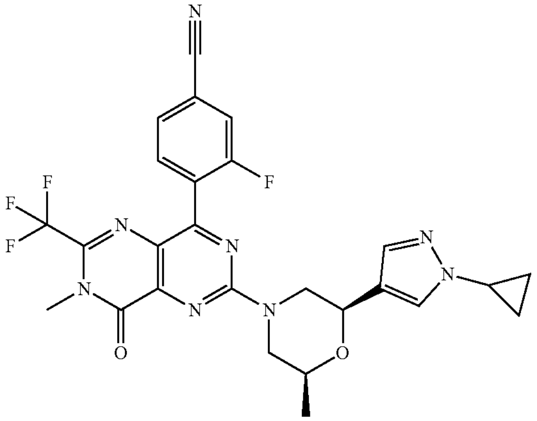

, or a pharmaceutically acceptable salt thereof.

5. The compound of claim 1, wherein the compound is:

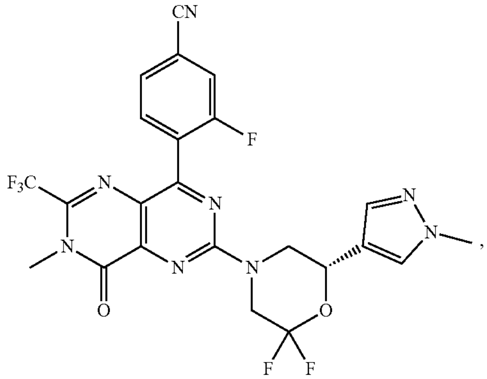

, or a pharmaceutically acceptable salt thereof.

6. The compound of claim 1, wherein the compound is:

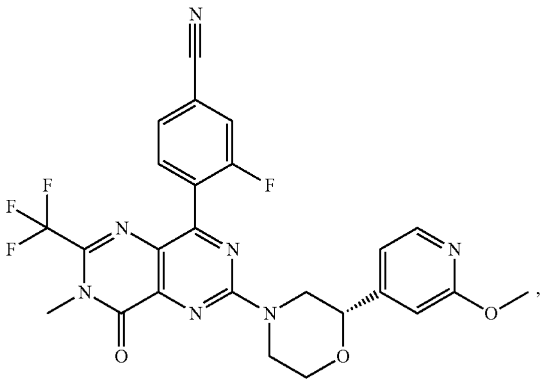 [SMILES: COc1cc([C@H]2CN(c3nc(-c4ccc(C#N)cc4F)c4nc(C(F)(F)F)n(C)c(=O)c4n3)CCO2)ccn1]

or a pharmaceutically acceptable salt thereof.

7. The compound of claim 1, wherein the compound is:

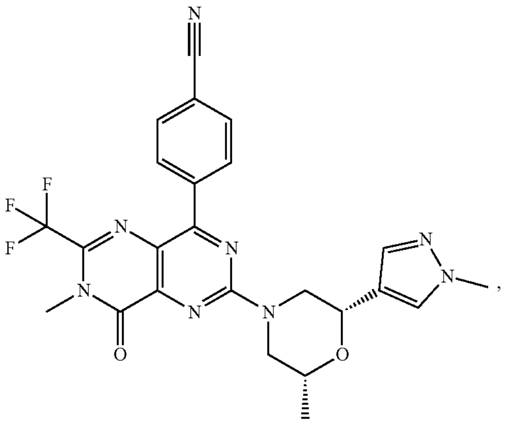 [SMILES: C[C@@H]1CN(c2nc(-c3ccc(C#N)cc3)c3nc(C(F)(F)F)n(C)c(=O)c3n2)C[C@H](c2cnn(C)c2)O1]

or a pharmaceutically acceptable salt thereof.

8. The compound of claim 1, wherein the compound is:

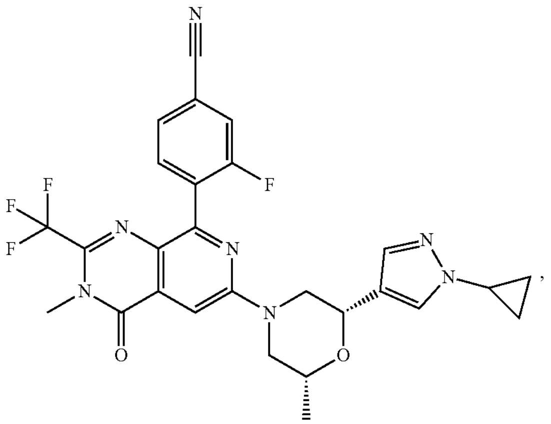

or a pharmaceutically acceptable salt thereof.

9. The compound of claim 1, wherein the compound is:

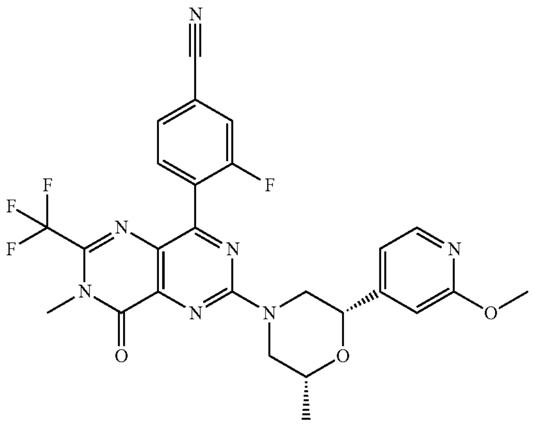

or a pharmaceutically acceptable salt thereof.

10. The compound of claim 1, wherein the compound is:

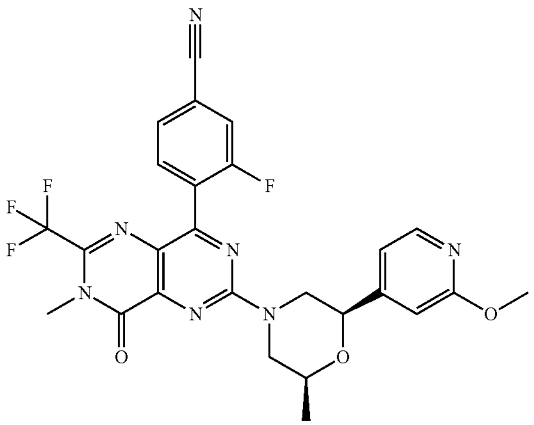 [SMILES: COc1cc([C@@H]2CN(c3nc(-c4ccc(C#N)cc4F)c4nc(C(F)(F)F)n(C)c(=O)c4n3)C[C@H](C)O2)ccn1]

or a pharmaceutically acceptable salt thereof.

11. The compound of claim 1, wherein the compound is:

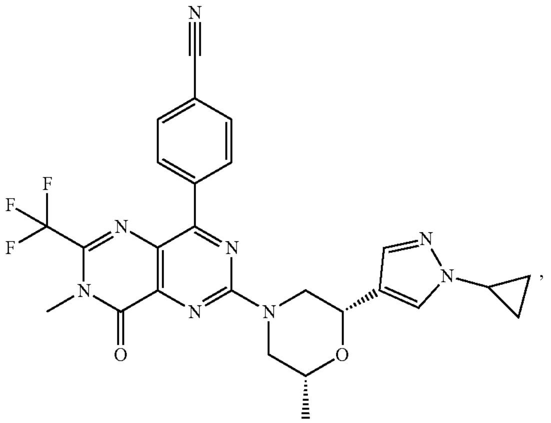

or a pharmaceutically acceptable salt thereof.

12. A pharmaceutical composition comprising a compound of claim 1, or a pharmaceutically acceptable salt thereof, and one or more pharmaceutically acceptable carriers, excipients and/or diluents.

13. A pharmaceutical composition comprising a compound of claim 2, or a pharmaceutically acceptable salt thereof, and one or more pharmaceutically acceptable carriers, excipients and/or diluents.

14. A pharmaceutical composition comprising a compound of claim 3, or a pharmaceutically acceptable salt thereof, and one or more pharmaceutically acceptable carriers, excipients and/or diluents.

15. A pharmaceutical composition comprising a compound of claim 4, or a pharmaceutically acceptable salt thereof, and one or more pharmaceutically acceptable carriers, excipients and/or diluents.

16. A pharmaceutical composition comprising a compound of claim 5, or a pharmaceutically acceptable salt thereof, and one or more pharmaceutically acceptable carriers, excipients and/or diluents.

17. A pharmaceutical composition comprising a compound of claim 6, or a pharmaceutically acceptable salt thereof, and one or more pharmaceutically acceptable carriers, excipients and/or diluents.

18. A pharmaceutical composition comprising a compound of claim 7, or a pharmaceutically acceptable salt thereof, and one or more pharmaceutically acceptable carriers, excipients and/or diluents.

19. A pharmaceutical composition comprising a compound of claim 8, or a pharmaceutically acceptable salt thereof, and one or more pharmaceutically acceptable carriers, excipients and/or diluents.

20. A pharmaceutical composition comprising a compound of claim 9, or a pharmaceutically acceptable salt thereof, and one or more pharmaceutically acceptable carriers, excipients and/or diluents.

21. A pharmaceutical composition comprising a compound of claim 10, or a pharmaceutically acceptable salt thereof, and one or more pharmaceutically acceptable carriers, excipients and/or diluents.

22. A pharmaceutical composition comprising a compound of claim 11, or a pharmaceutically acceptable salt thereof, and one or more pharmaceutically acceptable carriers, excipients and/or diluents.

23. A method of treating a condition associated with a loss of function of TREM2 comprising administering to a subject a therapeutically effective amount of a compound of claim 1, or a pharmaceutically acceptable salt thereof, wherein the condition is a neurodegenerative disease, and wherein the neurodegenerative disease is Alzheimer's Disease.

* * * * *